(12) United States Patent
Sherman et al.

(10) Patent No.: US 7,229,814 B2
(45) Date of Patent: Jun. 12, 2007

(54) NUCLEIC ACIDS AND POLYPEPTIDES INVOLVED IN THE PRODUCTION OF CRYPTOPHYCIN

(75) Inventors: David H. Sherman, Ann Arbor, MI (US); Nathan Magarvey, Minneapolis, MN (US); Zachary Q. Beck, Ann Arbor, MI (US)

(73) Assignees: Regents of the University of Minnesota, Saint Paul, MN (US); Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 11/122,396

(22) Filed: May 5, 2005

(65) Prior Publication Data

US 2006/0057698 A1 Mar. 16, 2006

Related U.S. Application Data

(60) Provisional application No. 60/568,334, filed on May 5, 2004.

(51) Int. Cl.
| C12N 9/10 | (2006.01) |
| C12N 1/20 | (2006.01) |
| C12N 15/00 | (2006.01) |
| C12N 5/02 | (2006.01) |
| C12N 9/16 | (2006.01) |
| C12P 21/06 | (2006.01) |
| C07H 21/04 | (2006.01) |

(52) U.S. Cl. ................. 435/193; 435/69.1; 435/252.3; 435/320.1; 435/325; 435/196; 536/23.2

(58) Field of Classification Search ............. 435/320.1, 435/183, 69.1, 193, 252.3; 536/23.2
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,845,085 A | 7/1989 | Sesin |
| 4,845,086 A | 7/1989 | Sesin |
| 4,874,748 A | 10/1989 | Katz et al. |
| 4,965,188 A | 10/1990 | Mullis et al. |
| 5,063,155 A | 11/1991 | Cox et al. |
| 5,098,837 A | 3/1992 | Beckmann et al. |
| 5,149,639 A | 9/1992 | Katz et al. |
| 5,672,491 A | 9/1997 | Khosla et al. |
| 5,712,146 A | 1/1998 | Khosla et al. |
| 5,830,750 A | 11/1998 | Khosla et al. |
| 5,843,718 A | 12/1998 | Khosla et al. |
| 5,945,315 A | 8/1999 | Moore et al. |
| 5,952,298 A | 9/1999 | Moore et al. |
| 5,962,290 A | 10/1999 | Khosla et al. |
| 6,013,626 A | 1/2000 | Moore et al. |
| 6,022,731 A | 2/2000 | Khosla et al. |
| 6,090,601 A | 7/2000 | Gustafsson et al. |
| 6,399,789 B1 | 6/2002 | Santi et al. |
| 6,492,562 B1 | 12/2002 | Ashley et al. |
| 6,524,841 B1 | 2/2003 | McDaniel et al. |
| 6,589,968 B2 | 7/2003 | Arslanian et al. |
| 6,660,862 B2 | 12/2003 | Reeves et al. |
| 2002/0065261 A1 | 5/2002 | Corbett et al. |
| 2003/0219872 A1 | 11/2003 | Hucul et al. |

FOREIGN PATENT DOCUMENTS

| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 98/27203 | 6/1998 |
| WO | WO 98/49315 | 11/1998 |

OTHER PUBLICATIONS

Seffernick et al., Mealamine deaminase and atrazine chlorhydrolase: 98 percent identical but functionally different. J. Bacteriol., 2001, vol. 183 (8): 2405-2410.*

"NiceZyme View of Enzyme: EC 1.3.99.15," [online]. [retrieved on Mar. 20, 2004]. Retrieved from the Internet: <URL: www.expasy.org/cgi-bin/nicezyme.pl? 1.3.99.15>, 2 pages.

Boddy et al., "Epothilone C Macrolactonization and Hydrolysis Are Catalyzed by the Isolated Thioesterase Domain of Epothilone Polyketide Synthase," J. Am. Chem. Soc., 2003, 125:3428-3429.

Challis et al., "Predictive, structure-based model of amino acid recognition by nonribosomal peptide synthetase adenylation domains," Chem. Biol., 2000, 7:211-224.

Chiu et al., "Molecular cloning and sequence analysis of the complestatin biosynthetic gene cluster," Proc. Natl. Acad. Sci. USA, 2001, 98(15):8548-8553.

Dayhoff et al., "A Model of Evolutionary Change in Proteins," Atlas of Protein Sequence and Structure, 1978, 5(Suppl. 3):345-352.

Eaton, "Organization and Evolution of Naphthalene Catabolic Pathways: Sequence of the DNA Encoding 2-Hydroxychromene-2-Carboxylate Isomerase and trans-o-Hydroxybenzylidenepyruvate Hydratase-Aldolase from the NAH7 Plasmid," J. Bacteriol., 1994, 176(24):7757-7762.

Fu et al., "Engineered Biosynthesis of Novel Polyketides: Stereochemical Course of Two Reactions Catalyzed by a Polyketide Synthase," Biochemistry, 1994, 33:9321-9326.

Eggen et al., "Total Synthesis of Cryptophycin-24 (Arenastatin A) Amenable to Structural Modifications in the C16 Side Chain," J. Org. Chem., 2000, 65:7792-7799.

(Continued)

Primary Examiner—Rebecca E. Prouty
Assistant Examiner—Ganapathirama Raghu
(74) Attorney, Agent, or Firm—Fish & Richardson P.C.

(57) ABSTRACT

The present invention provides polypeptides involved in cryptophycin biosynthesis and the nucleic acid molecules that encode such polypeptides. The nucleic acid molecules and polypeptides of the invention or variants thereof can be used in the methods of the invention to produce cryptophycins.

9 Claims, 39 Drawing Sheets

OTHER PUBLICATIONS

Golakoti et al., "Structure Determination, Conformational Analysis, Chemical Stability Studies, and Antitumor Evaluation of the Cryptophycins. Isolation of 18 New Analogs from *Nostoc* sp. Strain GSV 224," J. Am. Chem. Soc., 1995, 117:12030-12049.

Hans et al., "2-Hydroxyglutaryl-CoA dehydratase from *Clostridium symbiosum*," Eur. J. Biochem., 1999, 265:404-414.

Ishikawa and Hotta, "FramePlot: a new implementation of the Frame analysis for predicting protein-coding regions in bacterial DNA with a high G+C content," FEMS Microbiol. Lett., 1999, 174:251-253.

Jacobsen et al., "Spindly, a tetratricopeptide repeat protein involved in gibberellin signal transduction in *Arabidopsis*," Proc. Natl. Acad. Sci. USA, 1996, 93:9292-9296.

Kim et al., "Evidence for the role of 2-hydroxychromene-2-carboxylate isomerase in the degradation of anthracene by *Sphingomonas yanoikuyae* B1," FEMS Microbiol. Lett., 1997, 153:479-484.

Kinzie et al., "Posttranslational Hydroxylation of Human Phenylalanine Hydroxylase Is a Novel Example of Enzyme Self-Repair within the Second Coordinaiton Sphere of Catalytic Iron," J. Am. Chem. Soc., 2003, 125:4710-4711.

Kneller et al., "Improvements in Protein Secondary Structure Prediction by An Enhanced Neural Network," J. Mol. Biol., 1990, 214:171-182.

Kohli et al., "Chemoenzymatic Route to Macrocyclic Hybrid Peptide/Polyketide-like Molecules," J. Am. Chem. Soc., 2003, 125:7160-7161.

Kohli et al., "Biomimetic synthesis and optimization of cyclic peptide antibiotics," Nature, 2002, 418:658-661.

Lamb et al., "Tetratrico peptide repeat interactions: to TPR or not to TPR?" Trends Biosci., 1995, 20:257-259.

Landegren et al., "A Ligase-Mediated Gene Detection Technique," Science, 1988, 241:1077-1080.

Leahy et al., "A Method for Attachment of Peptides to a Solid Surface with Enhanced Immunoreactivity," BioTechniques, 1992, 13(5):738-743.

Littlechild, "Haloperoxidases and their role in biotransformation reactions," Curr. Opin. Chem. Biol., 1999, 3:28-34.

Marahiel et al., "Modular Peptide Synthetases Involved in Nonribosomal Peptide Synthesis," Chem. Rev., 1997, 97:2651-2673.

Martinez et al., "A Structural Approach into Human Tryptophan Hydroxylase and its Implications for the Regulation of Serotonin Biosynthesis," Curr. Med. Chem., 2001-8:1077-1091.

McDaniel et al., "Engineered Biosynthesis of Novel Polyketides," Science, 1993, 262:1546-1550.

Nakazawa et al., "UV and skin cancer: Specific p53 gene mutation in normal skin as a biologically relevant exposure measurement," Proc. Natl. Acad. Sci. USA, 1994, 91:360-364.

Neilan et al., "Nonribosomal Peptide Synthesis and Toxigenicity of Cyanobacterial," J. Bacteriol., 1999, 181(13):4089-4097.

Pattern et al., "Applications of DNA shuffling to pharmaceuticals and vaccines," Curr. Op. Biotechnol., 1997, 8:724-733.

Ramjee et al., "*Escherichia coli* L-aspartate-α-decarboxylase: preprotein processing and observation of reaction intermediates by electrospray mass spectrometry," Biochem. J., 1997, 323:661-669.

Rohr, "Combinatorial Biosynthesis—An Approach in the Near Future?" Angew. Chem. Int. Ed. Engl., 1995, 34(8):881-885.

Ryle et al., "Interconversion of two oxidized forms of taurine/α-ketoglutarate dioxygenase, a non-heme iron hydroxylase: Evidence for bicarbonate binding," Proc. Natl. Acad. Sci. USA, 2003, 100(7):3790-3795.

Saitoh et al., "Mammalian thioredoxin is a direct inhibitor of apoptosis signal-regulating kinase (ASK) 1," EMBO J., 1998, 17(9):2596-2606.

Schwarzer et al., "Nonribosomal peptides: from genes to products,"Nat. Prod. Rep., 2003, 20:275-287.

Sikorski et al., "TPR Proteins as Essential Components of the Yeast Cell Cycle," Cold Spring Harbor Symp. Quant. Biol., 1991, 56:663-673.

Smith and Johnson, "Single-step purification of polypeptides expressed in *Escherichia coli* as fusions with glutathione S-transferase," Gene, 1988, 67:31-40.

Solomon et al., "Non-heme iron enzymes: Contrasts to heme catalysis," Proc. Natl. Acad. Sci. USA, 2003, 100(7):3589-3594.

Subbaraju et al., "Three New Cryptophycins from *Nostoc* sp. GSV 224," J. Nat. Prod., 1997, 60:302-305.

Tang et al., "Cloning and Heterologous Expression of the Epothilone Gene Cluster," Science, 2000, 287:640-642.

Trimurtulu et al., "Total Structures of Cryptophycins, Potent Antitumor Depsipeptides from the Blue-Green Alga *Nostoc* sp. Strain GSV 224," J. Am. Chem. Soc., 1994, 116:4729-4737.

van Pée and Unversucht, "Biological dehalogenation and halogenation reactions," Chemosphere, 2003, 52:299-312.

Waugh and Long, "Prospects for generating new antibiotics," Science Progress, 2002, 85(1):73-88.

Williamson and Brown, "Purification and Properties of L-Aspartate-α-decarboxylase, an Enzyme That Catalyzes the Formation of β-Alanine in *Escherichia coli*," J. Biol. Chem., 1979, 254(16):8074-8082.

Wilson et al., "Analysis of Promoters Recognized by PvdS, an Extracytoplasmic-Function Sigma Factor Protein from *Pseudomonas aeruginosa*," J. Bacteriol., 2001, 183(6):2151-2155.

Wu et al., "Biomimetic Synthesis of Gramicidin S and Analogues by Enzymatic Cyclization of Linear Precursors on Solid Support," Org. Lett., 2003, 5(10):1749-1752.

\* cited by examiner

FIG. 5-1

PDAM163
TGATATTAGATGTTTAATATCTTAGGAAATTTTGATAAACAGGAAAGCTTATGACTGTCAGTTGCGAGAAC
GGTAAATTTTTAAACATATTTGCTCAACTTTCTCAACCACCAAATACTTTGCCTTCAGCTTAAAAAGCAAA
TATACTTCTTATTCGCTTTGGATATAACGAAAGTTCATATCCCCCTTGTAGCCAGAAGCTTTCGCAAGATC
CTTAAAGTTTTGCACGCCGGTATACTGATGTCCATTGATAACCCAAGTTGGTACACCTGGGACTTTCGCCG
CATTGCACAAGTCTGGGTGGGGATTGATACCTCTCTTATCGCACTCAACTTTAATACTGTCGTTGATTATT
TGGTAGGCTTGCTTCCCAAAGATTAACTTTTGTTCGTGACAGTGAGGACACCACCAAGAAACATATTCTTT
TGCCCCGATATACACCAAATGCTTCGCCAAGGCTAGTTCTGCCTTCCCTGAAGTGGTAGTGATTTCCCAAC
CGACTCCGGTCTGAGGTCGTTCTTTGGGCAGGAAGAAAATAATCGATGGGGACTTTTGGTTGTCTGTTTGT
TGAGCAATATCTGTCAGTAGTGCAGAGCCAGAACTCGTACCAACACAAATAATGGAGAGCGTTAACAGTGC
AAATAAAAAAGGGTGTTTGATAGCCATATTAAATATATACTTTGATTGAATAGTTGTCGAAGCTAACAATT
GTATGTTTAAGATTGTAGTATTTTGTATAACTGATAATACGAAGCCAGAKRATCCCCATCTTATCTTCGTC
ATAATCGAAATTATCATCACCATGTTCTTCATACCACTTTCTTTCTTCCTCCAAAGCGATTTCTCTCTCGA
TGATTTTTCTTTCTAGAATTTCACTTTCTAGAATTTCACTTTCAAGCTTTTCTCTTTCAAATCTTTCTCTT
TCTATTCTTTCTCTTCTCTGCCTTTCTTTCTCTTCTCTTTCTCTCTCAAGTTGAATTAATCGCTGCTCCAC
TCTCTCACAGTAAAAATCCAAGGCTTTACCAGTGGCTGCTCCGGTAATTGCACCACCAGCCAAAAATATTA
TTACAGTTTTCCAGCCTTGAATGGGATTACCGCTCCACTCCAAACTACCCTCATTGAGCCACACTAGTAGG
AAGTAAACGAGAATTCCAATAACAGTATTGATCGGTGCAAAAACTCTCGGTGTCATCTGGGTTTGACGAAG
TATCAGCCATTGCGCCAGGGTGAGAATCACACCAAAGATTGCCGCAGCAATTCTGAGAGAATCAGATTAC
CTGGGAAACTAAACGGATCTACTGTAAATCTAATGATTAGCGTGATAATAATCGGGGCAGAGAGCAAAAAG
CTCAGAAGTAAGCTAGCGCTAATCGCAAGAAACCAGTAGCGACCGAGATAACCCAGGCGAAATTCTAACAA
CGACTCTTGTACTTCCAAACAAAGTCATCCAAAATGCAATACTCGCGGTCAAATAATCAAGCATTAGCCGT
TGTTTTACCCGTGTGTTGAAGAGGGTATTTTCTAGAATACGCCCAAACAGTATTTTGTTGTTGTGGTGGCT
CTGGTGTGGTGTTTTTTTTTTGATAATTGCTCTATGAGATTTTTCAATGAGTTTTATATTTGGTAGTGCT
TTAAGGCTGCAAAATATAAAAAGCAACGAAAAACCCCATCCTTCATACAGGTTGGGGGGATAGATAAAAAA
CATATATTCCATGATGACACAATTCAATATTTGTTCGACTGCTGTCAGCCTAGAGGTGGGGCAATGAACAA
ACCACCATCCAGACGCAAGAAAATTACCCCTGCGACATCTGAGGAACCAAAGCTAGCAACTGACCCTGCTC
AGGAAAATACTTCTTTGCACGAAAATCCAGGGGGAGCAACTATCACGGTGACGGCTGTTGAAGTAACAGAT
TTGACCCAGGAAGAACAAAGCTTACGCCTGCATTTAGAACACCGTGTGGAGAGAGCATTTTTGGAGGCGGG
TCAAGCGTTGATGGAGTTGCGGGACAGACGGCTGTACCGTTCCACGCACCGGACTTTTGAAGAATACTGCC
GCGAACGCTTCAATTATAGTCGTGACGCGGCTTACTTGAAGATTTCGGCTACTGTGGTTTATGAGAATCTT
CAAAAGTTTTTGCCGACCATTGGTCGGCAAATTCCAATGCCGACCAACGAACGACAATTGCGTTTTTGGC
GAAAGCCGAGTTGGAACCGGCTGTGCAAGCGGATGTATGGCGGCAGGCAGTGGAGCAAGCTGGCAATAAGA
TTCCATCCGGTCGCATAGTGAAAGATGTTGTAGATAGGATACGCGAAAGGACGAAAGTACCCAATCCTTAC
CACGTTGGGGAGATATGCGTTCTTCTACCCAAAGATAATGCAGACTTGAGAGGTAAAGCGGGTTATTGGGG
CGTGGTCAGCCATGTTGGAGAATACAGTTGTACACTCCAGATATGGGACGGTGACTATACCGTAAAAATCG
AACACCTGAAATCACTGGAATTACTTGATGAAGATTGCCAATTCATGCAGCAGTTATGTGTGAGGTTACGG
CAGTTGCATCAAGTGGACAGGCGTGACGAGGCTGTGGATTGGCTGTTGCAGTGGTTGGGGAAACAGGCCAA
ACCTTATCTGTCATCCTTGCAGTCAAAGCTGCTGGCGTTTGTTGAGAGAGTACAACCTGGTTTGGAAGC
AGCAGAAGTGATGAGATAGCTAGTAAACAATAGGTTAATCCAACAAATACACAATGCAACAATTAACTCAT
TGCATGAAAGCGGTAAGCGATCGCGGAGGGTCTGGTAGAGTTGCCATGCTGGAAGGCTTATCGGTTCAAGA
AGAAATCTGAGTAGGTCATGGGGAGTGTCCTTTTATAGCCGCCATAACCGGACAGTTACCATTTTTCCCTC
ATGACATAGCACTAAATCTTACCAGCACTTCAAATTAAAGGTAAAGCAGTGCTAGTCATCAGTCACGATGA
TAAATATTTCCATTTAGCATCTCGCATTGTAAGGCTGGATTACGGACATCTTAAGTATGAGTCATGAAAAT
TATGTATTCCAAACCCGACAACTTACTGCATCCACTGTACCCAATCAGGCGCAGATGTCATCAATTGACTA
AACTTATCAGTGTAAGTATCGTCAAACTCTAGCATCACTCCCCATCGCTCATCACTCGTGAATCGGAAAAT
TGGAACTGAAGCCGATGCAGAGGAACATAACCGCCACAAAGCTGAAGTAAGCGCAGCAGATGATTAGCTCT
ACGATCCAGCCCTCTCAATATTGACAAATAGTACACTATGTGAGTTTTCTAAGAAGGTAAGACTAAAACTG
CACTTAAGCGCTTATGTTATCTCCCCTATTTGATGCTTTTGTAGAGGCAAGCCCCGTCAGTGTAATGATGC
GAGTCCTAATGGAAAACATTTTTAATTCCTCGCGAATGAATCAAATATTTGATACATCAAGCGTTCGCCAA
TACTCTCAAGAGCTACTGTTTTCGACTCAGGTGGATTTGATGAGTCTAGTAGTGTGTGGGATGTATCCCTC
GGTTCATGCAGCCTATCAGAAGAAGGCAGTGGAGGTAAGTGTCAGCGCCACAGCGTTATACAACAAACTGC
AACGGATTGAACTGCCTGTAAGTCGGGCATTAGTGCATGAGACAGCATCTGACCTCCAGCAGTTGCTGTTG

FIG. 5-2

```
ATGTTGAATGTGGAACGCCCCAGTCCTCTAGGAAAACAATATCGGTTGCGGATTGTAGATGGCAGTTGTTT
AGCCGGAACCGAACGCAGACTAGCAGCGCTGCGCCCCATGCAGCCAAACCATTACCCGGAAAAACAATCG
CCATTCTCGACCCAGGGACAAAACTGGTGGTTGATGTGATTCCTTGTGAAGACGGTCATTCCCAAGAACGC
TCCAAGTTTCATCAGGTTTTGGCACAAGTGCAACCCCAACAGGTATGGATTGCAGACCGTAACTTTTGTAC
CGCAGGATTTCTCCATACTATTGCCAAACTTGGAGCGTTTTTTGTGATTCGTCAACACGGGGTTTAGGAT
ACGAGCCTTTTGGTGAGTTACAAGCTGTTGGGTTGTGCCAAACAGGAACTGTGTTTGAACAACAGGTGGAA
ATTGTCCATGAGGGAGGGACTTTTCGGTGTCGCCGTATCGTAGTTAAGTTGACTCGTCCCACCCGTGACCA
AGAGTGGGAAATTGCCATTTTTACCAACTTACCACCCACTGACGCAGACGGCATTCTGGTGGCACAACTCT
ATCAAGGGCGGTGGAGTGTGGAAACTTTATTCCAAACTGTGACCCAAAACTTTCATGGAGAAATTGAAACC
CTAGCTTATCCTAAAGCTGCCTTATTCTCCTACTGCATGGCACTGTCAGCCTACAACCTTTTAGCGACACT
TAAAGCAGTTCTTGGCAGTGTACATGGGGTAGACAAAATCGATATTGGGCTATCCGATTTTTACCTAGTAG
ATGATATCCATTCCATCTATCGGGGCATGATGATTGCTATTCCTCCGGTTCATTGGCAATTCTTTGAGGAG
TTTACCAACATTCAGATGGTAGACGTTCTCCAGCATCTAGCAACCAAAGTACATCTCAAATCTTTTCGCAA
ACACCCCAGAAGTCCCAAAAAGAAACGACCACCACTCTCTGTTGATGGCAAACATTCCCACTGTTCCACTA
CTCGAAAGCTCAAGCAATACAAAGCAGCTCTTGATGCTATCCCGTGAAGCAATTTCATAAAATATGTTATT
TGTCAATATTGAGAGGGCTGGCTCTACGATCCTAACGTGGCAAAACTTACTAGAGAAGAGTAAAAATCCTG
TAATCTTGACCTTGTAGCGAAATAATGGTGCGAAAACTTGGCATGAAATTGTCTAAAACCAGAGGCAACAT
CGTTTGAAGTACTCGATTGTGTTCAAAAAAAATGCCCTTCGTGCGGTCAAGCAATGTGGAATGAATACAAT
AATCCTCGACATATAAGAACGTTAAACGGGGTAGTAGAACTACAACTAAAAATTCGTCGATGTCAAAATAA
TTCATGTCTGCGGTACAAAAAAGCATATCGACCAGAGCAAGAAGGGTCACTCGCTCTACCACAAAACGAAT
TTGGTTTGGATGTGATTTTATAAGGAGCATTACGCTACCAGGAACATAGAAGTGTTCCCCAAATACACGCT
CACCTCGAATTAAAAGGTATATGTATAAGTCAACGAACGGTCACGCACCTAATTGACAGATATGACGAGTT
ACTTTCTTTATGGCTAAAAGACCATAAAAGGTTAAAAGCAATAGTGGCTAATCAAGGACGGGTTATATTAG
CGATCGATGGAATGCAGCCAGAAATTGGACATGAGGTATTATGTATGCTTTGAATCATAATGTGAGAAAAA
TTTTGATCCATAAATTAGAAAAAGTTAACGAAAATTCAGGCTTTCGTGCTAATCAAAAATTAAAACTTTG
AATCAAATTATGAGTGAGAGTTGAAATTCTGAATCATAACTAGAGAATGAGTTGAAAAAACACAATTGGAC
AAAACTTGCACAAAAAATCCCTGACAAAATTTCTCTAACTTAAACTTTCAATTCAGAATATGGTTCAAATA
CCAATGTTATGGTTCAAAACTTTTACACAAGCTGTTAGGGTAGCATTACTTAGTATTGCTCATGGTTTATG
TCATTATCATTACCTGAAGGAAGCAATTAAACCCATATATGAGGCGGATCGACATGCAAAAAAGGAATAAA
AAAAAAGGTTAGAGGATTACGAGACATTGAATGTAGTGTTGTCAATGAAGATCAGAAAATGGCGACTATTA
TTGAAGATTATTGCTCGGCAGTACGTAGTTCTATAACCAATGATGGTCAAACCAATTCGCAATTGACAATT
CGCAATTCGCAGTTGAATTCAAAGTTAGCTCTGAACCCACCCCTGAATTGAGTCTACTGATTTAGAGAATC
AGAGTTAGCTCTGAGACCCATTAATTAACAATTCAACAATTAAGTAATTTCTTGTCTTTAATTGCGAATTG
CGAATTGACAATTGTTTCGGTCATCCACCGTTAGAGGCATCTGGATTAAAGTTACAAGAAAATTTGACGTT
GATAGAACAAAGCTTAGAACGGATGGAAAAAAAGTGCTWTACCACCACCTTTAGTCAACCTAAAATACTGA
TAGCCAAGGGATTATCTGCGACTGTATCTTTATTTTCACTTGTTAGGGTTGCATATCAGTGGGTTGATAAA
GCTAGTTATATTCTCAACAATAAAATAGCTTTTGATGCTGCTGGAGTCAAACAAAGTTATCAACAACTGTT
AACAGAAATGTCCCAACAAAATAGAAAGCTGGTACACTGAATACCGCAATCGATAACTTTATAAAACCA
CCCATAACTACTGGTCTAGACTTTTTCATTGTTACGAAATTGAAGATTTTCCAGAACTAATAATGACTTA
GAACATGCTTTTGGTATGTTACGTCATCATCAACGTCGTTGTACTGGTCGTAAGGTTGCTCCCTCATCCCT
CGTTATTCGTGGCTCTGTCAAACTTGCCTGTGCGTAGGCGTAGCCCGTCGTAGACATCGCTACTAAGCTTC
ACTCTTTTACCGCATCTGATTTAGCACAAGTTGATATTCATACTTGGCTCGAATTACGATCTCAACTGCAA
AAACACCACAAAGCCAGAATTGAACAATATCGATTTCTCAGAGACCCCAAGGGTTACTTGGCTAATTTAGA
GAGTCGTCTTCTCTAGTAAGTTTTACCATACTAGGTTTTTCTTGTTCTCAAATCCTGTTGCCATGACTCGG
ATCTTGCAGCTAGATGGTAAGAATTATACCCTAGCTCGCATAGTGCCACTTTCAACCCGACGTTGCAGTTC
AGGTAAGTCCGCTTGTCAATAGGGTTTGAGACGCGCTAACCCTGGGGTATGAAGACTTAAACGATCATGAA
CAATTACGTCATGACAAGATGTTCGTCTTGGCGAGCAGCATCGCATAAATTTTACCATTTTTAGTATTTC
CAGGCTCTAAGTGTGGAGCAAAGAGTTTCTTTGGAGAGGGATTACCTGTACCAATCCTAATTTTGGCTGAG
TTGTAACATATAGACCATCAACTGCCCCAACTGCCGATAGTATGGAAAATCCCTCGACTGCATTGAAAAAC
TGGGCATTTGTCTTCATTACCTCGTTACCTTTTTCCCTTTCGATTGCCAACGCCTGCTTGTCTTGCCTAAT
GCTGTGGCTTGACTGAATCCGCTGAGACATCTCTGCCATAACAAAATCGGCAATCCCCTCCTTAGCGTCCT
CCAAGTCCTCGACGCCGGACACCAGATTCAAGAATGCTAGCTTTAGGTTAGAACTGCCGAAGTCACGGCGA
CTAAGCCGTTGTGCCTCCCAGAAATAGGAATCCTTGCCACGGTTTTGATCGTAGAAGGCTGATACGAACAC
TAAGAAACGCAAATAAGCCTGCCGATAGCTCTGATCGTAGAAGAAGCAGCTTGTGACTCAGTCACCTCGC
```

FIG. 5-3

```
CACGTATAACACTTGTGATACTGGCTGCGGCTAACAAAGCGCTATAAGTAGCAAGATGCACCCCACTCGAT
AGTAGGGGGTCTAGGAAGCAAGCAGCGTCTCCCGATATGAAGTAGGCTGGTCCTGAAAAGGAGTCGGAAGT
GTAAGAGTAATCTTGCTCAACTTTCACGTCTGAGACTAGCTCCCCTAGTGCAACCAGATCCGCTATCAAGG
GACACTCTGCAATCGCCTCCACGTAGATATCCTTCAAGTTCTTAGTCAGTCTCTCCTTGTAGGTTGACTTA
TGCATCACTACACCAACGCTCATAATTTCCTCATCCAAAGGAATTCCCCACACCCAACCATCTGGAATGGA
GCCCAAGGCAATCGCACCCGACTGACCTTTAGGTAGTCTCAAGGCGTTTTTCCAGTACCCCCAGATGCCAA
CATTCTGGAATACGTCGTGTAGACGGCGGTTTTTCAGATACTCCGTCGCCATGATCCCAGCACGACCTGAA
GCGTCAATCATAAAGTCAAAAGAAATCTCCCCGGTAGTATCATTTGATTGTGACCAAGTAGCGCTGCGCGG
GCGATCGCCATCAAAAGACAACTGGCGAATTTTAGTCCCTTCAAAAACCTTCACACCCTGGCTCTTTGAAT
GCTCTAAAAGCAAGTGGTCGAATTCGTCACGGCGAACTTGGAAGCTGTAGGTGTTGTCCCCGTAAGTTCC
CCAAAATTGAGGCTCCACTTTTCCGTTCCCCATTCTATGTACGCTCCAGGTTTACGCTGAAAGCCATAAGC
TTCAATTTTCTCGCGTACGCCAAGCAGGTCAAAAATTTCTAAAGCAGAGGGCAAAAGAGATTCCCCAACGT
GGTAACGCGGGAATACCTCTCGTTCTAACAGCGTTACATCAAAGCCCTCACGAGCCAATAGGGTAGCAGCA
GTAGATCCAGAAGGTCCCCCTCCGATAATTAGAATCTGTGTGGAATTAGGCAGTGTAGACATTGCAGGTTT
CTTCTCCAAAAGATACAGTATTTTCGCAACAATGGCGGTTGTGTCGCCTAGGGACAAACAATCTGTCTTAC
TCGTGTGGCATTAAGCGACAACTCCAAAGATTTCTTTGATAAACTTGGCTTGAGCTACACTGTTCCCCGGC
CGATAAAGATACTTCCACTCCCCTTTAACTTGGATGTAAGTTTCGTCTACCCGCCATGAATCATTCGTCTG
CTTCAAATAAATGAGGACGAATCCGAAATCCAGTTCCAAGCCGCATTTCAACACCCATCAATTCAGGGTGG
AATGATCCACGTCTATGCCTCGCTCCTACATCATCTCCTCCAAGTCCCAATAGAACAACGAGCGGCAGTAC
CAACGCACATTAAGCAGGATGATTTCTGGCAAAAGGTGACGCCATTTGAACAGGGAGCGAGTGGAAATGGA
AAGCTAAGAGCCTGTCAAGAAACAACTTTTACAATTTATTATCTAGAAAGCTTACTGAGAAAGCATTTCTA
GCTCAAAAGAGGCAAGGTTGTTACATGACAAGCTCTAAGCATTAACGACAAGGATTTCCTACCCTGCACTA
TCTCACTCAGCTTTTTGCGACACAACCTTTAAAAGCACACTTTTAAAATGCGATGGGCTTACGCCTTACAG
GTACTTGAGAAACTTGTTGTTTTCATCCACGATAATTTTTTTCGGTTCCTTGATTTCGTCAGTTACCTCGA
ATGCTAGCAATGTGATAAGGTCTCCTGAATTGACTAGGTGGGCGGAGCCACCGTTCATACAGATTACCCCG
GAATTTTCCTCACCTTCTAGGACATAGGTTTCTAGACGATTACCATTAGTGTTGTCCACCACCATAACCTT
TTCACCCGGTAGTATGTCTGCCTTTTCCATCAGAACTTTGTCTACTGTAATACTTCCGATGTAGTTAACGT
TGGCTTCCGTCACCGTCGCTCTGTGAATTTTCGACTTCAACATAATACGCATCGTTTCTTTCCTCATGTGG
CTTTAAATTTCAATTGAGTTGACTGAGAAATATCTGAGCCTATATCTATTTGAGATGGCTGATACTTTTA
GCAAATAAACTCAAGTTTTTTGGGGCTATAGAAATACCAAACTTTAAATTTATAATATCAGATTGTCCATC
AAACCAAAGTCGATTTAGTAGCCTATACTCTTGTTTGGAAAATGCAGTTCTTCCATGCAAAACTCTAGTAT
TATCTACAATAATTATTTGGTTTTGTGCAAGTTTAAAAATTACTTGATTGTCAGGATTATTTACAAAGTTT
TCAAATGATTTAAATGCCGCAAAACTTTTCGATTCAACCGAAACATGAGCTGCATTATCTGCTCTAAACCT
TACAATAAGCCCAGCATGATGTTCTTCAAAAATAGGTTTAGTTGCTTTTTTATTATCTCTTTTGACTGTAA
TCGCATCAGGATTAAACAAAGTTAACAATCCAACTGGGTTTGTCCGCTTTAGATGTTCATATACCAGCTTG
CCATCAATAAGCTTGGTGAACCCGCCATTTGCAGCAGCAATCTGGCACTGCATTGCCATTACTTTTGGTGG
AGTAATTGTGAACGCTCCATCCGTATGTAACGATAAATCTGTAGTTGTAGTATTTACATATTCTGGATAAC
TATCAACAGGACTGATGGGAACAATTCCCTGTGAATCAGAATGTTCGTGCTGAATAATTGTTCCAAAATAA
TCAGACAATTTTAATAAGTTATTCTTAGGTGTTGCTGAAGGTTCGTGTTCTAGTATTACGAATCCAAACTC
ATTAAATTTATTTGCCATCTCAGCTTCTTTAGAAACTGGCATTTCTAATACACTTTTCACTCTAATTATTA
GATTTTCAATTTTTATTGAATACATTTTTAATTTTCTCCTGGATGTCACTGCTCTGCTACAACTAGCTTAA
TTTTTTTAGAATTCTCATGTTTACAATAAATACGTTTTCAAAAAAAATACTATAAGTCTTGCTGATATAGG
TTGTAAATCCCTCGATATAGCTAGGTAATAATCAAACATAAAATTAAATGCCTCTATTGCATGTTTATTTA
GAGCATGATAAGTATGTTTAAACAGAATTATTTACATTCAGTAGACCAAAAAGCTTTCCAAAAGACTTACC
AGCTATTGATTTCCTTGGGAATGCAATAATCCGCCGATATAAGCTTTTAAGAGGATGTTTAAAAAATTGG
GAGTTGAGTAAAAAATATTTTAAACATCCTCTAATAGTTTAAAATTCAGTTTTTTACAATACAACCATTTT
TAATCCACCTTGAGGATAAATTGAGAAAATATCTCGTACTGGTTTTAAAGGAGGTTTGCCTACCAATTCCA
ATTGCCAATTCCGCAAAATATTAGCCAATACTAACTTCATTTTAAACTGAGCAAATGCCATACCAATGCAA
GTTCGGTTACCGCCACCGAAAGGGAAATACTCATAATTTAAAAATTTATTATCTAGAAAACGTTCTGGCTT
AAACTGTTTAGAGTTAGGATATAGTTCTTCCCGGTGGTGAATTAGATAAATACATGGATAAAGACAAGTTC
CTACCTCAAATTGATGACCTCCAATTTCTATTGGCGATTTTACAATTCGAGGAAAAGTAGTTAGACCAACT
GGATATATTCTCAAGGTTTCAGCACAAACTGCATTGAGATAAGGTAATTTGCTTATTTCCGTTGGGTCTGG
ATTATCTCCTAACTCATCTAATTCTTGCAATAACTTGGCTCTTATCTCTGGTAAGTAATGAATCCAATAAT
ATGCCCATGTTATTGCTGCAGATGTAGTTTCATATCCAGAAAAGATAAGTGTCATTAACTCATCTTGCAAC
```

FIG. 5-4

```
TCCTCATCTGTCATTTTTCCTCCATTTTCATCTCGTGCTGCCATCAGCATACTGAGGATATCATTGTTGTA
ATTGTTACAATTTTCTCTACGTTCTTTGATTTCTGCAGAAATGATATTTGCAATCTGACGTTGGCAACGTA
AAAGATTACCCCAGGCACTCCAAGAACCCCAGTCTCTTCTAAACACATTGAAGAAAAGAGAGCTAGAAGCA
AAGGGATTAGTTATAGTGGATACTATTTGATTAACTATCAATTTGAGTTGTTGATAACGTTCCGTTTTATC
TGAACCCAGTAAAACCGTTAACATCGCTCGCAGCGTAATTTCTTTGACTTCCTTGTAAATAATCAATCTTT
GACCAGGTTGCCAATTAGAAGTAACCTGCTTCGTTGCATGGCATATTAGTTCTCCATAGTTAGATATATTT
TGACCATGAAAAGCAGGCATCAGTAGTTTACGCTGTCGTTTATGACTACTTCCATCAAGCAAGGTGACGGA
ATTGTTGCCTAAAAAAAATCCTGCTAAATCGTTAGCTTTAGCTTTTCCACTGTCAAAATACTTGTGTTTAT
CAAAAATTTCTTTTATATCCTTAGGATTACTAATAAGTACTAAAGGTTCAAAACCAATAGCTTTGAAGGTA
AAAGTGTCTCCATAGCGTGCTCGACACTCTTCCAAAAATTCACAAGGATTATTAAGCCATTGCAATAAGTT
CCACCAAGATGGTGTAGTGGGACCAGGAAGTAATGAGGATTTAGCAGTATTAATCATTTTAGTTATGCTGG
ATTTGGCGTAAATTTACTAATTAGACTTTGGACACTATTGAATTTCATTTTTCCAATTGATGGGTTTTCTG
TGCTTGTTCAAGAGATATTTGCATTTGTTGAGCCAATACCTTGACATGAGGCTCACTCAGCATTGAAACAT
GATTACCCGGAACTATATGGATTTCCACTTCTCCATCAGAAACTGATTCCAACCCCATGTTGGCTCTTGG
AAAATGTGAGAATAACTTTCTTGCTCTGGATTTATCTCCCTCGCACAAAACAAAGTGATTGGAGTTTTATA
AGTCTTTTCCGGTTCATACTTAATTTGACATTGAGTTTGGAAAACTTGTAATAAACCACGAACAATTTTGA
TATCTGTTTGAGCAGGCAAAAAACCAACTATTTCTAACTTTTGCTTGAAATAATTTAATTGTTGCTCCCAA
GTTAGAGAAGTTAGAGTTTCATAAGATAAAAATAGATTTTCTCCAACAATATCTTCAATAACCTCAGCCAT
TCGACATATCCACTTTGCATTATCCCAGTTAGAAAAATCATTCTGATGATTAGCTTGAGAAGTTGGTGCAG
GAGTATCTAAAATTCCAACATAAGCAACAGACTTTCCAATAAGTTGTAGTTGATTCGCCATTTCAAATACT
ACATGACTGCCAAAGGAATGACCAGCCAAGAAGTAAGGACCAACTGGTTGAACTGTTTGAATTGCTTTAAT
GTGTTGGGAGGCTATTTCTTCAACACTTTTATGAGGTTCGGTTTCACCATCAAGACCTTGTGCTTGTAAAC
CGTATAACGGTTGATTATTTCCAAGATATTGTGCTAAGTGGTGGAAGTAGAGAACATTTCCACCTGCTCCT
GGTACACAGAACAAAGGTGGTAATGAACCGTTTTGTTGAATTGGTACTAATGGAGACCAAAGTTCGGCTCC
GGAATCGGAACCAACAAGAAGTGCTAGTCGTTCAATGGTGGGATTTTGAAAAAGAGTGGCTAAAGGTAAAT
TTTTCTGGAATTGTTGTTGAATCTCGGACATTAGACGGACAGCTAGAAGGGAATGTCCTCCTAAGCTAAAG
AAGTTGTCATGAATACCAATAGAGGGTAGATTGAGAACTTCTTGGAAAATCTCAACTAACTGACGTTCTGT
TTGATTCCGTGGTTTTGTCTGCTCAGAAGTATTCAAACCTCCATATATAGCAGCAATTTGTTCCCGATTAA
TTTCTCCTCTTTGAGTAAGGGGTATTTGTTCAAGTTGGACAAAGTTAATTTGATTGGGTATCCCAAAGCGA
TCGTGTAGTTGTAACTCTTGTAAGGAGAGTGCAGCAAGTTCTGGTGTGGGAGAGGTGAAGTAAGCAGTTAA
TTTCTGCTTGGGCTGACAATCACGAATCAAATGTTCAACATTTGTTTTAGTTCCATCCAATCCGATTAATA
GATTATGTTCCGAACCAGATAAAGCTGCTAAAAATGAGTAAAATCCTTGTTGAGGAGTAATAATAAAATAG
CCCTTAGCACGACTGAGTTCTTGGAATTGATAGCCATGACTTATTCCGGTTTCATTCCACATACTCCAAGA
GCAGCAATAGCTTTGGAAACCGTTTGTTGTTGATAATCGCTCCATGCTGACTGAAAACTATTTGCTGCAC
TATAAGCTGCAACATTGGTTCCTCCAAAGAAACCATTTACAGAACAAAAGTGGACAAATAAAGCATTTTCT
TTATCCTTGAGCAATTGATGCAATACCCAAGTACCGCTAACTTTAGGACGTAAAACAGCAGCGATATTCC
TGGGGTTTCTTTCTCGATTGGCGTTTCCTGAATAATCCCAGCCATATGAAATACCCCATCAAGTTGAGTCC
TCCATTCTTGTGTTGCTTTTTCTACTACCTGTTGTAAACCTACTAAATCACAAATATCTACAGTTTGATAA
ATTATTGAACCTGGTAGTTTTTCTAATTCTTGATACCTCTGCAATTTTGTGCTAGCTTCCTCATTATTATC
TTCAATTTGAGTTCTACCAACTAATATTAAATTTGCTTGATAATGTTCTAATAAGTACTTTGCAATAACAG
TCCCAATTCCTCCAAGCCCTCCTGTAAGTAGATACGTTCCTCCTGGTAGAATCGGAATTTTTTGTTTTTCC
TTAGCAGTCATATCTACTGGTTCCAGACCAGACACAAAACGTTCTCTATTGCGTATAGCAACTTCCAATTC
TTTATCAGCAGAATACAGTTCTTGCCAAATATAACTATTGTTGAGTTCTGGTGCTAATGGTAAATCTAAAT
GACGAGTAGTTAACCAAGGCATTTCTTGACTAACAGTTTAAGTAAGCCTAAAACAGTGGATTTTCGGGT
TGAATTTTATCTGTGGGATGAACTAATTGGCTTTGATTAGCAATCCATAATAATTTGACTGCTTGCTGTTT
GCCTTGAATTTCTTCTAAAGCTTGTACTAAAATAGTAAACTGTAAATTCCTTGTTGTTGAGTGGACTCTA
AATTTTCCAAGCTAGAAATTTTTTCAGTCTGCTCGTTGTAGTTCCAAAGATGAAGAATTTGACTAATTACT
TGGCTATTTTGCCTCAAAGAATCAATTAACAAGCGATAGTGTTGTGGATTTCCAGGAACAACAGAATAATG
ATTTGGGCTAATTTGAGCAAAATTTGAACCAATAGTAACTTGAGCATATGGTTGAACAGTTTGGGACATTC
CTCGGTTATCTTGTTGCCAACCCAAATTATCTGTAAATATTAGGGTTAAAGTTTTCTGAGAAGAATAATTG
AGTAAAGTATTTTTACTTTCTTTAATTTGCCATACTTTACGGTAAAACCAGTTGGGAATAGTATTAGTATT
ATCAAGCAACAAGTCTACACGCTGTCTGAGAGATTTAAACTCACCACATTCAAAACGTTGCTTAAGGAGGG
AACGTTGAATTTTACCGATGGAAGTTTTGGGAATCAGTTCTTTATCTATGGGTATTAAATAACTTGGATTT
ATCCCGCAGTATTTTATAACTTGTTCCCTAACCTTTTTCAAAAGCTCTAATAATTGATTCTTCTCAGATAC
```

FIG. 5-5

```
ATACGGAGTGAAAAAGATTACTAATTCTTCGGTATTATTGCTAGCAACGCAGACTCCACAGGCTGCGGTAT
AAGAAACTTCAACCTCTCCTAATTCTTCAACAACAGCTTCTATTTCATGACTATAATAATTAACTCCATTA
ATAATAATGATATCTTTTTGTCGTCCTGTAATCGTTAAGCATCCATCTTTTATAAATCCTAAATCACCTGT
ATTAAACCAACCATCTTCGGTAAATGCTTCCTTATTTGCTTTTGGATTTTGATAATAACCAGAAGTAACGG
TTAATCCTTTGACCTGAAGTAAACCAATTTCACCTTCTGATAATACTTCCATGTCTTGATTGACTATTCTC
AGACAAGTACCCCTAATCGGTTTTCCAAGATTTACAAAGGAATTATCATCTGAACTTGATAAGAGTGAAAA
ATTGTCAGAATAAGTAATACCAGAGGAAACCTCAGCCATTCCCCAAGATGGAGTCATAGCATCCCCAGGTA
AGCCAAAGGGAGCAAGTAATTTCAAAAAACGTCTTGCTGTTGCTGCAACAATTTGTTCCGCACCATTTAAC
ATCAAGCGAATAGAAGATAAATTCCAATTCTGCTTTTCTATTTCTTGAACAAAATCATTAATTAAACTATA
AGCAAAGTTAGGAGCAAAAGTAACAGTGACACCAAAAGTATCAATCCAATCCAACCATCTTAAAGGTTTTT
CAATCACTAATTGACTAGTAGCATGAATTTGTTTACATCCTAAATAAATATCCCGGATATGAAAATATATT
AAACCTGCAACATGGTCTAAGGGCATCCAATTTAAGGTTATATCTTCTGGGGTAAAATTATTCATTTGTAT
TGAACCAATAGTCCTACTCAGTAGATTAAATGGCTCAACTGTACCACCTTAGACATACCTGTACTACCGG
AAGTAAGCATGAACAGTGCTAAATCTTCTGGTTGGGCATTATAGTAATCTTTATCTGTTGAGAACTTTTGT
AAACTTTCAATAGTTTCTAACTTAAAGTTGTCGTCATTTAGATTTTGAGACCATTTCTTTAGTTCTGACAA
TGATTTTTTATCTGTTAAAATCAAAGGTCTTTCTAACATCTGCCAACTATTTTGTAATTTATTTAGATTGA
CATTGGGCTGGTCATAGCTTACAGGAATTACAACGGGTACGGGAATAAAGCCTCCCAACACACAACCCCAA
AAAGCACTAATAAAATCTTTATTTTCTTTTAATTGCAAAATAACTTTATCTTGTGGCTTAATTCCCAGTTT
TCTGAAGCCACCTAGAATTCTTTGAGCATCTTCTAATAACTGGGCATATGATTGAACTTGTTCGGAACCAT
CAGAGTTAATATAAGTGATTCCTTTGTGAGGAAATTTCCCAGCAGTTTTTTGCAGCATCTCCCCTAAAGTT
TCTGGAGATGATTCTGGAAAGATTAATACTTCTTCGTGGCTGATGGCAGGTGATTTATTTCTAATAGGGA
ACTACTCTCTTTTCCCCTAGCAGTTCTGGGAGTTTCAACTGGAGTAGAACCTTGATTGAAAATAGCTTGGA
TTGATGGTAAAAGTTCTTCTAAATGTATCGGAGAAATCGTTTTTACATTTGGCTCAATAAAAACAGCAACT
TTATCAATTTCCGCCTGAGAACCTATTTGTTCTTCCCAAGTGTTAATTAACTCAGAATCAATTATGCTAAT
AGAAGCTAAACCTACTTCATCAACTTCTCCAAAACTTGTCAATGGTAAAGCAGATACTGGTACATAGATGC
AGGGTAATGGGTATCCAGGTAACTGAGATTTAAATAATGGTGTAAAAACTCCCTAGCCCAAGAACCATCT
TTGACTACGTAAGCGACTAATTTTTGATTGCGTACCATTACATAGCAATCTTCTACCCCTTTCGCTGTTTG
TAAAGCTTGTTCAATACGTTGTAGGTTAATTCGTTGTCCATTAACTGTGACAATTCGATGCTCTTTTCCTA
GCAATTCCAGAGAACCATCGACTCGACGACAACCCCATTCCCCTGTTTTAATAACTTACCCAGTTGGGTA
TGTTCTATGAAACTTATAAATTTTTCTGGTTCTGGATGTAACTTGTCTGGGAGTAAATCGCAATTCCCCAA
ATAAATTTCTCCTTCTACACTCAAAGGAACTAATTGTTGATGGTTATCTAAAATGTAAATTTGTAAATTAT
TTGAACTCAGGAAATGAACATATTTATCCAGCAGGTAAGTTGTAGCGATGTTATTGTAACTGTGCAGTACC
TGCTCTTGCTCAGAATCTGTGAATAATGGTAATTCACTTATCTTTTGTTGGGGATTTTCTACAATCGCGCT
ACACAGATTCTGGAAATGAGCAGTCATGCGCTCAATAGTTGACCCATCAAATAAGTCAGTGTTGTATTCCC
ATGAACCCACTAGTGCTTCGGAAGTTTGCTGCATTGATACTGTTAAATCAAACCGGGCTGTTTCTGTTTGA
GAACTCAATAAATTAAGGGTCACACCAGGTAATTCTAATTCACCCATGGGTGCATTCTGCAACACAAACAT
TACCTGGAATAAGGGTGCATAACTCAAAGAGCGTTGTGGTTGTAGTACTTCAACTACCTGTTCAAAAGGCA
CATCCTGATGTTCATAAGCTTCAAGTGTAGTTTCCCTAACTTGTGCCAGCAAATTCTCAAAACTGGGATTA
TCTTCAAAACGGGTTTTCAATACCAAAGTATTGGCAAAAAAGCCAATCAAAGACTCAATTTCACTGCAGTT
GCGATTGGCAATGGGTGAACCAATTAAAATATCTAATTGACCGCTGTAGCGATAGAGTAAAGTGGCAAACG
CTGCGTGCAGGGTCATAAATAAGGTAGTACCCGAGTTCCGAGACAGGGTTTGCAACTTCTCTTTTAAATCA
GTATTTAAACTAAAACTTTGAGTAGTACCCCGGAAAGTTTGCACGGTTGGACGAGGACGGTCAGTAGGTAA
TTGTAACAATTCTGGTGCACCCTCTAACTGAGAAAGCCAGTAATTGAGTTGAGTTTCTAGTACCTTTCCAC
TTAACCATTGTCTTTGCCAAACTGCAAAGTCTGCATACTGGATTGGTAATTCTGCCAAGGGGATGGTTTT
CCTGCACTAAAAGCTTGATATAAAGTAGATAGTTCTTGGCTGAATATCCCATTGACCAACCATCAGAGAC
AATGTGGTGCATCGTCAGTAATAACACATATTCTCTGGCATCTAACTGCAATAAACTACACCTGATTAGTG
GTGCAGTTTCTAAGTCAAAGGGGGTAATTGCTGCAAGTTGTGCTTGTTGGTGAAGGACACTTTCCCGTTCT
GTTGCTTCTAGTTGCTGTAAGTCCGCCACACTGATGTTCATGGTGGCTTCTGGGTGAATTACCTGTATTGG
TGTGCCATTCACAGTTCGGAAGCTGGTGCGTAGTACTTCATGACGGCGGACTATTTCTGATAATGCTTGTT
GCAAGGCATTAATATCCAACTTTCCAGTGACACGAATTGCTCCTGGCATGTTATAAGTGGCACTTGACCCT
TCAAGTTGGTTGAGGAACCACAACCGGTCTTGTGCAAAAGATAGGGGTAATTGTTGGTTCTGTGTTCTTGG
CTGAATGGGGGGAAGACTTAATGCGCTATTAGTAGTACGTAATTGGGTTAATGTTTGCTCTAATTGAGCTA
CAGTGGGAGAGGAAAAGACTGCACTTAGTTCTATTTCTACTTCAAAGGCAACTCTGAGTCGGGAAATTAAT
CGGGTTGCTAGTAGGGAATGTCCTCCCAATTCAAAGAAGTTGTCATGGATTCCAACATTTTGCACACCTAG
```

FIG. 5-6

```
AATAGAAGCGAAGATGTTGGCTATTATTTCTTCACCCGATGTACGTGGTGGGACATATTCATGTTCTCGGC
TAATTTCTCCATCAGGTGCTGGAAGGGCTTTACGGTCTATTTTACCGCTGGGTGTCAACGGTAAGGTGTCT
AAGATGACAAAGGCACTGGGCATCATGTATTCTGGTAGCTTTTGTTTGAGGAATTCACGCAGGTGATAGGT
ACTTAGTGATTCATCCTCACAGACTATGTAGGCTACTAAACGTTTGCTACCTGGAATATCTTCTATGGCAA
TGACAACGACTTGTTGGATTTGGGGGTGGGTACTGAGGACTGCTTCGATTTCTCCAAGTTCAATGCGGAAG
CCCCGCACCTTCACTTGGTGATCGATACGCCCTACAAATTCGATATTACCATCCGGCAGCCAGCGGGCTAG
GTCTCCAGTCCTAAACAATCTTTCTGCTTGTGCCTTTTTACTTTTCCCCCTGTCCTTCACAAACGGGTTGG
GGATAAACTTTTCCCGCGTTAACTCGGGCAGATTTAAATACCCTTTTGCAAGCCCATCTCCGCCGACGTAT
AGCTCACCCGTAACACCAGGTGGCAAAAGATCGCCATACTTGTCGAGGATGTAAATTTGTGTGTTTGAAAT
CGGTTTTCCAATCGGAATCGTATTTCTTTTCAGATATTCTTCTAGAGCTTCTCCTAAATCTGCTCTTCGCT
CGTCTGCCAACTGCAAATGTATTATTTCTTTATGCAGGACAGCAGTTTCCCTATCCCCTGAGCCACTAGGA
AGATTTTTAAAGCATCAAGTTTCTCTTTACTTTTTGCTTCAATTTGATTTGCGATTCTCAGTTTGACTTC
AAAGCATGTAACATCAGCGGCAACTTCTGAAGAGCCGTAGAGATTGAACAATCTGGCAGAGCTGATTTTCT
GGTGAAATTCCTTAGCCAAGGTTAGCGGTAAGACTTCACCGCTGCAAAAGACATATTTGAGATATCGAAGT
TTTGTCAGTTGTTGGGGCGCATTTTCCAGTATCGCTTTTAATAGCGATGGAACGAGAACAATTCTAGTTAC
CTTTCGATCGCTCAACAGGCTCATTAGCCTGGGAATATTGCCCGTATATCATCTGGAACGATCACAAGGG
GAATTCCTTTGAGAAGGGGAGAAAATATTTCCGCAACATGATCGCCAAAATTGATGGATGTTTTCTGAGAG
CAAATCTCATCTGCCCCAAATGGTAGCATTTCCCAGATCCAATGCAAGCGATTGACAATGCCGCAAGCGT
GCCGAGAACGGCTTTGGGTTTTCCAGTAGAACCAGACGTATAGATTGCGTATGCAAGGTCATCCAGTGTTG
TTTGCCGATCCAGATTTTCAACGCCTTCCCTAGCAATGACATCCCTATCCCTGTCCAGGCAAACGATATGG
GCATTTTGAGGGGAAATCTTTTCGAGCAGAGGCTGCTGGGTCAATATGATATGCACATTGGAATCTTCCTG
CATGAACGCCAGTCGTTCTTGCGGATAGTTCGGATCTAACGGCACATATACACCACCAGCTTTAAGTATCC
CCAACAGTCCTACAATCATATCAATGGAGTATTCTATGCAAATACCCACCAGCACTTCTGGTTTCACTCCC
AGAGTTTGTAGATAATGTGCTAATTGGTTCGCTTTTTGATTTAATTGTTGGTAGGTTGATTGTTCTTCTTC
AAACACCACTGCTATGGAGTTGGGGTTTTTTTCTACCTGTTGCTCAAATAACTGATGAATACATTTATCAG
ATGGGTAATCCGTTGCAGTGTTATTCCACTCAACCAATAACTGATGACGTTCTACTTCACTTAATAAAGGT
AATTGAGCTACCTTATGTGAAGGATTTTCCACAATTGCAATTGCTGATAAAACAGTTTGCAGATATCCTAA
AATCCACTCAATAGTATTTGAAGAGAAACGAGCAGTATCGTAACTAATCCTAACTGACAACTTATCCCCAG
GAACTGCAACTAAAGTTAGTGGATAATTAGTTTGTTCAAAAACCTCTATATCACCTAAGTGTAATGAACCT
TCTTCATTCAACAAAGAATTATCAATTGGATAATTCTCAAACACCACAATGCTCTCAAACAAAGGTATTCC
ACCTGGTATCTCAGAAGTAGCTTGAATATCAACAAGAGGAGTATAAAAATACTCTTGTAATTCAACCATTG
ACTGTTGTATTTTTTGCAACCAAGGTATGAGTTGCTCCTGGGTGGATACTTGTACTCGTAAGGGAAGGGTG
TTAATAAACAGTCCTACCATATTTTCTATCTCAGAGAGGCTAGGAGGACGACCAGAAACAGTCACACCAAA
TACTACATCTTTCTCACCACTATAACGACTCAATAGTAAAGCCCAAGCAGCTTGTACTACAGTTGATAAAG
TCACATGATGTTGTTGTGCTATATGAAGTAACTTCTGAGTGCATTCAGGGGATAAACTACTTGTTCTCTCC
TGATAATCCGCAGTTTTATACTGTTGCTCTTTCAGAAATTGAGTTTTATCCATTACCAATGGAGTGGGAGC
ACTAAAACCTTGTAAAGTTTGTTGCCAAAACTCAATTGCTGCTGATTTGTCTTGAGAATTCAACCAAGCAA
TATAATCCTGGTAAGGACGTGGTTTTGGCAATTGGCAATTTTCACCAAGCAGATGTGCTTTATAGAAAATT
AAAATTTCTTTAAAAATAATTGATAAACACCATCCATCCATAAGGATGTGGTGATGACTCCAGATAAATTT
GTAATTATCTTCGCCTAGCCTGACTAACGTACACCGCATTAATGGTGCTTGGGATAAGTTAAAACCTTGTT
CTCTTTGTGTTTGCAATAATTGTTTTAATTGTTGTTGTTGATCATTAGAAGAAAGTTCTCGCCAATCAAGA
GTATTCCAAGGAACATTAACCTGTTTTAGTACTACTTGTAATGGAGTTTGGCGATTTTCCCAAACAAAAAA
TGTACGTAGAATTGAATGTCTATCTAAAACTTTTTGCCAAGCTCTTTCAAAAGCAGCAACATTGATATTCC
CCTTCAAACCCCAGGTCATCTGTTCAAGATATACCCCACTATAAGGTGCATAAAGACTGTGGAACAGCATC
CCTTGTTGCATGGGAGAAAGTGGATAAATTGAAGAGATATTTCTTCTAATTCTTCGTTGCTCATTGTTCT
CTCTTTTTTATCTATATTTTTATATTTACACTATTTGCCCAAGTTTTTAATAACTCATCAAGTTCTAA
TTGATTTAACTGTGCATCTGGGAAATCACTAGCTGTATATCCAAAACCATTTTCTGACTGGCAATGTTCTA
TTATTGACTTAATTGCTTGAATATAGCTTTGTGTCAAATTTTTTACTGTATCATGAGTATGAAAATTACTA
CTATAAGTCCAATCAATTTGTAATTCACCTTCTACCACCAGACTATTAATCTCTAATAGATGGTGACGAGT
TTGCTTTGAACTATGATTATCTCCAGTAGATTCTGGCGCAAATTTCCAACCCGTTTCCGATTGTATTTGGT
CAAATTGTCCTAGGTAGTTAAAACTAATTTCTGGAGTAGGAATTGTCTGTAGTTTTTGGGTTACAGTAGTA
TCTTCACACAAGTAACGCAATATACCAAAGCCAATACCACGATGGGGAATCTCTCGTAATTGTTCTTTAAT
TGACTTGATAACTTCTGCTGGTTGTTTATCGTCTGGTAATCGCAATAATACTGGGAATAAACTGGTAAACC
AACCTATTGTTCTTGATAAGTCTACATCTGAAAATAGTTCTTCTCTGCCATGTCCTTCTAGGTCAATTAGT
```

FIG. 5-7

```
ACTTTTGAATCTCCCGTCCACTCTGCCAAGGAAACTACTAATGCACTGAGGAGGATATCGTTAATTTGTGT
GTTATAAGCTGAGTTTACTGACCCCAGCAAAGCGCGGGTTTCTTCTGGACTCAATTTCACTCTATAATTAA
TCGCACTATCAACTGTTTTTTCTGCTTGAGTGTGAGCAGAATCTAATGGTAGTGGTGTTGTTTCTGACCAA
GGTTGGTTGAGCCAATAGTCTAACTCTTGTTTGATTTTTTCTGATTGTGCATAATTTTTCAATTTCTCTGC
CCAATCAATAAATGCTGTTGTTTTCGCATTTAGCTGTATTGATTGTTGAGCGATTAGTTGTTGATAGATTG
TTTCTAAGTCTGATAGTAAAATTCGCCAACTCACACCATCTACTGCTAGGTGATGAATAATAATCAGTAAA
CGGGCATCAACTTCACTACCTAAGTTAAACATCACCACTTGCATTAAAGGTCCCTCTGAGAGGTTTAAACT
TGCTTGATATTCCGTGGCGATCTGTGATAAAGCTTGTGGTTGTTCAATGACAGGAGTTGATGATAAATCAA
CTACAGTAAATGCTACGGGATCATCAAAGCCATGGTTTATTTGTTTGTACTCAGATGCAACTGATGTGAAT
CGTAAACGCAGAGCATCGTGATGCTCTAATAATTTTTTCAAGGCTGTTTCGATTAATTCAGTTTGCAGATG
ATTGGGAATCTGCAATAAAACTGATTGGTTGTAATGGTGTGCTTCTTGGCTATTTGTGCAAAGAACCACT
GTTGAATTGGTGTTAGGGGTGCAACTCCAGTAACTATACCTTGGTTAGCACTGACAGTAACTGTTGTATTG
GCTACTAATGCTAGTTTGGCGATGGTTTGATTTTGGAATATTTGTTTGGGAGTGATTTGTATTCCTAAGTT
TTTGGCACGAGAAACTACTTGAATACCAAGGATGGAGTCGCCACCAATTTCAAAGAAGTTGTCATGGATGC
TGACTTGTTCTTTAAGGAGCAGTTCWTGCCAAATGTTGGTTAAGATTTGTTCTATTTCTGTGCGTGGTGCG
ACATATTCATCCTCTCGGCTAACTTCCCCATCAGGTGCACTTAGGGCTTTGCGGTCTACTTTACCGTTGGG
TGTCAACGGTAGGGTGTCTAAGATGACAAAGCTAGAGGGGAGCATATATTCTGGCAATTTAGACTTTAGGT
AGGAGCGCAATTCATTGCTACTCAGTACCTTACGTTCAGGCTTTGACTTATTAATTGTGTAATCTTCTAGA
TTATTTTCAGCAAACAATCGTTGATAAAAAGGGTTTTGCTTAAACAATTGTTTCCAATGATATGAGATGTA
TTCAAACTCAATCTCTTTTCCAGTTTTTTTAAAAGACGACCTCGAAGAGTATAATCTGGATTCAAATTAT
TTTCACAAAGCGTTCTCGTACAAACAGCTTCGATGATATCTCCTTCATTTACATAAATTCCTGGTTCAAAC
ACTGGAAGATAAACTGGTAACCAGCAATGTTCATTTCTAAAATATCTATACATTCTCCTTCAATTGTGTG
TAAGTTTAATCCCACTGAAAAACCATCTAATCTTCCTGATTTTTCAATAGTTAATTTAATTTGGTGAGTAG
ATTCTGTGCTAACAAGCTTGCTAAAGTCTAAATCCTCAAAAACTCCTCGATTGGACAACCAGTTTACTTGA
TTTAATCCTTTAATACATACTCGTAAATCAAAAGGATATCCAACTTGCTCAAATATCTTCTGGGTATAATA
ACCTGAAACTTTTGTAAATTGGGGTTGATTTAGTAATTCATCAGGAAGAGTTACTGCAATAATTTGAGTCA
CACTTCTTTGGGGAATCATTACACCATCTGATTTGAGAAATCTTCTGGCGTTGTTGATAATTACTGCTGCT
CCTTCAGATCCACCAATGGGTCCCACAATTTCAGAAACACATACATCAACTTCTTCTGGTAAGTTGGCTGT
AGTAGCGTCTCCATGTATGATTTGAATTTGTTCTGATAACCCCAACTCTTGCACGCAAGCTGAAGCTAACT
TACTGGTTTGCTCGTCTCTCAATTGCGTAGACTTTCTTAGCACCTGCTTCTGCACAAAATCTGGCTATA
ATTGCATCCTTGCCCGTGCCAATTTCAACAACTACTTTATCTTTAACCATTTGATTAATTGCGACTTGGTA
ACTCTGGTTTCGACGATGATCATTGGTCATCGCATAGTACAAGAGCTCATCATAAACGTAGAATTCTGCTA
CTGAGGGCCAAAGTTCAATTCCTGTCTGGGGCTGGGATCTTTTTCTTTTGACTGAAGAGGAACTAAATAT
GCTACCAACCGTTTGTGACCCGGAGTATCTTCCCTTTCGGTGACTGCGACTTGCTGTACTTGAGGATGGGT
ACTCAGAACTGATTCTATTTCTCCTAGTTCTATGCGGAAACCACGTATTTTCACCTGGTTATCAAGACGAC
CAAGAAACTCAATATTACCATCTGGTAAGTATCGAGCTAAATCTCCAGTTTTATATAGTTTTGATCTGCTA
TTGAAGGGGTTAGGGATGAATTTCTCTAAAGTTAATTCCGGTCGGTTGAGGTAACCTCTGGCTAAGCCATA
ACCTCCGATGTATAATTCTCCGGATACACTTATGGGTACTGGTTCTAAGTGCTTATCTAAGATATAGATTT
GGGTGTTTGCAATGGGGCGACCGATAGTAACTTTCTCGCTACCATGGCTGATTTGAGCCACTGCAGCACCA
ATAGTAGACTCAGTAGGCCCATAACCATTAAACAAACGACGACCAACAGACCACTGATTGGCCAATTCKAM
WYTASAAGSWTCCCCTGCCACAATTATCTGACCCAAGGCTGGAAATTCATCAGTAGCTAGTACTGCCAGGG
CAGAGGGAGGTAACGTAACATGAGTTACACATCTTTCTTGTAAAATTTGCTTTAAATCCGAACCCGGGATT
AACTCAGAAGCTATAGCCAAAATTAGCATTGCTCCAGAAGTCAAAGCGATAAATATTTCCGAAACTGAAGC
ATCAAAACTTATAGAAGCAAATTGAAGAACACGACTATTTGGTTCTAGATAAAATAAATTTTTCTGTGCTT
GAATAAGGTTGCACAAAGAAAATGTTCAATCCCAACCCCCTTGGGAACTCCAGTAGAACCAGAAGTATAA
ATCACATAAGCCAAATTATCTGAACATACCCCAACATCAAGATTCTCCTGACTGTGTTGCTCAATCACTCC
CCAATCACTATCCAAACAAACCACCTGTGCAGTATGTGACGGCAAAGATTCCAGTAGGGACTTTTGAGCCA
ACAACACCTCAACACCTGAATCCGCCAACATATAACTCAACCGTTCTTGGGGATAATTGGGGTCAAGGGGT
ACATAAGCCCCACCAGCCTTGAGTATCCCCAAGAGCCCTACCACCATTTCAAAAGAACGCTCCACGTAAAT
CCCTACCAGCACCTCTGGTTCGACTCGCAAGGAAAGCAGGTGATGTGCTAGTTGGTTGGCTTTTTGATTTA
ATTGTTGGTAGGTTAACTGCTGATTCTCAAATACCACCGCGACTGCATCCGGTGTTCTCTCTACCTGCTCT
TCAAACAATTGATGGATACATTTACTGGGATATTCCCTTGCTGTATCATTCCACTCCACCAACAACTGATG
CCGTTCTACTTCACTCAATAGGGGTGATTCACTTACCTTTTGTTGAGGATTTTCCACAATCGCTGACAATA
AATTCTGGAAATGACCAGCCATGCGCTCAATGGTTGACTCATCAAACAAGTCAGTGTTGTACTTAAAAACC
```

FIG. 5-8

```
CCAAAAACAGATGAACTCCCCTCCACCATTTCTAAACCTAAATCTAACTGACCTTCCTGTTGAGGTATTTC
ATAAGGTTTTATCTTCAATTCTCCCCAATCAACATAGGTTTCTATTTGATTTACAAACAACTTCTGTATAT
CTTGAGATTTTTGGAACTGCAGTAGAGAAAAAGAAGCCTGAAAAATCGGCGAACGACTGGGGTCGCGGTGT
GGCTGTAGCTTTTCTACCAATAGAGCAAATGGGTAATCTTGATGAGCAAGTGCTTCCAATACGGTTTGGCG
TACTTGGGCGAGGAAATCTTTGAAACTGGGATTTCCCGATAAATTTGCTCGCATAACAACAGGATCAACAA
AGTAGCCCAAGATCGAAGCAAACTTAGCTTGACTCCTACCTGAGGTGGGAGAACCGACTAAAATATCCTCC
TGGCCTGTGTAACGATACAAAAACACCTGAAAAGTTGCTAAGAGCATCATGTAAAGTGTTGCTCCCGAGTT
TAAAGCCAGCTCCTTGAGTTGCTTAGTGAGCTTGTCAGATAATTTGAAGTGATGGGAAGCACCATTATAAG
TTTTTATCGGTGGTCGCTGTCTTGAGGTTGCTAGGTTTAGTGCTGGCAAATCGCCTGTCAGTTTTTGCTGC
CAGTAGTTCCAGAGTCTTTCCCCTTCAGTCTCCTGCAAAATATTCCTCTGCCAACGAACGTAATCTTGGTA
AGAATGCTTTAGAGGAGAAAGGGGTGTCTTAAAATCAGCCCATTGTACTTGGTAGAGTTGTGGCAACTCCT
GTATTAACATATCTAAAGACCAGGCATCGCAAGCAATGTGGTGTATGGTTAGCAACAGGACATGTTCTTTC
TTGGAACGAGTAAACCACCGAACTCGCATAACAGGCCCTCGTTCGAGGTCAAAATATTGTTGATGGCTCTC
AATCACTTTCCCTTTCAGTTCATCTTCACTCCAAGCAGAAGCATCAATTTGCAAGAAATTTAATTCCTGAA
AATTATTTACCTGTTGGATTGACTCAGATCCGAGTTTGGGATAATTTGTACGCAATATCGGATGCCGTTCT
ATTAGTTTCTCAAATGCCTTTTGCATTGCTGTAATATCTACTGTTGAGCAAATACGAGCGACAAATGATAC
GTTATAAGCATGACTTTCTGGTGCTAATTGCCACAAAAACCAAAGTGCCCGTTGACCGTAAGAAAGGGGAT
AGACGTTTAAAATATCTGGGCGATCGCGCAGCAATTGTAATATTTCGGTTTTGTATTGTTTCAGTTGAGCT
AATACTAAAGCAGTTGATTCTTCTTGAGGAGCATCGTAACAAAGCCGTTCGCCCTCACTCCACACTTGCCA
ACCTTTTATTGAAATATCTTGTAAAAATTCGATTAAATTCATAATTCACCTCTTATCCGCTCGTTTTCTTT
CCTATTGCTTTGGTAGAGTTGCCCATTATTTTCTGACTCAACTCCTTGATTCTGAGCAACTTGGCTCAGTT
GCTCATTCACTTCAGTGGCTAAATCAACGATACTGATATCTTCTATAAATTTGACTATAGATATATCCACG
AGCAAGTCAGTTTGAAGCCTATTGTGCAATTCCACAGCCATTAGAGAATCAAGCCCCATAGTGTTCAGGGG
CTGTTGCATATCAATTTGAGAAGTGCTCAAAGAAAGTACTTGAGAAATTTCATCTTTAATGTAAATTATCA
AAAGCTTTTCTCTTTCTCTTGGTAAAGCAGCTTTTAGCTGTTCTAAAAATTCATTGTGCTTTGTCTTTGTT
TTGAGGGCTTTTTGCTGTGATTTGCTTTCTTTTACCAATTGGGACAGCAATGGTATTTGATTACCAAAACT
AAATTGCTCTTGGAACACTGACCATTGAATTGGTAGGACTCCTACTTGTGGTATGGATTGTTCGAGTAATT
GTCCTAGAACCTGCAATCCCTGTTCTGAAGACAAAAAAGTCATTCCCTTGGACACCATTCTATCTTGATGA
GGACTATCCAAATTTGCTGCCATTCCCTCTTGTGCCCATGGTCCCCAGTTAATGCTCAAGCCAGGTAAACC
CATACCCCGTCGATGATGGGCTAAACCATCCATGAAAGCATTAGCAGCAGCATAATTCCCTTGACCAGGCG
AACCCAATATTGAAGCCATAGAGGAAAAACAAACAAAAAGTCCAAAGGTAGATTCTGAGTCAAATTATGC
AAATGCCAAGCCCCTTGTACTTTTGGTGCCATCACCTGTGTAAATTTTTCCCAATTCATGTTTAACAGCAA
ACCATCATCCAATATCCCAGCAGCATGAATTATTCCTCGTAATGCTGGCAAAGATACTTTGATTGACTCTA
TAATTCTTGCCACATTTTCTTGTTGGGAAATATCTCCACACAGGACTAATACTTGCGCTCCTGCCTTCTGT
AATTGTTCAATGGTTTGTTGAGCTTTTGCTGATGGCTGCCTACGTCCGGTAAGTACTAAATATTTGACCCC
TTGTTGTACCATCCACTCAGCGGTTTTTAACCCCAGTGCTCCCAGACCTCCGGTAATTAAGTAACTGGCTT
CGGCTTGGATTAGGTTGTCTAAAGACTTATATTCTGATAGCTTCAGTTGAAATGGTTGTTGCGAGGAAATT
TGTAATCCGGACTGTGTAGATGTACTCATTTTTGTTGCCGCTCTAACCGGGCAACGTGACGTACCCCTTG
ACAGTAAGCAATTTGGTTTTCATCACCAGGAGATAATAGTTCCTCTAACAAAGCAGCTACTGTTTGGGAAT
CTTCCATAGTTGGATCTAAGTCTAAACACCGGCATTGTAATTCCCTATGTTCCTGGGCAATTACTCGACCT
AACCCCCATAAAGGTGTTTGTTGGAATTGTATAGGAAGGGACTCATTACCCACAGATTGTGAGCCTTGAGT
CACTAACCATAATGGGGCACTTTCCATATCTTGATTTTTACTAAGGCTTGGACTAAATGAAGTACGCTGC
CACAGCCCAGTTCTTGGGATTTTTGCAACTCCTGTGCCCCAGTCCTTAGTGCTATTGTTGAGTCCAAACTC
CACAGGTGAATAATTCCTCGTAATGGGGGTTGCTGCTCCAAGCTTGATTGCAATAGGTGCAGGAATTCCTC
AGGATGGTTGGGGTTGATTTGATAATGTTGAGATTCTAACTGCTGGTAATTTTCCCCTGGTGTTACTAATA
TACAATGCCAACCTTGTTGTTCTAAGGATTCTACCAGATGTTTGCCTATACCTGTGGGTGGGAAAACAAT
AACCAGCTACCTGATTTTGTTAAGTCAATTGATTGGTTATGGGGTGAAATTGATTGGGTTTGCCAATGGAT
TTGATATAACCAATTATTAAATTTTGGTTCAATATTACGCAACAAAGCCTCGCGAGAAGTACGTAATAAAG
TTAAACCTTCAACTCTTGCTACTACTATTCCTTGTTCATCCAATAAACAAACTTTACCGCTCAAAGTTTGT
TTATTAGTTTCTGTTGCACCTATCTCTACTTGAGTCCACAAACTATTACTACCACTCCGATAAATTTGTAG
TCGTTTTATTTCCAATGGCAAATAAGTTTCTTGGTTGTCCGTTTTACCCATAACTGCTGCTAACACCTGGA
AGCTAGCATCTAAAAGAATTGGGTGCAGTTGGTATAAAGTTGCAACATTCACCTCAGTTTCTGGTAACTGA
ATTTCACCTAGTGCTTTTCCTTCGCTGTGCCACAGTTGTTTAACGGCTTGGAAAGAAGAACCGTAATTAAG
ACCCCATTCTTCAAATTTTTGGTAGAATTCAGTAGGTAATATCTGTTGGTTATACTCGTCTTTAATCGCTT
```

FIG. 5-9

```
TTAAGTTTGTTGTTTCTAATTGGGGGTCTTTATTACCTACTAATATTTTTCCTTCAATATGTAGAATCCAT
TTAGGTTCTGAAGAATTAGTGTTTATATCCAAACTGAAAATTTGGAATTTATAGCTTTGTACTAACTGTAA
ATTTAAAACTATCTGAATTGTATTAATTTCATCCTTTGATAAAATTAATACTTTTTGGATTGCTATATCTT
CTAGGATTAAATCATCTGAATTGAATAAAATTGAACCTGCTGCTAAGGCTATTTCCAAGTAAGCTGCTGCT
GGGAAAACAGGTTGAGAAAAAACACAGTGGTGTTGCAGGTAAGTTGGTTGAGAAGCACTAATTTGACATTC
AAAACGAATTTGCTGTTCTAAGGCTGCTAAATGTAATCTTTGACCGAGTAGAGGGTGAAGATTTTTATGAT
TTGATAAAAACTGTTTTGATGTATTAGATTATTATTTGTCTCAATCCAATAACGTTGCCGTTGAAAGGGA
TAAGTCGGCAATACTACCTTGCTACGAGAATAATCTTTATCAAACCCTAACCAATCAACTTTAACTCCATG
CACATATAGTTCAGCCAAACTTTGTAGCATTTGCTGCCAGTCTTCTTGACCTGGTTTCAAAGAAGGCAACC
AAACTCCCACATCTTCTGGCAAGCACTGTCTTCCCATGCCTAACAAAGTTGGTTTGGGTCCAATTTCTAAG
AAGATGGAATAACCTTCTTGCTGTAATGTGTCCATACTTTGGGCAAATTTCACCGGTTGCCGGACATGATT
TACCCAATAGCTTGCTGTGGCAATACTATTCTCTGCCCTAGCTCCCGTTACATTTGATACTAATGGAATAT
TTGGTTGATTGTAGGTTATTTCTGATGCTACTGCTTCAAAGTCCGCCAACATTGGTTCCATCAAATGTGAA
TGGAATGCGTGGGATACTTGCAGTCGTTTTGTCTTAATGTCTTCTGCTTCTAAGCTATTTTGAACCGCTCC
AATTGCTTCTGCCTCACCAGAAATGACAATGCTTTGGGGTCCGTTAATCGATGCGATCGCTACTTTTTGAG
AGTATGGTGCAATTAGTTGATTTACCTTTTCAATTGAAGCCATTACAGATAACATTTCACCCCCAGAGGGT
AACTGTTGCATTAGTCTTCCTCTATGAGCAATCAGTTTTAAACCATCTTCTAAACTAAATATTCCTGCTAC
TGTGGCTGCCACATATTCCCCAGCACTATGCCCCATAACCACATCCGGTTTTATTCCCCAGGATTCCCATA
GTTTATAAAGAGCATATTCTATTGCAAATAAAGCTACTTGGGTATAGGCGGTTTGAGCTAGGACATTTTCC
TGTACTTGAGCGACATCAAGTATTTCTAATAAAGGTTTGTCTAAGTAGTTTTCTAATATTTGGGCACATTG
ATCGCTAGTACCTCTCCATAAAACTTGGTATACGCAACTAATTGCTTCACCAATTCCGGTTGATACTTTAA
TATTCCTGCGTCTACCACCGCAACTATTTTCTTCGGCTTTGTCTCCTCATCTGCCGAAATTACTTGCGCTA
GCGTCGGGTTTTTCAACTCAAATAAATTTTGGGTGAAGTAAATCTCATAGTTAAAAGTAACCGAAACACGT
TGATGAATTAATCTATTTTTTTGCTTGATGTCAACTATCATATTTTTGCAGGTATATCTAAAAGTGCAGTA
CTATTCAAAGCTTCAAGGAAAACCTCAACCGAGTGAGAACCATTTACCTTGACTTGATTATTCATGATGAA
AAACGGCACGCTGTTGATGCCATTTAAGCGAGCAAATGCCGATTCAGCAACAACTGTATCAACGACATCGC
GATCGTTTAATTGCAACTTTAATTCGGTAGCATCCATCTGGTATGCTGTACCGATGGCAACAATAACGTTA
ATATCTCCAATATTCAAACCCTCTTCAAAGTAAGCTCTATAAATAGCTTCAACGACATCATTTTTTATGTT
TGTCGGTGCTAATGCAATCAGTTGGTGAGCAAGCTTAGTATTGACAGCCAAACGGATTTTTTCAAAATCTA
GCTTAACCCCAGCCGCCTCCCCTGCGCGTTGCGTATAATCAAACATCTGTTGCATTTCTGGCGCTTTAATG
CCTTTTCTATTTTGCATAAAGCTACTAAATTCGTACCCCTCAGCAGGAACAGTATCATCCAGAAGAAAGGG
ATGCCATCGGATATTTACTTCTTGTTCTTGCCATTGTGCCAGTGCATCAAATAGATGTTTTTTCCCAATTC
TGCACCAAGGGCAAACGGTATCATGAAAGATATCTATCAGCATAGTTTTGTCACTCAAATGCTAATATTT
GTGTGCATCTGGGGTTTAAAATCTCGTTGCAGAGCCGTTGTATTTAAAGGCTGGAGAAAACTATTAATTTT
CTCTTCAAAAAACTTTGAGTATTTTCAAACTCTTTAATTAATGCCTCTCTATCCTTCCTAGCCACCAGTC
TAGCCAATCGGCTGTAAGTTTTAGCTAAAAGCTAATAGCATTACACCTTTCTTCAGTCGCTAGCATAATA
TCAACGCATAAATTAGGATTTTGCGAAAATAAACGTTTTACAATATCAATCTCTTGACGATAGTTAGGAGT
TGACATTGTTAAACTCTGCTCTATCTCTACTCTTGATTGTGCTAAGAAAACACCAAGACTAAATCTACAGA
AATGCTGCGTGGCTTGAATAATCACCATCATT (SEQ ID NO:1)
```

FIG. 6-1 crpA

```
ATGGGGCATAGTGCTGGGGAATATGTGGCAGCCACAGTAGCAGGAATATTTAGTTTAGAAGATGGTTTAAA
ACTGATTGCTCATAGAGGAAGACTAATGCAACAGTTACCCTCTGGGGGTGAAATGTTATCTGTAATGGCTT
CAATTGAAAAGGTAAATCAACTAATTGCACCATACTCTCAAAAAGTAGCGATCGCATCGATTAACGGACCC
CAAAGCATTGTCATTTCTGGTGAGGCAGAAGCAATTGGAGCGGTTCAAAATAGCTTAGAAGCAGAAGACAT
TAAGACAAAACGACTGCAAGTATCCCACGCATTCCATTCACATTTGATGGAACCAATGTTGGCGGACTTTG
AAGCAGTAGCATCAGAAATAACCTACAATCAACCAAATATTCCATTAGTATCAAATGTAACGGGAGCTAGG
GCAGAGAATAGTATTGCCACAGCAAGCTATTGGGTAAATCATGTCCGGCAACCGGTGAAATTTGCCCAAAG
TATGGACACATTACAGCAAGAAGGTTATTCCATCTTCTTAGAAATTGGACCCAAACCAACTTTGTTAGGCA
TGGGAAGACAGTGCTTGCCAGAAGATGTGGGAGTTTGGTTGCCTTCTTTGAAACCAGGTCAAGAAGACTGG
CAGCAAATGCTACAAAGTTTGGCTGAACTATATGTGCATGGAGTTAAAGTTGATTGGTTAGGGTTTGATAA
AGATTATTCTCGTAGCAAGGTAGTATTGCCGACTTATCCCTTTCAACGGCAACGTTATTGGATTGAGACAA
ATAATAATCTAATACATCAAAAACAGTTTTTATCAAATCATAAAAATCTTCACCCTCTACTCGGTCAAAGA
TTACATTTAGCAGCCTTAGAACAGCAAATTCGTTTTGAATGTCAAATTAGTGCTTCTCAACCAACTTACCT
GCAACACCACTGTGTTTTTTCTCAACCTGTTTTCCCAGCAGCAGCTTACTTGGAAATAGCCTTAGCAGCAG
GTTCAATTTTATTCAATTCAGATGATTTAATCCTAGAAGATATAGCAATCCAAAAAGTATTAATTTTATCA
AAGGATGAAATTAATACAATTCAGATAGTTTTAAATTTACAGTTAGTACAAAGCTATAAATTCCAAATTTT
CAGTTTGGATATAAACACTAATTCTTCAGAACCTAAATGGATTCTACATATTGAAGGAAAAATATTAGTAG
GTAATAAAGACCCCCAATTAGAAACAACAAACTTAAAAGCGATTAAAGACGAGTATAACCAACAGATATTA
CCTACTGAATTCTACCAAAAATTTGAAGAATGGGGTCTTAATTACGGTTCTTCTTTCCAAGCCGTTAAACA
ACTGTGGCACAGCGAAGGAAAAGCACTAGGTGAAATTCAGTTACCAGAAACTGAGGTGAATGTTGCAACTT
TATACCAACTGCACCCAATTCTTTTAGATGCTAGCTTCCAGGTGTTAGCAGCAGTTATGGGTAAAACGGAC
AACCAAGAAACTTATTTGCCATTGGAAATAAAACGACTACAAATTTATCGGAGTGGTAGTAATAGTTTGTG
GACTCAAGTAGAGATAGGTGCAACAGAAACTAATAAACAAACTTTGAGCGGTAAAGTTTGTTTATTGGATG
AACAAGGAATAGTAGTAGCAAGAGTTGAAGGTTTAACTTTATTACGTACTTCTCGCGAGGCTTTGTTGCGT
AATATTGAACCAAAATTTAATAATTGGTTATATCAAATCCATTGGCAAACCCAATCAATTTCACCCCATAA
CCAATCAATTGACTTAACAAAATCAGGTAGCTGGTTATTGTTTTCCCCACCCACAGGTATAGGCAAACATC
TGGTAGAATCCTTAGAACAACAAGGTTGGCATTGTATATTAGTAACACCAGGGGAAAATTACCAGCAGTTA
GAATCTCAACATTATCAAATCAACCCCAACCATCCTGAGGAATTCCTGCACCTATTGCAATCAAGCTTGGA
GCAGCAACCCCCATTACGAGGAATTATTCACCTGTGGAGTTTGGACTCAACAATAGCACTAAGGACTGGGG
CACAGGAGTTGCAAAAATCCCAAGAACTGGGCTGTGGCAGCGTACTTCATTTAGTCCAAGCCTTAGTAAAA
AATCAAGATATGGAAAGTGCCCCATTATGGTTAGTGACTCAAGGCTCACAATCTGTGGGTAATGAGTCCCT
TCCTATACAATTCCAACAAACACCTTTATGGGGGTTAGGTCGAGTAATTGCCCAGGAACATAGGGAATTAC
AATGCCGGTGTTTAGACTTAGATCCAACTATGGAAGATTCCCAAACAGTAGCTGCTTTGTTAGAGGAACTA
TTATCTCCTGGTGATGAAAACCAAATTGCTTACTGTCAAGGGGTACGTCACGTTGCCCGGTTAGAGCGGCA
ACAAAAAATGAGTACATCTACACAGTCCGGATTACAAATTTCCTCGCAACAACCATTTCAACTGAAGCTAT
CAGAATATAAGTCTTTAGACAACCTAATCCAAGCCGAAGCCAGTTACTTAATTACCGGAGGTCTGGGAGCA
CTGGGGTTAAAAACCGCTGAGTGGATGGTACAACAAGGGGTCAAATATTTAGTACTTACCGGACGTAGGCA
GCCATCAGCAAAAGCTCAACAAACCATTGAACAATTACAGAAGGCAGGAGCGCAAGTATTAGTCCTGTGTG
GAGATATTTCCCAACAAGAAATGTGGCAAGAATTATAGAGTCAATCAAAGTATCTTTGCCAGCATTACGA
GGAATAATTCATGCTGCTGGGATATTGGATGATGGTTTGCTGTTAAACATGAATTGGGAAAAATTTACACA
GGTGATGGCACCAAAAGTACAAGGGGCTTGGCATTTGCATAATTTGACTCAGAATCTACCTTTGGACTTTT
TTGTTTGTTTTTCCTCTATGGCTTCAATATTGGGTTCGCCTGGTCAAGGGAATTATGCTGCTGCTAATGCT
TTCATGGATGGTTTAGCCCATCATCGACGGGTATGGGTTTACCTGGCTTGAGCATTAACTGGGGACCATG
GGCACAAGAGGGAATGGCAGCAAATTTGGATAGTCCTCATCAAGATAGAATGGTGTCCAAGGGAATGACTT
TTTTGTCTTCAGAACAGGGATTGCAGGTTCTAGGACAATTACTCGAACAATCCATACCACAAGTAGGAGTC
CTACCAATTCAATGGTCAGTGTTCCAAGAGCAATTTAGTTTTGGTAATCAAATACCATTGCTGTCCCAATT
GGTAAAAGAAAGCAAATCACAGCAAAAAGCCCTCAAAACAAAGACAAAGCACAATGAATTTTTAGAACAGC
TAAAAGCTGCTTTACCAAGAGAAAGAGAAAAGCTTTTGATAATTTACATTAAAGATGAAATTTCTCAAGTA
CTTTCTTTGAGCACTTCTCAAATTGATATGCAACAGCCCCTGAACACTATGGGGCTTGATTCTCTAATGGC
TGTGGAATTGCACAATAGGCTTCAAACTGACTTGCTCGTGGATATATCTATAGTCAAATTTATAGAAGATA
TCAGTATCGTTGATTTAGCCACTGAAGTGAATGAGCAACTGAGCCAAGTTGCTCAGAATCAAGGAGTTGAG
TCAGAAAATAATGGGCAACTCTACCAAAGCAATAGGAAAGAAAACGAGCGGATAAGAGGTGAATTATGA
```
(SEQ ID NO:2)

FIG. 6-2

CrpA
MGHSAGEYVAATVAGIFSLEDGLKLIAHRGRLMQQLPSGGEMLSVMASIEKVNQLIAPYSQKVAIASINGP
QSIVISGEAEAIGAVQNSLEAEDIKTKRLQVSHAFHSHLMEPMLADFEAVASEITYNQPNIPLVSNVTGAR
AENSIATASYWVNHVRQPVKFAQSMDTLQQEGYSIFLEIGPKPTLLGMGRQCLPEDVGVWLPSLKPGQEDW
QQMLQSLAELYVHGVKVDWLGFDKDYSRSKVVLPTYPFQRQRYWIETNNNLIHQKQFLSNHKNLHPLLGQR
LHLAALEQQIRFECQISASQPTYLQHHCVFSQPVFPAAAYLEIALAAGSILFNSDDLILEDIAIQKVLILS
KDEINTIQIVLNLQLVQSYKFQIFSLDINTNSSEPKWILHIEGKILVGNKDPQLETTNLKAIKDEYNQQIL
PTEFYQKFEEWGLNYGSSFQAVKQLWHSEGKALGEIQLPETEVNVATLYQLHPILLDASFQVLAAVMGKTD
NQETYLPLEIKRLQIYRSGSNSLWTQVEIGATETNKQTLSGKVCLLDEQGIVVARVEGLTLLRTSREALLR
NIEPKFNNWLYQIHWQTQSISPHNQSIDLTKSGSWLLFSPPTGIGKHLVESLEQQGWHCILVTPGENYQQL
ESQHYQINPNHPEEFLHLLQSSLEQQPPLRGIIHLWSLDSTIALRTGAQELQKSQELGCGSVLHLVQALVK
NQDMESAPLWLVTQGSQSVGNESLPIQFQQTPLWGLGRVIAQEHRELQCRCLDLDPTMEDSQTVAALLEEL
LSPGDENQIAYCQGVRHVARLERQQKMSTSTQSGLQISSQQPFQLKLSEYKSLDNLIQAEASYLITGGLGA
LGLKTAEWMVQQGVKYLVLTGRRQPSAKAQQTIEQLQKAGAQVLVLCGDISQQENVARIIESIKVSLPALR
GIIHAAGILDDGLLLNMNWEKFTQVMAPKVQGAWHLHNLTQNLPLDFFVCFSSMASILGSPGQGNYAAANA
FMDGLAHHRRGMGLPGLSINWGPWAQEGMAANLDSPHQDRMVSKGMTFLSSEQGLQVLGQLLEQSIPQVGV
LPIQWSVFQEQFSFGNQIPLLSQLVKESKSQQKALKTKTKHNEFLEQLKAALPREREKLLIIYIKDEISQV
LSLSTSQIDMQQPLNTMGLDSLMAVELHNRLQTDLLVDISIVKFIEDISIVDLATEVNEQLSQVAQNQGVE
SENNGQLYQSNRKENERIRGEL (SEQ ID NO:3)

crpB
ATGAATTTAATCGAATTTTTACAAGATATTTCAATAAAAGGTTGGCAAGTGTGGAGTGAGGGCGAACGGCT
TTGTTACGATGCTCCTCAAGAAGAATCAACTGCTTTAGTATTAGCTCAACTGAAACAATACAAAACCGAAA
TATTACAATTGCTGCGCGATCGCCCAGATATTTTAAACGTCTATCCCCTTTCTTACGGTCAACGGGCACTT
TGGTTTTTGTGGCAATTAGCACCAGAAAGTCATGCTTATAACGTATCATTTGTCGCTCGTATTTGCTCAAC
AGTAGATATTACAGCAATGCAAAAGGCATTTGAGAAACTAATAGAACGGCATCCGATATTGCGTACAAATT
ATCCCAAACTCGGATCTGAGTCAATCCAACAGGTAAATAATTTTCAGGAATTAAATTTCTTGCAAATTGAT
GCTTCTGCTTGGAGTGAAGATGAACTGAAAGGGAAGTGATTGAGAGCCATCAACAATATTTTGACCTCGA
ACGAGGGCCTGTTATGCGAGTTCGGTGGTTTACTCGTTCCAAGAAAGAACATGTCCTGTTGCTAACCATAC
ACCACATTGCTTGCGATGCCTGGTCTTTAGATATGTTAATACAGGAGTTGCCACAACTCTACCAAGTACAA
TGGGCTGATTTTAAGACACCCCTTTCTCCTCTAAAGCATTCTTACCAAGATTACGTTCGTTGGCAGAGGAA
TATTTTGCAGGAGACTGAAGGGAAAGACTCTGGAACTACTGGCAGCAAAAACTGACAGGCGATTTGCCAG
CACTAAACCTAGCAACCTCAAGACAGCGACCACCGATAAAAACTTATAATGGTGCTTCCCATCACTTCAAA
TTATCTGACAAGCTCACTAAGCAACTCAAGGAGCTGGCTTTAAACTCGGGAGCAACACTTTACATGATGCT
CTTAGCAACTTTTCAGGTGTTTTTGTATCGTTACACAGGCCAGGAGGATATTTTAGTCGGTTCTCCCACCT
CAGGTAGGAGTCAAGCTAAGTTTGCTTCGATCTTGGCTACTTTGTTGATCCTGTTGTTATGCGAGCAAAT
TTATCGGGAATCCCAGTTTCAAAGATTTCCTCGCCCAAGTACGCCAAACCGTATTGGAAGCACTTGCTCA
TCAAGATTACCCATTTGCTCTATTGGTAGAAAAGCTACAGCCACACCGCGACCCCAGTCGTTCGCCGATTT
TTCAGGCTTCTTTTTCTCTACTGCAGTTCCAAAAATCTCAAGATATACAGAAGTTGTTTGTAAATCAAATA
GAAACCTATGTTGATTGGGGAGAATTGAAGATAAAACCTTATGAAATACCTCAACAGGAAGGTCAGTTAGA
TTTAGGTTTAGAAATGGTGGAGGGGAGTTCATCTGTTTTTGGGGTTTTTAAGTACAACACTGACTTGTTTG
ATGAGTCAACCATTGAGCGCATGGCTGGTCATTTCCAGAATTTATTGTCAGCGATTGTGGAAAATCCTCAA
CAAAAGGTAAGTGAATCACCCCTATTGAGTGAAGTAGAACGGCATCAGTTGTTGGTGGAGTGGAATGATAC
AGCAAGGGAATATCCCAGTAAATGTATCCATCAATTGTTTGAAGAGCAGGTAGAGAGAACACCGGATGCAG
TCGCGGTGGTATTTGAGAATCAGCAGTTAACCTACCAACAATTAAATCAAAAGCCAACCAACTAGCACAT
CACCTGCTTTCCTTGCGAGTCGAACCAGAGGTGCTGGTAGGGATTTACGTGGAGCGTTCTTTTGAAATGGT
GGTAGGGCTCTTGGGATACTCAAGGCTGGTGGGCTTATGTACCCCTTGACCCCAATTATCCCCAAGAAC
GGTTGAGTTATATGTTGGCGGATTCAGGTGTTGAGGTGTTGTTGGCTCAAAAGTCCCTACTGGAATCTTTG
CCGTCACATACTGCACAGGTGGTTTGTTTGGATAGTGATTGGGGAGTGATTGAGCAACACAGTCAGGAGAA
TCTTGATGTTGGGGTATGTTCAGATAATTTGGCTTATGTGATTTATACTTCTGGTTCTACTGGAGTTCCCA
AGGGGGTTGGGATTGAACATTTTTCTTTGTGCAACCTTATTCAAGCACAGAAAAATTTATTTTATCTAGAA
CCAAATAGTCGTGTTCTTCAATTTGCTTCTATAAGTTTTGATGCTTCAGTTTCGGAAATATTTATCGCTTT
GACTTCTGGAGCAATGCTAATTTTGGCTATAGCTTCTGAGTTAATCCCGGGTTCGGATTTAAAGCAAATTT
TACAAGAAAGATGTGTAACTCATGTTACGTTACCTCCCTCTGCCCTGGCAGTACTAGCTACTGATGAATTT

FIG. 6-3

```
CCAGCCTTGGGTCAGATAATTGTGGCAGGGGAWSCTTSTAYWMTKGAATTGGCCAATCAGTGGTCTGTTGG
TCGTCGTTTGTTTAATGGTTATGGGCCTACTGAGTCTACTATTGGTGCTGCAGTGGCTCAAATCAGCCATG
GTAGCGAGAAAGTTACTATCGGTCGCCCCATTGCAAACACCCAAATCTATATCTTAGATAAGCACTTAGAA
CCAGTACCCATAAGTGTATCCGGAGAATTATACATCGGAGGTTATGGCTTAGCCAGAGGTTACCTCAACCG
ACCGGAATTAACTTTAGAGAAATTCATCCCTAACCCCTTCAATAGCAGATCAAAACTATATAAAACTGGAG
ATTTAGCTCGATACTTACCAGATGGTAATATTGAGTTTCTTGGTCGTCTTGATAACCAGGTGAAAATACGT
GGTTTCCGCATAGAACTAGGAGAAATAGAATCAGTTCTGAGTACCCATCCTCAAGTACAGCAAGTCGCAGT
CACCGAAAGGGAAGATACTCCGGGTCACAAACGGTTGGTAGCATATTTAGTTCCTCTTCAGTCAAAAGAAA
AAGATCCCCAGCCCCAGACAGGAATTGAACTTTGGCCCTCAGTAGCAGAATTCTACGTTTATGATGAGCTC
TTGTACTATGCGATGACCAATGATCATCGTCGAAACCAGAGTTACCAAGTCGCAATTAATCAAATGGTTAA
AGATAAAGTAGTTGTTGAAATTGGCACGGGCAAGGATGCAATTATAGCCAGATTTTGTGCAGAAGCAGGTG
CTAAGAAAGTCTACGCAATTGAGAGAGACGAGCAAACCAGTAAGTTAGCTTCAGCTTGCGTGCAAGAGTTG
GGGTTATCAGAACAAATTCAAATCATACATGGAGACGCTACTACAGCCAACTTACCAGAAGAAGTTGATGT
ATGTGTTTCTGAAATTGTGGGACCCATTGGTGGATCTGAAGGAGCAGCAGTAATTATCAACAACGCCAGAA
GATTTCTCAAATCAGATGGTGTAATGATTCCCCAAGAAGTGTGACTCAAATTATTGCAGTAACTCTTCCT
GATGAATTACTAAATCAACCCCAATTTACAAAAGTTTCAGGTTATTATACCCAGAAGATATTTGAGCAAGT
TGGATATCCTTTTGATTTACGAGTATGTATTAAAGGATTAAATCAAGTAAACTGGTTGTCCAATCGAGGAG
TTTTTGAGGATTTAGACTTTAGCAAGCTTGTTAGCACAGAATCTACTCACCAAATTAAATTAACTATTGAA
AAATCAGGAAGATTAGATGGTTTTTCAGTGGGATTAAACTTACACACAATTGAAGGAGAATGTATAGATAT
TTTAGAAAATGAACATTGCTGGTTACCAGTTTATCTTCCAGTGTTTGAACCAGGAATTTATGTAAATGAAG
GAGATATCATCGAAGCTGTTTGTACGAGAACGCTTTGTGAAAATAATTTGAATCCAGATTATACTCTTCGA
GGTCGTCTTTTAAAAAAAACTGGAAAAGAGATTGAGTTTGAATACATCTCATATCATTGGAAACAATTGTT
TAAGCAAAACCCTTTTTATCAACGATTGTTTGCTGAAAATAATCTAGAAGATTACACAATTAATAAGTCAA
AGCCTGAACGTAAGGTACTGAGTAGCAATGAATTGCGCTCCTACCTAAAGTCTAAATTGCCAGAATATATG
CTCCCCTCTAGCTTTGTCATCTTAGACACCCTACCGTTGACACCCAACGGTAAAGTAGACCGCAAAGCCCT
AAGTGCACCTGATGGGGAAGTTAGCCGAGAGGATGAATATGTCGCACCACGCACAGAAATAGAACAAATCT
TAACCAACATTTGGCAWGAACTGCTCCTTAAAGAACAAGTCAGCATCCATGACAACTTCTTTGAAATTGGT
GGCGACTCCATCCTTGGTATTCAAGTAGTTTCTCGTGCCAAAAACTTAGGAATACAAATCACTCCCAAACA
AATATTCCAAAATCAAACCATCGCCAAACTAGCATTAGTAGCCAATACAACAGTTACTGTCAGTGCTAACC
AAGGTATAGTTACTGGAGTTGCACCCCTAACACCAATTCAACAGTGGTTCTTTGCACAAAATAGCCAAGAA
GCACACCATTACAACCAATCAGTTTTATTGCAGATTCCCAATCATCTGCAAACTGAATTAATCGAAACAGC
CTTGAAAAAATTATTAGAGCATCACGATGCTCTGCGTTTACGATTCACATCAGTTGCATCTGAGTACAAAC
AAATAAACCATGGCTTTGATGATCCCGTAGCATTTACTGTAGTTGATTTATCATCAACTCCTGTCATTGAA
CAACCACAAGCTTTATCACAGATCGCCACGGAATATCAAGCAAGTTTAAACCTCTCAGAGGGACCTTTAAT
GCAAGTGGTGATGTTTAACTTAGGTAGTGAAGTTGATGCCCGTTTACTGATTATTATTCATCACCTAGCAG
TAGATGGTGTGAGTTGGCGAATTTTACTATCAGACTTAGAAACAATCTATCAACAACTAATCGCTCAACAA
TCAATACAGCTAAATGCGAAAACAACAGCATTTATTGATTGGGCAGAGAAATTGAAAAATTATGCACAATC
AGAAAAAATCAAACAAGAGTTAGACTATTGGCTCAACCAACCTTGGTCAGAAACAACACCACTACCATTAG
ATTCTGCTCACACTCAAGCAGAAAAACAGTTGATAGTGCGATTAATTATAGAGTGAAATTGAGTCCAGAA
GAAACCCGCGCTTTGCTGGGGTCAGTAAACTCAGCTTATAACACACAAATTAACGATATCCTCCTCAGTGC
ATTAGTAGTTTCCTTGGCAGAGTGGACGGGAGATTCAAAAGTACTAATTGACCTAGAAGGACATGGCAGAG
AAGAACTATTTTCAGATGTAGACTTATCAAGAACAATAGGTTGGTTTACCAGTTTATTCCCAGTATTATTG
CGATTACCAGACGATAAACAACCAGCAGAAGTTATCAAGTCAATTAAAGAACAATTACGAGAGATTCCCCA
TCGTGGTATTGGCTTTGGTATATTGCGTTACTTGTGTGAAGATACTACTGTAAC
CCAAAAACTACAGACAATTCCTACTCCAGAAATTAGTTTTAACTACCTAGGACAATTTGACCAAATACAAT
CGGAAACGGGTTGGAAATTTGCGCCAGAATCTACTGGAGATAATCATAGTTCAAAGCAAACTCGTCACCAT
CTATTAGAGATTAATAGTCTGGTGGTAGAAGGTGAATTACAAATTGATTGGACTTATAGTAGTAATTTTCA
TACTCATGATACAGTAAAAAATTTGACACAAAGCTATATTCAAGCAATTAAGTCAATAATAGAACATTGCC
AGTCAGAAAATGGTTTTGGATATACAGCTAGTGATTTCCCAGATGCACAGTTAAATCAATTAGAACTTGAT
GAGTTATTAAAAAACTTGGGCAAATAG (SEQ ID NO:4)
```

CrpB

MNLIEFLQDISIKGWQVWSEGERLCYDAPQEESTALVLAQLKQYKTEILQLLRDRPDILNVYPLSYGQRAL
WFLWQLAPESHAYNVSFVARICSTVDITAMQKAFEKLIERHPILRTNYPKLGSESIQQVNNFQELNFLQID

FIG. 6-4

ASAWSEDELKGKVIESHQQYFDLERGPVMRVRWFTRSKKEHVLLLTIHHIACDAWSLDMLIQELPQLYQVQ
WADFKTPLSPLKHSYQDYVRWQRNILQETEGERLWNYWQQKLTGDLPALNLATSRQRPPIKTYNGASHHFK
LSDKLTKQLKELALNSGATLYMMLLATFQVFLYRYTGQEDILVGSPTSGRSQAKFASILGYFVDPVVMRAN
LSGNPSFKDFLAQVRQTVLEALAHQDYPFALLVEKLQPHRDPSRSPIFQASFSLLQFQKSQDIQKLFVNQI
ETYVDWGELKIKPYEIPQQEGQLDLGLEMVEGSSSVFGVFKYNTDLFDESTIERMAGHFQNLLSAIVENPQ
QKVSESPLLSEVERHQLLVEWNDTAREYPSKCIHQLFEEQVERTPDAVAVVFENQQLTYQQLNQKANQLAH
HLLSLRVEPEVLVGIYVERSFEMVVGLLGILKAGGAYVPLDPNYPQERLSYMLADSGVEVLLAQKSLLESL
PSHTAQVVCLDSDWGVIEQHSQENLDVGVCSDNLAYVIYTSGSTGVPKGVGIEHFSLCNLIQAQKNLFYLE
PNSRVLQFASISFDASVSEIFIALTSGAMLILAIASELIPGSDLKQILQERCVTHVTLPPSALAVLATDEF
PALGQIIVAGXXXXXELANQWSVGRRLFNGYGPTESTIGAAVAQISHGSEKVTIGRPIANTQIYILDKHLE
PVPISVSGELYIGGYGLARGYLNRPELTLEKFIPNPFNSRSKLYKTGDLARYLPDGNIEFLGRLDNQVKIR
GFRIELGEIESVLSTHPQVQQVAVTEREDTPGHKRLVAYLVPLQSKEKDPQPQTGIELWPSVAEFYVYDEL
LYYAMTNDHRRNQSYQVAINQMVKDKVVVEIGTGKDAIIARFCAEAGAKKVYAIERDEQTSKLASACVQEL
GLSEQIQIIHGDATTANLPEEVDVCVSEIVGPIGGSEGAAVIINNARRFLKSDGVMIPQRSVTQIIAVTLP
DELLNQPQFTKVSGYYTQKIFEQVGYPFDLRVCIKGLNQVNWLSNRGVFEDLDFSKLVSTESTHQIKLTIE
KSGRLDGFSVGLNLHTIEGECIDILENEHCWLPVYLPVFEPGIYVNEGDIIEAVCTRTLCENNLNPDYTLR
GRLLKKTGKEIEFEYISYHWKQLFKQNPFYQRLFAENNLEDYTINKSKPERKVLSSNELRSYLKSKLPEYM
LPSSFVILDTLPLTPNGKVDRKALSAPDGEVSREDEYVAPRTEIEQILTNIWXELLLKEQVSIHDNFFEIG
GDSILGIQVVSRAKNLGIQITPKQIFQNQTIAKLALVANTTVTVSANQGIVTGVAPLTPIQQWFFAQNSQE
AHHYNQSVLLQIPNHLQTELIETALKKLLEHHDALRLRFTSVASEYKQINHGFDDPVAFTVVDLSSTPVIE
QPQALSQIATEYQASLNLSEGPLMQVVMFNLGSEVDARLLIIIHHLAVDGVSWRILLSDLETIYQQLIAQQ
SIQLNAKTTAFIDWAEKLKNYAQSEKIKQELDYWLNQPWSETTPLPLDSAHTQAEKTVDSAINYRVKLSPE
ETRALLGSVNSAYNTQINDILLSALVVSLAEWTGDSKVLIDLEGHGREELFSDVDLSRTIGWFTSLFPVLL
RLPDDKQPAEVIKSIKEQLREIPHRGIGFGILRYLCEDTTVTQKLQTIPTPEISFNYLGQFDQIQSETGWK
FAPESTGDNHSSKQTRHHLLEINSLVVEGELQIDWTYSSNFHTHDTVKNLTQSYIQAIKSIIEHCQSENGF
GYTASDFPDAQLNQLELDELLKNLGK (SEQ ID NO:5)

crpC

ATGAGCAACGAAGAAATTAGAAGAAATATCTCTTCAATTTATCCACTTTCTCCCATGCAACAAGGGATGCT
GTTCCACAGTCTTTATGCACCTTATAGTGGGGTATATCTTGAACAGATGACCTGGGGTTTGAAGGGGAATA
TCAATGTTGCTGCTTTTGAAAGAGCTTGGCAAAAAGTTTTAGATAGACATTCAATTCTACGTACATTTTTT
GTTTGGGAAAATCGCCAAACTCCATTACAAGTAGTACTAAAACAGGTTAATGTTCCTTGGAATACTCTTGA
TTGGCGAGAACTTTCTTCTAATGATCAACAACAACAATTAAAACAATTATTGCAAACACAAGAGAACAAG
GTTTTAACTTATCCCAAGCACCATTAATGCGGTGTACGTTAGTCAGGCTAGGCGAAGATAATTACAAATTT
ATCTGGAGTCATCACCACATCCTTATGGATGGATGGTGTTTATCAATTATTTTTAAAGAAATTTTAATTTT
CTATAAAGCACATCTGCTTGGTGAAAATTGCCAATTGCCAAAACCACGTCCTTACCAGGATTATATTGCTT
GGTTGAATTCTCAAGACAAATCAGCAGCAATTGAGTTTGGCAACAAACTTTACAAGGTTTTAGTGCTCCC
ACTCCATTGGTAATGGATAAAACTCAATTTCTGAAAGAGCAACAGTATAAAACTGCGGATTATCAGGAGAG
AACAAGTAGTTTATCCCCTGAATGCACTCAGAAGTTACTTCATATAGCACAACAACATCATGTGACTTTAT
CAACTGTAGTACAAGCTGCTTGGGCTTTACTATTGAGTCGTTATAGTGGTGAGAAAGATGTAGTATTTGGT
GTGACTGTTTCTGGTCGTCCTCCTAGCCTCTCTGAGATAGAAAATATGGTAGGACTGTTTATTAACACCCT
TCCCTTACGAGTACAAGTATCCACCCAGGAGCAACTCATACCTTGGTTGCAAAAAATACAACAGTCAATGG
TTGAATTACAAGAGTATTTTTATACTCCTCTTGTTGATATTCAAGCTACTTCTGAGATACCAGGTGGAATA
CCTTTGTTTGAGAGCATTGTGGTGTTTGAGAATTATCCAATTGATAATTCTTTGTTGAATGAAGAAGGTTC
ATTACACTTAGGTGATATAGAGGTTTTTGAACAAACTAATTATCCACTAACTTTAGTTGCAGTTCCTGGGG
ATAAGTTGTCAGTTAGGATTAGTTACGATACTGCTCGTTTCTCTTCAAATACTATTGAGTGGATTTTAGGA
TATCTGCAAACTGTTTTATCAGCAATTGCAATTGTGGAAAATCCTTCACATAAGGTAGCTCAATTACCTTT
ATTAAGTGAAGTAGAACGTCATCAGTTATTGGTTGAGTGGAATAACACTGCAACGGATTACCCATCTGATA
AATGTATTCATCAGTTATTTGAGCAACAGGTAGAAAAAACCCCAACTCCATAGCAGTGGTGTTTGAAGAA
GAACAATCAACCTACCAACAATTAAATCAAAAGCGAACCAATTAGCACATTATCTACAAACTCTGGGAGT
GAAACCAGAAGTGCTGGTGGGTATTTGCATAGAATACTCCATTGATATGATTGTAGGACTGTTGGGGATAC
TTAAAGCTGGTGGTGTATATGTGCCGTTAGATCCGAACTATCCGCAAGAACGACTGGCGTTCATGCAGGAA
GATTCCAATGTGCATATCATATTGACCCAGCAGCCTCTGCTCGAAAAGATTTCCCCTCAAATGCCCATAT
CGTTTGCCTGGACAGGGATAGGGATGTCATTGCTAGGGAAGGCGTTGAAAATCTGGATCGGCAAACAACAC

FIG. 6-5

```
TGGATGACCTTGCATACGCAATCTATACGTCTGGTTCTACTGGAAAACCCAAAGCCGTTCTCGGCACGCTT
CGCGGCATTGTCAATCGCTTGCATTGGATCTGGGAAATGCTACCATTTGGGGCAGATGAGATTTGCTCTCA
GAAAACATCCATCAATTTTGGCGATCATGTTGCGGAAATATTTTCTCCCCTTCTCAAAGGAATTCCCCTTG
TGATCGTTCCAGATGATATACGGGGCAATATTCCCAGGCTAATGAGCCTGTTGAGCGATCGAAAGGTAACT
AGAATTGTTCTCGTTCCATCGCTATTAAAAGCGATACTGGAAAATGCGCCCCAACAACTGACAAAACTTCG
ATATCTCAAATATGTCTTTTGCAGCGGTGAAGTCTTACCGCTAACCTTGGCTAAGGAATTTCACCAGAAAA
TCAGCTCTGCCAGATTGTTCAATCTCTACGGCTCTTCAGAAGTTGCCGCTGATGTTACATGCTTTGAAGTC
AAACTGAGAATCGCAAATCAAATTGAAGCAAAAGTAAAGAGAAACTTGATGCTTTAAAAAATCTTCCTAG
TGGCTCAGGGGATAGGGAAACTGCTGTCCTGCATAAAGAAATAATACATTTGCAGTTGGCAGACGAGCGAA
GAGCAGATTTAGGAGAAGCTCTAGAAGAATATCTGAAAAGAAATACGATTCCGATTGGAAAACCGATTTCA
AACACACAAATTTACATCCTCGACAAGTATGGCGATCTTTTGCCACCTGGTGTTACGGGTGAGCTATACGT
CGGCGGAGATGGGCTTGCAAAAGGGTATTTAAATCTGCCCGAGTTAACGCGGGAAAAGTTTATCCCCAACC
CGTTTGTGAAGGACAGGGGGAAAAGTAAAAAGGCACAAGCAGAAAGATTGTTTAGGACTGGAGACCTAGCC
CGCTGGCTGCCGGATGGTAATATCGAATTTGTAGGGCGTATCGATCACCAAGTGAAGGTGCGGGCTTCCG
CATTGAACTTGGAGAAATCGAAGCAGTCCTCAGTACCCACCCCAAATCCAACAAGTCGTTGTCATTGCCA
TAGAAGATATTCCAGGTAGCAAACGTTTAGTAGCCTACATAGTCTGTGAGGATGAATCACTAAGTACCTAT
CACCTGCGTGAATTCCTCAAACAAAAGCTACCAGAATACATGATGCCCAGTGCCTTTGTCATCTTAGACAC
CTTACCGTTGACACCCAGCGGTAAAATAGACCGTAAAGCCCTTCCAGCACCTGATGGAGAAATTAGCCGAG
AACATGAATATGTCCCACCACGTACATCGGGTGAAGAAATAATAGCCAACATCTTCGCTTCTATTCTAGGT
GTGCAAAATGTTGGAATCCATGACAACTTCTTTGAATTGGGAGGACATTCCCTACTAGCAACCCGATTAAT
TTCCCGACTCAGAGTTGCCTTTGAAGTAGAAATAGAACTAAGTGCAGTCTTTTCCTCTCCCACTGTAGCTC
AATTAGAGCAAACATTAACCCAATTACGTACTACTAATAGCGCATTAAGTCTTCCCCCCATTCAGCCAAGA
ACACAGAACCAACAATTACCCCTATCTTTTGCACAAGACCGGTTGTGGTTCCTCAACCAACTTGAAGGGTC
AAGTGCCACTTATAACATGCCAGGAGCAATTCGTGTCACTGGAAAGTTGGATATTAATGCCTTGCAACAAG
CATTATCAGAAATAGTCCGCCGTCATGAAGTACTACGCACCAGCTTCCGAACTGTGAATGGCACACCAATA
CAGGTAATTCACCCAGAAGCCACCATGAACATCAGTGTGGCGGACTTACAGCAACTAGAAGCAACAGAACG
GGAAAGTGTCCTTCACCAACAAGCACAACTTGCAGCAATTACCCCCTTTGACTTAGAAACTGCACCACTAA
TCAGGTGTAGTTTATTGCAGTTAGATGCCAGAGAATATGTGTTATTACTGACGATGCACCACATTGTCTCT
GATGGTTGGTCAATGGGATATTCAGCCAAGAACTATCTACTTTATATCAAGCTTTTAGTGCAGGAAAACC
ATCCCCCTTGGCAGAATTACCAATCCAGTATGCAGACTTTGCAGTTTGGCAAAGACAATGGTTAAGTGGAA
AGGTACTAGAAACTCAACTCAATTACTGGCTTTCTCAGTTAGAGGGTGCACCAGAATTGTTACAATTACCT
ACTGACCGTCCTCGTCCAACCGTGCAAACTTTCCGGGGTACTACTCAAAGTTTTAGTTTAAATACTGATTT
AAAAGAGAAGTTGCAAACCCTGTCTCGGAACTCGGGTACTACCTTATTTATGACCCTGCACGCAGCGTTTG
CCACTTTACTCTATCGCTACAGCGGTCAATTAGATATTTTAATTGGTTCACCCATTGCCAATCGCAACTGC
AGTGAAATTGAGTCTTTGATTGGCTTTTTTGCCAATACTTTGGTATTGAAAACCCGTTTTGAAGATAATCC
CAGTTTTGAGAATTTGCTGGCACAAGTTAGGGAAACTACACTTGAAGCTTATGAACATCAGGATGTGCCTT
TTGAACAGGTAGTTGAAGTACTACAACCACAACGCTCTTTGAGTTATGCACCCTTATTCCAGGTAATGTTT
GTGTTGCAGAATGCACCCATGGGTGAATTAGAATTACCTGGTGTGACCCTTAATTTATTGAGTTCTCAAAC
AGAAACAGCCCGGTTTGATTTAACAGTATCAATGCAGCAAACTTCCGAAGCACTAGTGGGTTCATGGGAAT
ACAACACTGACTTATTTGATGGGTCAACTATTGAGCGCATGACTGCTCATTTCCAGAATCTGTGTAGCGCG
ATTGTAGAAAATCCCCAACAAAGATAAGTGAATTACCATTATTCACAGATTCTGAGCAAGAGCAGGTACT
GCACAGTTACAATAACATCGCTACAACTTACCTGCTGGATAAATATGTTCATTTCCTGAGTTCAAATAATT
TACAAATTTACATTTTAGATAACCATCAACAATTAGTTCCTTTGAGTGTAGAAGGAGAAATTTATTTGGGG
AATTGCGATTTACTCCCAGACAAGTTACATCCAGAACCAGAAAAATTTATAAGTTTCATAGAACATACCCA
ACTGGGTAAGTTATTAAAAACAGGGGAATGGGGTTGTCGTCGAGTCGATGGTTCTCTGGAATTGCTAGGAA
AAGAGCATCGAATTGTCACAGTTAATGGACAACGAATTAACCTACAACGTATTGAACAAGCTTTACAAACA
GCGAAAGGGGTAGAAGATTGCTATGTAATGGTACGCAATCAAAAATTAGTCGCTTACGTAGTCAAAGATGG
TTCTTGGGCTAGGGAGTTTTTACACCATTATTTAAAATCTCAGTTACCTGGATACCCATTACCCTGCATCT
ATGTACCAGTATCTGCTTTACCATTGACAAGTTTTGGAGAAGTTGATGAAGTAGGTTTAGCTTCTATTAGC
ATAATTGATTCTGAGTTAATTAACACTTGGGAAGAACAAATAGGTTCTCAGGCGGAAATTGATAAAGTTGC
TGTTTTTATTGAGCCAAATGTAAAAACGATTTCTCCGATACATTTAGAAGAACTTTTACCATCAATCCAAG
CTATTTTCAATCAAGGTTCTACTCCAGTTGAAACTCCCAGAACTGCTAGGGGAAAAGAGAGTAGTTCCCTA
TTAGAAATAAAATCACCTGCCATCAGCCACGAAGAAGTATTAATCTTTCCAGAATCATCTCCAGAAACTTT
AGGGGAGATGCTGCAAAAAACTGCTGGGAAATTTCCTCACAAAGGAATCACTTATATTAACTCTGATGGTT
```

FIG. 6-6

```
CCGAACAAGTTCAATCATATGCCCAGTTATTAGAAGATGCTCAAAGAATTCTAGGTGGCTTCAGAAAACTG
GGAATTAAGCCACAAGATAAAGTTATTTTGCAATTAAAAGAAAATAAAGATTTTATTAGTGCTTTTTGGGG
TTGTGTGTTGGGAGGCTTTATTCCCGTACCCGTTGTAATTCCTGTAAGCTATGACCAGCCCAATGTCAATC
TAAATAAATTACAAATAGTTGGCAGATGTTAGAAAGACCTTTGATTTTAACAGATAAAAATCATTGTCA
GAACTAAAGAAATGGTCTCAAAATCTAAATGACGACAACTTTAAGTTAGAAACTATTGAAAGTTTACAAAA
GTTCTCAACAGATAAAGATTACTATAATGCCCAACCAGAAGATTTAGCACTGTTCATGCTTACTTCCGGTA
GTACAGGTATGTCTAAGGTGGTACAGTTGAGCCATTTAAATCTACTGAGTAGGACTATTGGTTCAATACAA
ATGAATAATTTTACCCCAGAAGATATAACCTTAAATTGGATGCCCTTAGACCATGTTGCAGGTTTAATATA
TTTTCATATCCGGGATATTTATTTAGGATGTAAACAAATTCATGCTACTAGTCAATTAGTGATTGAAAAAC
CTTTAAGATGGTTGGATTGGATTGATACTTTTGGTGTCACTGTTACTTTTGCTCCTAACTTGCTTATAGT
TTAATTAATGATTTTGTTCAAGAAATAGAAAAGCAGAATTGGAATTTATCTTCTATTCGCTTGATGTTAAA
TGGTGCGGAACAAATTGTTGCAGCAACAGCAAGACGTTTTTGAAATTACTTGCTCCCTTTGGCTTACCTG
GGGATGCTATGACTCCATCTTGGGGAATGGCTGAGGTTTCCTCTGGTATTACTTATTCTGACAATTTTCA
CTCTTATCAAGTTCAGATGATAATTCCTTTGTAAATCTTGGAAAACCGATTAGGGGTACTTGTCTGAGAAT
AGTCAATCAAGACATGGAAGTATTATCAGAAGGTGAAATTGGTTTACTTCAGGTCAAAGGATTAACCGTTA
CTTCTGGTTATTATCAAAATCCAAAAGCAAATAAGGAAGCATTTACCGAAGATGGTTGGTTTAATACAGGT
GATTTAGGATTTATAAAAGATGGATGCTTAACGATTACAGGACGACAAAAAGATATCATTATTATTAATGG
AGTTAATTATTATAGTCATGAAATAGAAGCTGTTGTTGAAGAATTAGGAGAGGTTGAAGTTTCTTATACCG
CAGCCTGTGGAGTCTGCGTTGCTAGCAATAATACCGAAGAATTAGTAATCTTTTTCACTCCGTATGTATCT
GAGAAGAATCAATTATTAGAGCTTTTGAAAAAGGTTAGGGAACAAGTTATAAAATACTGCGGGATAAATCC
AAGTTATTTAATACCCATAGATAAAGAACTGATTCCCAAAACTTCCATCGGTAAAATTCAACGTTCCCTCC
TTAAGCAACGTTTTGAATGTGGTGAGTTTAAATCTCTCAGACAGCGTGTAGACTTGTTGCTTGATAATACT
AATACTATTCCCAACTGGTTTTACCGTAAAGTATGGCAAATTAAAGAAAGTAAAATACTTTACTCAATTA
TTCTTCTCAGAAAACTTTAACCCTAATATTTACAGATAATTTGGGTTGGCAACAAGATAACCGAGGAATGT
CCCAAACTGTTCAACCATATGCTCAAGTTACTATTGGTTCAAATTTTGCTCAAATTAGCCCAAATCATTAT
TCTGTTGTTCCTGGAAATCCACAACACTATCGCTTGTTAATTGATTCTTTGAGGCAAAATAGCCAAGTAAT
TAGTCAAATTCTTCATCTTTGGAACTACAACGAGCAGACTGAAAAAATTTCTAGCTTGGAAAATTTAGAGT
CCACTCAACAACAAGGAATTTACAGTTTACTATTTTTAGTACAAGCTTTAGAAGAAATTCAAGGCAAACAG
CAAGCAGTCAAATTATTATGGATTGCTAATCAAAGCCAATTAGTTCATCCCACAGATAAAATTCAACCCGA
AAAATCCACTGTTTTAGGCTTACTTAAAACTGTTAGTCAAGAAATGCCTTGGTTAACTACTCGTCATTTAG
ATTTACCATTAGCACCAGAACTCAACAATAGTTATATTTGGCAAGAACTGTATTCTGCTGATAAAGAATTG
GAAGTTGCTATACGCAATAGAGAACGTTTTGTGTCTGGTCTGGAACCAGTAGATATGACTGCTAAGGAAAA
ACAAAAAATTCCGATTCTACCAGGAGGAACGTATCTACTTACAGGAGGGCTTGGAGGAATTGGGACTGTTA
TTGCAAAGTACTTATTAGAACATTATCAAGCAAATTTAATATTAGTTGGTAGAACTCAAATTGAAGATAAT
AATGAGGAAGCTAGCACAAAATTGCAGAGGTATCAAGAATTAGAAAAACTACCAGGTTCAATAATTTATCA
AACTGTAGATATTTGTGATTTAGTAGGTTTACAACAGGTAGTAGAAAAAGCAACACAAGAATGGAGGACTC
AACTTGATGGGGTATTTCATATGGCTGGGATTATTCAGGAAACGCCAATCGAGAAAGAACCCCAGGAAAT
ATCGCTGCTGTTTTACGTCCTAAAGTTAGCGGTACTTGGGTATTGCATCAATTGCTCAAGGATAAAGAAAA
TGCTTTATTTGTCCACTTTTGTTCTGTAAATGGTTTCTTTGGAGGAACCAATGTTGCAGCTTATAGTGCAG
CAAATAGTTTTCAGTCAGCATGGAGCGATTATCAACAACAAAACGGTTTCCAAAGCTATTGCTGCTCTTGG
AGTATGTGGAATGAAACCGGAATAAGTCATGGCTATCAATTCCAAGAACTCAGTCGTGCTAAGGGCTATTT
TATTATTACTCCTCAACAAGGATTTTACTCATTTTTAGCAGCTTTATCTGGTTCGGAACATAATCTATTAA
TCGGATTGGATGGAACTAAAACAAATGTTGAACATTTGATTCGTGATTGTCAGCCCAAGCAGAAATTAACT
GCTTACTTCACCTCTCCCACACCAGAACTTGCTGCACTCTCCTTACAAGAGTTACAACTACACGATCGCTT
TGGGATACCCAATCAAATTAACTTTGTCCAACTTGAACAAATACCCCTTACTCAAAGAGGAGAAATTAATC
GGGAACAAATTGCTGCTATATATGGAGGTTTGAATACTTCTGAGCAGACAAAACCACGGAATCAAACAGAA
CGTCAGTTAGTTGAGATTTTCCAAGAAGTTCTCAATCTACCCTCTATTGGTATTCATGACAACTTCTTTAG
CTTAGGAGGACATTCCCTTCTAGCTGTCCGTCTAATGTCCGAGATTCAACAACAATTCCAGAAAATTTAC
CTTTAGCCACTCTTTTTCAAAATCCCACCATTGAACGACTAGCACTTCTTGTTGGTTCCGATTCCGGAGCC
GAACTTTGGTCTCCATTAGTACCAATTCAACAAAACGGTTCATTACCACCTTTGTTCTGTACCAGGAGC
AGGTGGAAATGTTCTCTACTTCCACCACTTAGCACAATATCTTGGAAATAATCAACCGTTATACGGTTTAC
AAGCACAAGGTCTTGATGGTGAAACCGAACCTCATAAAAGTGTTGAAGAAATAGCCTCCCAACACATTAAA
GCAATTCAAACAGTTCAACCAGTTGGTCCTTACTTCTTGGCTGGTCATTCCTTTGGCAGTCATGTAGTATT
TGAAATGGCGAATCAACTACAACTTATTGGAAAGTCTGTTGCTTATGTTGGAATTTTAGATACTCCTGCAC
```

FIG. 6-7

```
CAACTTCTCAAGCTAATCATCAGAATGATTTTTCTAACTGGGATAATGCAAAGTGGATATGTCGAATGGCT
GAGGTTATTGAAGATATTGTTGGAGAAAATCTATTTTTATCTTATGAAACTCTAACTTCTCTAACTTGGGA
GCAACAATTAAATTATTTCAAGCAAAAGTTAGAAATAGTTGGTTTTTTGCCTGCTCAAACAGATATCAAAA
TTGTTCGTGGTTTATTACAAGTTTTCCAAACTCAATGTCAAATTAAGTATGAACCGGAAAAGACTTATAAA
ACTCCAATCACTTTGTTTTGTGCGAGGGAGATAAATCCAGAGCAAGAAAGTTATTCTCACATTTTCCAAGA
GCCAACATGGGGTTGGAATCAGTTTTCTGATGGAGAAGTGGAAATCCATATAGTTCCGGGTAATCATGTTT
CAATGCTGAGTGAGCCTCATGTCAAGGTATTGGCTCAACAAATGCAAATATCTCTTGAACAAGCACAGAAA
ACCCATCAATTGGAAAAATGA (SEQ ID NO:6)
```

CrpC

```
MSNEEIRRNISSIYPLSPMQQGMLFHSLYAPYSGVYLEQMTWGLKGNINVAAFERAWQKVLDRHSILRTFF
VWENRQTPLQVVLKQVNVPWNTLDWRELSSNDQQQQLKQLLQTQREQGFNLSQAPLMRCTLVRLGEDNYKF
IWSHHHILMDGWCLSIIFKEILIFYKAHLLGENCQLPKPRPYQDYIAWLNSQDKSAAIEFWQQTLQGFSAP
TPLVMDKTQFLKEQQYKTADYQERTSSLSPECTQKLLHIAQQHHVTLSTVVQAAWALLLSRYSGEKDVVFG
VTVSGRPPSLSEIENMVGLFINTLPLRVQVSTQEQLIPWLQKIQQSMVELQEYFYTPLVDIQATSEIPGGI
PLFESIVVFENYPIDNSLLNEEGSLHLGDIEVFEQTNYPLTLVAVPGDKLSVRISYDTARFSSNTIEWILG
YLQTVLSAIAIVENPSHKVAQLPLLSEVERHQLLVEWNNTATDYPSDKCIHQLFEQQVEKNPNSIAVVFEE
EQSTYQQLNQKANQLAHYLQTLGVKPEVLVGICIEYSIDMIVGLLGILKAGGVYVPLDPNYPQERLAFMQE
DSNVHIILTQQPLLEKISPQNAHIVCLDRDRDVIAREGVENLDRQTTLDDLAYAIYTSGSTGKPKAVLGTL
RGIVNRLHWIWEMLPFGADEICSQKTSINFGDHVAEIFSPLLKGIPLVIVPDDIRGNIPRLMSLLSDRKVT
RIVLVPSLLKAILENAPQQLTKLRYLKYVFCSGEVLPLTLAKEFHQKISSARLFNLYGSSEVAADVTCFEV
KLRIANQIEAKSKEKLDALKNLPSGSGDRETAVLHKEIIHLQLADERRADLGEALEEYLKRNTIPIGKPIS
NTQIYILDKYGDLLPPGVTGELYVGGDGLAKGYLNLPELTREKFIPNPFVKDRGKSKKAQAERLFRTGDLA
RWLPDGNIEFVGRIDHQVKVRGFRIELGEIEAVLSTHPQIQQVVVIAIEDIPGSKRLVAYIVCEDESLSTY
HLREFLKQKLPEYMMPSAFVILDTLPLTPSGKIDRKALPAPDGEISREHEYVPPRTSGEEIIANIFASILG
VQNVGIHDNFFELGGHSLLATRLISRLRVAFEVEIELSAVFSSPTVAQLEQTLTQLRTTNSALSLPPIQPR
TQNQQLPLSFAQDRLWFLNQLEGSSATYNMPGAIRVTGKLDINALQQALSEIVRRHEVLRTSFRTVNGTPI
QVIHPEATMNISVADLQQLEATERESVLHQQAQLAAITPFDLETAPLIRCSLLQLDAREYVLLLTMHHIVS
DGWSMGIFSQELSTLYQAFSAGKPSPLAELPIQYADFAVWQRQWLSGKVLETQLNYWLSQLEGAPELLQLP
TDRPRPTVQTFRGTTQSFSLNTDLKEKLQTLSRNSGTTLFMTLHAAFATLLYRYSGQLDILIGSPIANRNC
SEIESLIGFFANTLVLKTRFEDNPSFENLLAQVRETTLEAYEHQDVPFEQVVEVLQPQRSLSYAPLFQVMF
VLQNAPMGELELPGVTLNLLSSQTETARFDLTVSMQQTSEALVGSWEYNTDLFDGSTIERMTAHFQNLCSA
IVENPQQKISELPLFTDSEQEQVLHSYNNIATTYLLDKYVHFLSSNNLQIYILDNHQQLVPLSVEGEIYLG
NCDLLPDKLHPEPEKFISFIEHTQLGKLLKTGEWGCRRVDGSLELLGKEHRIVTVNGQRINLQRIEQALQT
AKGVEDCYVMVRNQKLVAYVVKDGSWAREFLHHYLKSQLPGYPLPCIYVPVSALPLTSFGEVDEVGLASIS
IIDSELINTWEEQIGSQAEIDKVAVFIEPNVKTISPIHLEELLPSIQAIFNQGSTPVETPRTARGKESSSL
LEIKSPAISHEEVLIFPESSPETLGEMLQKTAGKFPHKGITYINSDGSEQVQSYAQLLEDAQRILGGFRKL
GIKPQDKVILQLKENKDFISAFWGCVLGGFIPVPVVIPVSYDQPNVNLNKLQNSWQMLERPLILTDKKSLS
ELKKWSQNLNDDNFKLETIESLQKFSTDKDYYNAQPEDLALFMLTSGSTGMSKVVQLSHLNLLSRTIGSIQ
MNNFTPEDITLNWMPLDHVAGLIYFHIRDIYLGCKQIHATSQLVIEKPLRWLDWIDTFGVTVTFAPNFAYS
LINDFVQEIEKQNWNLSSIRLMLNGAEQIVAATARRFLKLLAPFGLPGDAMTPSWGMAEVSSGITYSDNFS
LLSSSDDNSFVNLGKPIRGTCLRIVNQDMEVLSEGEIGLLQVKGLTVTSGYYQNPKANKEAFTEDGWFNTG
DLGFIKDGCLTITGRQKDIIIINGVNYYSHEIEAVVEELGEVEVSYTAACGVCVASNNTEELVIFFTPYVS
EKNQLLELLKKVREQVIKYCGINPSYLIPIDKELIPKTSIGKIQRSLLKQRFECGEFKSLRQRVDLLLDNT
NTIPNWFYRKVWQIKESKNTLLNYSSQKTLTLIFTDNLGWQQDNRGMSQTVQPYAQVTIGSNFAQISPNHY
SVVPGNPQHYRLLIDSLRQNSQVISQILHLWNYNEQTEKISSLENLESTQQQGIYSLLFLVQALEEIQGKQ
QAVKLLWIANQSQLVHPTDKIQPEKSTVLGLLKTVSQEMPWLTTRHLDLPLAPELNNSYIWQELYSADKEL
EVAIRNRERFVSGLEPVDMTAKEKQKIPILPGGTYLLTGGLGGIGTVIAKYLLEHYQANLILVGRTQIEDN
NEEASTKLQRYQELEKLPGSIIYQTVDICDLVGLQQVVEKATQEWRTQLDGVFHMAGIIQETPIEKETPGN
IAAVLRPKVSGTWVLHQLLKDKENALFVHFCSVNGFFGGTNVAAYSAANSFQSAWSDYQQQNGFQSYCCSW
SMWNETGISHGYQFQELSRAKGYFIITPQQGFYSFLAALSGSEHNLLIGLDGTKTNVEHLIRDCQPKQKLT
AYFTSPTPELAALSLQELQLHDRFGIPNQINFVQLEQIPLTQRGEINREQIAAIYGGLNTSEQTKPRNQTE
RQLVEIFQEVLNLPSIGIHDNFFSLGGHSLLAVRLMSEIQQQFQKNLPLATLFQNPTIERLALLVGSDSGA
ELWSPLVPIQQNGSLPPLFCVPGAGGNVLYFHHLAQYLGNNQPLYGLQAQGLDGETEPHKSVEEIASQHIK
```

FIG. 6-8

AIQTVQPVGPYFLAGHSFGSHVVFEMANQLQLIGKSVAYVGILDTPAPTSQANHQNDFSNWDNAKWICRMA
EVIEDIVGENLFLSYETLTSLTWEQQLNYFKQKLEIVGFLPAQTDIKIVRGLLQVFQTQCQIKYEPEKTYK
TPITLFCAREINPEQESYSHIFQEPTWGWNQFSDGEVEIHIVPGNHVSMLSEPHVKVLAQQMQISLEQAQK
THQLEK (SEQ ID NO:7)

crpF
ATGATTAATACTGCTAAATCCTCATTACTTCCTGGTCCCACTACACCATCTTGGTGGAACTTATTGCAATG
GCTTAATAATCCTTGTGAATTTTTGGAAGAGTGTCGAGCACGCTATGGAGACACTTTTACCTTCAAAGCTA
TTGGTTTTGAACCTTTAGTACTTATTAGTAATCCTAAGGATATAAAAGAAATTTTTGATAAACACAAGTAT
TTTGACAGTGGAAAAGCTAAAGCTAACGATTTAGCAGGATTTTTTTAGGCAACAATTCCGTCACCTTGCT
TGATGGAAGTAGTCATAAACGACAGCGTAAACTACTGATGCCTGCTTTTCATGGTCAAATATATCTAACT
ATGGAGAACTAATATGCCATGCAACGAAGCAGGTTACTTCTAATTGGCAACCTGGTCAAGATTGATTATT
TACAAGGAAGTCAAAGAAATTACGCTGCGAGCGATGTTAACGGTTTTACTGGGTTCAGATAAAACGGAACG
TTATCAACAACTCAAATTGATAGTTAATCAAATAGTATCCACTATAACTAATCCCTTTGCTTCAGCTCTC
TTTTCTTCAATGTGTTTAGAAGAGACTGGGGTTCTTGGAGTGCCTGGGGTAATCTTTTACGTTGCCAACGT
CAGATTGCAAATATCATTTCTGCAGAAATCAAAGAACGTAGAGAAAATTGTAACAATTACAACAATGATAT
CCTCAGTATGCTGATGGCAGCACGAGATGAAAATGGAGGAAAAATGACAGATGAGGAGTTGCAAGATGAGT
TAATGACACTTATCTTTTCTGGATATGAAACTACATCTGCAGCAATAACATGGGCATATTATTGGATTCAT
TACTTACCAGAGATAAGAGCCAAGTTATTGCAAGAATTAGATGAGTTAGGAGATAATCCAGACCCAACGGA
AATAAGCAAATTACCTTATCTCAATGCAGTTTGTGCTGAAACCTTGAGAATATATCCAGTTGGTCTAACTA
CTTTTCCTCGAATTGTAAAATCGCCAATAGAAATTGGAGGTCATCAATTTGAGGTAGGAACTTGTCTTTAT
CCATGTATTTATCTAATTCACCACCGGGAAGAACTATATCCTAACTCTAAACAGTTTAAGCCAGAACGTTT
TCTAGATAATAAATTTTTAAATTATGAGTATTTCCCTTTCGGTGGCGGTAACCGAACTTGCATTGGTATGG
CATTTGCTCAGTTTAAAATGAAGTTAGTATTGGCTAATATTTTGCGGAATTGGCAATTGGAATTGGTAGGC
AAACCTCCTTTAAAACCAGTACGAGATATTTTCTCAATTTATCCTCAAGGTGGATTAAAAATGGTTGTATT
GTAA (SEQ ID NO:8)

CrpF
MINTAKSSLLPGPTTPSWWNLLQWLNNPCEFLEECRARYGDTFTFKAIGFEPLVLISNPKDIKEIFDKHKY
FDSGKAKANDLAGFFLGNNSVTLLDGSSHKRQRKLLMPAFHGQNISNYGELICHATKQVTSNWQPGQRLII
YKEVKEITLRAMLTVLLGSDKTERYQQLKLIVNQIVSTITNPFASSSLFFNVFRRDWGSWSAWGNLLRCQR
QIANIISAEIKERRENCNNYNNDILSMLMAARDENGGKMTDEELQDELMTLIFSGYETTSAAITWAYYWIH
YLPEIRAKLLQELDELGDNPDPTEISKLPYLNAVCAETLRIYPVGLTTFPRIVKSPIEIGGHQFEVGTCLY
PCIYLIHHREELYPNSKQFKPERFLDNKFLNYEYFPFGGGNRTCIGMAFAQFKMKLVLANILRNWQLELVG
KPPLKPVRDIFSIYPQGGLKMVVL (SEQ ID NO:9)

crpG
ATGTATTCAATAAAAATTGAAAATCTAATAATTAGAGTGAAAAGTGTATTAGAAATGCCAGTTTCTAAAGA
AGCTGAGATGGCAAATAAATTTAATGAGTTTGGATTCGTAATACTAGAACACGAACCTTCAGCAACACCTA
AGAATAACTTATTAAAATTGTCTGATTATTTTGGAACAATTATTCAGCACGAACATTCTGATTCACAGGGA
ATTGTTCCCATCAGTCCTGTTGATAGTTATCCAGAATATGTAAATACTACAACTACAGATTTATCGTTACA
TACGGATGGAGCGTTCACAATTACTCCACCAAAAGTAATGGCAATGCAGTGCCAGATTGCTGCTGCAAATG
GCGGGTTCACCAAGCTTATTGATGGCAAGCTGGTATATGAACATCTAAAGCGGACAAACCCAGTTGGATTG
TTAACTTTGTTTAATCCTGATGCGATTACAGTCAAAAGAGATAATAAAAAAGCAACTAAACCTATTTTTGA
AGAACATCATGCTGGGCTTATTGTAAGGTTTAGAGCAGATAATGCAGCTCATGTTTCGGTTGAATCGAAAA
GTTTTGCGGCATTTAAATCATTTGAAAACTTTGTAAATAATCCTGACAATCAAGTAATTTTTAAACTTGCA
CAAAACCAAATAATTATTGTAGATAATACTAGAGTTTTGCATGGAAGAACTGCATTTTCCAAACAAGAGTA
TAGGCTACTAAATCGACTTTGGTTTGATGGACAATCTGATATTATAAATTTAAAGTTTGGTATTTCTATAG
CCCCAAAAAACTTGAGTTTATTTGCTAAAAAGTATCAGCCATCTCAAATAGATATAGGCTCAGATATTTCT
CAGTCAACTCAATTGAAATTTAAAGCCACATGA (SEQ ID NO:10)

CrpG
MYSIKIENLIIRVKSVLEMPVSKEAEMANKFNEFGFVILEHEPSATPKNNLLKLSDYFGTIIQHEHSDSQG
IVPISPVDSYPEYVNTTTTDLSLHTDGAFTITPPKVMAMQCQIAAANGGFTKLIDGKLVYEHLKRTNPVGL

FIG. 6-9

LTLFNPDAITVKRDNKKATKPIFEEHHAGLIVRFRADNAAHVSVESKSFAAFKSFENFVNNPDNQVIFKLA
QNQIIIVDNTRVLHGRTAFSKQEYRLLNRLWFDGQSDIINLKFGISIAPKNLSLFAKKYQPSQIDIGSDIS
QSTQLKFKAT (SEQ ID NO:11)

crpH
ATGTTGAAGTCGAAAATTCACAGAGCGACGGTGACGGAAGCCAACGTTAACTACATCGGAAGTATTACAGT
AGACAAAGTTCTGATGGAAAAGGCAGACATACTACCGGGTGAAAAGGTTATGGTGGTGGACAACACTAATG
GTAATCGTCTAGAAACCTATGTCCTAGAAGGTGAGGAAAATTCCGGGGTAATCTGTATGAACGGTGGCTCC
GCCCACCTAGTCAATTCAGGAGACCTTATCACATTGCTAGCATTCGAGGTAACTGACGAAATCAAGGAACC
GAAAAAAATTATCGTGGATGAAAACAACAAGTTTCTCAAGTACCTGTAA (SEQ ID NO:12)

CrpH
MLKSKIHRATVTEANVNYIGSITVDKVLMEKADILPGEKVMVVDNTNGNRLETYVLEGEENSGVICMNGGS
AHLVNSGDLITLLAFEVTDEIKEPKKIIVDENNKFLKYL (SEQ ID NO:13)

crpJ
ATGTCTACACTGCCTAATTCCACACAGATTCTAATTATCGGAGGGGGACCTTCTGGATCTACTGCTGCTAC
CCTATTGGCTCGTGAGGGCTTTGATGTAACGCTGTTAGAACGAGAGGTATTCCCGCGTTACCACGTTGGGG
AATCTCTTTTGCCCTCTGCTTTAGAAATTTTTGACCTGCTTGGCGTACGCGAGAAAATTGAAGCTTATGGC
TTTCAGCGTAAACCTGGAGCGTACATAGAATGGGGAACGGAAAAGTGGAGCCTCAATTTTGGGGAACTTAC
GGGGGACAACACCTACAGCTTCCAAGTTCGCCGTGACGAATTCGACCACTTGCTTTTAGAGCATTCAAAGA
GCCAGGGTGTGAAGGTTTTTGAAGGGACTAAAATTCGCCAGTTGTCTTTTGATGGCGATCGCCCGCGCAGC
GCTACTTGGTCACAATCAAATGATACTACCGGGGAGATTTCTTTTGACTTTATGATTGACGCTTCAGGTCG
TGCTGGGATCATGGCGACGAGTATCTGAAAAACCGCCGTCTACACGACGTATTCCAGAATGTTGGCATCT
GGGGGTACTGGAAAAACGCCTTGAGACTACCTAAAGGTCAGTCGGGTGCGATTGCCTTGGGCTCCATTCCA
GATGGTTGGGTGTGGGGAATTCCTTTGGATGAGGAAATTATGAGCGTTGGTGTAGTGATGCATAAGTCAAC
CTACAAGGAGAGACTGACTAAGAACTTGAAGGATATCTACGTGGAGGCGATTGCAGAGTGTCCCTTGATAG
CGGATCTGGTTGCACTAGGGGAGCTAGTCTCAGACGTGAAAGTTGAGCAAGATTACTCTTACACTTCCGAC
TCCTTTTCAGGACCAGCCTACTTCATATCGGGAGACGCTGCTTGCTTCCTAGACCCCCTACTATCGAGTGG
GGTGCATCTTGCTACTTATAGCGCTTTGTTAGCCGCAGCCAGTATCACAAGTGTTATACGTGGCGAGGTGA
CTGAGTCACAAGCTGCTTCTTTCTACGATCAGAGCTATCGGCAGGCTTATTTGCGTTTCTTAGTGTTCGTA
TCAGCCTTCTACGATCAAAACCGTGGCAAGGATTCCTATTTCTGGGAGGCACAACGGCTTAGTCGCCGTGA
CTTCGGCAGTTCTAACCTAAAGCTAGCATTCTTGAATCTGGTGTCCGGCGTCGAGGACTTGGAGGACGCTA
AGGAGGGGATTGCCGATTTTGTTATGGCAGAGATGTCTCAGCGGATTCAGTCAAGCCACAGCATTAGGCAA
GACAAGCAGGCGTTGGCAATCGAAAGGGAAAAAGGTAACGAGGTAATGAAGACAAATGCCCAGTTTTTCAA
TGCAGTCGAGGGATTTTCCATACTATCGGCAGTTGGGGCAGTTGATGGTCTATATGTTACAACTCAGCCAA
AATTAGGATTGGTACAGGTAATCCCTCTCCAAAGAAACTCTTTGCTCCACACTTAG (SEQ ID NO:14)

CrpJ
MSTLPNSTQILIIGGGPSGSTAATLLAREGFDVTLLEREVFPRYHVGESLLPSALEIFDLLGVREKIEAYG
FQRKPGAYIEWGTEKWSLNFGELTGDNTYSFQVRRDEFDHLLLEHSKSQGVKVFEGTKIRQLSFDGDRPRS
ATWSQSNDTTGEISFDFMIDASGRAGIMATEYLKNRRLHDVFQNVGIWGYWKNALRLPKGQSGAIALGSIP
DGWVWGIPLDEEIMSVGVVMHKSTYKERLTKNLKDIYVEAIAECPLIADLVALGELVSDVKVEQDYSYTSD
SFSGPAYFISGDAACFLDPLLSSGVHLATYSALLAAASITSVIRGEVTESQAASFYDQSYRQAYLRFLVFV
SAFYDQNRGKDSYFWEAQRLSRRDFGSSNLKLAFLNLVSGVEDLEDAKEGIADFVMAEMSQRIQSSHSIRQ
DKQALAIEREKGNEVMKTNAQFFNAVEGFSILSAVGAVDGLYVTTQPKLGLVQVIPLQRNSLLHT (SEQ
ID NO:15)

crpM
ATGTTATCTCCCCTATTTGATGCTTTTGTAGAGGCAAGCCCCGTCAGTGTAATGATGCGAGTCCTAATGGA
AAACATTTTTAATTCCTCGCGAATGAATCAAATATTTGATACATCAAGCGTTCGCCAATACTCTCAAGAGC
TACTGTTTTCGACTCAGGTGGATTTGATGAGTCTAGTAGTGTGTGGGATGTATCCCTCGGTTCATGCAGCC
TATCAGAAGAAGGCAGTGGAGGTAAGTGTCAGCGCCACAGCGTTATACAACAAACTGCAACGGATTGAACT

FIG. 6-10

```
GCCTGTAAGTCGGGCATTAGTGCATGAGACAGCATCTGACCTCCAGCAGTTGCTGTTGATGTTGAATGTGG
AACGCCCCAGTCCTCTAGGAAAACAATATCGGTTGCGGATTGTAGATGGCAGTTGTTTAGCCGGAACCGAA
CGCAGACTAGCAGCGCTGCGCCCCATGCAGCCAAACCATTACCCGGAAAAACAATCGCCATTCTCGACCC
AGGGACAAAACTGGTGGTTGATGTGATTCCTTGTGAAGACGGTCATTCCCAAGAACGCTCCAAGTTTCATC
AGGTTTTGGCACAAGTGCAACCCCAACAGGTATGGATTGCAGACCGTAACTTTTGTACCGCAGGATTTCTC
CATACTATTGCCAAACTTGGAGCGTTTTTTGTGATTCGTCAACACGGGGGTTTAGGATACGAGCCTTTTGG
TGAGTTACAAGCTGTTGGGTTGTGCCAAACAGGAACTGTGTTTGAACAACAGGTGGAAATTGTCCATGAGG
GAGGGACTTTTCGGTGTCGCCGTATCGTAGTTAAGTTGACTCGTCCCACCCGTGACCAAGAGTGGGAAATT
GCCATTTTTACCAACTTACCACCCACTGACGCAGACGGCATTCTGGTGGCACAACTCTATCAAGGGCGGTG
GAGTGTGGAAACTTTATTCCAAACTGTGACCCAAAACTTTCATGGAGAAATTGAAACCCTAGCTTATCCTA
AAGCTGCCTTATTCTCCTACTGCATGGCACTGTCAGCCACAACCTTTTAGCGACACTTAAAGCAGTTCTT
GGCAGTGTACATGGGGTAGACAAAATCGATATTGGGCTATCCGATTTTTACCTAGTAGATGATATCCATTC
CATCTATCGGGGCATGATGATTGCTATTCCTCCGGTTCATTGGCAATTCTTTGAGGAGTTTACCAACATTC
AGATGGTAGACGTTCTCCAGCATCTAGCAACCAAAGTACATCTCAAATCTTTTCGCAAACACCCCAGAAGT
CCCAAAAAGAAACGACCACCACTCTCTGTTGATGGCAAACATTCCCACTGTTCCACTACTCGAAAGCTCAA
GCAATACAAAGCAGCTCTTGATGCTATCCCGTGA (SEQ ID NO:16)
```

CrpM
```
MLSPLFDAFVEASPVSVMMRVLMENIFNSSRMNQIFDTSSVRQYSQELLFSTQVDLMSLVVCGMYPSVHAA
YQKKAVEVSVSATALYNKLQRIELPVSRALVHETASDLQQLLLMLNVERPSPLGKQYRLRIVDGSCLAGTE
RRLAALRPHAAKPLPGKTIAILDPGTKLVVDVIPCEDGHSQERSKFHQVLAQVQPQQVWIADRNFCTAGFL
HTIAKLGAFFVIRQHGGLGYEPFGELQAVGLCQTGTVFEQQVEIVHEGGTFRCRRIVVKLTRPTRDQEWEI
AIFTNLPPTDADGILVAQLYQGRWSVETLFQTVTQNFHGEIETLAYPKAALFSYCMALSAYNLLATLKAVL
GSVHGVDKIDIGLSDFYLVDDIHSIYRGMMIAIPPVHWQFFEEFTNIQMVDVLQHLATKVHLKSFRKHPRS
PKKKRPPLSVDGKHSHCSTTRKLKQYKAALDAIP (SEQ ID NO:17)
``` crpN
```
ATGAACAAACCACCATCCAGACGCAAGAAAATTACCCCTGCGACATCTGAGGAACCAAAGCTAGCAACTGA
CCCTGCTCAGGAAAATACTTCTTTGCACGAAAATCCAGGGGAGCAACTATCACGGTGACGGCTGTTGAAG
TAACAGATTTGACCCAGGAAGAACAAAGCTTACGCCTGCATTTAGAACACCGTGTGGAGAGCATTTTTG
GAGGCGGGTCAAGCGTTGATGGAGTTGCGGGACAGACGGCTGTACCGTTCCACGCACCGGACTTTTGAAGA
ATACTGCCGCGAACGCTTCAATTATAGTCGTGACGCGGCTTACTTGAAGATTTCGGCTACTGTGGTTTATG
AGAATCTTCAAAAGTTTTTGCCGACCATTGGTCGGCAAATTCCAATGCCGACCAACGAACGACAATTGCGT
TTTTTGGCGAAAGCCGAGTTGGAACCGGCTGTGCAAGCGGATGTATGGCGGCAGGCAGTGGAGCAAGCTGG
CAATAAGATTCCATCCGGTCGCATAGTGAAAGATGTTGTAGATAGGATACGCGAAAGGACGAAAGTACCCA
ATCCTTACCACGTTGGGGAGATATGCGTTCTTCTACCCAAAGATAATGCAGACTTGAGAGGTAAAGCGGGT
TATTGGGGCGTGGTCAGCCATGTTGGAGAATACAGTTGTACACTCCAGATATGGGACGGTGACTATACCGT
AAAAATCGAACACCTGAAATCACTGGAATTACTTGATGAAGATTGCCAATTCATGCAGCAGTTATGTGTGA
GGTTACGGCAGTTGCATCAAGTGGACAGGCGTGACGAGGCTGTGGATTGGCTGTTGCAGTGGTTGGGGAAA
CAGGCCAAACCTTATCTGTCATCCTTGCAGTCAAAGCTGCTGGCGTTTGTTGAGAGAGAGTACAACCTGGT
TTGGAAGCAGCAGAAGTGA (SEQ ID NO:18)
```

CrpN
```
MNKPPSRRKKITPATSEEPKLATDPAQENTSLHENPGGATITVTAVEVTDLTQEEQSLRLHLEHRVERAFL
EAGQALMELRDRRLYRSTHRTFEEYCRERFNYSRDAAYLKISATVVYENLQKFLPTIGRQIPMPTNERQLR
FLAKAELEPAVQADVWRQAVEQAGNKIPSGRIVKDVVDRIRERTKVPNPYHVGEICVLLPKDNADLRGKAG
YWGVVSHVGEYSCTLQIWDGDYTVKIEHLKSLELLDEDCQFMQQLCVRLRQLHQVDRRDEAVDWLLQWLGK
QAKPYLSSLQSKLLAFVEREYNLVWKQQK (SEQ ID NO:19)
``` crpP
```
ATGACGAAGWTAAGATGGGGATRKTCTYGKMTCGWARTATCAGTTATACAAAATACTACAATCTTAAACAT
ACAATTGTTAGCTTCGACAACTATTCAATCAAAGTATATATTTAATATGGCTATCAAACACCCTTTTTTAT
TTGCACTGTTAACGCTCTCCATTATTTGTGTTGGTACGAGTTCTGGCTCTGCACTACTGACAGATATTGCT
CAACAAACAGACAACCAAAAGTCCCCATCGATTATTTTCTTCCTGCCCAAAGAACGACCTCAGACCGGAGT
```

FIG. 6-11

CGGTTGGGAAATCACTACCACTTCAGGGAAGGCAGAACTAGCCTTGGCGAAGCATTTGGTGTATATCGGGG
CAAAAGAATATGTTTCTTGGTGGTGTCCTCACTGTCACGAACAAAAGTTAATCTTTGGGAAGCAAGCCTAC
CAAATAATCAACGACAGTATTAAAGTTGAGTGCGATAAGAGAGGTATCAATCCCCACCCAGACTTGTGCAA
TGCGGCGAAAGTCCCAGGTGTACCAACTTGGGTTATCAATGGACATCAGTATACCGGCGTGCAAAACTTTA
AGGATCTTGCGAAAGCTTCTGGCTACAAGGGGGATATGAACTTTCGTTATATCCAAAGCGAATAA (SEQ
ID NO:20)

CrpP

MTKXRWGXSXXXXSVIQNTTILNIQLLASTTIQSKYIFNMAIKHPFLFALLTLSIICVGTSSGSALLTDIA
QQTDNQKSPSIIFFLPKERPQTGVGWEITTTSGKAELALAKHLVYIGAKEYVSWWCPHCHEQKLIFGKQAY
QIINDSIKVECDKRGINPHPDLCNAAKVPGVPTWVINGHQYTGVQNFKDLAKASGYKGDMNFRYIQSE
(SEQ ID NO:21)*** crpU

ATGATACAGTGTAATTTTTCGTTGCCACCTGAGTATGTTCTTCGTAAGGCCAAGCCTTTTGATATGTGGTT
AATAGTATTTTTTGTGTTTAGAGCAAGGCTAGACCCCAGTCAATTAAGATGGCAGCAATTTTGGGTCATTG
AATGTGATGGACATTTAGTAGCCTTCGGGCAGATCCGAAACTTTCACTTAGCACAAGAGCTAGGCAGTTTA
TTTGTTGCACCGACTTGGCGAAACCGTGGTTTAGGGACTGTTTTGATACAGCATTTAATTACTCAAGCTAG
TCAACCGCTTTATTTAAAATGCTTAAAATATCAATTGGTGAATTTTTACATTAAAAGAGGCTTTGTATCCG
TTAATTTTAAAGATTTACCACCATCCCTCAAGCCAAAGTTTGGACTATCCCAATTACGAAAGAGGTTAACG
AAAGCTTTTGTGCTGTTTATGAAGTATGAATATCCCAACTGA (SEQ ID NO:22)

CrpU

MIQCNFSLPPEYVLRKAKPFDMWLIVFFVFRARLDPSQLRWQQFWVIECDGHLVAFGQIRNFHLAQELGSL
FVAPTWRNRGLGTVLIQHLITQASQPLYLKCLKYQLVNFYIKRGFVSVNFKDLPPSLKPKFGLSQLRKRLT
KAFVLFMKYEYPN (SEQ ID NO:23)

crpV

ATGTCAGTGCCAGTTAGCGCACAGATTATACCAGATAAAACACTACCTATTAATTCCAATGTTGAACATGA
AGGTAATACTAACCGCATAGAAGGTGGCACTATAAAAGGGAGCAACTTGTTCCACAGTTTTGAACAATTYT
CCGTGCTTACTGGAAATGAAGCTTACTTTAACAACGATATAAATATCCAAAACATTATTACTCGTATTACT
GGGAAGTCTATTTCTAATATCGATGGCATTCTCAAAGCCAATGGCACGGCTAATTTGTTTCTGCTCAATCC
CAATGGCATTATTTTTGGTAATAATGCCAAACTAAATATTGGTGGTTCATTTCTAGCTACTACTGCAAATC
AAATTAATTTTGCTGATGATACTAAATTTAGTACAAACAATCCCCAACCTAATCCTTTACTGACAGTAAGT
GTGCCTATAGGACTGCAAATTGATAGCAACCCCGGTACAATTCGCATCCAAGGTACAGGTCACAATCTAAT
TGGCCCTCCTTTTTCTCCTCTAATCACAAGTAGTAGCGCCGCAAATTTACAAGTGCAACCAGAAAGAACTG
TAGCAATTGTTGGTGGTGATGTAATTTTAGAGGGAGGTGTGATAACGGCTAGGGAGGGCGAATTGAATTG
GGTAGCCTCAGCAATGGTTCAGTCAGTATTAATCCTACGACCTCTGGTTGGAAACTGGGCTATGAAAATGT
ACCTTATTTCCAAGATATTAACCTCTCAAAACGCGCTKTAGTTAATACTAGTGGCATTGGCAGTGGATCTA
TACAGATAGAGGGACGCAKAGTTACGCTTACAGATGGCTCAGTAATCTTAAATCAAAATCAAGGAACACTA
CCAGGAGGCACACTAAACGTGAATGCTTCGGAGTCTTTGTCAGTGAGTGGTAGCGATCCAATTGCTAGGAC
AGCTGGTGGTTTGCGGAGCGAAACTTTGGGATTYGGCAAAGCTGGAGACATTGCAATTTCAACCAAACAGG
TAATTATTAAAAATGGAGGACAAATAAATAATTTAACCTTTGGTGCTGCAACAAGTGGCAATATAAATGTG
AATGCCTCTGATTCTATACAATTGCTTGGGGTTTCGCCTTTTGACCCTGCTGTTTTAGTACTATCAGCAC
TGCAACTTTCAATTCTGGAAACGCAAACAATATTACAGTGTCAACAGGACAATTCGTTGCCACGGATGGAG
GTAACTTGTCCTCTTCAACCTTTGGAACTGGTAGAGGAGGAGATGTCACTGTAAGTGCAACTGACTCTATA
GAAATAATAGGAGCTTCACCAATAACCTTTCAGCCAAGTATTTTATCTTCCATATCGCTCAATGCTGGCAA
AGCTGGCAGCCTAACAATCAGTACATCAAAGTTGATGGTTCAAGATGGCGGGAGGGTTGACGCTTCTACTT
TAGCAAGTGGGGAGGGCGGTAGTGTTACGATTAACGCCTTTAAATCTGTAGAGGTAAGTGGTAAGATACTT
GGTTTTGGAGAGCCTAGTTTGGTGATCTCCAGTGCTAATATCGTCTCTCCAATCTTGCAAAAGTTATACAG
ACTCCCTTCAGTGCCTTCTGGAAAATCTGGAAACGTGACGATTAATACTGGTCAGTTGAGTGTTACAGACG
GTGCTGAAGTTAACGTGAGAAATGACGGTTCTARCGATGCTGGAACACTCAGAATCAATGCTGTTTCTGTT
TCTTTAAACAAACAAAGTGCCATTACAGCAACTACTGCTAACGGCGAAGGCGGTAATATTTCGTGAATAC
ACGGTATTTGCAGCTAAGTAATTACAGTGTTGTAACGACGACCGCAGGTAGTAGAGGCAATGGCGGTAATA

FIG. 6-12

TAAACATCAATGCAGATATATTAAGTGCTTGGGGGAAGAGCAGTATTGCTGCCAATGCTTTCTATGGGTAT
GGAGGAAATGTACTAATTAATACTAGAGGACTTTTTATTGCTCGTGACAGTCAAATTTCTGCAAGTTCTAA
ATACGGAATTAACGGCACTGTTAGCATTAACAATACTGGTGGTGAAATTTATCCTACTAAACTCAAATCAG
AATCGATTCCAGTAGCTCCTCAAATAGCATCAGTTTGTCAAAAAAATTCAGATATACCAATCAGTAAATTT
GTGAATGTTGGCACCGGTGGACTGCCAGCTAATTCTGATGATATGCCATATATGAATTATGAACAGCAAAA
TAACTCTGTTTCAATCCACAATAATAATAACTTAGAGGCATCGAAGGCATCACAAACTGAAGAACCTATAC
AGATAATAGAAGCTCAGGGTTGGATAATAAATCTTGATGGGGAATGTCGTCTTAACTGCACAAAACAATAC
AGCAACCCCTAA (SEQ ID NO:24)

CrpV
MSVPVSAQIIPDKTLPINSNVEHEGNTNRIEGGTIKGSNLFHSFEQXSVLTGNEAYFNNDINIQNIITRIT
GKSISNIDGILKANGTANLFLLNPNGIIFGNNAKLNIGGSFLATTANQINFADDTKFSTNNPQPNPLLTVS
VPIGLQIDSNPGTIRIQGTGHNLIGPPFSPLITSSSAANLQVQPERTVAIVGGDVILEGGVITARGGRIEL
GSLSNGSVSINPTTSGWKLGYENVPYFQDINLSKRAXVNTSGIGSGSIQIEGRXVTLTDGSVILNQNQGTL
PGGTLNVNASESLSVSGSDPIARTAGGLRSETLGXGKAGDIAISTKQVIIKNGGQINNLTFGAATSGNINV
NASDSIQLLGVSPFDPAVFSTISTATFNSGNANNITVSTGQFVATDGGNLSSSTFGTGRGGDVTVSATDSI
EIIGASPITFQPSILSSISLNAGKAGSLTISTSKLMVQDGGRVDASTLASGEGGSVTINAFKSVEVSGKIL
GFGEPSLVISSANIVSPILQKLYRLPSVPSGKSGNVTINTGQLSVTDGAEVNVRNDGSXDAGTLRINAVSV
SLNKQSAITATTANGEGGNIFVNTRYLQLSNYSVVTTTAGSRGNGGNININADILSAWGKSSIAANAFYGY
GGNVLINTRGLFIARDSQISASSKYGINGTVSINNTGGEIYPTKLKSESIPVAPQIASVCQKNSDIPISKF
VNVGTGGLPANSDDMPYMNYEQQNNSVSIHNNNNLEASKASQTEEPIQIIEAQGWIINLDGECRLNCTKQY
SNP (SEQ ID NO:25)

crpX
ATGGTGATTATTCAAGCCACGCAGCATTTCTGTAGATTTAGTCTTGGTGTTTTCTTAGCACAATCAAGAGT
AGAGATAGAGCAGAGTTTAACAATGTCAACTCCTAACTATCGTCAAGAGATTGATATTGTAAAACGTTTAT
TTTCGCAAAATCCTAATTTATGCGTTGATATTATGCTAGCGACTGAAGAAAGGTGTAATGCTATTAGCTTT
TTAGCTAAAACTTACAGCCGATTGGCTAGACTGGTGGCTAGGAAGGATAGAGAGGCATTAATTAAAGAGTT
TGAAAATACTCAAAGTTTTTTTGAAGAGAAAATTAATAGTTTTCTCCAGCCTTTAAATACAACGGCTCTGC
AACGAGATTTTAAACCCCAGATGCACACAAATATTAGCATTTGA (SEQ ID NO:26)

CrpX
MVIIQATQHFCRFSLGVFLAQSRVEIEQSLTMSTPNYRQEIDIVKRLFSQNPNLCVDIMLATEERCNAISF
LAKTYSRLARLVARKDREALIKEFENTQSFFEEKINSFLQPLNTTALQRDFKPQMHTNISI (SEQ ID
NO:27)

crpY
ATGCTGATAGATATCTTTCATGATACCGTTTGCCCTTGGTGCAGAATTGGGAAAAAACATCTATTTGATGC
ACTGGCACAATGGCAAGAACAAGAAGTAAATATCCGATGGCATCCCTTTCTTCTGGATGATACTGTTCCTG
CTGAGGGGTACGAATTTAGTAGCTTTATGCAAAATAGAAAGGCATTAAAGCGCCAGAAATGCAACAGATG
TTTGATTATACGCAACGCGCAGGGGAGGCGGCTGGGGTTAAGCTAGATTTTGAAAAAATCCGTTTGGCTGT
CAATACTAAGCTTGCTCACCAACTGATTGCATTAGCACCGACAAACATAAAAAATGATGTCGTTGAAGCTA
TTTATAGAGCTTACTTTGAAGAGGGTTTGAATATTGGAGATATTAACGTTATTGTTGCCATCGGTACAGCA
TACCAGATGGATGCTACCGAATTAAAGTTGCAATTAAACGATCGCGATGTCGTTGATACAGTTGTTGCTGA
ATCGGCATTTGCTCGCTTAAATGGCATCAACAGCGTGCCGTTTTCATCATGAATAATCAAGTCAAGGTAA
ATGGTTCTCACTCGGTTGAGGTTTTCCTTGAAGCTTTGAATAGTACTGCACTTTTAGATATACCTGCAAAA
ATATGA (SEQ ID NO:28)

CrpY
MLIDIFHDTVCPWCRIGKKHLFDALAQWQEQEVNIRWHPFLLDDTVPAEGYEFSSFMQNRKGIKAPEMQQM
FDYTQRAGEAAGVKLDFEKIRLAVNTKLAHQLIALAPTNIKNDVVEAIYRAYFEEGLNIGDINVIVAIGTA
YQMDATELKLQLNDRDVVDTVVAESAFARLNGINSVPFFIMNNQVKVNGSHSVEVFLEALNSTALLDIPAK
I (SEQ ID NO:29)

FIG. 6-13 crpZ
ATGATAGTTGACATCAAGCAAAAAAATAGATTAATTCATCAACGTGTTTCGGTTACTTTTAACTATGAGAT
TTACTTCACCCAAAATTTATTTGAGTTGAAAAACCCGACGCTAGCGCAAGTAATTTCGGCAGATGAGGAGA
CAAAGCCGAAGAAAATAGTTGCGGTGGTAGACGCAGGAATATTAAAGTATCAACCGGAATTGGTGAAGCAA
TTAGTTGCGTATACCAAGTTTTATGGAGAGGTACTAGCGATCAATGTGCCCAAATATTAG (SEQ ID NO:30)

CrpZ
MIVDIKQKNRLIHQRVSVTFNYEIYFTQNLFELKNPTLAQVISADEETKPKKIVAVVDAGILKYQPELVKQ
LVAYTKFYGEVLAINVPKY (SEQ ID NO:31)

FIG. 7-1

```
ATGGGGCATAGAGCTTGGGGATATCTGGGAGGGACAGTCGCAGGTATGTTCACTTTGGAAGATTTTTTAAG
AGTGATTCGTCATAGTGGTAGACCAATGGCACAGGTACCCTGAGGAGGCGAAACGTTATCTATAAGGAGTT
CAATCGTAAAGATAAGTGAAGTAATCGCGCCATACGCTCCAAACGTCGCGATCTCATAAATTGACGGGCCC
CCAAGCACTGTCAATTCAGGTGGGCCAGTTGCAATTGGAACGCTTCGAAATCTCTTAGCCGCAGTAGAGAT
TTTGACACGACGACGGGAAGTATCCCGCGCGTTCAATGCATATCCGATGAAACGAACGTTAACGGAGTTTG
AAGCAGCAGCACCAGCCCTAACGTACGATCCACTAAACATACCATCAGTACCAAATGTATCGGGAGCGATT
GCGGAGCAGAGTATAACCTGAGCAAGCGGTTGCCTAATTCATCACCGGCTACCGCAGAAATTTGCGCATAG
TACGGACAGATAACAGCACGAAGGTTAATACCTCTGCGTAGACCTTGGACCAGAACCAGCTTTCTTAAGCG
TGGCAAGACAGTACCCGCCAGAGGACGTGGGTCCTTGGGTGCGATCTGTCATACTAGGACAAGTACACTCG
CATCCAATGCTAGAAACTTAGGCTCAACTTTATGCGCAAGGAGTTAAACATGATTGGTTACGGTTCATTAA
AGATTATTGTGGTAGTACGGAAGTAGTCTCGACTTTTGCCTTCCATCGCCAACGTTATTGGTAGGAGAGAT
ATAATAGTCTCATAGATAAGGAACAGATTTCATAAAATCATATTAATCTCCAAGCTCTAGTCGGTAATAGA
TCACAAGTAGCAGCGTTTGAAAAGTGAATTCGGTTTAAATGCCAAAATGGTGCTTCTCATCCAAGTTACCA
GCTACAGCAGTGAGTCTTTCCTGTACCTCTTTACCAAGCTACAGATTAGTTGGTAATACCCATACCAGGAG
GTACAACTTTATTTAAGTCAGGTGATAGAACCCTATAAGATATTGTAATAGAAAAGGCATGAATTTATCG
ACGGTTAAAATTCAGAGAATTCAAATAGTGTTAATCTTACGGTTACTACAGAGATATAGATTACATATTTT
TGGTCTGGAAACAAATACTGCTACTTAAGAACCTAGCTGGATACTACATGTTCAAGGATAAATGTTAGTAA
GGAACAAAGTCCCAGAATTAGAGACCACATACTTGAAAGCGGTCAAAGAAGGGTATAAGGAAAAGATTTTA
CCTAATGAGTTTTACAAGAAACATGAAGAAAGGCGGCTTTATAACGCTGCTTCTATCTAAGCCGTTGGACA
ACTGAGGCAGAGCGATAGCAAAAGACTAAGTGGAATTTAGTTGCCAAAAACACAGGTCATAGTTGCAAATT
TATGACAACTGCGCCTAAATGTTTAAGATGATATGTTCCAGGTATTTCCAGCTGTTGTGGTTAGAACGGAC
AAGCATGGAGCTTATGTGCACTTGGAAAGAAACCGTCAACAAATATAGCGGACTGTTAGTAATGGTTCGTC
GACAGAAGTATAGGTAGATGTAGCAGAACCTAAGAAAACCACTTTGAGATGTAACGTTGATTCATTATATG
AACGCGGAATAGTATGAGCAAGAATTCAAGCTTAAAGTTTATTATGTAGTTCACGGGAGGCATTGTGTTGT
AGTATCGAGCCGCAAGTTAACAAGGGGTTATAACACATCCAGTGGCAGACCCGATCACTTGCACCACATCA
CGAAACAATTGACTTGACAAACTCAGGTGGCTAGTTTTTGGCTTCACCAGCCACCGGGATAGAGAATCATA
TGGTGGAATCGTTCGCACTGCAAAGCTGACATTGTATATTTGTAGGACCAGGGCAGAACTTCCAGGAGTTA
GAAACTCCACAGTATCATATCGACCGCAATCAACCAGACGAATTCATGGACTTGATGAAAGCACGGTTGGT
GCAGCAACCCCAGGTACCAGCAATTATGCACCTACGGGGTTTCGACTAAACAATATCACTAAAGACTGGTG
CGCAGCACTTGCTAAATTAACGAGTACTCGGTTGTGGCAACGAACTGCATCGAGTCAAGGCCTTCGTAATA
GATCGAGATAAGGAGAGTGCCCCCTTATTGTAAGTGGCTCAAGCCTCTCATTCTGAGGGAAATGAATAACT
ACCGATACCATTCCGACAAGCAACTATGTGCGCGTTATGTGGAGTATTTGCACGGGGCCAAAGGCAATTAG
AAAGCCAGTGTTTAGGCTTACATCCATCTAAGGAAGCTTCCGAAAGATTAGCAGCTATCTTTGAGGGACTA
TTCTCTTCTGCTGATGAGAACGTAAATGCTAACTCTCAATGGTTAAGTCGCGTTCCTGAGTAAGAGAGGCG
ATAAAGAATGAGAACATGTACACATTCCGAATGAGAAATATCGTCGCATCAATCATGTCTACTGCAGCTAG
CAGTATATAGCTCATTGGACACCCTTATCGAACTCGAGGCCATTTACTCAATTGCCGTAAGTCTGAGAGCT
CCGGGCTAAAAAGCCGCTAAGTGGTTGATACCACAAGCGGTAATAAATTTCGTGCTTACTGGACATACGCA
GGCAACAGTAAGAGGTCTGCAAACCCTTGATCAAATACACATGGCAGAAGCGCCAGTGTTATTCATCTGGT
GAGAAATTTCGCATCAAGAGACTGTCGCAAGATTTATAAAGTCCAGCAAAGCATTATTGCGAGCACTATCA
GGAAAAATACAGGCCGCCGGGAAATGGGTTGGTGGTCTTCTGTTAGATATCAAGTGGGTTAAAGTTACATA
CGTGGTGGAACATAAACTACATCGGACTTGGTATTTCCAGAATATGACTCTGAATCTGCCTATGGACCTTG
TTTTATGTTTTGCCTCCATTGATTCGATCTTTGGTTCGACTGGTCGCGGGTATTAAGCTGGTGCCATTGAG
TTTATGGGTGGTTTATCCCATAATGGACGTGATATGCGATAACCTGGGTCGAGTATTAAATGGCGATCATG
GCCACTAGAAGCAATGGCTGCAAATATGGGTAGCCGTCTTCGAGATTGAGCGGTGACCAAGGCAATGTCTG
TTATGGTTTCAGAGCAGGGAATGCAGCTTCGAAGTCAAAAACTCTAAGAATCATTAGCACAAGTGGGAGTG
CTTCCAAATGAATGGCCAGTGATCCAAGGGCCATTAAGGTTCGGTGATCAATTAGCATTACTCCTAAAT
GGGCAATGGAAGCAAAACACACCATATAGCCATCGAGACTCAGACACAGTACAATGGGTTCTAAGAACACC
TAAAAGCTGCTGTACAAAGAGTAAGACATAAGATTGTGTTAAATTACGTCAAAGGTGTAATATCTAAACTA
TTTTGTTAGAGCATATCTCGACTTGTTATGGATCACCCCCTCAACACAATCGGTCTAGATTCTTTAAAGGC
CGTCCAAGTGCACACTAGTCTTCGAACTGATTTGCTCCTGAATATGTCGCTAGTCATAATTGTATAAAATA
CCTGTATCGTACATATAGGCTCTGAACTGTATCAGCAAGTGAGCCTAATTACGCAGACTCAATGAGATGAG
TGAGACAATAATGGTAAACTCGACCAAACTAAAAGCAACGATAAAGACCGCATTAGTAGTGGATTACGT
(SEQ ID NO:32)
```

FIG. 7-2

```
ATGGGGCATTATGCCGGGGAATCTGTGCCAGCCATAGTGGCTGGACTATTTGGTCTAGAAGACGTTTTAAA
CCCGCTTGCTTATATAGGACGACTAATCCATCAATTACCATCTGGGAGTGAGATCTTATCTGTAATTGCAT
CTATTGAACAGCTAAATCAGCTATTTGCATCATACCCTCAGAGAGTAGTGATCGCTTCGATCAACGTACAC
CAATGCATAGTCATCTCTGCTGATGCAGACGCATTTGGACCGGGTCAACATAGCTAAGTAGCACAAGACAG
GAAGACAACACGAGTGCAAATATGCCACCCATTTCATACACATCTGCTGGAATCAAAGTTGGTGGAATTTG
ACGCAGTCGCTTCAGACATAACGTACGATCATCCAACTATTCGATTAGCATGAAATGTATCTGGAGCGAGC
GCAGAGAATCGTTTAGCGACAGCAAGCTCTTTGGGTAATCACGTCTGGCTACCGGTGTAACTTGCCAAAAG
AATGCACAAATTACAGAATGAAGGCTATTACATCATCTTATAAATCGGACCAAAACCTACATTGTAAGGCA
TCAGAAGCCAGTGCATGTCAGAACATGAGGGAGTATGGGTGCCATCATTGAAGCTAGCGCAAGACGACTGA
CGGCACATGCCACGAAGCTTGGCAGAATTATCTGTCCATGGCGTTATAGTTCATTGTTTAGCGTTAGATAA
CGAATATTCTCCTAGAAAGGGAGTATTACCTACTTGTCCCTGTCAATGGCAGCGCTATTGCATTGTGACAG
ATAATCATCTAATTCACCAGAGACAGTTTCAATCAAATCATAAGAGTCTTCATCATCTACTCAGTCATACA
TTACATATAGAAGCATTAGATCAGCATATACGGTTTGAATGACATATTAGTGCATCACTACCAGCTTACGT
TCAACACCGCTGCGTTTTATCACAACCTGTTATCCTAGAAGCTGCTTACTAGGTAATCGCCTTAGGAGCGG
GTACAATATTAATCAATGCAGAGGATTTCATCCTACATGATATATCAAACTAAAAGTAGTAACTTTATCT
AAAGAAGAAGTTAATACACTTCATAAAGGTTTAAACTTACAGTTTATACAAGGCTATCAATTCCTGATCTT
CAGTATGGCTATAAGCACTAATTGATCCGAACCTAGATGCATTCAACATGTTGAAGGACAGATAATAGTGG
GTAATCAATACCCCGAATTACAAACACCAATCTTCAACGCGATTACAGAGGAGTAGAACTAACGGATACTA
CCTGCTGCATTCTACCGAACATTTGCAGACTGGTGTCTTAACTCCGGTCCTTCGTTCTAAGCCGTTCAACT
ACTGCGGGACAGCGCAGGATAAGCATTAGATGTAATTCCGTTACGAGACACCGAGATGAATGTAACAACTT
CATACTAACTACACCTAATTCGTTTCGATGCTCGCTGCCACGTGTTCGCAGCATTTAGGGGTAACACGCAC
AGCCATGAATCTTATATGCGATTGCAAATAGAACGATTACGAATTCATCGGAGTGGTACTAATCGTTTCTG
GACTCAAGGAGAGATCGGTGCGACACAACCTAGTAAACAAGCTTTGACCGGTCAAGTGCGTTTATTCGCTG
ATCAAGGCATAGGAGTAGGATGAGTTGCAGGTGTAACCGTATTACGTGCTTTTCGCGCGGGTTTGTTGCCT
ATTATTGAAGCAATATGTATTAATTGCTTAGATCACATCCACTGGCTAATCCAATCATTTTCGCCGCATAT
CCAAGCAATCGACTGAACCAAATCAGGTACGTGTCTAGTGTTTTCGGCACCCACACGTAAAGGCCAACTTC
TGGGAGACTCCTTATAACAACAAGCTCGGCATTGTAGACTAGTAACACAACGGGACATTTACCAGGAGCTA
GAACCGCAACATGAACAAATCAACCTCAGCCAACTTGAGGAATTCGGGCACCCATGGCAATCCAGCTCGGA
GGAGTAACCCCCAGGACGAGGCATTGTTCACCTGCGGACTTGGTACTCAACCATACCACTAACCACTGGGG
GACACGAGTTGCTACAATCCCATGAGCTGGCCGGTGGCAGCGTACGACATTTAGACGAAGGATTAGTAAAG
ATTCAAGATACGCAAAGTGGGCCATTATGGTAATTGACTCAATGCTGACACTCTGGGGGTAATAACTCCCT
GCATATACAATTGCATCAGACATCTTTACGCGGGTTAGGTCGCGGAATCGCCCAAGAATACAGGGAATTAC
TATTCCGCTTTTTAGACATATATCCAAGTATAGAAGATCCCAAAACAGCAGGTGCTTCGTTATAGGATCTA
TCATCTCATGGTCATGTTAACCAAATAGTTTACTGTCATGAGGTACGTCACTTTACCATGTTAGAGCGGCA
ATAGAGAACGAGTACGTCTATACAGTCGGCATTACCATTTTCCTCGCTACAAGCATATCAGCTGAAGCTAG
CAGCTTACAAGTCTTAAGTCAACCTAGTCCTAGCCGATGCGAGTTACGTAGTTAGCGGATGTCTGGCAGTA
CTGGGGTTAATTACGGCCGAGTGGACGGTAGAACATGGGGTGAGATGTTTAGTACTCACCCGACGTCGGGA
GCGATCAGAAAAGGGTCAACAATCCAGTGAACCATTGCAGAAGCCAGGGCGGAAATATTAGTCCAGTGGG
GCGGTATTTCCCGACACGAAAGTGTGACAAGGATTCTAGAGACATTCAAAGGATCCTTGCCGGCCTTACGA
GAAATGATTCCTACTGCTGGCATATTAGATCATGATTTGCGGTCAAACATGACTGGGGAACCATTTACACG
GTAATGGCGCCCAAAGTACTAGGTGCTTGTCATGTGCATACCTTGACTCATAATGTACCGTGGGACTTTG
TTCTTTGTTCTTGCTCTATGCCTTGAATAATCGGTTCGCGTGGCCAAGGGACTAATGCGGCTACTAATGCA
TACATGGTTAGTTTAGCCGATCACCGACGAGGTACGGGCTTAGCTGGCTGGAGGATTATCTGGGAACCATG
GACACGAGCGGAAATGGCACCTAATTTGCATTGTCCTCATCGACATAGTATGCTGTCCATGGGTATGACTA
TTATGTCTATAGAACAGTGATTCCAGCTTATAGGACAGTTACCCGAACAGTCGATACCACGAGTCGCAGTG
CTACCACTTGAATGGTCACTGATCCAAGAACATTTTAGTTGTGGTACTCAAGTACCACTGCGGTCCTAGTT
GGTGACAGAAAGCATATCACGGCACCAAGCCCTCAATTCAAAGACATAGCAGAATGAAGTTATAGGATAGC
TAACAGCAGCTTTACCAGGACAAGGAGCAAAGCATATGATAATGTACATTATAGATGCAGTTTCCCGAGTA
CTATCTCTGAGCAGTTATCAAAGTCATATGCATCAGCTCCTGAGCAGTATGGCCCTTGATTCTCAATTGGC
TGTCCAATTGCACATTACGCTACAAGCTGACATGCTGGTGGAGATAACTATACTCAGATTTATACCAGATT
TCACTATCGTTGCTATAGCCAGTGATGTGCATGAGGAACTGACCCTAGTTGCTTAGCATCAACGAGATGAG
TCAGCATATACCGGGCAACTCTACGATAGCATTAGGTAAGCAAGCGAGCGGATTAGACGTCAATAATGA
(SEQ ID NO:33)
```

FIG. 7-3

```
ATGGGGCATAGCGCTGGGGAATATGTTGCAGCAACAGTACCATGAATTTTTAGATTAGGAGATGGTTCAAA
ACAGATTGCTCAGAGAGCAAGACTTATGCAACAATTACCGTCTGGCGGTTAAATGTTTTCTGTAAAGGCTT
GAATCGTAAAAGTGAATCAACTCATTGCACTATACTCTCAATAAGTAGCGGTCGCATCGATTGACCGACCT
CAAAGCATTGACATGTCTGGCGAGGCAGTAGCAAATGGAGCGGCTGAAAAAAGCTTGGAACCAGAAGACAT
AAAGACAAAATGACTGCAAGTGTCACAGGCATTCCTTTCACGTTTGTTGGACCCAATGTTAGCGGACATTG
AAGCGGTAGCCTCAGAATTAACCTACAGTCAAGCAAATATTTCATAAGGATCAAATGTAAGGGTAGCTAAG
GCAGCGAATAGTATTTCCAAAGCAACCTATTGGTTATATCGTGTCCGGCAACCGGTGAATTTTGCGCAATG
TATGGTCACAATATAGCAAGAAGATTATTCCTTCTTGTTAGAAATTGCACACAAATCAACTTTGTAAGGCG
TGGGCAGACAGTGCTTGCCAGATGATGTTGTAGTATGGGTGCCTCCGTTGAAACCAGGTCAAGAATACTTG
CAGCAGATGCTCCAAAGTATGGCTTAACCATTTGTGCATGCAGTTTAAGTTGATTGGTTTGGGTTTAATAA
GGATTATTCTCCTAGTAAAGTAGTATGGCCGATTTATCCCTATCAACCGCAACGATATTGGAGTGCGACAA
ATTATAATCTAAAACAGCAGAAACAGCTATTATCAAATCATAAGAATCCTCACCCTCAACTCGGTGAAAGA
TAACATTCTGCAGCCTTAGTACTGCAAATTCATTTTGAGTGTCGAATTAGTGCATCTCAAGCAACTTACCC
GCAACACTACTGGTTTTTTTTCAGCCTCTTTTCTCAGCAGTAGCTTGCTTCGAAAAAGCCTTACCAGCAG
GTGCAATTATATTCAAGTCAGATGATTTCATCCTATAAGGTATAGCAATCCCAAAAGTATTTATTATATGA
AACGATGAAAATAATGCAATTCCGATAGTATTGAAATTACATTTAGTGCAAAGCCATAAATACCAAATTCT
CAGTTTGGATGTAATCACTAGTTCTCCAAAACCCAAATGGATTCTACGTATTGAAAGAAAATTATTAGAAG
GTAGTAAAGCCTCCCAATTAAAAACAACAAACTTAGAAGCGCTTTAAGACGGGTATTACCTACAGATAATA
CCTGCTGAATTCTCCTAAAAATTTGAAGGATGCGGTCTTATTTACGGATCGTCTCTCCAAGCCTTTAAACA
AATGTGGCACACCGAAGTAAAGGCACCAGGTAAAATTCCGTGACCAAAAACTGAGGTAAATGTGGCATCTT
CATACGAACTGCACCCAAATCTATTAGATCCTAGCTTCCGGGTGTTTGCTGCAGTAATGCGTAAATCGGAC
AGCCAAGAAGCTAATTGGCCATTGGAAATACAACGACTACAATTTTATCGCAATGGTGGTAACAGTATGAG
GACTCGAGTAGCGATAGGTGCTACAGAAACTAGTACACAGACTTTAAGCGGCAAGGATTGTTTACTGGATG
AACGAGGAACAGTAGTAACAAGAGTTCAAGGTTTATCTTTATAACGTACTACTCGCCAGGCTTAGTTACGT
GATATTCAACCTAAATTTAATAAATGGTTATGTCAAATGCATAGGCAAACCCGATCAATCTCTCCGCATAA
CCAAACAATTGACTTGACAAATTCAGGAAGGTGGTTATTGTTTCCCCCACTCACAAGTATAGGCAAGCATC
TCGTAGTAACCTTACAACGACAAGGATGGCATTGTGTATTAGCAACACCTGGGGAAGATTAGCACCAGTTA
GAATCACTACATTATCAATTCAACCCCTACCATCCAGAGGGATTCCTGGACCTATAGCAATCCAGCTTGGA
ACAGGAACCGCCATAACGAGGAGTTATTTACCTGTAGAGTTACGACTCAACAATTGCACAAAGGGCTGGGG
CACACGACTTGCTAAATTCCCAAGGAGTGGGCTTTGGCAGCGTGCTTCCTTTAGAGCAAGCCATAGTAGAA
AACCAAGATATGGAAAGTTCCCCATTGTGGTTACTGACACAACGCTCACAGTCTTTGGGTCATGAGTCCCT
TCCTGTACCATTCCAACATACACCGTTATGGGGATTACGTCGGGTAATTGCCTAGGGACATTGGAAATTAC
ATTGCCCGTGTTTTGACTTAGGTCCAACTATATAAGATTGCGAAACAGTAGCTTCTTAGTTAGAGGAAATA
TTATGTCCTGGTTATCAAATCCAAATTGATTACTGGCAAGGGGTGCGTCACGTTTCCCGGTTAGGGCGGCA
ACAACATATGAGTGCATCTACATAGTCAGGATAACTAATTTCCTTGCAACACCCGTTTCTACTGAAGCTAG
CAGAATGTAACTCTTTAGGCAACCTACTCCATGCCGGAGCCAGTTAGTTAATTACAGGACGTCTGGTAGCA
CTGGGGTTGAAAACTGCTGGGTGGATGGTCCAACAAGCGGTTAAATTTTTACTACTTTCCGGTGGTAGCCA
GCCATCTGCAAAAGCTCAACAAAGCATTGTACAATTACGGAAGGCAGGACCGCATGTGTTCGTCATGTGTG
GAGAAAATTGCCAACAAGATAAAGTGGCAGCAATTATATAGTCAAGCAAACTATCTTTGCCACCATTACGT
GGTATAATTCATGCTGGTGGGAAATTGGGTGATGGTATGCTCTTAATCATGAGTTGGGTAAAATTAACACA
GGTGATGGCACAAAAAGTACAGGGGGCCTGGCGTTTGCATTATTTGACTGAGAATGTACGTTACGACTTTT
TTGTGTGTTATTCCGGTATGGTTTCAATATTGGGTACGCCTCGTCAAGGGGATTATTATGCTGCGAATGCT
TCCATGGATGGTTTAGCTCATCGTCGACGGGGTATGCGTTTATTTGGCTTGGGCATTAAGTGCGGACTATG
GCCACAGGAGGGATTGGCAGCGAATTTGCATAGTCCTCAACAAGGTAGAAAGGTGTCCAAGGGAATGAGGT
TCTTGTCATCAGAACAGGGATTCCAGCTTCTAGGTCAAATACTCGAAGAATCTATAACACAAGTACGAGTC
CAACCAGTCCAATGGTGAGTGATCGAAGAGCAATTTAGTTGTGGTAATGAAATACCATAGCTCTCCCGATT
GGAAAAGGACAGCATATCTCAGCAAAAAACCCTCAAGACCAAGACTAAGCACAATGAGTTTATAGAACAGC
TTAAGGCTGCTTTACCAACAGAAAAGGAAAGCATTTGAAAATTGACACTAAAGATGAAGTTTCTAAAGTG
CTTACTTTGAGCCCTTCTGAAATAGATATGCATCAGCGCCTGAACTCTATGGGCTTGAATCTCTAATCGC
TGTAGAAGTGCACATTAGCCTTCAGACTGACTTGCTGGTGTATATATCAAGAGTCTAATTTACAGAAAGTA
TCAGTACCGTTGGTTTAGCCACTGATGTGAATGGGCAACCGAGCCAAGCTACTCACAATCAAGGTGTTAAG
TCAGGAAATCAAGGGCAGCTTTACCAAAACAATACGAAAGATAACGTGCGGGTAAGAGGTGAAATATGA
(SEQ ID NO:34)
```

FIG. 7-4

```
ATGGGGCATAGTGGTGGGGAATATATCGCAGCCACTGTAGAAGGAATATTTAGGTTAGAAGATGGCTTAAA
ACTTATTGCACATAGAGGAAGACTAAGGCAACCGTTACCCTCTTGGGGTGAAATATTATCTGTGATGGCTT
CACTTGAAAAGGTAATTCAAATAATTGCACCAGACTCTCAAACAGTAGCGATCGCATTGATTAAAGGACCC
CAAGGCATTGTCACTTCTGTTGAGGCAGAAACAATTGGAGCGGGTCAAAATAGCCTAGAAGCTGAAGACAT
AAAGACAAAGCGACTGCAACTATCCCACGTATTCCATTCAAATTTGATGGAGCCAATGCTGGCGGACTTTT
AAGCAGTAGCAACAGAAATAAGCTACAATCACCCAAATATTTCATTAGAATCAAATGTGACGGGAGCTCGG
GCAGAGATTAGTATTGCAACAGCAAGCGATTGGGTAACTCATGTCCGTCAACCGGTAAAATTTGCCGAAAG
TATGGCCACATTACATCAAGAAGGTAATTCCATCTTGTTAGAAATTCGACCCAAACTAACTTTGTAAGGCA
TGGGGAGACAGTGCCTGCCAGAAGTTGTGGGAGTATGGTTGCCTGCTTTGAAACCCGGTCAAGAATACTGG
CAGCAAAAGCTACAAAGGTTGGCTGACCTATATGTGCTTGGAGTAAAAGTTGATGGGTTAGGGTCTGATAA
AGTTTATTCTCGAAGCAAGGTAGGATTGCCGACTCATCCCTTCTACGGCAACGATATTGGATGGAGACAA
ATCATAATCTAATTCATCAAAAAAGTTTTTAGCAAATCATAACAATCTTCACTCTCTACTCGGACAAAGA
TTAGATTTAGCACCCTTAGAACTGCAAATTCGATTTGAATGTGAAATTAGTCCTTCTCAACTAACTTACCT
ACAACACCACGGTGTTTTCCTCAACCTGTTTTTCCAGCAGCAACTTACTTGGGAATAGCCTTCGCAGCAG
TTTCAATATTATTCAATGCAGATGATTCAATCCTAGATGATATAGCAAACCAAAAAGTGTTAATTTTACCA
AAGGATGTAATTAATACAATACAGATAGTTGTAAATTTACCGTTAGTACAATGCTATAAATACCAAATTTT
GAGTTTGGATCTAAACACTATTTCTTCAAAACCTAAAGGGATTCTACCTATTGAAGGTAAAATATTAATAG
GTAATAGAGACCCCCACTTAGAAACATCAAACTTAAAAGAGATTAAAGAGGAGTATAACCCACAGATATTT
CCTACTGAAATCTACCAAAGATTTGAAGCATGGGTCTTTATTACGGTTATTCTTTCCAGGCCGTTAACCA
ACTGTGGTACAGCGAAGAAAAGCACTGGGTGAAATCCAGTTACCTGAAACTGAGGAGAATGTTGCAGCTT
TATCCCAACTGTACCCAATTCTATTAGATGCTGGCTTCCAGGCGTTAGCAGCTGTTATGGGTAAAACAGAC
AACCGAGAAACTTACTTGCCATTGTAAATAAAACAACTACAAATGTATCGGAGTCGTAGTAATATTTGTG
GACACAAGTAGAGGTAGGTGCACCAGAAACTATTAAACAAACATTGAGCGGTGAAGTTTGTTCATTGGATG
ATCAAGGAATAATAGTAGCAAGGGTTGAAGGTCTAACTTTATTACGTACTTCACGCGAGGCTTGGTTGCGT
ACTATTGAACCTAAATTTAAAAATTGGTGATATCAAATCCCTTGGCAAACTCAATCAATATCACCCCATAG
CCAATCAATCGACTTAACAATATCAGGTAGATGGTTATTGTGTTCCCCACCTACAGGTATGGGCAAACATG
TGGTAGAATGCTTAGAACAGCAAGGTTGGGATTGTATATGAGTAACACCGGGGAAAATGACCAGCAGTGA
GAATCTCAGCATTATCAAGTCAACCCCAGCCATCCTGGGGAATTCCGGCACCTATTGGAATCAAGCTGGGA
GCAGCAGCCCCCATTAGGAGGAATTATGCACCTGTGGGGTTTGGACTGAACAATAGCGCTAAGGACGGGG
CACAGGGGTTGCAAAAGTCCCAAGAACGGGGCTGTGGGAGCGTACTTGATTTAGTCCGAGCCTTAGTGAAA
AATCAAGGTATGGAAAGGGCCCATTAGGGTTAGTGAGTCAAGGCTCGCAATCTGGGGGTAATGGGTCCCT
TCCGATACAATTCGAACAAACACGTTTATGGGGGTAGGTCGAGGAATTGCCCAAGAACATAGGAAATTAC
AAAGCCGGTGTTAAGACTTAGAACCAACTATGAAAGATTCCAAAACAGTAGATGCTTTGTTAAAGGAACTA
TAATCTCCTGGAGATGAAAACAAAATTGCTTAATGTCAAGGGATACGTCACGATGCCCGGTAAGAGCGGCA
AAAAAAAATGACTACATCTACCCAGTCCGGTTTACAAATTTTCTCGCAACATCCATTTCAATTGAAGCTAT
TAGAATATAATTCTTTAGACTACCTAATCCTAGCCGAAGCTAGTTACTTATTTACCGGAGTTCTGGGAGCT
CTGGGGTTATAAACCGCTGTGTGGATGGTTCAACAAGGGTTCAAATATCTTGTACTTACTGGACGTAGGTA
GCCATCAGCTAAAGCTCAACTAACCATTGATCAATTACAGTAGGCAGGAGTGCAAGTATTTGTCCTGTGTT
GAGATATTTTCCAACAAGATAATGTGGCTAGAATTATTGAGTCAATCTAAGTATCTTTTCCAGCATTACTA
GGAATATTTCATGCTGTCGGGATATTTGATGATGGTTTGCTGTTAAATATGAATTGGGTAAAATTTAAACA
GGTGATAGCACCAAAAATACAAGGGGATTGGCATTTACATAATTTAACTCAGAATATACCTTTGAACTTTT
TTGTATGTTTTTCCACTATGGCTTAAATATTGGGATCGCCTGGTAAAGGGAATTATGCTGCTGCAAATGCT
TTCAAGGAAGGTTTAGCCAATCATCGACCGGGTATGGGCTTACCTGGCCTGAGCATTACCTGGGGACCCTG
GCACAACAGGGAATGGCCGCAAATTTCGATAGTCCTCCTCAAGATACAATGGTGTCCCAGGGAATGCCTT
TTTTGTCCTCAGAACACGGATTGCAGCTTCTAGGACCATTACTCGACCAATCCATACCCCAAGTAGCAGTC
CTACCCATTCAATGGCCAGTGTTCCCAGAGCAATTCAGTTTTGGTCATCAAATACCCTTGCTGTCCCCATT
GGTACAAGAAAGCACATCACAGCACAAAGCCCTCCAAACAAAGACCAAGCACAACGAATTTTTAGGACAGC
TAAGAGCTGCTTTGCCAAGAGAAGGAGAAAAGCGTTTGATATTGTACATTAAAGGTGAAATTTGTCAAGTA
CTGTCTTTGAGCGCTTCTCAAAGTGATATGCAGCAGCCCCTGGACACTATGGGGTTGATTCGCTAATGGC
TGGGGAATTGCGCAATAGGCTGCAAACTGACGTGCTCGTGGGTATATCTATGGTCAAATTTGTAGAAGATA
GCAGTATCGTGGATTTAGCCGCTGAAGTGAGTGAGCAACTGGGCCAAGTTGGTCAGAATCAGGGAGTTGAG
GCAGAAAATAGTGGGCAACTGTACCAAAGGAATAGGAAAGGAAACGAGCGGGTAAGAGGGGAATTATGA
(SEQ ID NO:35)
```

FIG. 7-5

```
ATGGGGCATGGTGCTGGGGAATATGTGGCAGCCACAGTAGCAGGAATATTAAGTTAAGAAGATTGTTTAAA
ACTGATTGCTCATAGAGGAAGACTCATGCAACAGATACCCTCTGGGGGTAAAATGTTATCTGTAATGGCTT
CAATTGGAAAGGTTAATCAACTAATTGCACCATACTCTCAAAAAGCAGCGATCGCATCGATTAACGGACCC
CGAAGCTTTGTCATTTCTGGTGAGGCAGAAGAAATTGGAGCGCTTCAAAAAAGCTTAGAAGCAGAAGACAT
TAAGACAAAACGACTGCAAGTAACCCGCGCATTCCTTTCACATTTGATGGAACCAATGTTGGCGGCCTTTG
AAGCAGGAGCATCAGAAATAACCTACAATCAACCAAATATTCCATTAGTAACAAATGTAACGGGAGAAGG
GCAGAGAATAGTATTGCCACAGCAAGCAATTGGGTAAATCATGTCCGGCAACCGGTGAAATTTGCCAAAAG
TATGGACACATCACAGCCAGAAGGTTATTCCATCTTCTTAGAAATTGGACCCCAACCACCTTTGTTAGGCA
TGGGAAGACAGTGCTTGCCAGAAGATCTGGGAGTTTGGTTTCCTTCTTTGAATCCAGGTCAAGAAGACTGG
CAGCAAATGTTACAATGTTTGGCTGAACTATATGTGCATGGAGTTAAAGTTGATTTGTTAGGGTTTGATAA
AGATTATTCTCGTAGCGAGGTAGTATTGCCGACTTATCCCTTTCAGGGGCAACGTGATTGGATTGAGACAA
ATAATAATCTAATACAGCAAAAACAGTTTTTATCAAAACAAAAAAATCTTCACCCTCTACTCGGACAAAGA
ATACATTTAGCAGCCTTAGAACAGCAAATTCGTATTGAATGTCAAATTAGTGCTTCTCACCCAACTCACCT
GCCACACCACTGTGTTTTTTCTCAACCTGTCTTCCCCGCAGCAGCTTACTTGGAAATAGCCTTAGCAGCAG
GTTCAATTTTATTCGATGCAGATGATTTAATCCTAGAAGATATAGCAATCCAAAAGGTATTAATTGTATCA
AAGGATGAAATTAATACAATTCAGATAGTTTTAGATTTACAGTTAGTATAAAGCTTTAAATTCCAAATTTT
CAGTTTGGATATAAACACTTATTCTTCATAACCTAAATGGATTCTACATATTGAAGGAATAATATTAGTAG
GTGATAAAGACCCCCAATTAGAAACAACAAACTTAAAAGCGAGTAAGGACGAGTATAACCAACAGATATTA
CCTACTGAATTCTAGCAGAAATTAGAAGAATGGGGTCTTAATTACGGTTCTTCTTTCCAAGCCATAAAACA
ACAGTGGCACAGCGAAGGAAAAGCACTAGGTGAAAATCAGTTACCAGAAACAGAGATGAATGTTGCAACTT
TATACCAACTGCACCCAATACTTATAGATGCTAGCTTCCAGGTGTTAGCAGCAGTTATAGGTAAAACGGAC
AACCAAGAAGGGGATTTGCCATTGGAAATAAAACGACTACAAATTTATGGGAGTGGTAGTAATAGTTTGTG
GACTCAAGTAGAGATAGGTGCAACAGAAACTAATAAACAAATTTTGTGTGGTAAAGTTTGTTTATTGGATA
AACAAGGAATAGTTGTATCAAGAGTTGAAGGTTTAACTTTATTACGTACTTCTCGCGAGGCTTTGTTAAAA
AAAATTGAACCAAAATTTAATAATTGGTTATATCAAATCCATTGGCAAACCCAATCAATTTCACCCCATAA
CCAATCAATTGACTTAACAAAATCAGGTAGGGGGTTGGTGTTTTCCCCACCCACAGGTATAGGCAAACATC
GGGTAGAATCCTTAGAACAACAAGGTTGGCATTGTATATTAGTAACACCAGGGGAAATTTACCAGCATTTA
GAATCTCAACATTATCAAATCAACCCTAACCTTCCTGAGGAATTCCTGCACCTATTGCAATCAAGCTTGGA
GTAGCAACCCCCATAACGAGGAATTATTCACATGTGGAGTTTGAACTCAACAATAGCACTAAGGACTGAGG
CACAGGAGTAGCAAAAATCCCAAGAACTGGGCTGTGGCAGCGTCCTTCATTTAGTCCAAGCCTTAGTACAC
AATCAAGATATGCAACGTGCCCCATTATGGTTAGTGACTCAAGGCTCACAATCTGTGGGTAATGAGTCCCT
TCATATACAATTCCAACAAACACCTTTATGGGAGTTAGGTCAAGTAATTGCCCAGGAACATAGGGAATTAC
AATGCCGGTATTTAGACTTAGATACAACTTTGGAATATTCCCAAACAGTAGCTGCTTTGTTAGAGGAACTA
TTATCTCCTGGTGATGATAACCATATTGCTTACTGTCAAGGTGTACGTCACGTTGCCCGTTTAGAGCGGCA
ACATATAATGAGTACATCTACATAGTCCGGATTACTAATTTCCTCGCAACAACCATTTCAACTGAAGCTAT
CAGAATATAAGTCTTAAGACAACCTAATCCAAGCCGAAGCCAGTTAATTAATTACCGGAGGTCTGGGAGAA
CTGGAGTTAAAAACCGCTGAGTGGATGGTACAACAAGAGGTCAAATATTTAGTACTTACCGGACGTAGGCC
GCCATCAGCAAAAGCCCAACAAACCATTGAACACTTACAGACGGCAGGAGCGCAAGTATTAGTCCTGTGTG
CAAATATTTCCCAAAAAGAAAATGTGGCAAGAATTATAGAGTCAATCAAAGTATCTTTGACAGCATTACAA
GGAATAATTCATGCTGCTGGGAAATTGGATGATGGTTTGCTGTTAAACATGAATTGTGATAAATTTACACA
GGTGATGGCACCTAAAGTACAATGGTCTTGGCATTTGCATAATTTGACTCAGAATCTACCATTGGACTTTA
TTGTTTGTATTACCTCTATGGCTTCAATATTGGGTTCGCCTGGTCAAGGGAATTATGCTGCTGCTAATGCT
TTCATGGATGGTTTAGCCAATCATCGACGGGGTATGGATTTACCAGGCTTGAGCATTAAATGGGGACCATG
AGCACAAGAGGGAATGGCAGCAAATTTGGATAGTCCTCATCAAGATAGCATGGTGTCCAAGGGAATGACTC
TTCTGTCTTCAGAACACGGATTGCAGGTCTAGGACAATTACTCGAACAATCCATACCACAAGTAGCAGTC
CTACCATTTCAATGGTCAGTGTTTCAAGATCAATTTAGTTTTGGTAATCAAATTCCATTGCTGTCCCAATT
GGTAAAAGAAAGCAAATCACAGCAAAAAGCCTTCCAACCAAAGACAAAGCACAATGAACTTTTAGAACAGC
TAAAAGCTGCTTTACCAAGAGAAAGACAACAGCTTTTGATAATTTACATTAAAGATGAAATTTGTCAAGTA
CTTTCTTTGAGCACGTCTCAAATTGATATGCGACAGCCCCTGAACACTAGGGGGCTTGATGCTCTAATGGC
TGTGGAATTGCACAATAGGCTACAAACTGACTTGCTCGTGGATAAATCTATAGTCAAATTTATAGAAGATA
TCAATATCGTAGATATAGCCACTGAAGTGAATGAGCAACTGAGCCAAGTTGCTCAGAATCAAGGAGTTGAG
TCAGATAATATTGGGCAACTCTACCTAAGCAATAGGATAGTAAACGAGCGGATAAGAGGTGAATTATGA
(SEQ ID NO:36)
```

FIG. 7-6

```
ATGGGGCATAGTGCTGGGGAATATGTGGCAGCCACAGTAGCAGGAATATTTAGTTTAGAAGATGGTTTAAA
ACTGATTGCTCATAGAGGAAGACTAATGCGACAGTTACCCTCTGGGGGTGAAATGTTATCTGTAATGGCTT
CAATTGAAAAGGTAAATCAACTAATTGCACCATACTCTCAAAAAGTAGCGATCGCATCGATTAACGGACCC
CAAAGCATTGTCATTTCTGGTGAGGCAGAAGCAATTGGAGCGGTTCAAAATAGCTTAGGAGCAGAAGACAT
TAAGACAAAACGACTGGAAGTATCCCACGCATTCCATTCACATTTGATGGAACCAATGTTGGCGGACTTTG
AAGCAGTAGCATCAGAAATAACCTACAATCAACCAAATATTCCATGAGTATCAAATGTAACGGGAGCTAGG
GCAGAGAATAGTATTGCCACAGCAAGCTATTGGGTAAATCATGTCCGGCAACCGGTGAAATTTGCCCAAAG
TATGGGCACATTACAGCAAGAAGGTTATTCCATCTTCTTAGAAATTGGACCCAAACCAACTTTGTTAGGCA
TGGGAAGACAGTGCTTGCCAGAAGATGTGGGAGGTTGGTTGCCTTCTTTGAAACCAGGTCAAGAAGACTGG
CAGCAAATGCTACAAAGTTTGGCTGAACTATATGTGCATGGAGTTAAAGTTGATTGGTTAGGGTTTGATAA
AGATTATTCTCGTAGCAAGGTAGTATTGCCGACTTATCCCTTTCAACGGCAACGTTATTGGGTTGAGACAA
ATAATAATCTAATACATCAACAACAGTTTTTATCAAATCATAAAAATCTTCACCCTCTACTCGGTCAAAGA
TTACATTTAGCAGCCTTAGAACAGCAAATTCGTTTTGAATGTCAAATTCGTGCTTCTCAACCAACTTACCT
GCAACACCACTGTGTTTTTCTCAACCTGTTTTCCCAGCAGCAGCTTACTTGGAAATAGCCTTAGCAGCAG
GTTCAACTTTATTCAATTCAGATGATTTAATCCTAGAAGATATAGCAATCCAAAAGTATTAATTTTATCA
AAGGATGAAATTAATACAATTCAGATAGTTTTAAACTTACAGTTAGTACAAAGCTATAAATTCCAAATTTT
CAGTTTGGATATAAACACTAATTCTTCAGAACCTAAATGGATTCTACATATTGAAGGAAAAATACTAGTAG
GTAATAAAGACCCCCAATTAGAAACAACAAACTTAAAAGCGATTAAAGACGAGTATAACCAACAGATATTA
CCTACTGAATTCTACCAAAAATCTGAAGAATGGGGTCTTAATTACGGTTCTTCTTTCCAAGCCGTTAAACA
ACTGTGGCACAGCGAAGGAAAAGCACTAGGTGAAATTCAGTTACCAGAAACCGAGGTGAATGTTGCAACTT
TATACCAACTGCACCCAATTCTTTTAGATGCTAGCTTCCAGGTGTTAGCAGCAGTTATGGGTAAAACGGAC
AACCAAGAACCTTATTTGCCATTGGAAATAAAACGACTACAAATTTATCGGAGTGGTAGTAATAGTTTGTG
GACTCAAGTAGAGATAGGTGCAACAGAAACTAATAAACCAACTTTGAGCGGTAAAGTTTGTCTATTGGATG
AACAAGGAATAGTAGTAGCAAGAGTTGAAGGTTTAACTTTATTACGTACTTCTCGCGAGGCTTTGTTCCGT
AATATTGAACCAAAATTTAATAATTGGTTATATCAAATCCATTGGCAAACCCAATCAATTTCACCCCATAA
CCAATCAATTGACTTAACAAAATCACGTAGCTGGTTATTGTTTTCCCCACCCACAGGTATAGGCAAACATC
TGGTAGAATCCTTAGAACAACAAGGTTGGCATTGTATATTAGTAACACCAGGGGCAAATTACCAGCAGTTA
GAATCTCAACATTATCAAATCAACCCCAACCATCCTGAGGAATTCCTGCACCTATTGCAATCAAGCTTGGA
GCAGCAACCCCCCTTACGAGGAATTATTCACCTGTGGAGTTTGGACTCAACAATAGCACTAAGGACTGGGG
CACAGGAGTTGCAAAAATCCCAAGAACTGGGCTGTGGCAGCCTACTTCATTTAGTCCAAGCCTTAGTAAAA
AATCAAGATATGGAAAGTGCCCCATTATGGTTAGTGACTCAAGGCTCACAATCTGTGGGTAATGAGTCCCC
TCCTATACAATTCCAACAAACACCTTTATGGGGGTTAGGTCGAGTAATTGCCCAGGAACATAGGGAATTAC
AATGCCGGTGTTTAGACTTAGATCCAACCATGGAAGATTCCCAAACAGTAGCTGCTTTGTTAGAGGAACTA
TTATCTCCTGGTGATGAAAACCAAATTGCTTACTGTCAAGGGGTACGTCACGTTGCCCGGTTAGAGCGGCA
ACAAAAAATGAGTACATCTACACAGTCCGGATTACAAATTTCCTCGCAACAACCATTCCAACTGAAGCTAT
CAGAATATAAGTCTTCAGACAACCTAATCCAAGCCGAAGCCAGTTACTTAATTACCGGAGGTCTGGGAGCA
CTGGGGTTAAAAACCGCTGAGTGGATGGTACAACAAGGGGTCAACTATTTAGTACTTACCGGACGTAGGCA
GCCATCAGCAAAAGCTCAACAAACCATTGAACAATTACAGAAGGCAGGAGCGCAAGTATTAGTCCTGTGTG
GACATATTTCCCAACAAGAAAATGTGGCAAGAATTATAGAGTCAATCAAAGTATCTTTGCCAGCGTTACGA
GGAATAATTCATGCTGCTGGGATATTGGATGCTGGTTTGCTGTTAAACATGAATTGGGAAAAATTTACACA
GGTGATGGCACCAAAAGTACAAGGGGCTTGGCATTTGCATAATTTGACTCAGAATCTACCCTTGGACTTTT
TTGTTTGTTTTTCCTCTATGGCTTCAATATTGGGTTCGCCTGGTCAAGGGAATTATGCTGCTGCTAATGCT
TTCATGGATGGTTTAGCCCATCATCGACGGGGTATGGGTTTACCTGGCTTGAGCATTAACTGGGGACCATG
GGCACAAGAGGGAATGGCCGCAAATTTGGATAGTCCTCATCAAGATACAATGGTGTCCAAGGGAATGACTT
TTTTGTCTTCAGAACAGGGATTGCAGGTTCTAGGACAATTACTCGAACAATCCATACCACAAGTAGGAGTC
CTACCCATTCAATGGTCAGTGTTCCAAGAGCAATTTAGTTTTGGTAATCAAATACCATTGCTGTCCCAATT
GGTAAAAGAAAGCAAATCACAGCAAAAAGCCCTCCAAACAAAGACAAAGCACAATGAATTTTTAGAACAGC
TAAAAGCTGCTTTACCAAGAGAAAGAGAAAAGCTTTTGATAATTTACATTAAAGATGAAATTTCCCAAGTA
CTTTCTTTGAGCACTTCTCAAATTGATATGCAACAGCCCTGAACACTATGGGCTTGATTCTCTAATGGC
TGTGGAATTGCACAATAGGCTCCAAACTGACTTGCTCGTGGATATATCTATAGTCAAATTTATAGAAGATA
TCAGTATCGTTGATTTAGCCACTGAAGTGAATGAGCAACTGAGCCAAGTTGCTCAGAATCAAGGAGTTGAG
TCAGAAAATAATGGGCAACTCTACCAAAGCAATAGGAAAGAAAACGAGCGGATAAGAGGTGAATTATGA
```
(SEQ ID NO:37)

<sup>a</sup>Key a) PyBOP, DIPEA, HSNAC, DMF; b) 4 N HCl/dioxane; c) 50:50:1 TFA:CH$_2$Cl$_2$:Et$_3$SiH; d) 20:1 AcCN:48% aq. HF; e) PyBOP, DIPEA (3.0 eq), 3, and 6 or 9.

SEQUENCE LISTING

```
<160> NUMBER OF SEQ ID NOS: 41

<210> SEQ ID NO 1
<211> LENGTH: 33260
<212> TYPE: DNA
<213> ORGANISM: Nostoc species

<400> SEQUENCE: 1
tgatattaga tgtttaatat cttaggaaat tttgataaac aggaaagctt atgactgtca      60
gttgcgagaa cggtaaattt ttaaacatat ttgctcaact ttctcaacca ccaaatactt     120
tgccttcagc ttaaaaagca aatatacttc ttattcgctt tggatataac gaaagttcat     180
atcccccttg tagccagaag ctttcgcaag atccttaaag ttttgcacgc cggtatactg     240
atgtccattg ataacccaag ttggtacacc tgggactttc gccgcattgc acaagtctgg     300
gtggggattg atacctctct tatcgcactc aactttaata ctgtcgttga ttatttggta     360
```

-continued

```
ggcttgcttc ccaaagatta acttttgttc gtgacagtga ggacaccacc aagaaacata      420
ttcttttgcc ccgatataca ccaaatgctt cgccaaggct agttctgcct tccctgaagt      480
ggtagtgatt tcccaaccga ctccggtctg aggtcgttct ttgggcagga agaaaataat      540
cgatggggac ttttggttgt ctgtttgttg agcaatatct gtcagtagtg cagagccaga      600
actcgtacca acacaaataa tggagagcgt taacagtgca aataaaaaag ggtgtttgat      660
agccatatta aatatatact ttgattgaat agttgtcgaa gctaacaatt gtatgtttaa      720
gattgtagta ttttgtataa ctgataatac gaagccagak ratccccatc ttatcttcgt      780
cataatcgaa attatcatca ccatgttctt cataccactt tctttcttcc tccaaagcga      840
tttctctctc gatgattttt ctttctagaa tttcactttc tagaatttca ctttcaagct      900
tttctctttc aaatcttcct cttctctatt cttctcttct ctgcctttct ttctcttctc      960
tttctctctc aagttgaatt aatcgctgct ccactctctc acagtaaaaa tccaaggctt     1020
taccagtggc tgctccggta attgcaccac cagccaaaaa tattattaca gttttccagc     1080
cttgaatggg attaccgctc cactccaaac taccctcatt gagccacact agtaggaagt     1140
aaacgagaat tccaataaca gtattgatcg gtgcaaaaac tctcggtgtc atctgggttt     1200
gacgaagtat cagccattgc gccagggtga gaatcacacc aaagattgcc gcagcaattc     1260
ctgagagaat cagattacct gggaaactaa acggatctac tgtaaatcta atgattagcg     1320
tgataataat cggggcagag agcaaaaagc tcagaagtaa gctagcgcta atcgcaagaa     1380
accagtagcg accgagataa cccaggcgaa attctaacaa cgactcttgt acttccaaac     1440
aaagtcatcc aaaatgcaat actcgcggtc aaataatcaa gcattagccg ttgttttacc     1500
cgtgtgttga agagggtatt ttctagaata cgcccaaaca gtattttgtt gttgtggtgg     1560
ctctggtgtg gtgttttttt ttttgataat tgctctatga gattttttcaa tgagttttat     1620
atttggtagt gctttaaggc tgcaaaatat aaaaagcaac gaaaacccc atccttcata     1680
caggttgggg ggatagataa aaaacatata ttccatgatg acacaattca atatttgttc     1740
gactgctgtc agcctagagg tggggcaatg aacaaaccac catccagacg caagaaaatt     1800
accccctgcga catctgagga accaaagcta gcaactgacc ctgctcagga aaatacttct     1860
ttgcacgaaa atccagggg agcaactatc acggtgacgg ctgttgaagt aacagatttg     1920
acccaggaag aacaaagctt acgcctgcat ttagaacacc gtgtggagag agcattttg     1980
gaggcgggtc aagcgttgat ggagttgcgg gacagacggc tgtaccgttc cacgcaccgg     2040
acttttgaag aatactgccg cgaacgcttc aattatagtc gtgacgcggc ttacttgaag     2100
atttcggcta ctgtggttta tgagaatctt caaaagtttt tgccgaccat tggtcggcaa     2160
attccaatgc cgaccaacga acgacaattg cgttttttgg cgaaagccga gttggaaccg     2220
gctgtgcaag cggatgtatg gcggcaggca gtggagcaag ctggcaataa gattccatcc     2280
ggtcgcatag tgaaagatgt tgtagatagg atacgcgaaa ggacgaaagt acccaatcct     2340
taccacgttg gggagatatg cgttcttcta cccaaagata atgcagactt gagaggtaaa     2400
gcgggttatt ggggcgtggt cagccatgtt ggagaataca gttgtacact ccagatatgg     2460
gacggtgact ataccgtaaa aatcgaacac ctgaaatcac tggaattact tgatgaagat     2520
tgccaattca tgcagcagtt atgtgtgagg ttacggcagt tgcatcaagt ggacaggcgt     2580
gacgaggctg tggattggct gttgcagtgg ttggggaaac aggccaaacc ttatctgtca     2640
tccttgcagt caaagctgct ggcgtttgtt gagagagagt acaacctggt ttggaagcag     2700
cagaagtgat gagatagcta gtaaacaata ggttaatcca acaaatacac aatgcaacaa     2760
```

```
ttaactcatt gcatgaaagc ggtaagcgat cgcggagggt ctggtagagt tgccatgctg   2820
gaaggcttat cggttcaaga agaaatctga gtaggtcatg gggagtgtcc ttttatagcc   2880
gccataaccg gacagttacc attttttccct catgacatag cactaaatct taccagcact   2940
tcaaattaaa ggtaaagcag tgctagtcat cagtcacgat gataaatatt tccatttagc   3000
atctcgcatt gtaaggctgg attacggaca tcttaagtat gagtcatgaa aattatgtat   3060
tccaaacccg acaacttact gcatccactg tacccaatca ggcgcagatg tcatcaattg   3120
actaaactta tcagtgtaag tatcgtcaaa ctctagcatc actccccatc gctcatcact   3180
cgtgaatcgg aaaattggaa ctgaagccga tgcagaggaa cataaccgcc acaaagctga   3240
agtaagcgca gcagatgatt agctctacga tccagccctc tcaatattga caaatagtac   3300
actatgtgag ttttctaaga aggtaagact aaaactgcac ttaagcgctt atgttatctc   3360
ccctatttga tgcttttgta gaggcaagcc ccgtcagtgt aatgatgcga gtcctaatgg   3420
aaaacatttt taattcctcg cgaatgaatc aaatatttga tacatcaagc gttcgccaat   3480
actctcaaga gctactgttt tcgactcagg tggatttgat gagtctagta gtgtgtggga   3540
tgtatccctc ggttcatgca gcctatcaga agaaggcagt ggaggtaagt gtcagcgcca   3600
cagcgttata caacaaactg caacggattg aactgcctgt aagtcgggca ttagtgcatg   3660
agacagcatc tgacctccag cagttgctgt tgatgttgaa tgtggaacgc cccagtcctc   3720
taggaaaaca atatcggttg cggattgtag atggcagttg tttagccgga accgaacgca   3780
gactagcagc gctgcgcccc catgcagcca aaccattacc cggaaaaaca atcgccattc   3840
tcgacccagg gacaaaactg gtggttgatg tgattccttg tgaagacggt cattcccaag   3900
aacgctccaa gtttcatcag gttttggcac aagtgcaacc ccaacaggta tggattgcag   3960
accgtaactt tgtaccgca ggatttctcc atactattgc caaacttgga gcgttttttg   4020
tgattcgtca acacggggt ttaggatacg agccttttgg tgagttacaa gctgttgggt   4080
tgtgccaaac aggaactgtg tttgaacaac aggtggaaat tgtccatgag ggagggactt   4140
ttcggtgtcg ccgtatcgta gttaagttga ctcgtcccac ccgtgaccaa gagtgggaaa   4200
ttgccatttt taccaactta ccacccactg acgcagacgg cattctggtg cacaactct   4260 atcaagggcg gtggagtgtg gaaactttat tccaaactgt gacccaaaac tttcatggag   4320
aaattgaaac cctagcttat cctaaagctg ccttattctc ctactgcatg gcactgtcag   4380
cctacaacct tttagcgaca cttaaagcag ttccttggcag tgtacatggg gtagacaaaa   4440
tcgatattgg gctatccgat ttttacctag tagatgatat ccattccatc tatcggggca   4500
tgatgattgc tattcctccg gttcattggc aattctttga ggagtttacc aacattcaga   4560
tggtagacgt tctccagcat ctagcaacca agtacatct caaatctttt cgcaaacacc   4620
ccagaagtcc caaaaagaaa cgaccaccac tctctgttga tggcaaacat tcccactgtt   4680
ccactactcg aaagctcaag caatacaaag cagctcttga tgctatcccg tgaagcaatt   4740
tcataaaata tgttatttgt caatattgag agggctggct ctacgatcct aacgtggcaa   4800
aacttactag agaagagtaa aaatcctgta atcttgacct tgtagcgaaa taatggtgcg   4860
aaaacttggc atgaaattgt ctaaaaccag aggcaacatc gtttgaagta ctcgattgtg   4920
ttcaaaaaaa atgcccttcg tgcggtcaag caatgtggaa tgaatacaat aatcctcgac   4980
atataagaac gttaaacggg gtagtagaac tacaactaaa aattcgtcga tgtcaaaata   5040
attcatgtct gcggtacaaa aaagcatatc gaccagagca agaagggtca ctcgctctac   5100
```

```
cacaaaacga atttggtttg gatgtgattt tataaggagc attacgctac caggaacata    5160
gaagtgttcc ccaaatacac gctcacctcg aattaaaagg tatatgtata agtcaacgaa    5220
cggtcacgca cctaattgac agatatgacg agttactttc tttatggcta aaagaccata    5280
aaaggttaaa agcaatagtg gctaatcaag gacgggttat attagcgatc gatggaatgc    5340
agccagaaat tggacatgag gtattatgta tgctttgaat cataatgtga gaaaaatttt    5400
gatccataaa ttagaaaaaa gttaacgaaa attcaggctt tcgtgctaat caaaaattaa    5460
aactttgaat caaattatga gtgagagttg aaattctgaa tcataactag agaatgagtt    5520
gaaaaaacac aattggacaa aacttgcaca aaaaatccct gacaaaattt ctctaactta    5580
aactttcaat tcagaatatg gttcaaatac caatgttatg gttcaaaact tttacacaag    5640
ctgttagggt agcattactt agtattgctc atggtttatg tcattatcat tacctgaagg    5700
aagcaattaa acccatatat gaggcggatc gacatgcaaa aaaggaataa aaaaaaaggt    5760
tagaggatta cgagacattg aatgtagtgt tgtcaatgaa gatcagaaaa tggcgactat    5820
tattgaagat tattgctcgg cagtacgtag ttctataacc aatgatggtc aaaccaattc    5880
gcaattgaca attcgcaatt cgcagttgaa ttcaaagtta gctctgaacc caccccctgaa    5940 ttgagtctac tgatttagag aatcagagtt agctctgaga cccattaatt aacaattcaa    6000
caattaagta atttcttgtc tttaattgcg aattgcgaat tgacaattgt ttcggtcatc    6060
caccgttaga ggcatctgga ttaaagttac aagaaaattt gacgttgata gaacaaagct    6120
tagaacggat ggaaaaaaag tgctwtacca ccacctttag tcaacctaaa atactgatag    6180
ccaagggatt atctgcgact gtatctttat tttcacttgt tagggttgca tatcagtggg    6240
ttgataaagc tagttatatt ctcaacaata aaatagcttt tgatgctgct ggagtcaaac    6300
aaagttatca acaactgtta acagaaatgt cccaacaaaa atagaaagct ggtacactga    6360
ataccgcaat cgataacttt ataaaaacca cccataacta ctggtctaga ctttttcatt    6420
gttacgaaat tgaagatttt tccagaacta ataatgactt agaacatgct tttggtatgt    6480
tacgtcatca tcaacgtcgt tgtactggtc gtaaggttgc tccctcatcc ctcgttattc    6540
gtggctctgt caaacttgcc tgtgcgtagg cgtagcccgt cgtagacatc gctactaagc    6600
ttcactcttt taccgcatct gatttagcac aagttgatat tcatacttgg ctcgaattac    6660
gatctcaact gcaaaacac cacaaagcca gaattgaaca atatcgattt ctcagagacc    6720
ccaagggtta cttggctaat ttagagagtc gtcttctcta gtaagttta ccatactagg    6780 ttttcttgt tctcaaatcc tgttgccatg actcggatct tgcagctaga tggtaagaat    6840
tataccctag ctcgcatagt gccactttca acccgacgtt gcagttcagg taagtccgct    6900
tgtcaatagg gtttgagacg cgctaaccct ggggtatgaa gacttaaacg atcatgaaca    6960
attacgtcat gacaagatgt tcgtcttggc gagcagcatc gcataaattt ttaccatttt    7020
tagtatttcc aggctctaag tgtggagcaa agagtttctt tggagaggga ttacctgtac    7080
caatcctaat tttggctgag ttgtaacata tagaccatca actgccccaa ctgccgatag    7140
tatggaaaat ccctcgactg cattgaaaaa ctgggcattt gtcttcatta cctcgttacc    7200
tttttccctt tcgattgcca acgcctgctt gtcttgccta atgctgtggc ttgactgaat    7260
ccgctgagac atctctgcca taacaaaatc ggcaatcccc tccttagcgt cctccaagtc    7320
ctcgacgccg gacaccagat tcaagaatgc tagctttagg ttagaactgc cgaagtcacg    7380
gcgactaagc cgttgtgcct cccagaaata ggaatccttg ccacggtttt gatcgtagaa    7440
ggctgatacg aacactaaga aacgcaaata agcctgccga tagctctgat cgtagaaaga    7500
```

```
agcagcttgt gactcagtca cctcgccacg tataacactt gtgatactgg ctgcggctaa    7560
caaagcgcta taagtagcaa gatgcacccc actcgatagt aggggggtcta ggaagcaagc    7620 agcgtctccc gatatgaagt aggctggtcc tgaaaaggag tcggaagtgt aagagtaatc    7680
ttgctcaact ttcacgtctg agactagctc ccctagtgca accagatccg ctatcaaggg    7740
acactctgca atcgcctcca cgtagatatc cttcaagttc ttagtcagtc tctccttgta    7800
ggttgactta tgcatcacta caccaacgct cataatttcc tcatccaaag gaattcccca    7860
cacccaacca tctggaatgg agcccaaggc aatcgcaccc gactgacctt taggtagtct    7920
caaggcgttt ttccagtacc cccagatgcc aacattctgg aatacgtcgt gtagacggcg    7980
gtttttcaga tactccgtcg ccatgatccc agcacgacct gaagcgtcaa tcataaagtc    8040
aaaagaaatc tccccggtag tatcatttga ttgtgaccaa gtagcgctgc gcgggcgatc    8100
gccatcaaaa gacaactggc gaattttagt cccttcaaaa accttcacac cctggctctt    8160
tgaatgctct aaaagcaagt ggtcgaattc gtcacggcga acttggaagc tgtaggtgtt    8220
gtcccccgta agttcccaa aattgaggct ccacttttcc gttccccatt ctatgtacgc    8280
tccaggttta cgctgaaagc cataagcttc aattttctcg cgtacgccaa gcaggtcaaa    8340
aatttctaaa gcagagggca aaagagattc cccaacgtgg taacgcggga atacctctcg    8400
ttctaacagc gttacatcaa agccctcacg agccaatagg gtagcagcag tagatccaga    8460
aggtccccct ccgataatta gaatctgtgt ggaattaggc agtgtagaca ttgcaggttt    8520
cttctccaaa agatacagta ttttcgcaac aatggcggtt gtgtcgccta gggacaaaca    8580
atctgtctta ctcgtgtggc attaagcgac aactccaaag attttctttga taaacttggc    8640 ttgagctaca ctgttccccg gccgataaag atacttccac tcccctttaa cttggatgta    8700
agtttcgtct acccgccatg aatcattcgt ctgcttcaaa taaatgagga cgaatccgaa    8760
atccagttcc aagccgcatt tcaacaccca tcaattcagg gtggaatgat ccacgtctat    8820
gcctcgctcc tacatcatct cctccaagtc ccaatagaac aacgagcggc agtaccaacg    8880
cacattaagc aggatgattt ctggcaaaag gtgacgccat ttgaacaggg agcgagtgga    8940
aatggaaagc taagagcctg tcaagaaaca acttttacaa tttattatct agaaagctta    9000
ctgagaaagc atttctagct caaaagaggc aaggttgtta catgacaagc tctaagcatt    9060
aacgacaagg atttcctacc ctgcactatc tcactcagct ttttgcgaca caacctttaa    9120
aagcacactt ttaaaatgcg atgggcttac gccttacagg tacttgagaa acttgttgtt    9180
ttcatccacg ataatttttt tcggttcctt gatttcgtca gttacctcga atgctagcaa    9240
tgtgataagt tctcctgaat tgactaggtg ggcggagcca ccgttcatac agattacccc    9300
ggaattttcc tcaccttcta ggacataggt ttctagacga ttaccattag tgttgtccac    9360
caccataacc ttttcacccg gtagtatgtc tgccttttcc atcagaactt tgtctactgt    9420
aatacttccg atgtagttaa cgttggcttc cgtcaccgtc gctctgtgaa ttttcgactt    9480
caacataata cgcatcgttt ctttcctcat gtggctttaa atttcaattg agttgactga    9540
gaaatatctg agcctatatc tatttgagat ggctgatact tttttagcaaa taaactcaag    9600 tttttttgggg ctatagaaat accaaacttt aaatttataa tatcagattg tccatcaaac    9660
caaagtcgat ttagtagcct atactcttgt ttggaaaatg cagttcttcc atgcaaaact    9720
ctagtattat ctacaataat tatttggttt tgtgcaagtt taaaaattac ttgattgtca    9780
ggattattta caaagttttc aaatgattta atgccgcaa aacttttcga ttcaaccgaa    9840
```

-continued

```
acatgagctg cattatctgc tctaaacctt acaataagcc cagcatgatg ttcttcaaaa    9900
ataggtttag ttgcttttt attatctctt ttgactgtaa tcgcatcagg attaaacaaa    9960
gttaacaatc caactgggtt tgtccgcttt agatgttcat ataccagctt gccatcaata   10020
agcttggtga acccgccatt tgcagcagca atctggcact gcattgccat tacttttggt   10080
ggagtaattg tgaacgctcc atccgtatgt aacgataaat ctgtagttgt agtatttaca   10140
tattctggat aactatcaac aggactgatg ggaacaattc cctgtgaatc agaatgttcg   10200
tgctgaataa ttgttccaaa ataatcagac aattttaata agttattctt aggtgttgct   10260
gaaggttcgt gttctagtat tacgaatcca aactcattaa atttatttgc catctcagct   10320
tctttagaaa ctggcatttc taatacactt ttcactctaa ttattagatt ttcaattttt   10380
attgaataca ttttaattt tctcctggat gtcactgctc tgctacaact agcttaattt   10440
ttttagaatt ctcatgttta caataaatac gttttcaaaa aaatactat aagtcttgct   10500
gataggtt gtaaatccct cgatatagct aggtaataat caaacataaa attaaatgcc   10560
tctattgcat gtttatttag agcatgataa gtatgttaa acagaattat ttacattcag   10620
tagaccaaaa agctttccaa aagacttacc agctattgat tttccttggg aatgcaataa   10680
tccgccgata taagctttta agaggatgtt taaaaattg ggagttgagt aaaaatatt    10740
ttaaacatcc tctaatagtt taaaattcag ttttttacaa tacaaccatt tttaatccac   10800
cttgaggata aattgagaaa atatctcgta ctggttttaa aggaggtttg cctaccaatt   10860
ccaattgcca attccgcaaa atattagcca atactaactt cattttaaac tgagcaaatg   10920
ccataccaat gcaagttcgg ttaccgccac cgaaagggaa atactcataa tttaaaaatt   10980
tattatctag aaaacgttct ggcttaaact gtttagagtt aggatatagt tcttcccggt   11040
ggtgaattag ataaatacat ggataaagac aagttcctac ctcaaattga tgacctccaa   11100
tttctattgg cgattttaca attcgaggaa agtagttag accaactgga tatattctca   11160
aggtttcagc acaaactgca ttgagataag gtaatttgct tatttccgtt gggtctggat   11220
tatctcctaa ctcatctaat tcttgcaata acttggctct tatctctggt aagtaatgaa   11280
tccaataata tgcccatgtt attgctgcag atgtagtttc atatccagaa aagataagtg   11340
tcattaactc atcttgcaac tcctcatctg tcattttcc tccattttca tctcgtgctg    11400
ccatcagcat actgaggata tcattgttgt aattgttaca atttctcta cgttctttga    11460
tttctgcaga aatgatattt gcaatctgac gttggcaacg taaagatta ccccaggcac    11520
tccaagaacc ccagtctctt ctaaacacat tgaagaaaag agagctagaa gcaaagggat   11580
tagttatagt ggatactatt tgattaacta tcaatttgag ttgttgataa cgttccgttt   11640
tatctgaacc cagtaaaacc gttaacatcg ctcgcagcgt aatttctttg acttccttgt   11700
aaataatcaa tctttgacca ggttgccaat tagaagtaac ctgcttcgtt gcatggcata   11760
ttagttctcc atagttagat atattttgac catgaaaagc aggcatcagt agtttacgct   11820
gtcgtttatg actacttcca tcaagcaagg tgacggaatt gttgcctaaa aaaaatcctg   11880
ctaaatcgtt agcttagct tttccactgt caaaatactt gtgtttatca aaatttctt    11940
ttatatcctt aggattacta ataagtacta aaggttcaaa accaatagct ttgaaggtaa   12000
aagtgtctcc atagcgtgct cgacactctt ccaaaaattc acaaggatta ttaagccatt   12060
gcaataagtt ccaccaagat ggtgtagtgg gaccaggaag taatgaggat ttagcagtat   12120
taatcatttt agttatgctg gatttggcgt aaatttacta attagacttt ggacactatt   12180
gaatttcatt tttccaattg atgggttttc tgtgcttgtt caagagatat ttgcatttgt   12240
```

```
tgagccaata ccttgacatg aggctcactc agcattgaaa catgattacc cggaactata   12300
tggatttcca cttctccatc agaaaactga ttccaacccc atgttggctc ttggaaaatg   12360
tgagaataac tttcttgctc tggatttatc tccctcgcac aaaacaaagt gattggagtt   12420
ttataagtct tttccggttc atacttaatt tgacattgag tttggaaaac ttgtaataaa   12480
ccacgaacaa ttttgatatc tgtttgagca ggcaaaaaac caactatttc taacttttgc   12540
ttgaaataat ttaattgttg ctcccaagtt agagaagtta gagtttcata agataaaaat   12600
agattttctc caacaatatc ttcaataacc tcagccattc gacatatcca ctttgcatta   12660
tcccagttag aaaaatcatt ctgatgatta gcttgagaag ttggtgcagg agtatctaaa   12720
attccaacat aagcaacaga cttttccaata agttgtagtt gattcgccat ttcaaatact   12780
acatgactgc caaaggaatg accagccaag aagtaaggac caactggttg aactgtttga   12840
attgctttaa tgtgttggga ggctatttct tcaacacttt tatgaggttc ggtttcacca   12900
tcaagaccct tgtgcttgtaa accgtataac ggttgattat ttccaagata ttgtgctaag   12960
tggtggaagt agagaacatt tccacctgct cctggtacac agaacaaagg tggtaatgaa   13020
ccgttttgtt gaattggtac taatggagac caaagttcgg ctccggaatc ggaaccaaca   13080
agaagtgcta gtcgttcaat ggtgggattt tgaaaagag tggctaaagg taaatttttc   13140
tggaattgtt gttgaatctc ggacattaga cggacagcta aagggaatg tcctcctaag   13200 ctaaagaagt tgtcatgaat accaatagag ggtagattga gaacttcttg gaaaatctca   13260
actaactgac gttctgtttg attccgtggt tttgtctgct cagaagtatt caaacctcca   13320
tatatagcag caatttgttc ccgattaatt tctcctcttt gagtaagggg tatttgttca   13380
agttggacaa agttaatttg attgggtatc ccaaagcgat cgtgtagttg taactcttgt   13440
aaggagagtg cagcaagttc tggtgtggga gaggtgaagt aagcagttaa tttctgcttg   13500
ggctgacaat cacgaatcaa atgttcaaca tttgtttttag ttccatccaa tccgattaat   13560
agattatgtt ccgaaccaga taaagctgct aaaaatgagt aaaatccttg ttgaggagta   13620
ataataaaat agcccttagc acgactgagt tcttggaatt gatagccatg acttattccg   13680
gtttcattcc acatactcca agagcagcaa tagctttgga aaccgttttg ttgttgataa   13740
tcgctccatg ctgactgaaa actatttgct gcactataag ctgcaacatt ggttcctcca   13800
aagaaaccat ttacagaaca aaagtggaca aataaagcat tttctttatc cttgagcaat   13860
tgatgcaata cccaagtacc gctaacttta ggacgtaaaa cagcagcgat atttcctggg   13920
gtttctttct cgattggcgt ttcctgaata atcccagcca tatgaaatac cccatcaagt   13980
tgagtcctcc attcttgtgt tgcttttttct actacctgtt gtaaacctac taaatcacaa   14040
atatctacag tttgataaat tattgaacct ggtagttttt ctaattcttg atacctctgc   14100
aattttgtgc tagcttcctc attattatct tcaatttgag ttctaccaac taatattaaa   14160
tttgcttgat aatgttctaa taagtacttt gcaataacag tcccaattcc tccaagccct   14220
cctgtaagta gatacgttcc tcctggtaga atcggaattt tttgtttttc cttagcagtc   14280
atatctactg gttccagacc agacacaaaa cgttctctat tgcgtatagc aacttccaat   14340 tcttatcag cagaatacag ttcttgccaa atataactat tgttgagttc tggtgctaat   14400
ggtaaatcta aatgacgagt agttaaccaa ggcatttctt gactaacagt tttaagtaag   14460
cctaaaacag tggattttc gggttgaatt ttatctgtgg gatgaactaa ttggctttga   14520
ttagcaatcc ataataattt gactgcttgc tgtttgcctt gaatttcttc taaagcttgt   14580
```

```
actaaaaata gtaaactgta aattccttgt tgttgagtgg actctaaatt ttccaagcta    14640 gaaattttt cagtctgctc gttgtagttc caaagatgaa gaatttgact aattacttgg    14700
ctattttgcc tcaaagaatc aattaacaag cgatagtgtt gtggatttcc aggaacaaca    14760
gaataatgat ttgggctaat ttgagcaaaa tttgaaccaa tagtaacttg agcatatggt    14820
tgaacagttt gggacattcc tcggttatct tgttgccaac ccaaattatc tgtaaatatt    14880
agggttaaag ttttctgaga agaataattg agtaaagtat ttttactttc tttaatttgc    14940
catactttac ggtaaaacca gttgggaata gtattagtat tatcaagcaa caagtctaca    15000
cgctgtctga gagatttaaa ctcaccacat tcaaaacgtt gcttaaggag ggaacgttga    15060
attttaccga tggaagtttt gggaatcagt tctttatcta tgggtattaa ataacttgga    15120
tttatcccgc agtatttat aacttgttcc ctaacctttt tcaaaagctc taataattga    15180
ttcttctcag atacatacgg agtgaaaaag attactaatt cttcggtatt attgctagca    15240
acgcagactc cacaggctgc ggtataagaa acttcaacct ctcctaattc ttcaacaaca    15300
gcttctattt catgactata ataattaact ccattaataa taatgatatc ttttttgtcgt    15360 cctgtaatcg ttaagcatcc atcttttata aatcctaaat cacctgtatt aaaccaacca    15420
tcttcggtaa atgcttcctt atttgctttt ggattttgat aataaccaga agtaacggtt    15480
aatcctttga cctgaagtaa accaatttca ccttctgata atacttccat gtcttgattg    15540
actattctca gacaagtacc cctaatcggt tttccaagat ttacaaagga attatcatct    15600
gaacttgata gagtgaaaaa attgtcagaa taagtaatac cagaggaaac ctcagccatt    15660 cccccaagatg gagtcatagc atccccaggt aagccaaagg gagcaagtaa tttcaaaaaa    15720
cgtcttgctg ttgctgcaac aatttgttcc gcaccattta acatcaagcg aatagaagat    15780
aaattccaat tctgcttttc tatttcttga acaaaatcat taattaaact ataagcaaag    15840
ttaggagcaa aagtaacagt gacaccaaaa gtatcaatcc aatccaacca tcttaaaggt    15900
ttttcaatca ctaattgact agtagcatga atttgtttac atcctaaata aatatcccgg    15960
atatgaaaat atattaaacc tgcaacatgg tctaagggca tccaatttaa ggttatatct    16020
tctggggtaa aattattcat ttgtattgaa ccaatagtcc tactcagtag atttaaatgg    16080
ctcaactgta ccaccttaga catacctgta ctaccggaag taagcatgaa cagtgctaaa    16140
tcttctggtt gggcattata gtaatctttt tctgttgaga acttttgtaa acttttcaata    16200 gtttctaact taaagttgtc gtcatttaga ttttgagacc atttctttag ttctgacaat    16260
gattttttat ctgttaaaat caaaggtctt tctaacatct gccaactatt ttgtaattta    16320
tttagattga cattgggctg gtcatagctt acaggaatta caacgggtac gggaataaag    16380
cctcccaaca cacaacccca aaaagcacta ataaaatctt tattttcttt taattgcaaa    16440
ataactttat cttgtggctt aattcccagt tttctgaagc cacctagaat tctttgagca    16500
tcttctaata actgggcata tgattgaact tgttcggaac catcagagtt aatataagtg    16560
attcctttgt gaggaaattt cccagcagtt ttttgcagca tctcccctaa agtttctgga    16620
gatgattctg gaaagattaa tacttcttcg tggctgatgg caggtgattt tatttctaat    16680
agggaactac tctcttttcc cctagcagtt ctgggagttt caactggagt agaaccttga    16740
ttgaaaatag cttggattga tggtaaaagt tcttctaaat gtatcggaga aatcgttttt    16800
acatttggct caataaaaac agcaacttta tcaatttccg cctgagaacc tatttgttct    16860
tcccaagtgt taattaactc agaatcaatt atgctaatag aagctaaacc tacttcatca    16920
acttctccaa aacttgtcaa tggtaaagca gatactggta catagatgca gggtaatggg    16980
```

-continued

```
tatccaggta actgagattt taaataatgg tgtaaaaact ccctagccca agaaccatct      17040
ttgactacgt aagcgactaa tttttgattg cgtaccatta catagcaatc ttctacccct      17100
ttcgctgttt gtaaagcttg ttcaatacgt tgtaggttaa ttcgttgtcc attaactgtg      17160
acaattcgat gctcttttcc tagcaattcc agagaaccat cgactcgacg acaacccat       17220
tcccctgttt taataactt acccagttgg gtatgttcta tgaaacttat aaatttttct       17280
ggttctggat gtaacttgtc tgggagtaaa tcgcaattcc ccaaataaat ttctccttct      17340
acactcaaag gaactaattg ttgatggtta tctaaaatgt aaatttgtaa attatttgaa      17400
ctcaggaaat gaacatattt atccagcagg taagttgtag cgatgttatt gtaactgtgc      17460
agtacctgct cttgctcaga atctgtgaat aatggtaatt cacttatctt ttgttggggga    17520
ttttctacaa tcgcgctaca cagattctgg aaatgagcag tcatgcgctc aatagttgac      17580
ccatcaaata agtcagtgtt gtattcccat gaacccacta gtgcttcgga agtttgctgc      17640
attgatactg ttaaatcaaa ccgggctgtt tctgtttgag aactcaataa attaagggtc      17700
acaccaggta attctaattc acccatgggt gcattctgca acacaaacat tacctggaat      17760
aagggtgcat aactcaaaga gcgttgtggt tgtagtactt caactacctg ttcaaaaggc      17820
acatcctgat gttcataagc ttcaagtgta gtttccctaa cttgtgccag caaattctca      17880
aaactgggat tatcttcaaa acgggttttc aataccaaag tattggcaaa aaagccaatc      17940
aaagactcaa tttcactgca gttgcgattg gcaatgggtg aaccaattaa aatatctaat      18000
tgaccgctgt agcgatagag taaagtggca aacgctgcgt gcagggtcat aaataaggta      18060
gtacccgagt tccgagacag ggtttgcaac ttctctttta aatcagtatt taaactaaaa      18120
cttttgagtag taccccggaa agtttgcacg gttggacgag gacggtcagt aggtaattgt      18180
aacaattctg gtgcaccctc taactgagaa agccagtaat tgagttgagt ttctagtacc      18240
tttccactta accattgtct ttgccaaact gcaaagtctg catactggat tggtaattct      18300
gccaagggggg atggttttcc tgcactaaaa gcttgatata agtagatag ttcttggctg       18360
aatatcccca ttgaccaacc atcagagaca atgtggtgca tcgtcagtaa taacacatat      18420
tctctggcat ctaactgcaa taaactacac ctgattagtg gtgcagtttc taagtcaaag      18480
ggggtaattg ctgcaagttg tgcttgttgg tgaaggacac tttcccgttc tgttgcttct      18540
agttgctgta agtccgccac actgatgttc atggtggctt ctgggtgaat tacctgtatt      18600
ggtgtgccat tcacagttcg gaagctggtg cgtagtactt catgacggcg gactatttct      18660
gataatgctt gttgcaaggc attaatatcc aactttccag tgacacgaat tgctcctggc      18720
atgttataag tggcacttga cccttcaagt tggttgagga accacaaccg gtcttgtgca      18780
aaagataggg gtaattgttg gttctgtgtt cttggctgaa tgggggggaag acttaatgcg      18840
ctattagtag tacgtaattg ggttaatgtt tgctctaatt gagctacagt gggagaggaa      18900
aagactgcac ttagttctat ttctacttca aaggcaactc tgagtcggga aattaatcgg      18960
gttgctagta gggaatgtcc tcccaattca agaagttgt catggattcc aacatttgc        19020
acacctagaa tagaagcgaa gatgttggct attatttctt cacccgatgt acgtggtggg      19080
acatattcat gttctcggct aatttctcca tcaggtgctg gaagggcttt acggtctatt      19140
ttaccgctgg gtgtcaacgg taaggtgtct aagatgacaa aggcactggg catcatgtat      19200
tctggtagct tttgtttgag gaattcacgc aggtgatagg tacttagtga ttcatcctca      19260
cagactatgt aggctactaa acgtttgcta cctggaatat cttctatggc aatgacaacg      19320
```

```
acttgttgga tttgggggtg ggtactgagg actgcttcga tttctccaag ttcaatgcgg    19380
aagccccgca ccttcacttg gtgatcgata cgccctacaa attcgatatt accatccggc    19440
agccagcggg ctaggtctcc agtcctaaac aatcttctg cttgtgcctt tttacttttc     19500
cccctgtcct tcacaaacgg gttggggata aacttttccc gcgttaactc gggcagattt    19560 aaatacccctt ttgcaagccc atctccgccg acgtatagct cacccgtaac accaggtggc   19620
aaaagatcgc catacttgtc gaggatgtaa atttgtgtgt ttgaaatcgg ttttccaatc    19680
ggaatcgtat ttcttttcag atattcttct agagcttctc ctaaatctgc tcttcgctcg    19740
tctgccaact gcaaatgtat tatttcttta tgcaggacag cagtttccct atcccctgag    19800
ccactaggaa gattttttaa agcatcaagt ttctctttac tttttgcttc aatttgattt    19860
gcgattctca gtttgacttc aaagcatgta acatcagcgg caacttctga agagccgtag    19920
agattgaaca atctggcaga gctgattttc tggtgaaatt ccttagccaa ggttagcggt    19980
aagacttcac cgctgcaaaa gacatatttg agatatcgaa gttttgtcag ttgttggggc    20040
gcattttcca gtatcgcttt taatagcgat ggaacgagaa caattctagt tacctttcga    20100
tcgctcaaca ggctcattag cctgggaata ttgccccgta tatcatctgg aacgatcaca    20160
aggggaattc ctttgagaag gggagaaaat atttccgcaa catgatcgcc aaaattgatg    20220
gatgttttct gagagcaaat ctcatctgcc ccaaatggta gcattcccca gatccaatgc    20280
aagcgattga caatgccgcg aagcgtgccg agaacggctt tgggttttcc agtagaacca    20340
gacgtataga ttgcgtatgc aaggtcatcc agtgttgttt gccgatccag attttcaacg    20400
ccttccctag caatgacatc cctatccctg tccaggcaaa cgatatgggc attttgaggg    20460
gaaatctttt cgagcagagg ctgctgggtc aaatgatat gcacattgga atcttcctgc     20520
atgaacgcca gtcgttcttg cggatagttc ggatctaacg gcacatatac accaccagct    20580
ttaagtatcc ccaacagtcc tacaatcata tcaatggagt attctatgca aatacccacc    20640
agcacttctg gtttcactcc cagagtttgt agataatgtg ctaattggtt cgcttttttga  20700 tttaattgtt ggtaggttga ttgttcttct tcaaacacca ctgctatgga gttggggttt    20760
ttttctacct gttgctcaaa taactgatga atacatttat cagatgggta atccgttgca    20820
gtgttattcc actcaaccaa taactgatga cgttctactt cacttaataa aggtaattga    20880
gctaccttat gtgaaggatt ttccacaatt gcaattgctg ataaaacagt ttgcagatat    20940
cctaaaatcc actcaatagt atttgaagag aaacgagcag tatcgtaact aatcctaact    21000
gacaacttat ccccaggaac tgcaactaaa gttagtggat aattagtttg ttcaaaaacc    21060
tctatatcac ctaagtgtaa tgaaccttct tcattcaaca aagaattatc aattggataa    21120
ttctcaaaca ccacaatgct ctcaaacaaa ggtattccac ctggtatctc agaagtagct    21180
tgaatatcaa caagaggagt ataaaaatac tcttgtaatt caaccattga ctgttgtatt    21240
ttttgcaacc aaggtatgag ttgctcctgg gtggatactt gtactcgtaa gggaagggtg    21300
ttaataaaca gtcctaccat attttctatc tcagagaggc taggaggacg accagaaaca    21360
gtcacaccaa atactacatc tttctcacca ctataacgac tcaatagtaa agcccaagca    21420
gcttgtacta cagttgataa agtcacatga tgttgttgtg ctatatgaag taacttctga    21480
gtgcattcag gggataaaact acttgttctc tcctgataat ccgcagtttt atactgttgc    21540
tctttcagaa attgagtttt atccattacc aatggagtgg gagcactaaa accttgtaaa    21600
gtttgttgcc aaaactcaat tgctgctgat tgtcttgag aattcaacca agcaatataa     21660
tcctggtaag gacgtggttt tggcaattgg caattttcac caagcagatg tgctttatag    21720
```

```
aaaattaaaa tttctttaaa aataattgat aaacaccatc catccataag gatgtggtga  21780
tgactccaga taaatttgta attatcttcg cctagcctga ctaacgtaca ccgcattaat  21840
ggtgcttggg ataagttaaa accttgttct ctttgtgttt gcaataattg ttttaattgt  21900
tgttgttgat cattagaaga aagttctcgc caatcaagag tattccaagg aacattaacc  21960
tgttttagta ctacttgtaa tggagtttgg cgattttccc aaacaaaaaa tgtacgtaga  22020
attgaatgtc tatctaaaac ttttttgccaa gctctttcaa aagcagcaac attgatattc  22080
cccttcaaac cccaggtcat ctgttcaaga tataccccac tataaggtgc ataaagactg  22140
tggaacagca tcccttgttg catgggagaa agtggataaa ttgaagagat atttcttcta  22200
atttcttcgt tgctcattgt tctctctttt tttatctata ttttttatat ttacactatt  22260
tgcccaagtt ttttaataac tcatcaagtt ctaattgatt taactgtgca tctgggaaat  22320
cactagctgt atatccaaaa ccattttctg actggcaatg ttctattatt gacttaattg  22380
cttgaatata gctttgtgtc aaattttta ctgtatcatg agtatgaaaa ttactactat  22440
aagtccaatc aatttgtaat tcaccttcta ccaccagact attaatctct aatagatggt  22500
gacgagtttg ctttgaacta tgattatctc cagtagattc tggcgcaaat ttccaacccg  22560
tttccgattg tatttggtca aattgtccta ggtagttaaa actaatttct ggagtaggaa  22620
ttgtctgtag ttttttgggtt acagtagtat cttcacacaa gtaacgcaat ataccaaagc  22680
caataccacg atggggaatc tctcgtaatt gttcttaat tgacttgata acttctgctg  22740
gttgtttatc gtctggtaat cgcaataata ctgggaataa actggtaaac caacctattg  22800
ttcttgataa gtctacatct gaaaatagtt cttctctgcc atgtccttct aggtcaatta  22860
gtactttga atctcccgtc cactctgcca aggaaaactac taatgcactg aggaggatat  22920
cgttaatttg tgtgttataa gctgagttta ctgaccccag caaagcgcgg gtttcttctg  22980
gactcaattt cactctataa ttaatcgcac tatcaactgt tttttctgct tgagtgtgag  23040
cagaatctaa tggtagtggt gttgtttctg accaaggttg gttgagccaa tagtctaact  23100
cttgtttgat tttttctgat tgtgcataat ttttcaattt ctctgcccaa tcaataaatg  23160
ctgttgtttt cgcatttagc tgtattgatt gttgagcgat tagttgttga tagattgttt  23220
ctaagtctga tagtaaaatt cgccaactca caccatctac tgctaggtga tgaataataa  23280
tcagtaaacg ggcatcaact tcactaccta agttaaacat caccacttgc attaaaggtc  23340
cctctgagag gtttaaactt gcttgatatt ccgtggcgat ctgtgataaa gcttgtggtt  23400
gttcaatgac aggagttgat gataaatcaa ctacagtaaa tgctacggga tcatcaaagc  23460
catggtttat ttgtttgtac tcagatgcaa ctgatgtgaa tcgtaaacgc agagcatcgt  23520
gatgctctaa taatttttc aaggctgttt cgattaattc agtttgcaga tgattgggaa  23580
tctgcaataa aactgattgg ttgtaatggt gtgcttcttg gctattttgt gcaaagaacc  23640
actgttgaat tggtgttagg ggtgcaactc cagtaactat accttggtta gcactgacag  23700
taactgttgt attggctact aatgctagtt tggcgatggt ttgattttgg aatatttgtt  23760
tgggagtgat ttgtattcct aagttttgg cacgagaaac tacttgaata ccaaggatgg  23820
agtcgccacc aatttcaaag aagttgtcat ggatgctgac ttgttcttta aggagcagtt  23880
cwtgccaaat gttggttaag atttgttcta tttctgtgcg tggtgcgaca tattcatcct  23940
ctcggctaac ttccccatca ggtgcactta gggctttgcg gtctacttta ccgttgggtg  24000
tcaacggtag ggtgtctaag atgacaaagc tagaggggag catatattct ggcaatttag  24060
```

-continued

```
actttaggta ggagcgcaat tcattgctac tcagtacctt acgttcaggc tttgacttat      24120
taattgtgta atcttctaga ttattttcag caaacaatcg ttgataaaaa gggttttgct      24180
taaacaattg tttccaatga tatgagatgt attcaaactc aatctctttt ccagtttttt      24240
ttaaaagacg acctcgaaga gtataatctg gattcaaatt attttcacaa agcgttctcg      24300
tacaaacagc ttcgatgata tctccttcat ttacataaat tcctggttca aacactggaa      24360
gataaactgg taaccagcaa tgttcatttt ctaaaatatc tatacattct ccttcaattg      24420
tgtgtaagtt taatcccact gaaaaaccat ctaatcttcc tgattttca atagttaatt       24480 taatttggtg agtagattct gtgctaacaa gcttgctaaa gtctaaatcc tcaaaaactc      24540
ctcgattgga caaccagttt acttgattta atcctttaat acatactcgt aaatcaaaag     24600
gatatccaac ttgctcaaat atcttctggg tataataacc tgaaactttt gtaaattggg      24660
gttgatttag taattcatca ggaagagtta ctgcaataat ttgagtcaca cttctttggg     24720
gaatcattac accatctgat ttgagaaatc ttctggcgtt gttgataatt actgctgctc      24780
cttcagatcc accaatgggt cccacaattt cagaaacaca tacatcaact tcttctggta     24840
agttggctgt agtagcgtct ccatgtatga tttgaatttg ttctgataac cccaactctt      24900
gcacgcaagc tgaagctaac ttactggttt gctcgtctct ctcaattgcg tagactttct     24960
tagcacctgc ttctgcacaa aatctggcta taattgcatc cttgcccgtg ccaatttcaa      25020
caactacttt atctttaacc atttgattaa ttgcgacttg gtaactctgg tttcgacgat      25080
gatcattggt catcgcatag tacaagagct catcataaac gtagaattct gctactgagg      25140
gccaaagttc aattcctgtc tggggctggg gatctttttc ttttgactga agaggaacta     25200
aatatgctac caaccgtttg tgacccggag tatcttccct ttcggtgact gcgacttgct     25260
gtacttgagg atgggtactc agaactgatt ctatttctcc tagttctatg cggaaaccac     25320
gtattttcac ctggttatca agacgaccaa gaaactcaat attaccatct ggtaagtatc     25380
gagctaaatc tccagtttta tatagttttg atctgctatt gaagggggtta gggatgaatt      25440 tctctaaagt taattccggt cggttgaggt aacctctggc taagccataa cctccgatgt     25500
ataattctcc ggatacactt atgggtactg gttctaagtg cttatctaag atatagattt      25560
gggtgtttgc aatggggcga ccgatagtaa ctttctcgct accatggctg atttgagcca      25620
ctgcagcacc aatagtagac tcagtaggcc cataaccatt aaacaaacga cgaccaacag     25680
accactgatt ggccaattck amwytasaag swtcccctgc cacaattatc tgacccaagg     25740
ctggaaattc atcagtagct agtactgcca gggcagaggg aggtaacgta acatgagtta     25800
cacatctttc ttgtaaaatt tgctttaaat ccgaacccgg gattaactca gaagctatag    25860
ccaaaattag cattgctcca gaagtcaaag cgataaatat ttccgaaact gaagcatcaa      25920
aacttataga agcaaattga agaacacgac tatttggttc tagataaaat aaatttttct     25980
gtgcttgaat aaggttgcac aaagaaaaat gttcaatccc aaccccttg ggaactccaa       26040 tagaaccaga agtataaatc acataagcca aattatctga acatacccca acatcaagat     26100
tctcctgact gtgttgctca atcactcccc aatcactatc caaacaaacc acctgtgcag    26160
tatgtgacgg caaagattcc agtagggact tttgagccaa caacacctca acacctgaat     26220
ccgccaacat ataactcaac cgttcttggg gataattggg gtcaaggggt acataagccc      26280
caccagcctt gagtatcccc aagagcccta ccaccatttc aaaagaacgc tccacgtaaa      26340 tcccctaccag cacctctggt tcgactcgca aggaaagcag gtgatgtgct agttggttgg    26400
ctttttgatt taattgttgg taggttaact gctgattctc aaataccacc gcgactgcat     26460
```

```
ccggtgttct ctctacctgc tcttcaaaca attgatggat acatttactg ggatattccc    26520
ttgctgtatc attccactcc accaacaact gatgccgttc tacttcactc aatagggtg     26580 attcacttac cttttgttga ggattttcca caatcgctga caataaattc tggaaatgac    26640
cagccatgcg ctcaatggtt gactcatcaa acaagtcagt gttgtactta aaaccccaa     26700 aaacagatga actcccctcc accatttcta aacctaaatc taactgacct tcctgttgag    26760
gtatttcata aggttttatc ttcaattctc cccaatcaac ataggtttct atttgattta    26820
caaacaactt ctgtatatct tgagattttt ggaactgcag tagagaaaaa gaagcctgaa    26880
aaatcggcga acgactgggg tcgcggtgtg gctgtagctt ttctaccaat agagcaaatg    26940
ggtaatcttg atgagcaagt gcttccaata cggtttggcg tacttgggcg aggaaatctt    27000
tgaaactggg atttcccgat aaatttgctc gcataacaac aggatcaaca agtagccca     27060 agatcgaagc aaacttagct tgactcctac ctgaggtggg agaaccgact aaaatatcct    27120
cctggcctgt gtaacgatac aaaaacacct gaaaagttgc taagagcatc atgtaaagtg    27180
ttgctcccga gtttaaagcc agctccttga gttgcttagt gagcttgtca gataaatttga   27240 agtgatggga agcaccatta taagttttta tcggtggtcg ctgtcttgag gttgctaggt    27300
ttagtgctgg caaatcgcct gtcagttttt gctgccagta gttccagagt ctttccccttt   27360 cagtctcctg caaaatattc ctctgccaac gaacgtaatc ttgtaagaa tgctttagag     27420 gagaaagggg tgtcttaaaa tcagcccatt gtacttggta gagttgtggc aactcctgta    27480
ttaacatatc taaagaccag gcatcgcaag caatgtggtg tatggttagc aacaggacat    27540
gttctttctt ggaacgagta aaccaccgaa ctcgcataac aggccctcgt tcgaggtcaa    27600
aatattgttg atggctctca atcactttcc ctttcagttc atcttcactc caagcagaag    27660
catcaatttg caagaaattt aattcctgaa aattatttac ctgttggatt gactcagatc    27720
cgagtttggg ataatttgta cgcaatatcg gatgccgttc tattagtttc tcaaatgcct    27780
tttgcattgc tgtaatatct actgttgagc aaatacgagc gacaaatgat acgttataag    27840
catgactttc tggtgctaat tgccacaaaa accaaagtgc ccgttgaccg taagaaaggg    27900
gatagacgtt taaaatatct gggcgatcgc gcagcaattg taatatttcg gttttgtatt    27960
gtttcagttg agctaatact aaagcagttg attcttcttg aggagcatcg taacaaagcc    28020
gttcgccctc actccacact tgccaacctt ttattgaaat atcttgtaaa aattcgatta    28080
aattcataat tcacctctta tccgctcgtt ttctttccta ttgctttggt agagttgccc    28140
attattttct gactcaactc cttgattctg agcaacttgg ctcagttgct cattcacttc    28200
agtggctaaa tcaacgatac tgatatcttc tataaatttg actatagata tatccacgag    28260
caagtcagtt tgaagcctat tgtgcaattc cacagccatt agagaatcaa gccccatagt    28320
gttcaggggc tgttgcatat caatttgaga agtgctcaaa gaaagtactt gagaaatttc    28380
atctttaatg taaattatca aaagcttttc tctttctctt ggtaaagcag cttttagctg    28440
ttctaaaaat tcattgtgct ttgtctttgt tttgagggct ttttgctgtg atttgctttc    28500
ttttaccaat tgggacagca atggtatttg attaccaaaa ctaaattgct cttggaacac    28560
tgaccattga attggtagga ctcctacttg tggtatggat tgttcgagta attgtcctag    28620
aacctgcaat ccctgttctg aagacaaaaa agtcattccc ttggacacca ttctatcttg    28680
atgaggacta tccaaatttg ctgccattcc ctcttgtgcc catggtcccc agttaatgct    28740
caagccaggt aaacccatac cccgtcgatg atgggctaaa ccatccatga aagcattagc    28800
```

```
agcagcataa ttcccttgac caggcgaacc caatattgaa gccatagagg aaaaacaaac   28860
aaaaaagtcc aaaggtagat tctgagtcaa attatgcaaa tgccaagccc cttgtacttt   28920
tggtgccatc acctgtgtaa attttcccca attcatgttt aacagcaaac catcatccaa   28980
tatcccagca gcatgaatta ttcctcgtaa tgctggcaaa gatactttga ttgactctat   29040
aattcttgcc acattttctt gttgggaaat atctccacac aggactaata cttgcgctcc   29100
tgccttctgt aattgttcaa tggtttgttg agcttttgct gatggctgcc tacgtccggt   29160
aagtactaaa tatttgaccc cttgttgtac catccactca gcggttttta accccagtgc   29220
tcccagacct ccggtaatta agtaactggc ttcggcttgg attaggttgt ctaaagactt   29280
atattctgat agcttcagtt gaatggttg ttgcgaggaa atttgtaatc cggactgtgt   29340
agatgtactc attttttgtt gccgctctaa ccgggcaacg tgacgtaccc cttgacagta   29400
agcaatttgg ttttcatcac caggagataa tagttcctct aacaaagcag ctactgtttg   29460
ggaatcttcc atagttggat ctaagtctaa acaccggcat tgtaattccc tatgttcctg   29520
ggcaattact cgacctaacc cccataaagg tgtttgttgg aattgtatag aagggactc   29580 attacccaca gattgtgagc cttgagtcac taaccataat ggggcacttt ccatatcttg   29640 atttttact aaggcttgga ctaaatgaag tacgctgcca cagcccagtt cttgggattt   29700
ttgcaactcc tgtgccccag tccttagtgc tattgttgag tccaaactcc acaggtgaat   29760
aattcctcgt aatgggggtt gctgctccaa gcttgattgc aataggtgca ggaattcctc   29820
aggatggttg gggttgattt gataatgttg agattctaac tgctggtaat tttcccctgg   29880
tgttactaat atacaatgcc aaccttgttg ttctaaggat tctaccagat gtttgcctat   29940
acctgtgggt ggggaaaaca ataaccagct acctgatttt gttaagtcaa ttgattggtt   30000 atgggtgaa attgattggg tttgccaatg gatttgatat aaccaattat taaattttgg   30060
ttcaatatta cgcaacaaag cctcgcgaga agtacgtaat aaagttaaac cttcaactct   30120
tgctactact attccttgtt catccaataa acaaacttta ccgctcaaag tttgtttatt   30180
agtttctgtt gcacctatct ctacttgagt ccacaaacta ttactaccac tccgataaat   30240
ttgtagtcgt tttatttcca atggcaaata agtttcttgg ttgtccgttt tacccataac   30300
tgctgctaac acctgaaagc tagcatctaa aagaattggg tgcagttggt ataaagttgc   30360
aacattcacc tcagtttctg gtaactgaat ttcacctagt gcttttcctt cgctgtgcca   30420
cagttgttta acggcttgga aagaagaacc gtaattaaga ccccattctt caaattttg   30480 gtagaattca gtaggtaata tctgttggtt atactcgtct ttaatcgctt ttaagtttgt   30540
tgtttctaat tgggggtctt tattacctac taatattttt ccttcaatat gtagaatcca   30600
tttaggttct gaagaattag tgtttatatc caaactgaaa atttggaatt tatagctttg   30660
tactaactgt aaatttaaaa ctatctgaat tgtattaatt tcatcctttg ataaaattaa   30720 tacttttgg attgctatat cttctaggat taaatcatct gaattgaata aaattgaacc   30780
tgctgctaag gctatttcca gtaagctgc tgctgggaaa acaggttgag aaaaacaca   30840 gtggtgttgc aggtaagttg gttgagaagc actaatttga cattcaaaac gaatttgctg   30900
ttctaaggct gctaaatgta atctttgacc gagtagaggg tgaagatttt tatgatttga   30960 taaaactgt ttttgatgta ttagattatt atttgtctca atccaataac gttgccgttg   31020
aaagggataa gtcggcaata ctaccttgct acgagaataa tctttatcaa accctaacca   31080 atcaactta actccatgca catatagttc agccaaactt tgtagcattt gctgccagtc   31140
ttcttgacct ggtttcaaag aaggcaacca aactcccaca tcttctggca agcactgtct   31200
```

```
tcccatgcct aacaaagttg gtttgggtcc aatttctaag aagatggaat aaccttcttg    31260
ctgtaatgtg tccatacttt gggcaaattt caccggttgc cggacatgat ttacccaata    31320
gcttgctgtg gcaatactat tctctgccct agctcccgtt acatttgata ctaatggaat    31380
atttggttga ttgtaggtta tttctgatgc tactgcttca aagtccgcca acattggttc    31440
catcaaatgt gaatggaatg cgtgggatac ttgcagtcgt tttgtcttaa tgtcttctgc    31500
ttctaagcta ttttgaaccg ctccaattgc ttctgcctca ccagaaatga caatgctttg    31560
gggtccgtta atcgatgcga tcgctacttt ttgagagtat ggtgcaatta gttgatttac    31620
cttttcaatt gaagccatta cagataacat ttcaccccca gagggtaact gttgcattag    31680
tcttcctcta tgagcaatca gttttaaacc atcttctaaa ctaaatattc ctgctactgt    31740
ggctgccaca tattccccag cactatgccc cataaccaca tccggtttta ttccccagga    31800
ttcccatagt ttataaagag catattctat tgcaaataaa gctacttggg tataggcggt    31860
ttgagctagg acatttttcct gtacttgagc gacatcaagt atttctaata aggtttgtc    31920 taagtagttt tctaatattt gggcacattg atcgctagta cctctccata aaacttggta    31980
tacgcaacta attgcttcac caattccggt tgatactta atattcctgc gtctaccacc    32040
gcaactattt tcttcggctt tgtctcctca tctgccgaaa ttacttgcgc tagcgtcggg    32100
tttttcaact caaataaatt ttgggtgaag taaatctcat agttaaaagt aaccgaaaca    32160
cgttgatgaa ttaatctatt tttttgcttg atgtcaacta tcatattttt gcaggtatat    32220
ctaaaagtgc agtactattc aaagcttcaa ggaaaacctc aaccgagtga gaaccattta    32280
ccttgacttg attattcatg atgaaaaacg gcacgctgtt gatgccattt aagcgagcaa    32340
atgccgattc agcaacaact gtatcaacga catcgcgatc gtttaattgc aactttaatt    32400
cggtagcatc catctggtat gctgtaccga tggcaacaat aacgttaata tctccaatat    32460
tcaaaccctc ttcaaagtaa gctctataaa tagcttcaac gacatcattt tttatgtttg    32520
tcggtgctaa tgcaatcagt tggtgagcaa gcttagtatt gacagccaaa cggattttt    32580 caaaatctag cttaaccca gccgcctccc ctgcgcgttg cgtataatca acatctgtt    32640 gcatttctgg cgctttaatg ccttttctat tttgcataaa gctactaaat tcgtacccct    32700
cagcaggaac agtatcatcc agaagaaagg gatgccatcg gatatttact tcttgttctt    32760
gccattgtgc cagtgcatca aatagatgtt ttttcccaat tctgcaccaa gggcaaacgg    32820
tatcatgaaa gatatctatc agcatagttt ttgtcactca aatgctaata tttgtgtgca    32880
tctggggttt aaaatctcgt tgcagagccg ttgtatttaa aggctggaga aaactattaa    32940
ttttctcttc aaaaaaactt tgagtatttt caaactcttt aattaatgcc tctctatcct    33000
tcctagccac cagtctagcc aatcggctgt aagtttagc taaaaagcta atagcattac    33060
acctttcttc agtcgctagc ataatatcaa cgcataaatt aggattttgc gaaaataaac    33120
gttttacaat atcaatctct tgacgatagt taggagttga cattgttaaa ctctgctcta    33180
tctctactct tgattgtgct aagaaaacac caagactaaa tctacagaaa tgctgcgtgg    33240
cttgaataat caccatcatt                                                 33260

<210> SEQ ID NO 2
<211> LENGTH: 3690
<212> TYPE: DNA
<213> ORGANISM: Nostoc species

<400> SEQUENCE: 2
```

-continued

```
atgggcata gtgctgggga atatgtggca gccacagtag caggaatatt tagtttagaa      60
gatggtttaa aactgattgc tcatagagga agactaatgc aacagttacc ctctgggggt     120
gaaatgttat ctgtaatggc ttcaattgaa aaggtaaatc aactaattgc accatactct     180
caaaaagtag cgatcgcatc gattaacgga ccccaaagca ttgtcatttc tggtgaggca     240
gaagcaattg gagcggttca aaatagctta gaagcagaag acattaagac aaaacgactg     300
caagtatccc acgcattcca ttcacatttg atggaaccaa tgttggcgga ctttgaagca     360
gtagcatcag aaataaccta caatcaacca aatattccat tagtatcaaa tgtaacggga     420
gctagggcag agaatagtat tgccacagca agctattggg taaatcatgt ccggcaaccg     480
gtgaaatttg cccaaagtat ggacacatta cagcaagaag ttattccat cttcttagaa      540 attggaccca aaccaacttt gttaggcatg ggaagacagt gcttgccaga agatgtggga    600
gtttggttgc cttctttgaa accaggtcaa gaagactggc agcaaatgct acaaagtttg    660
gctgaactat atgtgcatgg agttaaagtt gattggttag ggtttgataa agattattct   720
cgtagcaagg tagtattgcc gacttatccc tttcaacggc aacgttattg gattgagaca   780
aataataatc taatacatca aaaacagttt ttatcaaatc ataaaaatct tcaccctcta   840
ctcggtcaaa gattacattt agcagcctta gaacagcaaa ttcgttttga atgtcaaatt   900
agtgcttctc aaccaactta cctgcaacac cactgtgttt tttctcaacc tgttttccca   960
gcagcagctt acttggaaat agccttagca gcaggttcaa ttttattcaa ttcagatgat  1020
ttaatcctag aagatatagc aatccaaaaa gtattaattt tatcaaagga tgaaattaat  1080
acaattcaga tagttttaaa tttacagtta gtacaaagct ataaattcca aattttcagt  1140
ttggatataa acactaattc ttcagaacct aaatggattc tacatattga aggaaaaata  1200
ttagtaggta ataaagaccc ccaattagaa acaacaaact taaaagcgat taaagacgag  1260
tataaccaac agatattacc tactgaattc taccaaaaat ttgaagaatg gggtcttaat  1320
tacggttctt cttttccaagc cgttaaacaa ctgtggcaca gcgaaggaaa agcactaggt  1380
gaaattcagt taccagaaac tgaggtgaat gttgcaactt ataccaact gcacccaatt    1440 cttttagatg ctagcttcca ggtgttagca gcagttatgg gtaaaacgga caaccaagaa  1500
acttatttgc cattggaaat aaaacgacta caaatttatc ggagtggtag taatagtttg  1560
tggactcaag tagagatagg tgcaacagaa actaataaac aaactttgag cggtaaagtt  1620
tgtttattgg atgaacaagg aatagtagta gcaagagttg aaggttttaac tttattacgt  1680 acttctcgcg aggctttgtt gcgtaatatt gaaccaaaat ttaataattg gttatatcaa  1740
atccattggc aaacccaatc aatttcaccc cataaccaat caattgactt aacaaaatca  1800
ggtagctggt tattgttttc cccacccaca ggtataggca acatctggt agaatcctta   1860 gaacaacaag gttggcattg tatattagta acaccagggg aaaattacca gcagttagaa  1920
tctcaacatt atcaaatcaa ccccaaccat cctgaggaat tcctgcacct attgcaatca  1980
agcttggagc agcaaccccc attacgagga attattcacc tgtggagttt ggactcaaca  2040
atagcactaa ggactggggc acaggagttg caaaaatccc aagaactggg ctgtggcagc  2100
gtacttcatt tagtccaagc cttagtaaaa aatcaagata tggaaagtgc cccattatgg  2160
ttagtgactc aaggctcaca atctgtgggt aatgagtccc ttcctataca attccaacaa  2220
acacctttat gggggttagg tcgagtaatt gcccaggaac atagggaatt acaatgccgg  2280
tgtttagact tagatccaac tatggaagat tcccaaacag tagctgcttt gttagaggaa  2340
ctattatctc ctggtgatga aaaccaaatt gcttactgtc aaggggtacg tcacgttgcc  2400
```

-continued

```
cggttagagc ggcaacaaaa aatgagtaca tctacacagt ccggattaca aatttcctcg    2460
caacaaccat ttcaactgaa gctatcagaa tataagtctt tagacaacct aatccaagcc    2520
gaagccagtt acttaattac cggaggtctg ggagcactgg ggttaaaaac cgctgagtgg    2580
atggtacaac aagggggtcaa atatttagta cttaccggac gtaggcagcc atcagcaaaa   2640
gctcaacaaa ccattgaaca attacagaag gcaggagcgc aagtattagt cctgtgtgga    2700
gatatttccc aacaagaaaa tgtggcaaga attatagagt caatcaaagt atctttgcca    2760
gcattacgag gaataattca tgctgctggg atattggatg atggtttgct gttaaacatg    2820
aattgggaaa aatttacaca ggtgatggca ccaaaagtac aaggggcttg gcatttgcat    2880
aatttgactc agaatctacc tttggacttt tttgtttgtt tttcctctat ggcttcaata    2940
ttgggttcgc ctggtcaagg gaattatgct gctgctaatg ctttcatgga tggtttagcc    3000
catcatcgac ggggtatggg tttacctggc ttgagcatta actggggacc atgggcacaa    3060
gagggaatgg cagcaaattt ggatagtcct catcaagata gaatggtgtc caagggaatg    3120
acttttttgt cttcagaaca gggattgcag gttctaggac aattactcga acaatccata    3180
ccacaagtag gagtcctacc aattcaatgg tcagtgttcc aagagcaatt tagttttggt    3240
aatcaaatac cattgctgtc ccaattggta aagaaaagca atcacagca aaaagccctc     3300 aaaacaaaga caaagcacaa tgaattttta gaacagctaa aagctgctttt accaagagaa   3360 agagaaaagc ttttgataat ttacattaaa gatgaaattt ctcaagtact ttctttgagc    3420
acttctcaaa ttgatatgca acagcccctg aacactatgg ggcttgattc tctaatggct    3480
gtggaattgc acaataggct tcaaactgac ttgctcgtgg atatatctat agtcaaattt    3540
atagaagata tcagtatcgt tgatttagcc actgaagtga atgagcaact gagccaagtt    3600
gctcagaatc aaggagttga gtcagaaaat aatgggcaac tctaccaaag caataggaaa    3660
gaaaacgagc ggataagagg tgaattatga                                     3690
```

<210> SEQ ID NO 3
<211> LENGTH: 1229
<212> TYPE: PRT
<213> ORGANISM: Nostoc species

<400> SEQUENCE: 3

```
Met Gly His Ser Ala Gly Glu Tyr Val Ala Thr Val Ala Gly Ile
  1               5                  10                  15

Phe Ser Leu Glu Asp Gly Leu Lys Leu Ile Ala His Arg Gly Arg Leu
                 20                  25                  30

Met Gln Gln Leu Pro Ser Gly Gly Glu Met Leu Ser Val Met Ala Ser
             35                  40                  45

Ile Glu Lys Val Asn Gln Leu Ile Ala Pro Tyr Ser Gln Lys Val Ala
         50                  55                  60

Ile Ala Ser Ile Asn Gly Pro Gln Ser Ile Val Ile Ser Gly Glu Ala
     65                  70                  75                  80

Glu Ala Ile Gly Ala Val Gln Asn Ser Leu Glu Ala Glu Asp Ile Lys
                 85                  90                  95

Thr Lys Arg Leu Gln Val Ser His Ala Phe His Ser His Leu Met Glu
                100                 105                 110

Pro Met Leu Ala Asp Phe Glu Ala Val Ala Ser Glu Ile Thr Tyr Asn
            115                 120                 125

Gln Pro Asn Ile Pro Leu Val Ser Asn Val Thr Gly Ala Arg Ala Glu
        130                 135                 140
```

-continued

```
Asn Ser Ile Ala Thr Ala Ser Tyr Trp Val Asn His Val Arg Gln Pro
145                 150                 155                 160

Val Lys Phe Ala Gln Ser Met Asp Thr Leu Gln Gln Glu Gly Tyr Ser
                165                 170                 175

Ile Phe Leu Glu Ile Gly Pro Lys Pro Thr Leu Leu Gly Met Gly Arg
                180                 185                 190

Gln Cys Leu Pro Glu Asp Val Gly Val Trp Leu Pro Ser Leu Lys Pro
            195                 200                 205

Gly Gln Glu Asp Trp Gln Gln Met Leu Gln Ser Leu Ala Glu Leu Tyr
    210                 215                 220

Val His Gly Val Lys Val Asp Trp Leu Gly Phe Asp Lys Asp Tyr Ser
225                 230                 235                 240

Arg Ser Lys Val Val Leu Pro Thr Tyr Pro Phe Gln Arg Gln Arg Tyr
                245                 250                 255

Trp Ile Glu Thr Asn Asn Asn Leu Ile His Gln Lys Gln Phe Leu Ser
                260                 265                 270

Asn His Lys Asn Leu His Pro Leu Leu Gly Gln Arg Leu His Leu Ala
            275                 280                 285

Ala Leu Glu Gln Gln Ile Arg Phe Glu Cys Gln Ile Ser Ala Ser Gln
    290                 295                 300

Pro Thr Tyr Leu Gln His His Cys Val Phe Ser Gln Pro Val Phe Pro
305                 310                 315                 320

Ala Ala Ala Tyr Leu Glu Ile Ala Leu Ala Ala Gly Ser Ile Leu Phe
                325                 330                 335

Asn Ser Asp Asp Leu Ile Leu Glu Asp Ile Ala Ile Gln Lys Val Leu
            340                 345                 350

Ile Leu Ser Lys Asp Glu Ile Asn Thr Ile Gln Ile Val Leu Asn Leu
    355                 360                 365

Gln Leu Val Gln Ser Tyr Lys Phe Gln Ile Phe Ser Leu Asp Ile Asn
    370                 375                 380

Thr Asn Ser Ser Glu Pro Lys Trp Ile Leu His Ile Glu Gly Lys Ile
385                 390                 395                 400

Leu Val Gly Asn Lys Asp Pro Gln Leu Glu Thr Thr Asn Leu Lys Ala
                405                 410                 415

Ile Lys Asp Glu Tyr Asn Gln Gln Ile Leu Pro Thr Glu Phe Tyr Gln
                420                 425                 430

Lys Phe Glu Glu Trp Gly Leu Asn Tyr Gly Ser Ser Phe Gln Ala Val
            435                 440                 445

Lys Gln Leu Trp His Ser Glu Gly Lys Ala Leu Gly Glu Ile Gln Leu
    450                 455                 460

Pro Glu Thr Glu Val Asn Val Ala Thr Leu Tyr Gln Leu His Pro Ile
465                 470                 475                 480

Leu Leu Asp Ala Ser Phe Gln Val Leu Ala Ala Val Met Gly Lys Thr
                485                 490                 495

Asp Asn Gln Glu Thr Tyr Leu Pro Leu Glu Ile Lys Arg Leu Gln Ile
            500                 505                 510

Tyr Arg Ser Gly Ser Asn Ser Leu Trp Thr Gln Val Glu Ile Gly Ala
    515                 520                 525

Thr Glu Thr Asn Lys Gln Thr Leu Ser Gly Lys Val Cys Leu Leu Asp
    530                 535                 540

Glu Gln Gly Ile Val Val Ala Arg Val Glu Gly Leu Thr Leu Leu Arg
545                 550                 555                 560
```

```
Thr Ser Arg Glu Ala Leu Leu Arg Asn Ile Glu Pro Lys Phe Asn Asn
            565                 570                 575
Trp Leu Tyr Gln Ile His Trp Gln Thr Gln Ser Ile Ser Pro His Asn
            580                 585                 590
Gln Ser Ile Asp Leu Thr Lys Ser Gly Ser Trp Leu Leu Phe Ser Pro
            595                 600                 605
Pro Thr Gly Ile Gly Lys His Leu Val Glu Ser Leu Glu Gln Gln Gly
            610                 615                 620
Trp His Cys Ile Leu Val Thr Pro Gly Glu Asn Tyr Gln Gln Leu Glu
625                 630                 635                 640
Ser Gln His Tyr Gln Ile Asn Pro Asn His Pro Glu Glu Phe Leu His
            645                 650                 655
Leu Leu Gln Ser Ser Leu Glu Gln Gln Pro Pro Leu Arg Gly Ile Ile
            660                 665                 670
His Leu Trp Ser Leu Asp Ser Thr Ile Ala Leu Arg Thr Gly Ala Gln
            675                 680                 685
Glu Leu Gln Lys Ser Gln Glu Leu Gly Cys Gly Ser Val Leu His Leu
            690                 695                 700
Val Gln Ala Leu Val Lys Asn Gln Asp Met Glu Ser Ala Pro Leu Trp
705                 710                 715                 720
Leu Val Thr Gln Gly Ser Gln Ser Val Gly Asn Glu Ser Leu Pro Ile
            725                 730                 735
Gln Phe Gln Gln Thr Pro Leu Trp Gly Leu Gly Arg Val Ile Ala Gln
            740                 745                 750
Glu His Arg Glu Leu Gln Cys Arg Cys Leu Asp Leu Asp Pro Thr Met
            755                 760                 765
Glu Asp Ser Gln Thr Val Ala Ala Leu Leu Glu Leu Leu Ser Pro
            770                 775                 780
Gly Asp Glu Asn Gln Ile Ala Tyr Cys Gln Gly Val Arg His Val Ala
785                 790                 795                 800
Arg Leu Glu Arg Gln Gln Lys Met Ser Thr Ser Thr Gln Ser Gly Leu
            805                 810                 815
Gln Ile Ser Ser Gln Gln Pro Phe Gln Leu Lys Leu Ser Glu Tyr Lys
            820                 825                 830
Ser Leu Asp Asn Leu Ile Gln Ala Glu Ala Ser Tyr Leu Ile Thr Gly
            835                 840                 845
Gly Leu Gly Ala Leu Gly Leu Lys Thr Ala Glu Trp Met Val Gln Gln
            850                 855                 860
Gly Val Lys Tyr Leu Val Leu Thr Gly Arg Arg Gln Pro Ser Ala Lys
865                 870                 875                 880
Ala Gln Gln Thr Ile Glu Gln Leu Gln Lys Ala Gly Ala Gln Val Leu
            885                 890                 895
Val Leu Cys Gly Asp Ile Ser Gln Gln Glu Asn Val Ala Arg Ile Ile
            900                 905                 910
Glu Ser Ile Lys Val Ser Leu Pro Ala Leu Arg Gly Ile Ile His Ala
            915                 920                 925
Ala Gly Ile Leu Asp Asp Gly Leu Leu Leu Asn Met Asn Trp Glu Lys
            930                 935                 940
Phe Thr Gln Val Met Ala Pro Lys Val Gln Gly Ala Trp His Leu His
945                 950                 955                 960
Asn Leu Thr Gln Asn Leu Pro Leu Asp Phe Phe Val Cys Phe Ser Ser
            965                 970                 975
Met Ala Ser Ile Leu Gly Ser Pro Gly Gln Gly Asn Tyr Ala Ala Ala
```

```
                        980             985             990
Asn Ala Phe Met Asp Gly Leu Ala His His Arg Arg Gly Met Gly Leu
        995                 1000            1005
Pro Gly Leu Ser Ile Asn Trp Gly Pro Trp Ala Gln Glu Gly Met Ala
        1010                1015            1020
Ala Asn Leu Asp Ser Pro His Gln Asp Arg Met Val Ser Lys Gly Met
1025            1030            1035            1040
Thr Phe Leu Ser Ser Glu Gln Gly Leu Gln Val Leu Gly Gln Leu Leu
            1045            1050            1055
Glu Gln Ser Ile Pro Gln Val Gly Val Leu Pro Ile Gln Trp Ser Val
        1060            1065            1070
Phe Gln Glu Gln Phe Ser Phe Gly Asn Gln Ile Pro Leu Leu Ser Gln
        1075            1080            1085
Leu Val Lys Glu Ser Lys Ser Gln Gln Lys Ala Leu Lys Thr Lys Thr
        1090            1095            1100
Lys His Asn Glu Phe Leu Glu Gln Leu Lys Ala Ala Leu Pro Arg Glu
1105            1110            1115            1120
Arg Glu Lys Leu Leu Ile Ile Tyr Ile Lys Asp Glu Ile Ser Gln Val
            1125            1130            1135
Leu Ser Leu Ser Thr Ser Gln Ile Asp Met Gln Gln Pro Leu Asn Thr
        1140            1145            1150
Met Gly Leu Asp Ser Leu Met Ala Val Glu Leu His Asn Arg Leu Gln
        1155            1160            1165
Thr Asp Leu Leu Val Asp Ile Ser Ile Val Lys Phe Ile Glu Asp Ile
        1170            1175            1180
Ser Ile Val Asp Leu Ala Thr Glu Val Asn Glu Gln Leu Ser Gln Val
1185            1190            1195            1200
Ala Gln Asn Gln Gly Val Glu Ser Glu Asn Asn Gly Gln Leu Tyr Gln
            1205            1210            1215
Ser Asn Arg Lys Glu Asn Glu Arg Ile Arg Gly Glu Leu
            1220            1225

<210> SEQ ID NO 4
<211> LENGTH: 5832
<212> TYPE: DNA
<213> ORGANISM: Nostoc species

<400> SEQUENCE: 4
atgaatttaa tcgaatttt  acaagatatt tcaataaaag gttggcaagt gtggagtgag     60
ggcgaacggc tttgttacga tgctcctcaa gaagaatcaa ctgctttagt attagctcaa    120
ctgaaacaat acaaaaccga atattacaa  ttgctgcgcg atcgcccaga tattttaaac    180
gtctatcccc tttcttacgg tcaacgggca ctttggtttt tgtggcaatt agcaccagaa    240
agtcatgctt ataacgtatc atttgtcgct cgtatttgct caacagtaga tattacagca    300
atgcaaaagg catttgagaa actaatagaa cggcatccga tattgcgtac aaattatccc    360
aaactcggat ctgagtcaat ccaacaggta ataattttc  aggaattaaa tttcttgcaa    420
attgatgctt ctgcttggag tgaagatgaa ctgaaaggga agtgattga  gagccatcaa    480
caatatttg  acctcgaacg agggcctgtt atgcgagttc ggtggtttac tcgttccaag    540
aaagaacatg tcctgttgct aaccatacac cacattgctt gcgatgcctg gtctttagat    600
atgttaatac aggagttgcc acaactctac caagtacaat gggctgattt taagacaccc    660
ctttctcctc taaagcattc ttaccaagat tacgttcgtt ggcagaggaa tattttgcag    720
```

-continued

```
gagactgaag gggaaagact ctggaactac tggcagcaaa aactgacagg cgatttgcca       780
gcactaaacc tagcaacctc aagacagcga ccaccgataa aaacttataa tggtgcttcc       840
catcacttca aattatctga caagctcact aagcaactca aggagctggc tttaaactcg       900
ggagcaacac tttacatgat gctcttagca acttttcagg tgttttttgta tcgttacaca      960 ggccaggagg atattttagt cggttctccc acctcaggta ggagtcaagc taagtttgct      1020
tcgatcttgg gctactttgt tgatcctgtt gttatgcgag caaatttatc gggaaatccc      1080
agtttcaaag atttcctcgc ccaagtacgc caaaccgtat ggaagcact tgctcatcaa       1140 gattacccat ttgctctatt ggtagaaaag ctacagccac accgcgaccc cagtcgttcg      1200 ccgattttc aggcttcttt ttctctactg cagttccaaa aatctcaaga tatacagaag       1260
ttgtttgtaa atcaaataga aacctatgtt gattggggag aattgaagat aaaaccttat      1320
gaaatacctc aacaggaagg tcagttagat ttaggtttag aaatggtgga ggggagttca      1380 tctgttttttg gggtttttaa gtacaacact gacttgtttg atgagtcaac cattgagcgc     1440
atggctggtc atttccagaa tttattgtca gcgattgtgg aaaatcctca acaaaaggta      1500
agtgaatcac ccctattgag tgaagtagaa cggcatcagt tgttggtgga gtggaatgat      1560
acagcaaggg aatatcccag taaatgtatc catcaattgt ttgaagagca ggtagagaga      1620
acaccggatg cagtcgcggt ggtatttgag aatcagcagt taacctacca acaattaaat      1680
caaaaagcca accaactagc acatcacctg ctttccttgc gagtcgaacc agaggtgctg      1740
gtagggattt acgtggagcg ttcttttgaa atggtggtag ggctcttggg gatactcaag      1800
gctggtgggg cttatgtacc ccttgacccc aattatcccc aagaacggtt gagttatatg      1860
ttggcggatt caggtgttga ggtgttgttg gctcaaaagt ccctactgga atctttgccg      1920
tcacatactg cacaggtggt ttgtttggat agtgattggg gagtgattga gcaacacagt      1980
caggagaatc ttgatgttgg ggtatgttca gataatttgg cttatgtgat ttatacttct      2040
ggttctactg gagttcccaa gggggttggg attgaacatt tttctttgtg caaccttatt      2100
caagcacaga aaaatttatt ttatctagaa ccaaatagtc gtgttcttca atttgcttct      2160
ataagttttg atgcttcagt ttcggaaata tttatcgctt tgacttctgg agcaatgcta      2220
attttggcta tagcttctga gttaatcccg ggttcggatt taaagcaaat tttacaagaa      2280
agatgtgtaa ctcatgttac gttacctccc tctgccctgg cagtactagc tactgatgaa      2340
tttccagcct tgggtcagat aattgtggca ggggawsctt staywmtkga attggccaat      2400
cagtggtctg ttggtcgtcg tttgttttaat ggttatgggc ctactgagtc tactattggt      2460
gctgcagtgg ctcaaatcag ccatggtagc gagaaagtta ctatcggtcg ccccattgca      2520
aacacccaaa tctatatctt agataagcac ttagaaccag tacccataag tgtatccgga      2580
gaattataca tcggaggtta tggcttagcc agaggttacc tcaaccgacc ggaattaact      2640
ttagagaaat tcatccctaa ccccttcaat agcagatcaa aactatataa aactggagat      2700
ttagctcgat acttaccaga tggtaatatt gagtttcttg gtcgtcttga taaccaggtg      2760
aaaatacgtg gtttccgcat agaactagga gaaatagaat cagttctgag tacccatcct      2820
caagtacagc aagtcgcagt caccgaaagg gaagatactc cgggtcacaa acggttggta      2880
gcatatttag ttcctcttca gtcaaaagaa aaagatcccc agcccagac aggaattgaa       2940 ctttggccct cagtagcaga attctacgtt tatgatgagc tcttgtacta tgcgatgacc      3000
aatgatcatc gtcgaaacca gagttaccaa gtcgcaatta atcaaatggt taaagataaa      3060
gtagttgttg aaattggcac gggcaaggat gcaattatag ccagattttg tgcagaagca      3120
```

```
ggtgctaaga aagtctacgc aattgagaga gacgagcaaa ccagtaagtt agcttcagct   3180
tgcgtgcaag agttggggtt atcagaacaa attcaaatca tacatggaga cgctactaca   3240
gccaacttac cagaagaagt tgatgtatgt gtttctgaaa ttgtgggacc cattggtgga   3300
tctgaaggag cagcagtaat tatcaacaac gccagaagat ttctcaaatc agatggtgta   3360
atgattcccc aaagaagtgt gactcaaatt attgcagtaa ctcttcctga tgaattacta   3420
aatcaacccc aatttacaaa agtttcaggt tattataccc agaagatatt tgagcaagtt   3480
ggatatcctt ttgatttacg agtatgtatt aaaggattaa atcaagtaaa ctggttgtcc   3540
aatcgaggag tttttgagga tttagacttt agcaagcttg ttagcacaga atctactcac   3600
caaattaaat taactattga aaaatcagga agattagatg ttttttcagt gggattaaac   3660
ttacacacaa ttgaaggaga atgtatagat atttttagaaa atgaacattg ctggttacca   3720
gtttatcttc cagtgtttga accaggaatt tatgtaaatg aaggagatat catcgaagct   3780
gtttgtacga gaacgctttg tgaaaataat ttgaatccag attatactct tcgaggtcgt   3840
cttttaaaaa aaactggaaa agagattgag tttgaataca tctcatatca ttggaaacaa   3900
ttgtttaagc aaaaccctt ttatcaacga ttgtttgctg aaaataatct agaagattac   3960
acaattaata agtcaaagcc tgaacgtaag gtactgagta gcaatgaatt gcgctcctac   4020
ctaaagtcta aattgccaga atatatgctc ccctctagct ttgtcatctt agacacccta   4080
ccgttgacac ccaacggtaa agtagaccgc aaagccctaa gtgcacctga tggggaagtt   4140
agccgagagg atgaatatgt cgcaccacgc acagaaatag aacaaatctt aaccaacatt   4200
tggcawgaac tgctccttaa agaacaagtc agcatccatg acaacttctt tgaaattggt   4260
ggcgactcca tccttggtat tcaagtagtt tctcgtgcca aaaacttagg aatacaaatc   4320
actcccaaac aaatattcca aaatcaaacc atcgccaaac tagcattagt agccaataca   4380
acagttactg tcagtgctaa ccaaggtata gttactggag ttgcacccct aacaccaatt   4440
caacagtggt tctttgcaca aaatagccaa gaagcacacc attacaacca atcagtttta   4500
ttgcagattc ccaatcatct gcaaactgaa ttaatcgaaa cagccttgaa aaaattatta   4560
gagcatcacg atgctctgcg tttacgattc acatcagttg catctgagta caaacaaata   4620
aaccatggct tgatgatcc cgtagcattt actgtagttg atttatcatc aactcctgtc   4680
attgaacaac cacaagcttt atcacagatc gccacggaat atcaagcaag tttaaacctc   4740
tcagagggac ctttaatgca agtggtgatg tttaacttag gtagtgaagt tgatgcccgt   4800
ttactgatta ttattcatca cctagcagta gatggtgtga gttggcgaat tttactatca   4860
gacttagaaa caatctatca acaactaatc gctcaacaat caatacagct aaatgcgaaa   4920
acaacagcat ttattgattg ggcagagaaa ttgaaaaatt atgcacaatc agaaaaaatc   4980
aaacaagagt tagactattg gctcaaccaa ccttggtcag aaacaacacc actaccatta   5040
gattctgctc acactcaagc agaaaaaaca gttgatagtg cgattaatta tagagtgaaa   5100
ttgagtccag aagaaacccg cgctttgctg gggtcagtaa actcagctta taacacacaa   5160
attaacgata tcctcctcag tgcattagta gtttccttgg cagagtggac gggagattca   5220
aaagtactaa ttgacctaga aggacatggc agagaagaac tattttcaga tgtagactta   5280
tcaagaacaa taggttggtt taccagtttta ttcccagtat tattgcgatt accagacgat   5340
aaacaaccag cagaagttat caagtcaatt aaagaacaat tacgagagat tccccatcgt   5400
ggtattggct ttggtatatt gcgttacttg tgtgaagata ctactgtaac ccaaaaacta   5460
```

```
cagacaattc ctactccaga aattagtttt aactacctag gacaatttga ccaaatacaa    5520
tcggaaacgg gttggaaatt tgcgccagaa tctactggag ataatcatag ttcaaagcaa    5580
actcgtcacc atctattaga gattaatagt ctggtggtag aaggtgaatt acaaattgat    5640
tggacttata gtagtaattt tcatactcat gatacagtaa aaaatttgac acaaagctat    5700
attcaagcaa ttaagtcaat aatagaacat tgccagtcag aaaatggttt tggatataca    5760
gctagtgatt tcccagatgc acagttaaat caattagaac ttgatgagtt attaaaaaac    5820
ttgggcaaat ag                                                        5832
```

<210> SEQ ID NO 5
<211> LENGTH: 1943
<212> TYPE: PRT
<213> ORGANISM: Nostoc species
<220> FEATURE:
<221> NAME/KEY: VARIANT
<222> LOCATION: 792-796  1402
<223> OTHER INFORMATION: Xaa = Unknown

<400> SEQUENCE: 5

```
Met Asn Leu Ile Glu Phe Leu Gln Asp Ile Ser Ile Lys Gly Trp Gln
 1               5                  10                  15

Val Trp Ser Glu Gly Glu Arg Leu Cys Tyr Asp Ala Pro Gln Glu Glu
             20                  25                  30

Ser Thr Ala Leu Val Leu Ala Gln Leu Lys Gln Tyr Lys Thr Glu Ile
         35                  40                  45

Leu Gln Leu Leu Arg Asp Arg Pro Asp Ile Leu Asn Val Tyr Pro Leu
     50                  55                  60

Ser Tyr Gly Gln Arg Ala Leu Trp Phe Leu Trp Gln Leu Ala Pro Glu
 65                  70                  75                  80

Ser His Ala Tyr Asn Val Ser Phe Val Ala Arg Ile Cys Ser Thr Val
                 85                  90                  95

Asp Ile Thr Ala Met Gln Lys Ala Phe Glu Lys Leu Ile Glu Arg His
            100                 105                 110

Pro Ile Leu Arg Thr Asn Tyr Pro Lys Leu Gly Ser Glu Ser Ile Gln
        115                 120                 125

Gln Val Asn Asn Phe Gln Glu Leu Asn Phe Leu Gln Ile Asp Ala Ser
    130                 135                 140

Ala Trp Ser Glu Asp Glu Leu Lys Gly Lys Val Ile Glu Ser His Gln
145                 150                 155                 160

Gln Tyr Phe Asp Leu Glu Arg Gly Pro Val Met Arg Val Arg Trp Phe
                165                 170                 175

Thr Arg Ser Lys Lys Glu His Val Leu Leu Leu Thr Ile His His Ile
            180                 185                 190

Ala Cys Asp Ala Trp Ser Leu Asp Met Leu Ile Gln Glu Leu Pro Gln
        195                 200                 205

Leu Tyr Gln Val Gln Trp Ala Asp Phe Lys Thr Pro Leu Ser Pro Leu
    210                 215                 220

Lys His Ser Tyr Gln Asp Tyr Val Arg Trp Gln Arg Asn Ile Leu Gln
225                 230                 235                 240

Glu Thr Glu Gly Glu Arg Leu Trp Asn Tyr Trp Gln Gln Lys Leu Thr
                245                 250                 255

Gly Asp Leu Pro Ala Leu Asn Leu Ala Thr Ser Arg Gln Arg Pro Pro
            260                 265                 270

Ile Lys Thr Tyr Asn Gly Ala Ser His His Phe Lys Leu Ser Asp Lys
        275                 280                 285
```

-continued

```
Leu Thr Lys Gln Leu Lys Glu Leu Ala Leu Asn Ser Gly Ala Thr Leu
    290                 295                 300

Tyr Met Met Leu Leu Ala Thr Phe Gln Val Phe Leu Tyr Arg Tyr Thr
305                 310                 315                 320

Gly Gln Glu Asp Ile Leu Val Gly Ser Pro Thr Ser Gly Arg Ser Gln
                325                 330                 335

Ala Lys Phe Ala Ser Ile Leu Gly Tyr Phe Val Asp Pro Val Val Met
            340                 345                 350

Arg Ala Asn Leu Ser Gly Asn Pro Ser Phe Lys Asp Phe Leu Ala Gln
        355                 360                 365

Val Arg Gln Thr Val Leu Glu Ala Leu Ala His Gln Asp Tyr Pro Phe
    370                 375                 380

Ala Leu Leu Val Glu Lys Leu Gln Pro His Arg Asp Pro Ser Arg Ser
385                 390                 395                 400

Pro Ile Phe Gln Ala Ser Phe Ser Leu Leu Gln Phe Gln Lys Ser Gln
                405                 410                 415

Asp Ile Gln Lys Leu Phe Val Asn Gln Ile Glu Thr Tyr Val Asp Trp
            420                 425                 430

Gly Glu Leu Lys Ile Lys Pro Tyr Glu Ile Pro Gln Gln Glu Gly Gln
        435                 440                 445

Leu Asp Leu Gly Leu Glu Met Val Glu Gly Ser Ser Val Phe Gly
    450                 455                 460

Val Phe Lys Tyr Asn Thr Asp Leu Phe Asp Glu Ser Thr Ile Glu Arg
465                 470                 475                 480

Met Ala Gly His Phe Gln Asn Leu Leu Ser Ala Ile Val Glu Asn Pro
                485                 490                 495

Gln Gln Lys Val Ser Glu Ser Pro Leu Leu Ser Glu Val Glu Arg His
            500                 505                 510

Gln Leu Leu Val Glu Trp Asn Asp Thr Ala Arg Glu Tyr Pro Ser Lys
        515                 520                 525

Cys Ile His Gln Leu Phe Glu Glu Gln Val Glu Arg Thr Pro Asp Ala
    530                 535                 540

Val Ala Val Phe Glu Asn Gln Gln Leu Thr Tyr Gln Gln Leu Asn
545                 550                 555                 560

Gln Lys Ala Asn Gln Leu Ala His His Leu Leu Ser Leu Arg Val Glu
                565                 570                 575

Pro Glu Val Leu Val Gly Ile Tyr Val Glu Arg Ser Phe Glu Met Val
            580                 585                 590

Val Gly Leu Leu Gly Ile Leu Lys Ala Gly Ala Tyr Val Pro Leu
        595                 600                 605

Asp Pro Asn Tyr Pro Gln Glu Arg Leu Ser Tyr Met Leu Ala Asp Ser
    610                 615                 620

Gly Val Glu Val Leu Leu Ala Gln Lys Ser Leu Leu Glu Ser Leu Pro
625                 630                 635                 640

Ser His Thr Ala Gln Val Val Cys Leu Asp Ser Asp Trp Gly Val Ile
                645                 650                 655

Glu Gln His Ser Gln Glu Asn Leu Asp Val Gly Val Cys Ser Asp Asn
            660                 665                 670

Leu Ala Tyr Val Ile Tyr Thr Ser Gly Ser Thr Gly Val Pro Lys Gly
        675                 680                 685

Val Gly Ile Glu His Phe Ser Leu Cys Asn Leu Ile Gln Ala Gln Lys
    690                 695                 700
```

-continued

```
Asn Leu Phe Tyr Leu Glu Pro Asn Ser Arg Val Leu Gln Phe Ala Ser
705                 710                 715                 720

Ile Ser Phe Asp Ala Ser Val Ser Glu Ile Phe Ile Ala Leu Thr Ser
                725                 730                 735

Gly Ala Met Leu Ile Leu Ala Ile Ala Ser Glu Leu Ile Pro Gly Ser
            740                 745                 750

Asp Leu Lys Gln Ile Leu Gln Glu Arg Cys Val Thr His Val Thr Leu
        755                 760                 765

Pro Pro Ser Ala Leu Ala Val Leu Ala Thr Asp Glu Phe Pro Ala Leu
    770                 775                 780

Gly Gln Ile Ile Val Ala Gly Xaa Xaa Xaa Xaa Glu Leu Ala Asn
785                 790                 795                 800

Gln Trp Ser Val Gly Arg Arg Leu Phe Asn Gly Tyr Gly Pro Thr Glu
                805                 810                 815

Ser Thr Ile Gly Ala Ala Val Ala Gln Ile Ser His Gly Ser Glu Lys
            820                 825                 830

Val Thr Ile Gly Arg Pro Ile Ala Asn Thr Gln Ile Tyr Ile Leu Asp
        835                 840                 845

Lys His Leu Glu Pro Val Pro Ile Ser Val Ser Gly Glu Leu Tyr Ile
    850                 855                 860

Gly Gly Tyr Gly Leu Ala Arg Gly Tyr Leu Asn Arg Pro Glu Leu Thr
865                 870                 875                 880

Leu Glu Lys Phe Ile Pro Asn Pro Phe Asn Ser Arg Ser Lys Leu Tyr
                885                 890                 895

Lys Thr Gly Asp Leu Ala Arg Tyr Leu Pro Asp Gly Asn Ile Glu Phe
            900                 905                 910

Leu Gly Arg Leu Asp Asn Gln Val Lys Ile Arg Gly Phe Arg Ile Glu
        915                 920                 925

Leu Gly Glu Ile Glu Ser Val Leu Ser Thr His Pro Gln Val Gln Gln
    930                 935                 940

Val Ala Val Thr Glu Arg Glu Asp Thr Pro Gly His Lys Arg Leu Val
945                 950                 955                 960

Ala Tyr Leu Val Pro Leu Gln Ser Lys Glu Lys Asp Pro Gln Pro Gln
                965                 970                 975

Thr Gly Ile Glu Leu Trp Pro Ser Val Ala Glu Phe Tyr Val Tyr Asp
            980                 985                 990

Glu Leu Leu Tyr Tyr Ala Met Thr Asn Asp His Arg Arg Asn Gln Ser
        995                 1000                1005

Tyr Gln Val Ala Ile Asn Gln Met Val Lys Asp Lys Val Val Glu
    1010                1015                1020

Ile Gly Thr Gly Lys Asp Ala Ile Ile Ala Arg Phe Cys Ala Glu Ala
1025                1030                1035                1040

Gly Ala Lys Lys Val Tyr Ala Ile Glu Arg Asp Glu Gln Thr Ser Lys
                1045                1050                1055

Leu Ala Ser Ala Cys Val Gln Glu Leu Gly Leu Ser Glu Gln Ile Gln
            1060                1065                1070

Ile Ile His Gly Asp Ala Thr Thr Ala Asn Leu Pro Glu Glu Val Asp
        1075                1080                1085

Val Cys Val Ser Glu Ile Val Gly Pro Ile Gly Gly Ser Glu Gly Ala
    1090                1095                1100

Ala Val Ile Ile Asn Asn Ala Arg Arg Phe Leu Lys Ser Asp Gly Val
1105                1110                1115                1120

Met Ile Pro Gln Arg Ser Val Thr Gln Ile Ile Ala Val Thr Leu Pro
```

-continued

```
                1125                1130                1135
Asp Glu Leu Leu Asn Gln Pro Gln Phe Thr Lys Val Ser Gly Tyr Tyr
            1140                1145                1150

Thr Gln Lys Ile Phe Glu Gln Val Gly Tyr Pro Phe Asp Leu Arg Val
            1155                1160                1165

Cys Ile Lys Gly Leu Asn Gln Val Asn Trp Leu Ser Asn Arg Gly Val
            1170                1175                1180

Phe Glu Asp Leu Asp Phe Ser Lys Leu Val Ser Thr Glu Ser Thr His
1185                1190                1195                1200

Gln Ile Lys Leu Thr Ile Glu Lys Ser Gly Arg Leu Asp Gly Phe Ser
            1205                1210                1215

Val Gly Leu Asn Leu His Thr Ile Glu Gly Glu Cys Ile Asp Ile Leu
            1220                1225                1230

Glu Asn Glu His Cys Trp Leu Pro Val Tyr Leu Pro Val Phe Glu Pro
            1235                1240                1245

Gly Ile Tyr Val Asn Glu Gly Asp Ile Ile Glu Ala Val Cys Thr Arg
            1250                1255                1260

Thr Leu Cys Glu Asn Asn Leu Asn Pro Asp Tyr Thr Leu Arg Gly Arg
1265                1270                1275                1280

Leu Leu Lys Lys Thr Gly Lys Glu Ile Glu Phe Glu Tyr Ile Ser Tyr
            1285                1290                1295

His Trp Lys Gln Leu Phe Lys Gln Asn Pro Phe Tyr Gln Arg Leu Phe
            1300                1305                1310

Ala Glu Asn Asn Leu Glu Asp Tyr Thr Ile Asn Lys Ser Lys Pro Glu
            1315                1320                1325

Arg Lys Val Leu Ser Ser Asn Glu Leu Arg Ser Tyr Leu Lys Ser Lys
            1330                1335                1340

Leu Pro Glu Tyr Met Leu Pro Ser Ser Phe Val Ile Leu Asp Thr Leu
1345                1350                1355                1360

Pro Leu Thr Pro Asn Gly Lys Val Asp Arg Lys Ala Leu Ser Ala Pro
            1365                1370                1375

Asp Gly Glu Val Ser Arg Glu Asp Glu Tyr Val Ala Pro Arg Thr Glu
            1380                1385                1390

Ile Glu Gln Ile Leu Thr Asn Ile Trp Xaa Glu Leu Leu Leu Lys Glu
            1395                1400                1405

Gln Val Ser Ile His Asp Asn Phe Phe Glu Ile Gly Gly Asp Ser Ile
            1410                1415                1420

Leu Gly Ile Gln Val Val Ser Arg Ala Lys Asn Leu Gly Ile Gln Ile
1425                1430                1435                1440

Thr Pro Lys Gln Ile Phe Gln Asn Gln Thr Ile Ala Lys Leu Ala Leu
            1445                1450                1455

Val Ala Asn Thr Thr Val Thr Val Ser Ala Asn Gln Gly Ile Val Thr
            1460                1465                1470

Gly Val Ala Pro Leu Thr Pro Ile Gln Gln Trp Phe Phe Ala Gln Asn
            1475                1480                1485

Ser Gln Glu Ala His His Tyr Asn Gln Ser Val Leu Leu Gln Ile Pro
            1490                1495                1500

Asn His Leu Gln Thr Glu Leu Ile Glu Thr Ala Leu Lys Lys Leu Leu
1505                1510                1515                1520

Glu His His Asp Ala Leu Arg Leu Arg Phe Thr Ser Val Ala Ser Glu
            1525                1530                1535

Tyr Lys Gln Ile Asn His Gly Phe Asp Asp Pro Val Ala Phe Thr Val
            1540                1545                1550
```

-continued

```
Val Asp Leu Ser Ser Thr Pro Val Ile Glu Gln Pro Gln Ala Leu Ser
        1555                1560                1565
Gln Ile Ala Thr Glu Tyr Gln Ala Ser Leu Asn Leu Ser Glu Gly Pro
    1570                1575                1580
Leu Met Gln Val Val Met Phe Asn Leu Gly Ser Glu Val Asp Ala Arg
1585                1590                1595                1600
Leu Leu Ile Ile Ile His His Leu Ala Val Asp Gly Val Ser Trp Arg
                1605                1610                1615
Ile Leu Leu Ser Asp Leu Glu Thr Ile Tyr Gln Gln Leu Ile Ala Gln
            1620                1625                1630
Gln Ser Ile Gln Leu Asn Ala Lys Thr Thr Ala Phe Ile Asp Trp Ala
        1635                1640                1645
Glu Lys Leu Lys Asn Tyr Ala Gln Ser Glu Lys Ile Lys Gln Glu Leu
    1650                1655                1660
Asp Tyr Trp Leu Asn Gln Pro Trp Ser Glu Thr Thr Pro Leu Pro Leu
1665                1670                1675                1680
Asp Ser Ala His Thr Gln Ala Glu Lys Thr Val Asp Ser Ala Ile Asn
                1685                1690                1695
Tyr Arg Val Lys Leu Ser Pro Glu Glu Thr Arg Ala Leu Leu Gly Ser
            1700                1705                1710
Val Asn Ser Ala Tyr Asn Thr Gln Ile Asn Asp Ile Leu Leu Ser Ala
        1715                1720                1725
Leu Val Val Ser Leu Ala Glu Trp Thr Gly Asp Ser Lys Val Leu Ile
    1730                1735                1740
Asp Leu Glu Gly His Gly Arg Glu Glu Leu Phe Ser Asp Val Asp Leu
1745                1750                1755                1760
Ser Arg Thr Ile Gly Trp Phe Thr Ser Leu Phe Pro Val Leu Leu Arg
                1765                1770                1775
Leu Pro Asp Asp Lys Gln Pro Ala Glu Val Ile Lys Ser Ile Lys Glu
            1780                1785                1790
Gln Leu Arg Glu Ile Pro His Arg Gly Ile Gly Phe Gly Ile Leu Arg
        1795                1800                1805
Tyr Leu Cys Glu Asp Thr Thr Val Thr Gln Lys Leu Gln Thr Ile Pro
    1810                1815                1820
Thr Pro Glu Ile Ser Phe Asn Tyr Leu Gly Gln Phe Asp Gln Ile Gln
1825                1830                1835                1840
Ser Glu Thr Gly Trp Lys Phe Ala Pro Glu Ser Thr Gly Asp Asn His
                1845                1850                1855
Ser Ser Lys Gln Thr Arg His His Leu Leu Glu Ile Asn Ser Leu Val
            1860                1865                1870
Val Glu Gly Glu Leu Gln Ile Asp Trp Thr Tyr Ser Ser Asn Phe His
        1875                1880                1885
Thr His Asp Thr Val Lys Asn Leu Thr Gln Ser Tyr Ile Gln Ala Ile
    1890                1895                1900
Lys Ser Ile Ile Glu His Cys Gln Ser Glu Asn Gly Phe Gly Tyr Thr
1905                1910                1915                1920
Ala Ser Asp Phe Pro Asp Ala Gln Leu Asn Gln Leu Glu Leu Asp Glu
                1925                1930                1935
Leu Leu Lys Asn Leu Gly Lys
            1940
```

<210> SEQ ID NO 6
<211> LENGTH: 10032

<212> TYPE: DNA
<213> ORGANISM: Nostoc species

<400> SEQUENCE: 6

```
atgagcaacg aagaaattag aagaaatatc tcttcaattt atccactttc tcccatgcaa    60
caagggatgc tgttccacag tctttatgca ccttatagtg gggtatatct tgaacagatg   120
acctggggtt tgaaggggaa tatcaatgtt gctgcttttg aaagagcttg caaaaagtt    180
ttagatagac attcaattct acgtacattt tttgtttggg aaaatcgcca aactccatta   240
caagtagtac taaaacaggt taatgttcct tggaatactc ttgattggcg agaactttct   300
tctaatgatc aacaacaaca attaaaacaa ttattgcaaa cacaaagaga caaggtttt    360
aacttatccc aagcaccatt aatgcggtgt acgttagtca ggctaggcga agataattac   420
aaatttatct ggagtcatca ccacatcctt atggatggat ggtgtttatc aattattttt   480
aaagaaattt taattttcta taaagcacat ctgcttggtg aaaattgcca attgccaaaa   540
ccacgtcctt accaggatta tattgcttgg ttgaattctc aagacaaatc agcagcaatt   600
gagttttggc aacaaacttt acaaggtttt agtgctccca ctccattggt aatggataaa   660
actcaatttc tgaaagagca acagtataaa actgcggatt atcaggagag aacaagtagt   720
ttatcccctg aatgcactca gaagttactt catatagcac aacaacatca tgtgactta    780
tcaactgtag tacaagctgc ttgggcttta ctattgagtc gttatagtgg tgagaaagat   840
gtagtatttg gtgtgactgt ttctggtcgt cctcctagcc tctctgagat agaaaatatg   900
gtaggactgt ttattaacac ccttccctta cgagtacaag tatccaccca ggagcaactc   960
ataccttggt tgcaaaaaat acaacagtca atggttgaat acaagagta tttttatact  1020
cctcttgttg atattcaagc tacttctgag ataccaggtg aatacccttt gtttgagagc  1080
attgtggtgt ttgagaatta tccaattgat aattctttgt tgaatgaaga aggttcatta  1140
cacttaggtg atatagaggt ttttgaacaa actaattatc cactaacttt agttgcagtt  1200
cctggggata agttgtcagt taggattagt tacgatactg ctcgtttctc ttcaaatact  1260
attgagtgga ttttaggata tctgcaaact gttttatcag caattgcaat tgtggaaaat  1320
ccttcacata aggtagctca attacctta ttaagtgaag tagaacgtca tcagttattg  1380
gttgagtgga taacactgc aacggattac ccatctgata aatgtattca tcagttattt  1440
gagcaacagg tagaaaaaaa ccccaactcc atagcagtgg tgtttgaaga agaacaatca  1500
acctaccaac aattaaatca aaaagcgaac caattagcac attatctaca aactctggga  1560
gtgaaaccag aagtgctggt gggtatttgc atagaatact ccattgatat gattgtagga  1620
ctgttgggga tacttaaagc tggtggtgta tatgtgccgt tagatccgaa ctatccgcaa  1680
gaacgactgg cgttcatgca ggaagattcc aatgtgcata tcatattgac ccagcagcct  1740
ctgctcgaaa agatttcccc tcaaaatgcc catatcgttt gcctggacag ggatagggat  1800
gtcattgcta gggaaggcgt tgaaaatctg gatcggcaaa acactggga tgaccttgca  1860
tacgcaatct atacgtctgg ttctactgga aaacccaaag ccgttctcgg cacgcttcgc  1920
ggcattgtca atcgcttgca ttggatctgg gaaatgctac catttggggc agatgagatt  1980
tgctctcaga aacatccat caattttggc gatcatgttg cggaaatatt ttctccctt   2040
ctcaaaggaa ttccccttgt gatcgttcca gatgatatac ggggcaatat tcccaggcta  2100
atgagcctgt tgagcgatcg aaaggtaact agaattgttc tcgttccatc gctattaaaa  2160
gcgatactgg aaaatgcgcc ccaacaactg acaaaacttc gatatctcaa atatgtcttt  2220
```

-continued

```
tgcagcggtg aagtcttacc gctaaccttg gctaaggaat ttcaccagaa aatcagctct    2280
gccagattgt tcaatctcta cggctcttca gaagttgccg ctgatgttac atgctttgaa    2340
gtcaaactga aatcgcaaa tcaaattgaa gcaaaaagta aagagaaact tgatgcttta    2400
aaaaatcttc ctagtggctc aggggatagg gaaactgctg tcctgcataa agaaataata    2460
catttgcagt tggcagacga gcgaagagca gatttaggag aagctctaga agaatatctg    2520
aaaagaaata cgattccgat tggaaaaccg atttcaaaca cacaaattta catcctcgac    2580
aagtatggcg atcttttgcc acctggtgtt acgggtgagc tatacgtcgg cggagatggg    2640
cttgcaaaag ggtatttaaa tctgcccgag ttaacgcggg aaaagtttat ccccaacccg    2700
tttgtgaagg acaggggaa aagtaaaaag gcacaagcag aaagattgtt taggactgga    2760
gacctagccc gctggctgcc ggatggtaat atcgaatttg tagggcgtat cgatcaccaa    2820
gtgaaggtgc ggggcttccg cattgaactt ggagaaatcg aagcagtcct cagtacccac    2880
ccccaaatcc aacaagtcgt tgtcattgcc atagaagata ttccaggtag caaacgttta    2940
gtagcctaca tagtctgtga ggatgaatca ctaagtacct atcacctgcg tgaattcctc    3000
aaacaaaagc taccagaata catgatgccc agtgcctttg tcatcttaga caccttaccg    3060
ttgacaccca gcggtaaaat agaccgtaaa gcccttccag cacctgatgg agaaattagc    3120
cgagaacatg aatatgtccc accacgtaca tcgggtgaag aaataatagc caacatcttc    3180
gcttctattc taggtgtgca aaatgttgga atccatgaca acttctttga attgggagga    3240
cattccctac tagcaacccg attaatttcc cgactcagag ttgcctttga agtagaaata    3300
gaactaagtg cagtcttttc ctctcccact gtagctcaat tagagcaaac attaacccaa    3360
ttacgtacta ctaatagcgc attaagtctt ccccccattc agccaagaac acagaaccaa    3420
caattacccc tatcttttgc acaagaccgg ttgtggttcc tcaaccaact tgaagggtca    3480
agtgccactt ataacatgcc aggagcaatt cgtgtcactg gaaagttgga tattaatgcc    3540
ttgcaacaag cattatcaga aatagtccgc cgtcatgaag tactacgcac cagcttccga    3600
actgtgaatg gcacaccaat acaggtaatt cacccagaag ccaccatgaa catcagtgtg    3660
gcggacttac agcaactaga agcaacagaa cgggaaagtg tccttcacca acaagcacaa    3720
cttgcagcaa ttacccccttt tgacttagaa actgcaccac taatcaggtg tagtttattg    3780
cagttagatg ccagagaata tgtgttatta ctgacgatgc accacattgt ctctgatggt    3840
tggtcaatgg ggatattcag ccaagaacta tctactttat atcaagcttt tagtgcagga    3900
aaaccatccc ccttggcaga attaccaatc cagtatgcag actttgcagt ttggcaaaga    3960
caatggttaa gtggaaaggt actagaaact caactcaatt actggctttc tcagttagag    4020
ggtgcaccag aattgttaca attacctact gaccgtcctc gtccaaccgt gcaaactttc    4080
cggggtacta ctcaaagttt tagtttaaat actgatttaa aagagaagtt gcaaaccctg    4140
tctcggaact cgggtactac cttatttatg acccctgcacg cagcgtttgc cactttactc    4200
tatcgctaca gcggtcaatt agatatttta attggttcac ccattgccaa tcgcaactgc    4260
agtgaaattg agtctttgat tggcttttttt gccaatactt tggtattgaa acccgtttt    4320 gaagataatc ccagttttga gaatttgctg gcacaagtta gggaaactac acttgaagct    4380
tatgaacatc aggatgtgcc ttttgaacag gtagttgaag tactacaacc acaacgctct    4440
ttgagttatg caccccttatt ccaggtaatg tttgtgttgc agaatgcacc catgggtgaa    4500
ttagaattac ctggtgtgac ccttaattta ttgagttctc aaacagaaac agcccggtttt    4560 gatttaacag tatcaatgca gcaaacttcc gaagcactag tgggttcatg ggaatacaac    4620
```

-continued

```
actgacttat tgatgggtc aactattgag cgcatgactg ctcatttcca gaatctgtgt    4680
agcgcgattg tagaaaatcc ccaacaaaag ataagtgaat taccattatt cacagattct    4740
gagcaagagc aggtactgca cagttacaat aacatcgcta caacttacct gctggataaa    4800
tatgttcatt tcctgagttc aaataattta caaatttaca ttttagataa ccatcaacaa    4860
ttagttcctt tgagtgtaga aggagaaatt tatttgggga attgcgtttt actcccagac    4920
aagttacatc cagaaccaga aaaatttata agtttcatag aacatacccca actgggtaag    4980
ttattaaaaa caggggaatg gggttgtcgt cgagtcgatg gttctctgga attgctagga    5040
aaagagcatc gaattgtcac agttaatgga caacgaatta acctacaacg tattgaacaa    5100
gctttacaaa cagcgaaagg ggtagaagat tgctatgtaa tggtacgcaa tcaaaaatta    5160
gtcgcttacg tagtcaaaga tggttcttgg gctagggagt ttttacacca ttatttaaaa    5220
tctcagttac ctggataccc attaccctgc atctatgtac cagtatctgc tttaccattg    5280
acaagttttg gagaagttga tgaagtaggt ttagcttcta ttagcataat tgattctgag    5340
ttaattaaca cttgggaaga acaaataggt tctcaggcgg aaattgataa agttgctgtt    5400
tttattgagc caaatgtaaa aacgatttct ccgatacatt tagaagaact tttaccatca    5460
atccaagcta ttttcaatca aggttctact ccagttgaaa ctcccagaac tgctagggga    5520
aaagagagta gttccctatt agaaataaaa tcacctgcca tcagccacga agaagtatta    5580
atctttccag aatcatctcc agaaacttta ggggagatgc tgcaaaaaac tgctgggaaa    5640
tttcctcaca aaggaatcac ttatattaac tctgatggtt ccgaacaagt tcaatcatat    5700
gcccagttat tagaagatgc tcaaagaatt ctaggtggct tcagaaaact gggaattaag    5760
ccacaagata aagttatttt gcaattaaaa gaaataaaag attttattag tgcttttttgg    5820
ggttgtgtgt tgggaggctt tattcccgta cccgttgtaa ttcctgtaag ctatgaccag    5880
cccaatgtca atctaaataa attacaaaat agttggcaga tgttagaaag acctttgatt    5940
ttaacagata aaaatcatt gtcagaacta agaaatggt ctcaaaatct aaatgacgac    6000
aactttaagt tagaaactat tgaaagttta caaaagttct caacagataa agattactat    6060
aatgcccaac cagaagattt agcactgttc atgcttactt ccggtagtac aggtatgtct    6120
aaggtggtac agttgagcca tttaaatcta ctgagtagga ctattggttc aatacaaatg    6180
aataatttta ccccagaaga tataacctta aattggatgc ccttagacca tgttgcaggt    6240
ttaatatatt tcatatccg ggatatttat ttaggatgta aacaaattca tgctactagt    6300
caattagtga ttgaaaaacc tttaagatgg ttggattgga ttgatacttt tggtgtcact    6360
gttacttttg ctcctaactt tgcttatagt ttaattaatg attttgttca agaaatagaa    6420
aagcagaatt ggaatttatc ttctattcgc ttgatgttaa atggtgcgga acaaattgtt    6480
gcagcaacag caagacgttt tttgaaatta cttgctcccct ttggcttacc tggggatgct    6540
atgactccat cttggggaat ggctgaggtt tcctctggta ttacttattc tgacaatttt    6600
tcactcttat caagttcaga tgataattcc tttgtaaatc ttggaaaacc gattaggggt    6660
acttgtctga aatagtcaa tcaagacatg gaagtattat cagaaggtga aattggttta    6720
cttcaggtca aaggattaac cgttacttct ggttattatc aaaatccaaa agcaaataag    6780
gaagcatttta ccgaagatgg ttggtttaat acaggtgatt taggatttat aaaagatgga    6840
tgcttaacga ttcaggacg acaaaaagat atcattatta ttaatggagt taattattat    6900
agtcatgaaa tagaagctgt tgttgaagaa ttaggagagg ttgaagtttc ttataccgca    6960
```

```
gcctgtggag tctgcgttgc tagcaataat accgaagaat tagtaatctt tttcactccg    7020
tatgtatctg agaagaatca attattagag cttttgaaaa aggttaggga acaagttata    7080
aaatactgcg ggataaatcc aagttattta atacccatag ataaagaact gattcccaaa    7140
acttccatcg gtaaaattca acgttccctc cttaagcaac gttttgaatg tggtgagttt    7200
aaatctctca gacagcgtgt agacttgttg cttgataata ctaatactat tcccaactgg    7260
ttttaccgta aagtatggca aattaaagaa agtaaaaata ctttactcaa ttattcttct    7320
cagaaaactt taaccctaat atttacagat aatttgggtt ggcaacaaga taaccgagga    7380
atgtcccaaa ctgttcaacc atatgctcaa gttactattg gttcaaattt tgctcaaatt    7440
agcccaaatc attattctgt tgttcctgga aatccacaac actatcgctt gttaattgat    7500
tctttgaggc aaaatagcca agtaattagt caaattcttc atctttggaa ctacaacgag    7560
cagactgaaa aaatttctag cttggaaaat ttagagtcca ctcaacaaca aggaatttac    7620
agtttactat ttttagtaca agctttagaa gaaattcaag gcaaacagca agcagtcaaa    7680
ttattatgga ttgctaatca aagccaatta gttcatccca cagataaaat tcaacccgaa    7740
aaatccactg ttttaggctt acttaaaact gttagtcaag aaatgccttg gttaactact    7800
cgtcatttag atttaccatt agcaccagaa ctcaacaata gttatatttg gcaagaactg    7860
tattctgctg ataaagaatt ggaagttgct atacgcaata gagaacgttt tgtgtctggt    7920
ctggaaccag tagatatgac tgctaaggaa aaacaaaaaa ttccgattct accaggagga    7980
acgtatctac ttacaggagg gcttggagga attgggactg ttattgcaaa gtacttatta    8040
gaacattatc aagcaaattt aatattagtt ggtagaactc aaattgaaga taataatgag    8100
gaagctagca caaaattgca gaggtatcaa gaattagaaa aactaccagg ttcaataatt    8160
tatcaaactg tagatatttg tgatttagta ggtttacaac aggtagtaga aaaagcaaca    8220
caagaatgga ggactcaact tgatgggta tttcatatgg ctgggattat tcaggaaacg    8280
ccaatcgaga aagaaacccc aggaaaatatc gctgctgttt tacgtcctaa agttagcggt    8340
acttgggtat tgcatcaatt gctcaaggat aaagaaaatg ctttatttgt ccacttttgt    8400
tctgtaaatg gtttctttgg aggaaccaat gttgcagctt atagtgcagc aaatagtttt    8460
cagtcagcat ggagcgatta tcaacaacaa aacggtttcc aaagctattg ctgctcttgg    8520
agtatgtgga atgaaaccgg aataagtcat ggctatcaat tccaagaact cagtcgtgct    8580
aagggctatt ttattattac tcctcaacaa ggattttact cattttttagc agctttatct    8640 ggttcggaac ataatctatt aatcggattg gatggaacta aaacaaatgt tgaacatttg    8700
attcgtgatt gtcagcccaa gcagaaatta actgcttact tcacctctcc cacaccagaa    8760
cttgctgcac tctccttaca agagttacaa ctacacgatc gctttgggat acccaatcaa    8820
attaactttg tccaacttga acaaataccc cttactcaaa gaggagaaat taatcgggaa    8880
caaattgctg ctatatatgg aggtttgaat acttctgagc agacaaaacc acggaatcaa    8940
acagaacgtc agttagttga gattttccaa gaagttctca atctaccctc tattggtatt    9000
catgacaact tctttagctt aggaggacat tcccttctag ctgtccgtct aatgtccgag    9060
attcaacaac aattccagaa aaatttacct ttagccactc ttttttcaaaa tcccaccatt    9120 gaacgactag cacttcttgt tggttccgat tccggagccg aactttggtc tccattagta    9180
ccaattcaac aaaacggttc attaccacct ttgttctgtg taccaggagc aggtggaaat    9240
gttctctact tccaccactt agcacaatat cttggaaata atcaaccgtt atacggttta    9300
caagcacaag gtcttgatgg tgaaaccgaa cctcataaaa gtgttgaaga aatagcctcc    9360
```

-continued

```
caacacatta aagcaattca aacagttcaa ccagttggtc cttacttctt ggctggtcat    9420
tcctttggca gtcatgtagt atttgaaatg gcgaatcaac tacaacttat tggaaagtct    9480
gttgcttatg ttggaatttt agatactcct gcaccaactt ctcaagctaa tcatcagaat    9540 gattttcta actgggataa tgcaaagtgg atatgtcgaa tggctgaggt tattgaagat    9600
attgttggag aaatctatt tttatcttat gaaactctaa cttctctaac ttgggagcaa    9660
caattaaatt atttcaagca aagttagaa atagttggtt ttttgcctgc tcaaacagat    9720
atcaaaattg ttcgtggttt attacaagtt ttccaaactc aatgtcaaat taagtatgaa    9780
ccggaaaaga cttataaaac tccaatcact ttgttttgtg cgagggagat aaatccagag    9840
caagaaagtt attctcacat tttccaagag ccaacatggg gttggaatca gttttctgat    9900
ggagaagtgg aaatccatat agttccgggt aatcatgttt caatgctgag tgagcctcat    9960
gtcaaggtat tggctcaaca aatgcaaata tctcttgaac aagcacagaa aacccatcaa   10020
ttggaaaaat ga                                                       10032
```

<210> SEQ ID NO 7
<211> LENGTH: 3343
<212> TYPE: PRT
<213> ORGANISM: Nostoc species

<400> SEQUENCE: 7

```
Met Ser Asn Glu Glu Ile Arg Arg Asn Ile Ser Ser Ile Tyr Pro Leu
 1               5                  10                  15

Ser Pro Met Gln Gln Gly Met Leu Phe His Ser Leu Tyr Ala Pro Tyr
                20                  25                  30

Ser Gly Val Tyr Leu Glu Gln Met Thr Trp Gly Leu Lys Gly Asn Ile
            35                  40                  45

Asn Val Ala Ala Phe Glu Arg Ala Trp Gln Lys Val Leu Asp Arg His
        50                  55                  60

Ser Ile Leu Arg Thr Phe Phe Val Trp Glu Asn Arg Gln Thr Pro Leu
65                  70                  75                  80

Gln Val Val Leu Lys Gln Val Asn Val Pro Trp Asn Thr Leu Asp Trp
                85                  90                  95

Arg Glu Leu Ser Ser Asn Asp Gln Gln Gln Leu Lys Gln Leu Leu
                100                 105                 110

Gln Thr Gln Arg Glu Gln Gly Phe Asn Leu Ser Gln Ala Pro Leu Met
            115                 120                 125

Arg Cys Thr Leu Val Arg Leu Gly Glu Asp Asn Tyr Lys Phe Ile Trp
        130                 135                 140

Ser His His Ile Leu Met Asp Gly Trp Cys Leu Ser Ile Ile Phe
145                 150                 155                 160

Lys Glu Ile Leu Ile Phe Tyr Lys Ala His Leu Leu Gly Glu Asn Cys
                165                 170                 175

Gln Leu Pro Lys Pro Arg Pro Tyr Gln Asp Tyr Ile Ala Trp Leu Asn
            180                 185                 190

Ser Gln Asp Lys Ser Ala Ala Ile Glu Phe Trp Gln Thr Leu Gln
        195                 200                 205

Gly Phe Ser Ala Pro Thr Pro Leu Val Met Asp Lys Thr Gln Phe Leu
    210                 215                 220

Lys Glu Gln Gln Tyr Lys Thr Ala Asp Tyr Gln Glu Arg Thr Ser Ser
225                 230                 235                 240

Leu Ser Pro Glu Cys Thr Gln Lys Leu Leu His Ile Ala Gln Gln His
```

-continued

```
                        245                 250                 255
His Val Thr Leu Ser Thr Val Val Gln Ala Ala Trp Ala Leu Leu Leu
                260                 265                 270
Ser Arg Tyr Ser Gly Glu Lys Asp Val Val Phe Gly Val Thr Val Ser
            275                 280                 285
Gly Arg Pro Pro Ser Leu Ser Glu Ile Glu Asn Met Val Gly Leu Phe
        290                 295                 300
Ile Asn Thr Leu Pro Leu Arg Val Gln Val Ser Thr Gln Glu Gln Leu
305                 310                 315                 320
Ile Pro Trp Leu Gln Lys Ile Gln Gln Ser Met Val Glu Leu Gln Glu
                325                 330                 335
Tyr Phe Tyr Thr Pro Leu Val Asp Ile Gln Ala Thr Ser Glu Ile Pro
            340                 345                 350
Gly Gly Ile Pro Leu Phe Glu Ser Ile Val Phe Glu Asn Tyr Pro
        355                 360                 365
Ile Asp Asn Ser Leu Leu Asn Glu Glu Gly Ser Leu His Leu Gly Asp
    370                 375                 380
Ile Glu Val Phe Glu Gln Thr Asn Tyr Pro Leu Thr Leu Val Ala Val
385                 390                 395                 400
Pro Gly Asp Lys Leu Ser Val Arg Ile Ser Tyr Asp Thr Ala Arg Phe
                405                 410                 415
Ser Ser Asn Thr Ile Glu Trp Ile Leu Gly Tyr Leu Gln Thr Val Leu
            420                 425                 430
Ser Ala Ile Ala Ile Val Glu Asn Pro Ser His Lys Val Ala Gln Leu
        435                 440                 445
Pro Leu Leu Ser Glu Val Glu Arg His Gln Leu Leu Val Glu Trp Asn
    450                 455                 460
Asn Thr Ala Thr Asp Tyr Pro Ser Asp Lys Cys Ile His Gln Leu Phe
465                 470                 475                 480
Glu Gln Gln Val Glu Lys Asn Pro Asn Ser Ile Ala Val Val Phe Glu
                485                 490                 495
Glu Glu Gln Ser Thr Tyr Gln Gln Leu Asn Gln Lys Ala Asn Gln Leu
            500                 505                 510
Ala His Tyr Leu Gln Thr Leu Gly Val Lys Pro Glu Val Leu Val Gly
        515                 520                 525
Ile Cys Ile Glu Tyr Ser Ile Asp Met Ile Val Gly Leu Leu Gly Ile
    530                 535                 540
Leu Lys Ala Gly Gly Val Tyr Val Pro Leu Asp Pro Asn Tyr Pro Gln
545                 550                 555                 560
Glu Arg Leu Ala Phe Met Gln Glu Asp Ser Asn Val His Ile Ile Leu
                565                 570                 575
Thr Gln Gln Pro Leu Leu Glu Lys Ile Ser Pro Gln Asn Ala His Ile
            580                 585                 590
Val Cys Leu Asp Arg Asp Arg Asp Val Ile Ala Arg Glu Gly Val Glu
        595                 600                 605
Asn Leu Asp Arg Gln Thr Thr Leu Asp Leu Ala Tyr Ala Ile Tyr
    610                 615                 620
Thr Ser Gly Ser Thr Gly Lys Pro Lys Ala Val Leu Gly Thr Leu Arg
625                 630                 635                 640
Gly Ile Val Asn Arg Leu His Trp Ile Trp Glu Met Leu Pro Phe Gly
                645                 650                 655
Ala Asp Glu Ile Cys Ser Gln Lys Thr Ser Ile Asn Phe Gly Asp His
            660                 665                 670
```

-continued

```
Val Ala Glu Ile Phe Ser Pro Leu Leu Lys Gly Ile Pro Leu Val Ile
            675                 680                 685

Val Pro Asp Ile Arg Gly Asn Ile Pro Arg Leu Met Ser Leu Leu
            690                 695                 700

Ser Asp Arg Lys Val Thr Arg Ile Val Leu Val Pro Ser Leu Leu Lys
705                 710                 715                 720

Ala Ile Leu Glu Asn Ala Pro Gln Gln Leu Thr Lys Leu Arg Tyr Leu
            725                 730                 735

Lys Tyr Val Phe Cys Ser Gly Glu Val Leu Pro Leu Thr Leu Ala Lys
            740                 745                 750

Glu Phe His Gln Lys Ile Ser Ser Ala Arg Leu Phe Asn Leu Tyr Gly
            755                 760                 765

Ser Ser Glu Val Ala Ala Asp Val Thr Cys Phe Glu Val Lys Leu Arg
770                 775                 780

Ile Ala Asn Gln Ile Glu Ala Lys Ser Lys Glu Lys Leu Asp Ala Leu
785                 790                 795                 800

Lys Asn Leu Pro Ser Gly Ser Gly Asp Arg Glu Thr Ala Val Leu His
            805                 810                 815

Lys Glu Ile Ile His Leu Gln Leu Ala Asp Glu Arg Arg Ala Asp Leu
            820                 825                 830

Gly Glu Ala Leu Glu Glu Tyr Leu Lys Arg Asn Thr Ile Pro Ile Gly
            835                 840                 845

Lys Pro Ile Ser Asn Thr Gln Ile Tyr Ile Leu Asp Lys Tyr Gly Asp
            850                 855                 860

Leu Leu Pro Pro Gly Val Thr Gly Glu Leu Tyr Val Gly Gly Asp Gly
865                 870                 875                 880

Leu Ala Lys Gly Tyr Leu Asn Leu Pro Glu Leu Thr Arg Glu Lys Phe
            885                 890                 895

Ile Pro Asn Pro Phe Val Lys Asp Arg Gly Lys Ser Lys Lys Ala Gln
            900                 905                 910

Ala Glu Arg Leu Phe Arg Thr Gly Asp Leu Ala Arg Trp Leu Pro Asp
            915                 920                 925

Gly Asn Ile Glu Phe Val Gly Arg Ile Asp His Gln Val Lys Val Arg
930                 935                 940

Gly Phe Arg Ile Glu Leu Gly Glu Ile Glu Ala Val Leu Ser Thr His
945                 950                 955                 960

Pro Gln Ile Gln Gln Val Val Ile Ala Ile Glu Asp Ile Pro Gly
            965                 970                 975

Ser Lys Arg Leu Val Ala Tyr Ile Val Cys Glu Asp Glu Ser Leu Ser
            980                 985                 990

Thr Tyr His Leu Arg Glu Phe Leu Lys Gln Lys Leu Pro Glu Tyr Met
            995                 1000                1005

Met Pro Ser Ala Phe Val Ile Leu Asp Thr Leu Pro Leu Thr Pro Ser
            1010                1015                1020

Gly Lys Ile Asp Arg Lys Ala Leu Pro Ala Pro Asp Gly Glu Ile Ser
1025                1030                1035                1040

Arg Glu His Glu Tyr Val Pro Pro Arg Thr Ser Gly Glu Ile Ile
            1045                1050                1055

Ala Asn Ile Phe Ala Ser Ile Leu Gly Val Gln Asn Val Gly Ile His
            1060                1065                1070

Asp Asn Phe Phe Glu Leu Gly Gly His Ser Leu Leu Ala Thr Arg Leu
            1075                1080                1085
```

-continued

```
Ile Ser Arg Leu Arg Val Ala Phe Glu Val Glu Ile Glu Leu Ser Ala
    1090                1095                1100

Val Phe Ser Ser Pro Thr Val Ala Gln Leu Glu Gln Thr Leu Thr Gln
1105                1110                1115                1120

Leu Arg Thr Thr Asn Ser Ala Leu Ser Leu Pro Pro Ile Gln Pro Arg
                1125                1130                1135

Thr Gln Asn Gln Gln Leu Pro Leu Ser Phe Ala Gln Asp Arg Leu Trp
            1140                1145                1150

Phe Leu Asn Gln Leu Glu Gly Ser Ser Ala Thr Tyr Asn Met Pro Gly
        1155                1160                1165

Ala Ile Arg Val Thr Gly Lys Leu Asp Ile Asn Ala Leu Gln Gln Ala
    1170                1175                1180

Leu Ser Glu Ile Val Arg Arg His Glu Val Leu Arg Thr Ser Phe Arg
1185                1190                1195                1200

Thr Val Asn Gly Thr Pro Ile Gln Val Ile His Pro Glu Ala Thr Met
                1205                1210                1215

Asn Ile Ser Val Ala Asp Leu Gln Gln Leu Glu Ala Thr Glu Arg Glu
            1220                1225                1230

Ser Val Leu His Gln Ala Gln Leu Ala Ala Ile Thr Pro Phe Asp
        1235                1240                1245

Leu Glu Thr Ala Pro Leu Ile Arg Cys Ser Leu Leu Gln Leu Asp Ala
    1250                1255                1260

Arg Glu Tyr Val Leu Leu Leu Thr Met His His Ile Val Ser Asp Gly
1265                1270                1275                1280

Trp Ser Met Gly Ile Phe Ser Gln Glu Leu Ser Thr Leu Tyr Gln Ala
                1285                1290                1295

Phe Ser Ala Gly Lys Pro Ser Pro Leu Ala Glu Leu Pro Ile Gln Tyr
            1300                1305                1310

Ala Asp Phe Ala Val Trp Gln Arg Gln Trp Leu Ser Gly Lys Val Leu
        1315                1320                1325

Glu Thr Gln Leu Asn Tyr Trp Leu Ser Gln Leu Glu Gly Ala Pro Glu
    1330                1335                1340

Leu Leu Gln Leu Pro Thr Asp Arg Pro Arg Pro Thr Val Gln Thr Phe
1345                1350                1355                1360

Arg Gly Thr Thr Gln Ser Phe Ser Leu Asn Thr Asp Leu Lys Glu Lys
                1365                1370                1375

Leu Gln Thr Leu Ser Arg Asn Ser Gly Thr Thr Leu Phe Met Thr Leu
            1380                1385                1390

His Ala Ala Phe Ala Thr Leu Leu Tyr Arg Tyr Ser Gly Gln Leu Asp
        1395                1400                1405

Ile Leu Ile Gly Ser Pro Ile Ala Asn Arg Asn Cys Ser Glu Ile Glu
    1410                1415                1420

Ser Leu Ile Gly Phe Phe Ala Asn Thr Leu Val Leu Lys Thr Arg Phe
1425                1430                1435                1440

Glu Asp Asn Pro Ser Phe Glu Asn Leu Leu Ala Gln Val Arg Glu Thr
                1445                1450                1455

Thr Leu Glu Ala Tyr Glu His Gln Asp Val Pro Phe Glu Gln Val Val
            1460                1465                1470

Glu Val Leu Gln Pro Gln Arg Ser Leu Ser Tyr Ala Pro Leu Phe Gln
        1475                1480                1485

Val Met Phe Val Leu Gln Asn Ala Pro Met Gly Glu Leu Glu Leu Pro
    1490                1495                1500

Gly Val Thr Leu Asn Leu Leu Ser Ser Gln Thr Glu Thr Ala Arg Phe
```

-continued

```
           1505                1510                1515                1520

Asp Leu Thr Val Ser Met Gln Gln Thr Ser Glu Ala Leu Val Gly Ser
                1525                1530                1535

Trp Glu Tyr Asn Thr Asp Leu Phe Asp Gly Ser Thr Ile Glu Arg Met
                1540                1545                1550

Thr Ala His Phe Gln Asn Leu Cys Ser Ala Ile Val Glu Asn Pro Gln
                1555                1560                1565

Gln Lys Ile Ser Glu Leu Pro Leu Phe Thr Asp Ser Glu Gln Glu Gln
            1570                1575                1580

Val Leu His Ser Tyr Asn Asn Ile Ala Thr Thr Tyr Leu Leu Asp Lys
1585                1590                1595                1600

Tyr Val His Phe Leu Ser Ser Asn Asn Leu Gln Ile Tyr Ile Leu Asp
                1605                1610                1615

Asn His Gln Gln Leu Val Pro Leu Ser Val Glu Gly Glu Ile Tyr Leu
                1620                1625                1630

Gly Asn Cys Asp Leu Leu Pro Asp Lys Leu His Pro Glu Pro Glu Lys
                1635                1640                1645

Phe Ile Ser Phe Ile Glu His Thr Gln Leu Gly Lys Leu Leu Lys Thr
            1650                1655                1660

Gly Glu Trp Gly Cys Arg Arg Val Asp Gly Ser Leu Glu Leu Leu Gly
1665                1670                1675                1680

Lys Glu His Arg Ile Val Thr Val Asn Gly Gln Arg Ile Asn Leu Gln
                1685                1690                1695

Arg Ile Glu Gln Ala Leu Gln Thr Ala Lys Gly Val Glu Asp Cys Tyr
                1700                1705                1710

Val Met Val Arg Asn Gln Lys Leu Val Ala Tyr Val Lys Asp Gly
                1715                1720                1725

Ser Trp Ala Arg Glu Phe Leu His His Tyr Leu Lys Ser Gln Leu Pro
            1730                1735                1740

Gly Tyr Pro Leu Pro Cys Ile Tyr Val Pro Val Ser Ala Leu Pro Leu
1745                1750                1755                1760

Thr Ser Phe Gly Glu Val Asp Glu Val Gly Leu Ala Ser Ile Ser Ile
                1765                1770                1775

Ile Asp Ser Glu Leu Ile Asn Thr Trp Glu Glu Gln Ile Gly Ser Gln
                1780                1785                1790

Ala Glu Ile Asp Lys Val Ala Val Phe Ile Glu Pro Asn Val Lys Thr
                1795                1800                1805

Ile Ser Pro Ile His Leu Glu Glu Leu Leu Pro Ser Ile Gln Ala Ile
            1810                1815                1820

Phe Asn Gln Gly Ser Thr Pro Val Glu Thr Pro Arg Thr Ala Arg Gly
1825                1830                1835                1840

Lys Glu Ser Ser Ser Leu Leu Glu Ile Lys Ser Pro Ala Ile Ser His
                1845                1850                1855

Glu Glu Val Leu Ile Phe Pro Glu Ser Ser Pro Glu Thr Leu Gly Glu
                1860                1865                1870

Met Leu Gln Lys Thr Ala Gly Lys Phe Pro His Lys Gly Ile Thr Tyr
            1875                1880                1885

Ile Asn Ser Asp Gly Ser Glu Gln Val Gln Ser Tyr Ala Gln Leu Leu
            1890                1895                1900

Glu Asp Ala Gln Arg Ile Leu Gly Gly Phe Arg Lys Leu Gly Ile Lys
1905                1910                1915                1920

Pro Gln Asp Lys Val Ile Leu Gln Leu Lys Glu Asn Lys Asp Phe Ile
                1925                1930                1935
```

```
Ser Ala Phe Trp Gly Cys Val Leu Gly Gly Phe Ile Pro Val Pro Val
            1940                1945                1950

Val Ile Pro Val Ser Tyr Asp Gln Pro Asn Val Asn Leu Asn Lys Leu
        1955                1960                1965

Gln Asn Ser Trp Gln Met Leu Glu Arg Pro Leu Ile Leu Thr Asp Lys
    1970                1975                1980

Lys Ser Leu Ser Glu Leu Lys Lys Trp Ser Gln Asn Leu Asn Asp Asp
1985                1990                1995                2000

Asn Phe Lys Leu Glu Thr Ile Glu Ser Leu Gln Lys Phe Ser Thr Asp
            2005                2010                2015

Lys Asp Tyr Tyr Asn Ala Gln Pro Glu Asp Leu Ala Leu Phe Met Leu
        2020                2025                2030

Thr Ser Gly Ser Thr Gly Met Ser Lys Val Val Gln Leu Ser His Leu
    2035                2040                2045

Asn Leu Leu Ser Arg Thr Ile Gly Ser Ile Gln Met Asn Asn Phe Thr
2050                2055                2060

Pro Glu Asp Ile Thr Leu Asn Trp Met Pro Leu Asp His Val Ala Gly
2065            2070                2075                2080

Leu Ile Tyr Phe His Ile Arg Asp Ile Tyr Leu Gly Cys Lys Gln Ile
            2085                2090                2095

His Ala Thr Ser Gln Leu Val Ile Glu Lys Pro Leu Arg Trp Leu Asp
        2100                2105                2110

Trp Ile Asp Thr Phe Gly Val Thr Val Thr Phe Ala Pro Asn Phe Ala
    2115                2120                2125

Tyr Ser Leu Ile Asn Asp Phe Val Gln Glu Ile Glu Lys Gln Asn Trp
        2130                2135                2140

Asn Leu Ser Ser Ile Arg Leu Met Leu Asn Gly Ala Glu Gln Ile Val
2145                2150                2155                2160

Ala Ala Thr Ala Arg Arg Phe Leu Lys Leu Leu Ala Pro Phe Gly Leu
            2165                2170                2175

Pro Gly Asp Ala Met Thr Pro Ser Trp Gly Met Ala Glu Val Ser Ser
        2180                2185                2190

Gly Ile Thr Tyr Ser Asp Asn Phe Ser Leu Leu Ser Ser Ser Asp Asp
    2195                2200                2205

Asn Ser Phe Val Asn Leu Gly Lys Pro Ile Arg Gly Thr Cys Leu Arg
        2210                2215                2220

Ile Val Asn Gln Asp Met Glu Val Leu Ser Glu Gly Glu Ile Gly Leu
2225                2230                2235                2240

Leu Gln Val Lys Gly Leu Thr Val Thr Ser Gly Tyr Tyr Gln Asn Pro
            2245                2250                2255

Lys Ala Asn Lys Glu Ala Phe Thr Glu Asp Gly Trp Phe Asn Thr Gly
        2260                2265                2270

Asp Leu Gly Phe Ile Lys Asp Gly Cys Leu Thr Ile Thr Gly Arg Gln
    2275                2280                2285

Lys Asp Ile Ile Ile Ile Asn Gly Val Asn Tyr Tyr Ser His Glu Ile
    2290                2295                2300

Glu Ala Val Val Glu Glu Leu Gly Glu Val Glu Val Ser Tyr Thr Ala
2305                2310                2315                2320

Ala Cys Gly Val Cys Val Ala Ser Asn Asn Thr Glu Glu Leu Val Ile
            2325                2330                2335

Phe Phe Thr Pro Tyr Val Ser Glu Lys Asn Gln Leu Leu Glu Leu Leu
        2340                2345                2350
```

-continued

```
Lys Lys Val Arg Glu Gln Val Ile Lys Tyr Cys Gly Ile Asn Pro Ser
        2355                2360                2365

Tyr Leu Ile Pro Ile Asp Lys Glu Leu Ile Pro Lys Thr Ser Ile Gly
        2370                2375                2380

Lys Ile Gln Arg Ser Leu Leu Lys Gln Arg Phe Glu Cys Gly Glu Phe
2385                2390                2395                2400

Lys Ser Leu Arg Gln Arg Val Asp Leu Leu Asp Asn Thr Asn Thr
        2405                2410                2415

Ile Pro Asn Trp Phe Tyr Arg Lys Val Trp Gln Ile Lys Glu Ser Lys
        2420                2425                2430

Asn Thr Leu Leu Asn Tyr Ser Gln Lys Thr Leu Thr Leu Ile Phe
        2435                2440                2445

Thr Asp Asn Leu Gly Trp Gln Gln Asp Asn Arg Gly Met Ser Gln Thr
        2450                2455                2460

Val Gln Pro Tyr Ala Gln Val Thr Ile Gly Ser Asn Phe Ala Gln Ile
2465                2470                2475                2480

Ser Pro Asn His Tyr Ser Val Val Pro Gly Asn Pro Gln His Tyr Arg
        2485                2490                2495

Leu Leu Ile Asp Ser Leu Arg Gln Asn Ser Gln Val Ile Ser Gln Ile
        2500                2505                2510

Leu His Leu Trp Asn Tyr Asn Glu Gln Thr Glu Lys Ile Ser Ser Leu
        2515                2520                2525

Glu Asn Leu Glu Ser Thr Gln Gln Gly Ile Tyr Ser Leu Leu Phe
        2530                2535                2540

Leu Val Gln Ala Leu Glu Glu Ile Gln Gly Lys Gln Gln Ala Val Lys
2545                2550                2555                2560

Leu Leu Trp Ile Ala Asn Gln Ser Gln Leu Val His Pro Thr Asp Lys
        2565                2570                2575

Ile Gln Pro Glu Lys Ser Thr Val Leu Gly Leu Leu Lys Thr Val Ser
        2580                2585                2590

Gln Glu Met Pro Trp Leu Thr Thr Arg His Leu Asp Leu Pro Leu Ala
        2595                2600                2605

Pro Glu Leu Asn Asn Ser Tyr Ile Trp Gln Glu Leu Tyr Ser Ala Asp
        2610                2615                2620

Lys Glu Leu Glu Val Ala Ile Arg Asn Arg Glu Arg Phe Val Ser Gly
2625                2630                2635                2640

Leu Glu Pro Val Asp Met Thr Ala Lys Glu Lys Gln Lys Ile Pro Ile
        2645                2650                2655

Leu Pro Gly Gly Thr Tyr Leu Leu Thr Gly Gly Leu Gly Gly Ile Gly
        2660                2665                2670

Thr Val Ile Ala Lys Tyr Leu Leu Glu His Tyr Gln Ala Asn Leu Ile
        2675                2680                2685

Leu Val Gly Arg Thr Gln Ile Glu Asp Asn Glu Glu Ala Ser Thr
        2690                2695                2700

Lys Leu Gln Arg Tyr Gln Glu Leu Glu Lys Leu Pro Gly Ser Ile Ile
2705                2710                2715                2720

Tyr Gln Thr Val Asp Ile Cys Asp Leu Val Gly Leu Gln Val Val
        2725                2730                2735

Glu Lys Ala Thr Gln Glu Trp Arg Thr Gln Leu Asp Gly Val Phe His
        2740                2745                2750

Met Ala Gly Ile Ile Gln Glu Thr Pro Ile Glu Lys Glu Thr Pro Gly
        2755                2760                2765

Asn Ile Ala Ala Val Leu Arg Pro Lys Val Ser Gly Thr Trp Val Leu
```

-continued

```
              2770                2775                2780
His Gln Leu Leu Lys Asp Lys Glu Asn Ala Leu Phe Val His Phe Cys
2785                2790                2795                2800

Ser Val Asn Gly Phe Phe Gly Gly Thr Asn Val Ala Ala Tyr Ser Ala
                2805                2810                2815

Ala Asn Ser Phe Gln Ser Ala Trp Ser Asp Tyr Gln Gln Asn Gly
                2820                2825                2830

Phe Gln Ser Tyr Cys Cys Ser Trp Ser Met Trp Asn Glu Thr Gly Ile
                2835                2840                2845

Ser His Gly Tyr Gln Phe Gln Glu Leu Ser Arg Ala Lys Gly Tyr Phe
    2850                2855                2860

Ile Ile Thr Pro Gln Gln Gly Phe Tyr Ser Phe Leu Ala Ala Leu Ser
2865                2870                2875                2880

Gly Ser Glu His Asn Leu Leu Ile Gly Leu Asp Gly Thr Lys Thr Asn
                2885                2890                2895

Val Glu His Leu Ile Arg Asp Cys Gln Pro Lys Gln Lys Leu Thr Ala
                2900                2905                2910

Tyr Phe Thr Ser Pro Thr Pro Glu Leu Ala Ala Leu Ser Leu Gln Glu
                2915                2920                2925

Leu Gln Leu His Asp Arg Phe Gly Ile Pro Asn Gln Ile Asn Phe Val
2930                2935                2940

Gln Leu Glu Gln Ile Pro Leu Thr Gln Arg Gly Glu Ile Asn Arg Glu
2945                2950                2955                2960

Gln Ile Ala Ala Ile Tyr Gly Gly Leu Asn Thr Ser Glu Gln Thr Lys
                2965                2970                2975

Pro Arg Asn Gln Thr Glu Arg Gln Leu Val Glu Ile Phe Gln Glu Val
                2980                2985                2990

Leu Asn Leu Pro Ser Ile Gly Ile His Asp Asn Phe Ser Leu Gly
                2995                3000                3005

Gly His Ser Leu Leu Ala Val Arg Leu Met Ser Glu Ile Gln Gln Gln
    3010                3015                3020

Phe Gln Lys Asn Leu Pro Leu Ala Thr Leu Phe Gln Asn Pro Thr Ile
3025                3030                3035                3040

Glu Arg Leu Ala Leu Leu Val Gly Ser Asp Ser Gly Ala Glu Leu Trp
                3045                3050                3055

Ser Pro Leu Val Pro Ile Gln Gln Asn Gly Ser Leu Pro Pro Leu Phe
                3060                3065                3070

Cys Val Pro Gly Ala Gly Gly Asn Val Leu Tyr Phe His His Leu Ala
                3075                3080                3085

Gln Tyr Leu Gly Asn Asn Gln Pro Leu Tyr Gly Leu Gln Ala Gln Gly
    3090                3095                3100

Leu Asp Gly Glu Thr Glu Pro His Lys Ser Val Glu Glu Ile Ala Ser
3105                3110                3115                3120

Gln His Ile Lys Ala Ile Gln Thr Val Gln Pro Val Gly Pro Tyr Phe
                3125                3130                3135

Leu Ala Gly His Ser Phe Gly Ser His Val Val Phe Glu Met Ala Asn
                3140                3145                3150

Gln Leu Gln Leu Ile Gly Lys Ser Val Ala Tyr Val Gly Ile Leu Asp
                3155                3160                3165

Thr Pro Ala Pro Thr Ser Gln Ala Asn His Gln Asn Asp Phe Ser Asn
    3170                3175                3180

Trp Asp Asn Ala Lys Trp Ile Cys Arg Met Ala Glu Val Ile Glu Asp
3185                3190                3195                3200
```

```
Ile Val Gly Glu Asn Leu Phe Leu Ser Tyr Glu Thr Leu Thr Ser Leu
                3205                3210                3215

Thr Trp Glu Gln Gln Leu Asn Tyr Phe Lys Gln Lys Leu Glu Ile Val
                3220                3225                3230

Gly Phe Leu Pro Ala Gln Thr Asp Ile Lys Ile Val Arg Gly Leu Leu
                3235                3240                3245

Gln Val Phe Gln Thr Gln Cys Gln Ile Lys Tyr Glu Pro Glu Lys Thr
            3250                3255                3260

Tyr Lys Thr Pro Ile Thr Leu Phe Cys Ala Arg Glu Ile Asn Pro Glu
3265                3270                3275                3280

Gln Glu Ser Tyr Ser His Ile Phe Gln Glu Pro Thr Trp Gly Trp Asn
                3285                3290                3295

Gln Phe Ser Asp Gly Glu Val Glu Ile His Ile Val Pro Gly Asn His
                3300                3305                3310

Val Ser Met Leu Ser Glu Pro His Val Lys Val Leu Ala Gln Gln Met
            3315                3320                3325

Gln Ile Ser Leu Glu Gln Ala Gln Lys Thr His Gln Leu Glu Lys
        3330                3335                3340

<210> SEQ ID NO 8
<211> LENGTH: 1353
<212> TYPE: DNA
<213> ORGANISM: Nostoc species

<400> SEQUENCE: 8
atgattaata ctgctaaatc ctcattactt cctggtccca ctacaccatc ttggtggaac    60
ttattgcaat ggcttaataa tccttgtgaa tttttggaag agtgtcgagc acgctatgga   120
gacactttta ccttcaaagc tattggtttt gaacctttag tacttattag taatcctaag   180
gatataaaag aaattttga taaacacaag tattttgaca gtggaaaagc taaagctaac    240
gatttagcag attttttttt aggcaacaat tccgtcacct tgcttgatgg aagtagtcat   300
aaacgacagc gtaaactact gatgcctgct tttcatggtc aaaatatatc taactatgga   360
gaactaatat gccatgcaac gaagcaggtt acttctaatt ggcaacctgg tcaaagattg   420
attatttaca aggaagtcaa agaaattacg ctgcgagcga tgttaacggt tttactgggt   480
tcagataaaa cggaacgtta tcaacaactc aaattgatag ttaatcaaat agtatccact   540
ataactaatc cctttgcttc tagctctctt ttcttcaatg tgtttagaag agactggggt   600
tcttggagtg cctgggtaa tcttttacgt tgccaacgtc agattgcaaa tatcatttct   660
gcagaaatca agaacgtag agaaaattgt aacaattaca acaatgatat cctcagtatg   720
ctgatggcag cacgagatga aaatggagga aaaatgacag atgaggagtt gcaagatgag   780
ttaatgacac ttatctttc tggatatgaa actacatctg cagcaataac atgggcatat   840
tattggattc attacttacc agagataaga gccaagttat gcaagaatt agatgagtta   900 ggagataatc cagacccaac ggaaataagc aaattacctt atctcaatgc agtttgtgct   960
gaaaccttga gaatatatcc agttggtcta actactttc ctcgaattgt aaaatcgcca  1020
atagaaattg gaggtcatca atttgaggta ggaacttgtc tttatccatg tatttatcta  1080
attcaccacc gggaagaact atatcctaac tctaaacagt ttaagccaga acgttttcta  1140
gataataaat ttttaaatta tgagtatttc cctttcggtg gcggtaaccg aacttgcatt  1200
ggtatggcat tgctcagtt taaaatgaag ttagtattgg ctaatatttt gcggaattgg  1260
caattggaat tggtaggcaa acctccttta aaaccagtac gagatatttt ctcaatttat  1320
```

```
cctcaaggtg gattaaaaat ggttgtattg taa                                    1353
```

<210> SEQ ID NO 9
<211> LENGTH: 450
<212> TYPE: PRT
<213> ORGANISM: Nostoc species

<400> SEQUENCE: 9

```
Met Ile Asn Thr Ala Lys Ser Ser Leu Leu Pro Gly Pro Thr Thr Pro
  1               5                  10                  15

Ser Trp Trp Asn Leu Leu Gln Trp Leu Asn Asn Pro Cys Glu Phe Leu
             20                  25                  30

Glu Glu Cys Arg Ala Arg Tyr Gly Asp Thr Phe Thr Phe Lys Ala Ile
         35                  40                  45

Gly Phe Glu Pro Leu Val Leu Ile Ser Asn Pro Lys Asp Ile Lys Glu
     50                  55                  60

Ile Phe Asp Lys His Lys Tyr Phe Asp Ser Gly Lys Ala Lys Ala Asn
 65                  70                  75                  80

Asp Leu Ala Gly Phe Phe Leu Gly Asn Asn Ser Val Thr Leu Leu Asp
                 85                  90                  95

Gly Ser Ser His Lys Arg Gln Arg Lys Leu Leu Met Pro Ala Phe His
            100                 105                 110

Gly Gln Asn Ile Ser Asn Tyr Gly Glu Leu Ile Cys His Ala Thr Lys
        115                 120                 125

Gln Val Thr Ser Asn Trp Gln Pro Gly Gln Arg Leu Ile Ile Tyr Lys
    130                 135                 140

Glu Val Lys Glu Ile Thr Leu Arg Ala Met Leu Thr Val Leu Leu Gly
145                 150                 155                 160

Ser Asp Lys Thr Glu Arg Tyr Gln Gln Leu Lys Leu Ile Val Asn Gln
                165                 170                 175

Ile Val Ser Thr Ile Thr Asn Pro Phe Ala Ser Ser Leu Phe Phe
            180                 185                 190

Asn Val Phe Arg Arg Asp Trp Gly Ser Trp Ser Ala Trp Gly Asn Leu
        195                 200                 205

Leu Arg Cys Gln Arg Gln Ile Ala Asn Ile Ile Ser Ala Glu Ile Lys
    210                 215                 220

Glu Arg Arg Glu Asn Cys Asn Asn Tyr Asn Asn Asp Ile Leu Ser Met
225                 230                 235                 240

Leu Met Ala Ala Arg Asp Glu Asn Gly Gly Lys Met Thr Asp Glu Glu
                245                 250                 255

Leu Gln Asp Glu Leu Met Thr Leu Ile Phe Ser Gly Tyr Glu Thr Thr
            260                 265                 270

Ser Ala Ala Ile Thr Trp Ala Tyr Tyr Trp Ile His Tyr Leu Pro Glu
        275                 280                 285

Ile Arg Ala Lys Leu Leu Gln Glu Leu Asp Glu Leu Gly Asp Asn Pro
    290                 295                 300

Asp Pro Thr Glu Ile Ser Lys Leu Pro Tyr Leu Asn Ala Val Cys Ala
305                 310                 315                 320

Glu Thr Leu Arg Ile Tyr Pro Val Gly Leu Thr Thr Phe Pro Arg Ile
                325                 330                 335

Val Lys Ser Pro Ile Glu Ile Gly Gly His Gln Phe Glu Val Gly Thr
            340                 345                 350

Cys Leu Tyr Pro Cys Ile Tyr Leu Ile His His Arg Glu Glu Leu Tyr
        355                 360                 365
```

```
Pro Asn Ser Lys Gln Phe Lys Pro Glu Arg Phe Leu Asp Asn Lys Phe
        370                 375                 380

Leu Asn Tyr Glu Tyr Phe Pro Phe Gly Gly Gly Asn Arg Thr Cys Ile
385                 390                 395                 400

Gly Met Ala Phe Ala Gln Phe Lys Met Lys Leu Val Leu Ala Asn Ile
                405                 410                 415

Leu Arg Asn Trp Gln Leu Glu Leu Val Gly Lys Pro Pro Leu Lys Pro
            420                 425                 430

Val Arg Asp Ile Phe Ser Ile Tyr Pro Gln Gly Gly Leu Lys Met Val
        435                 440                 445

Val Leu
    450

<210> SEQ ID NO 10
<211> LENGTH: 885
<212> TYPE: DNA
<213> ORGANISM: Nostoc species

<400> SEQUENCE: 10
atgtattcaa taaaaattga aaatctaata attagagtga aaagtgtatt agaaatgcca      60
gtttctaaag aagctgagat ggcaaataaa tttaatgagt ttggattcgt aatactagaa     120
cacgaacctt cagcaacacc taagaataac ttattaaaat tgtctgatta ttttggaaca     180
attattcagc acgaacattc tgattcacag ggaattgttc ccatcagtcc tgttgatagt     240
tatccagaat atgtaaatac tacaactaca gatttatcgt tacatacgga tggagcgttc     300
acaattactc caccaaaagt aatggcaatg cagtgccaga ttgctgctgc aaatggcggg     360
ttcaccaagc ttattgatgg caagctggta tatgaacatc taaagcggac aaacccagtt     420
ggattgttaa ctttgtttaa tcctgatgcg attacagtca aaagagataa taaaaaagca     480
actaaaccta ttttgaaga acatcatgct gggcttattg taaggtttag agcagataat      540
gcagctcatg tttcggttga atcgaaaagt tttgcggcat ttaaatcatt tgaaaacttt     600
gtaaataatc ctgacaatca agtaattttt aaacttgcac aaaaccaaat aattattgta     660
gataatacta gagttttgca tggaagaact gcattttcca acaagagta taggctacta      720 aatcgacttt ggtttgatgg acaatctgat attataaatt taaagtttgg tatttctata     780
gccccaaaaa acttgagttt atttgctaaa aagtatcagc catctcaaat agatataggc     840
tcagatattt ctcagtcaac tcaattgaaa tttaaagcca catga                     885

<210> SEQ ID NO 11
<211> LENGTH: 294
<212> TYPE: PRT
<213> ORGANISM: Nostoc species

<400> SEQUENCE: 11

Met Tyr Ser Ile Lys Ile Glu Asn Leu Ile Ile Arg Val Lys Ser Val
  1               5                  10                  15

Leu Glu Met Pro Val Ser Lys Glu Ala Glu Met Ala Asn Lys Phe Asn
                20                  25                  30

Glu Phe Gly Phe Val Ile Leu Glu His Glu Pro Ser Ala Thr Pro Lys
            35                  40                  45

Asn Asn Leu Leu Lys Leu Ser Asp Tyr Phe Gly Thr Ile Ile Gln His
        50                  55                  60

Glu His Ser Asp Ser Gln Gly Ile Val Pro Ile Ser Pro Val Asp Ser
 65                  70                  75                  80
```

```
Tyr Pro Glu Tyr Val Asn Thr Thr Thr Asp Leu Ser Leu His Thr
                85                  90                  95

Asp Gly Ala Phe Thr Ile Thr Pro Pro Lys Val Met Ala Met Gln Cys
            100                 105                 110

Gln Ile Ala Ala Ala Asn Gly Gly Phe Thr Lys Leu Ile Asp Gly Lys
            115                 120                 125

Leu Val Tyr Glu His Leu Lys Arg Thr Asn Pro Val Gly Leu Leu Thr
            130                 135             140

Leu Phe Asn Pro Asp Ala Ile Thr Val Lys Arg Asp Asn Lys Lys Ala
145                 150                 155                 160

Thr Lys Pro Ile Phe Glu His His Ala Gly Leu Ile Val Arg Phe
                165                 170                 175

Arg Ala Asp Asn Ala Ala His Val Ser Val Glu Ser Lys Ser Phe Ala
                180                 185                 190

Ala Phe Lys Ser Phe Glu Asn Phe Val Asn Asn Pro Asp Asn Gln Val
            195                 200                 205

Ile Phe Lys Leu Ala Gln Asn Gln Ile Ile Ile Val Asp Asn Thr Arg
            210                 215                 220

Val Leu His Gly Arg Thr Ala Phe Ser Lys Gln Glu Tyr Arg Leu Leu
225                 230                 235                 240

Asn Arg Leu Trp Phe Asp Gly Gln Ser Asp Ile Ile Asn Leu Lys Phe
                245                 250                 255

Gly Ile Ser Ile Ala Pro Lys Asn Leu Ser Leu Phe Ala Lys Lys Tyr
            260                 265                 270

Gln Pro Ser Gln Ile Asp Ile Gly Ser Asp Ile Ser Gln Ser Thr Gln
            275                 280                 285

Leu Lys Phe Lys Ala Thr
        290
```

```
<210> SEQ ID NO 12
<211> LENGTH: 333
<212> TYPE: DNA
<213> ORGANISM: Nostoc species

<400> SEQUENCE: 12
atgttgaagt cgaaaattca cagagcgacg gtgacggaag ccaacgttaa ctacatcgga     60
agtattacag tagacaaagt tctgatggaa aaggcagaca tactaccggg tgaaaaggtt    120
atggtggtgg acaacactaa tggtaatcgt ctagaaacct atgtcctaga aggtgaggaa    180
aattccgggg taatctgtat gaacggtggc tccgcccacc tagtcaattc aggagacctt    240
atcacattgc tagcattcga ggtaactgac gaaatcaagg aaccgaaaaa aattatcgtg    300
gatgaaaaca acaagtttct caagtacctg taa                                 333

<210> SEQ ID NO 13
<211> LENGTH: 110
<212> TYPE: PRT
<213> ORGANISM: Nostoc species

<400> SEQUENCE: 13
```

```
Met Leu Lys Ser Lys Ile His Arg Ala Thr Val Thr Glu Ala Asn Val
1               5                   10                  15

Asn Tyr Ile Gly Ser Ile Thr Val Asp Lys Val Leu Met Glu Lys Ala
            20                  25                  30

Asp Ile Leu Pro Gly Glu Lys Val Met Val Val Asp Asn Thr Asn Gly
        35                  40                  45
```

```
Asn Arg Leu Glu Thr Tyr Val Leu Glu Gly Glu Asn Ser Gly Val
 50                  55                  60
Ile Cys Met Asn Gly Gly Ser Ala His Leu Val Asn Ser Gly Asp Leu
 65                  70                  75                  80
Ile Thr Leu Leu Ala Phe Glu Val Thr Asp Glu Ile Lys Glu Pro Lys
                 85                  90                  95
Lys Ile Ile Val Asp Glu Asn Asn Lys Phe Leu Lys Tyr Leu
            100                 105                 110

<210> SEQ ID NO 14
<211> LENGTH: 1476
<212> TYPE: DNA
<213> ORGANISM: Nostoc species

<400> SEQUENCE: 14
atgtctacac tgcctaattc cacacagatt ctaattatcg agggggacc ttctggatct      60
actgctgcta ccctattggc tcgtgagggc tttgatgtaa cgctgttaga acgagaggta    120
ttcccgcgtt accacgttgg ggaatctctt ttgccctctg cttttagaaat ttttgacctg   180
cttggcgtac gcgagaaaat tgaagcttat ggctttcagc gtaaacctgg agcgtacata   240
gaatggggaa cggaaaagtg gagcctcaat tttggggaac ttacggggga caacacctac   300
agcttccaag ttcgccgtga cgaattcgac cacttgcttt tagagcattc aaagagccag   360
ggtgtgaagg ttttgaagg gactaaaaatt cgccagttgt cttttgatgg cgatcgcccg   420
cgcagcgcta cttggtcaca atcaaatgat actaccgggg agatttcttt tgactttatg   480
attgacgctt caggtcgtgc tgggatcatg gcgacggagt atctgaaaaa ccgccgtcta   540
cacgacgtat tccagaatgt tggcatctgg ggtactggaa aaacgccttt agactacct    600
aaaggtcagt cgggtgcgat tgccttgggc tccattccag atggttgggt gtggggaatt   660
cctttggatg aggaaattat gagcgttggt gtagtgatgc ataagtcaac ctacaaggag   720
agactgacta agaacttgaa ggatatctac gtggaggcga ttgcagagtg tcccttgata   780
gcggatctgg ttgcactagg ggagctagtc tcagacgtga agttgagca agattactct    840
tacacttccg actccttttc aggaccagcc tacttcatat cgggagacgc tgcttgcttc   900
ctagacccc tactatcgag tggggtgcat cttgctactt atagcgcttt gttagccgca    960
gccagtatca aagtgttat acgtggcgag gtgactgagt cacaagctgc ttctttctac   1020
gatcagagct atcggcaggc ttatttgcgt ttcttagtgt tcgtatcagc cttctacgat  1080
caaaaccgtg gcaaggattc ctatttctgg gaggcacaac ggcttagtcg ccgtgacttc  1140
ggcagttcta acctaaagct agcattcttg aatctggtgt ccggcgtcga ggacttggag  1200
gacgctaagg aggggattgc cgatttgtt atggcagaga tgtctcagcg gattcagtca   1260
agccacagca ttaggcaaga caagcaggcg ttggcaatcg aaagggaaaa aggtaacgag  1320
gtaatgaaga caaatgccca gttttttcaat gcagtcgagg atttttccat actatcggca  1380
gttgggggcag ttgatggtct atatgttaca actcagccaa aattaggatt ggtacaggta  1440
atccctctcc aaagaaactc tttgctccac acttag                             1476

<210> SEQ ID NO 15
<211> LENGTH: 491
<212> TYPE: PRT
<213> ORGANISM: Nostoc species

<400> SEQUENCE: 15
```

```
Met Ser Thr Leu Pro Asn Ser Thr Gln Ile Leu Ile Gly Gly Gly
  1               5                  10                 15

Pro Ser Gly Ser Thr Ala Ala Thr Leu Leu Ala Arg Glu Gly Phe Asp
             20                  25                  30

Val Thr Leu Leu Glu Arg Glu Val Phe Pro Arg Tyr His Val Gly Glu
         35                  40                  45

Ser Leu Leu Pro Ser Ala Leu Glu Ile Phe Asp Leu Leu Gly Val Arg
 50                  55                  60

Glu Lys Ile Glu Ala Tyr Gly Phe Gln Arg Lys Pro Gly Ala Tyr Ile
 65              70                  75                  80

Glu Trp Gly Thr Glu Lys Trp Ser Leu Asn Phe Gly Glu Leu Thr Gly
                 85                  90                  95

Asp Asn Thr Tyr Ser Phe Gln Val Arg Arg Asp Glu Phe Asp His Leu
            100                 105                 110

Leu Leu Glu His Ser Lys Ser Gln Gly Val Lys Val Phe Glu Gly Thr
            115                 120                 125

Lys Ile Arg Gln Leu Ser Phe Asp Gly Asp Arg Pro Arg Ser Ala Thr
130                 135                 140

Trp Ser Gln Ser Asn Asp Thr Thr Gly Glu Ile Ser Phe Asp Phe Met
145                 150                 155                 160

Ile Asp Ala Ser Gly Arg Ala Gly Ile Met Ala Thr Glu Tyr Leu Lys
                165                 170                 175

Asn Arg Arg Leu His Asp Val Phe Gln Asn Val Gly Ile Trp Gly Tyr
            180                 185                 190

Trp Lys Asn Ala Leu Arg Leu Pro Lys Gly Gln Ser Gly Ala Ile Ala
        195                 200                 205

Leu Gly Ser Ile Pro Asp Gly Trp Val Trp Gly Ile Pro Leu Asp Glu
    210                 215                 220

Glu Ile Met Ser Val Gly Val Val Met His Lys Ser Thr Tyr Lys Glu
225                 230                 235                 240

Arg Leu Thr Lys Asn Leu Lys Asp Ile Tyr Val Glu Ala Ile Ala Glu
            245                 250                 255

Cys Pro Leu Ile Ala Asp Leu Val Ala Leu Gly Glu Leu Val Ser Asp
            260                 265                 270

Val Lys Val Glu Gln Asp Tyr Ser Tyr Thr Ser Asp Ser Phe Ser Gly
        275                 280                 285

Pro Ala Tyr Phe Ile Ser Gly Asp Ala Ala Cys Phe Leu Asp Pro Leu
    290                 295                 300

Leu Ser Ser Gly Val His Leu Ala Thr Tyr Ser Ala Leu Leu Ala Ala
305                 310                 315                 320

Ala Ser Ile Thr Ser Val Ile Arg Gly Glu Val Thr Glu Ser Gln Ala
                325                 330                 335

Ala Ser Phe Tyr Asp Gln Ser Tyr Arg Gln Ala Tyr Leu Arg Phe Leu
            340                 345                 350

Val Phe Val Ser Ala Phe Tyr Asp Gln Asn Arg Gly Lys Asp Ser Tyr
        355                 360                 365

Phe Trp Glu Ala Gln Arg Leu Ser Arg Arg Asp Phe Gly Ser Ser Asn
    370                 375                 380

Leu Lys Leu Ala Phe Leu Asn Leu Val Ser Gly Val Glu Asp Leu Glu
385                 390                 395                 400

Asp Ala Lys Glu Gly Ile Ala Asp Phe Val Met Ala Glu Met Ser Gln
                405                 410                 415

Arg Ile Gln Ser Ser His Ser Ile Arg Gln Asp Lys Gln Ala Leu Ala
```

```
                420             425             430
Ile Glu Arg Glu Lys Gly Asn Glu Val Met Lys Thr Asn Ala Gln Phe
        435                 440                 445

Phe Asn Ala Val Glu Gly Phe Ser Ile Leu Ser Ala Val Gly Ala Val
    450                 455                 460

Asp Gly Leu Tyr Val Thr Thr Gln Pro Lys Leu Gly Leu Val Gln Val
465                 470                 475                 480

Ile Pro Leu Gln Arg Asn Ser Leu Leu His Thr
                485                 490

<210> SEQ ID NO 16
<211> LENGTH: 1383
<212> TYPE: DNA
<213> ORGANISM: Nostoc species

<400> SEQUENCE: 16
atgttatctc ccctatttga tgcttttgta gaggcaagcc ccgtcagtgt aatgatgcga    60
gtcctaatgg aaaacatttt taattcctcg cgaatgaatc aaatatttga tacatcaagc   120
gttcgccaat actctcaaga gctactgttt tcgactcagg tggatttgat gagtctagta   180
gtgtgtggga tgtatccctc ggttcatgca gcctatcaga agaaggcagt ggaggtaagt   240
gtcagcgcca cagcgttata caacaaactg aacggattg aactgcctgt aagtcgggca    300
ttagtgcatg agacagcatc tgacctccag cagttgctgt tgatgttgaa tgtggaacgc   360
cccagtcctc taggaaaaca atatcggttg cggattgtag atggcagttg tttagccgga   420
accgaacgca gactagcagc gctgcgcccc catgcagcca aaccattacc cggaaaaaca   480
atcgccattc tcgacccagg acaaaaactg gtggttgatg tgattccttg tgaagacggt   540
cattcccaag aacgctccaa gtttcatcag gttttggcac aagtgcaacc ccaacaggta   600
tggattgcag accgtaactt tgtaccgca ggatttctcc atactattgc caaacttgga    660
gcgttttttg tgattcgtca acacgggggt ttaggatacg agccttttgg tgagttacaa   720
gctgttgggt tgtgccaaac aggaactgtg tttgaacaac aggtggaaat tgtccatgag   780
ggagggactt ttcggtgtcg ccgtatcgta gttaagttga ctcgtcccac ccgtgaccaa   840
gagtgggaaa ttgccatttt taccaactta ccacccactg acgcagacgg cattctggtg   900
gcacaactct atcaagggcg gtggagtgtg gaaactttat tccaaactgt gacccaaaac   960
tttcatggag aaattgaaac cctagcttat cctaaagctg ccttattctc ctactgcatg  1020
gcactgtcag cctacaacct tttagcgaca cttaaagcag ttcttggcag tgtacatggg  1080
gtagacaaaa tcgatattgg gctatccgat ttttacctag tagatgatat ccattccatc  1140
tatcggggca tgatgattgc tattcctccg gttcattggc aattctttga ggagtttacc  1200
aacattcaga tggtagacgt tctccagcat ctagcaacca agtacatct caaatctttt   1260
cgcaaacacc ccagaagtcc aaaaagaaa cgaccaccac tctctgttga tggcaaacat   1320
tcccactgtt ccactactcg aaagctcaag caatacaaag cagctcttga tgctatcccg  1380
tga                                                                1383

<210> SEQ ID NO 17
<211> LENGTH: 460
<212> TYPE: PRT
<213> ORGANISM: Nostoc species

<400> SEQUENCE: 17

Met Leu Ser Pro Leu Phe Asp Ala Phe Val Glu Ala Ser Pro Val Ser
```

-continued

```
  1               5                  10                 15
Val Met Met Arg Val Leu Met Glu Asn Ile Phe Asn Ser Ser Arg Met
              20                 25                 30

Asn Gln Ile Phe Asp Thr Ser Ser Val Arg Gln Tyr Ser Gln Glu Leu
              35                 40                 45

Leu Phe Ser Thr Gln Val Asp Leu Met Ser Leu Val Val Cys Gly Met
  50                 55                 60

Tyr Pro Ser Val His Ala Ala Tyr Gln Lys Lys Ala Val Glu Val Ser
65                 70                 75                 80

Val Ser Ala Thr Ala Leu Tyr Asn Lys Leu Gln Arg Ile Glu Leu Pro
              85                 90                 95

Val Ser Arg Ala Leu Val His Glu Thr Ala Ser Asp Leu Gln Gln Leu
              100                105                110

Leu Leu Met Leu Asn Val Glu Arg Pro Ser Pro Leu Gly Lys Gln Tyr
              115                120                125

Arg Leu Arg Ile Val Asp Gly Ser Cys Leu Ala Gly Thr Glu Arg Arg
              130                135                140

Leu Ala Ala Leu Arg Pro His Ala Ala Lys Pro Leu Pro Gly Lys Thr
145                150                155                160

Ile Ala Ile Leu Asp Pro Gly Thr Lys Leu Val Val Asp Val Ile Pro
              165                170                175

Cys Glu Asp Gly His Ser Gln Glu Arg Ser Lys Phe His Gln Val Leu
              180                185                190

Ala Gln Val Gln Pro Gln Gln Val Trp Ile Ala Asp Arg Asn Phe Cys
              195                200                205

Thr Ala Gly Phe Leu His Thr Ile Ala Lys Leu Gly Ala Phe Phe Val
              210                215                220

Ile Arg Gln His Gly Gly Leu Gly Tyr Glu Pro Phe Gly Glu Leu Gln
225                230                235                240

Ala Val Gly Leu Cys Gln Thr Gly Thr Val Phe Glu Gln Gln Val Glu
              245                250                255

Ile Val His Glu Gly Gly Thr Phe Arg Cys Arg Arg Ile Val Val Lys
              260                265                270

Leu Thr Arg Pro Thr Arg Asp Gln Glu Trp Glu Ile Ala Ile Phe Thr
              275                280                285

Asn Leu Pro Pro Thr Asp Ala Asp Gly Ile Leu Val Ala Gln Leu Tyr
              290                295                300

Gln Gly Arg Trp Ser Val Glu Thr Leu Phe Gln Thr Val Thr Gln Asn
305                310                315                320

Phe His Gly Glu Ile Glu Thr Leu Ala Tyr Pro Lys Ala Ala Leu Phe
              325                330                335

Ser Tyr Cys Met Ala Leu Ser Ala Tyr Asn Leu Leu Ala Thr Leu Lys
              340                345                350

Ala Val Leu Gly Ser Val His Gly Val Asp Lys Ile Asp Ile Gly Leu
              355                360                365

Ser Asp Phe Tyr Leu Val Asp Asp Ile His Ser Ile Tyr Arg Gly Met
              370                375                380

Met Ile Ala Ile Pro Pro Val His Trp Gln Phe Phe Glu Glu Phe Thr
385                390                395                400

Asn Ile Gln Met Val Asp Val Leu Gln His Leu Ala Thr Lys Val His
              405                410                415

Leu Lys Ser Phe Arg Lys His Pro Arg Ser Pro Lys Lys Lys Arg Pro
              420                425                430
```

```
Pro Leu Ser Val Asp Gly Lys His Ser His Cys Ser Thr Thr Arg Lys
        435                 440                 445

Leu Lys Gln Tyr Lys Ala Ala Leu Asp Ala Ile Pro
    450                 455                 460

<210> SEQ ID NO 18
<211> LENGTH: 942
<212> TYPE: DNA
<213> ORGANISM: Nostoc species

<400> SEQUENCE: 18
atgaacaaac caccatccag acgcaagaaa attacccctg cgacatctga ggaaccaaag      60
ctagcaactg accctgctca ggaaaatact tctttgcacg aaaatccagg ggagcaact     120 atcacggtga cggctgttga agtaacagat ttgacccagg aagaacaaag cttacgcctg    180
catttagaac accgtgtgga gagagcattt ttggaggcgg gtcaagcgtt gatggagttg    240
cgggacagac ggctgtaccg ttccacgcac cggactttg aagaatactg ccgcgaacgc     300
ttcaattata gtcgtgacgc ggcttacttg aagatttcgg ctactgtggt ttatgagaat    360
cttcaaaagt ttttgccgac cattggtcgg caaattccaa tgccgaccaa cgaacgacaa    420
ttgcgttttt tggcgaaagc cgagttggaa ccggctgtgc aagcggatgt atggcggcag    480
gcagtggagc aagctggcaa taagattcca tccggtcgca tagtgaaaga tgttgtagat    540
aggatacgcg aaaggacgaa agtacccaat cctaccacg ttggggagat atgcgttctt     600
ctacccaaag ataatgcaga cttgagaggt aaagcgggtt attggggcgt ggtcagccat    660
gttggagaat acagttgtac actccagata tgggacggtg actataccgt aaaaatcgaa    720
cacctgaaat cactggaatt acttgatgaa gattgccaat tcatgcagca gttatgtgtg    780
aggttacggc agttgcatca agtggacagg cgtgacgagg ctgtggattg gctgttgcag    840
tggttgggga acaggccaa accttatctg tcatccttgc agtcaaagct gctggcgttt     900
gttgagagag agtacaacct ggtttggaag cagcagaagt ga                       942

<210> SEQ ID NO 19
<211> LENGTH: 313
<212> TYPE: PRT
<213> ORGANISM: Nostoc species

<400> SEQUENCE: 19

Met Asn Lys Pro Pro Ser Arg Arg Lys Lys Ile Thr Pro Ala Thr Ser
  1               5                  10                  15

Glu Glu Pro Lys Leu Ala Thr Asp Pro Ala Gln Glu Asn Thr Ser Leu
             20                  25                  30

His Glu Asn Pro Gly Gly Ala Thr Ile Thr Val Thr Ala Val Glu Val
         35                  40                  45

Thr Asp Leu Thr Gln Glu Glu Gln Ser Leu Arg Leu His Leu Glu His
    50                  55                  60

Arg Val Glu Arg Ala Phe Leu Glu Ala Gly Gln Ala Leu Met Glu Leu
 65                  70                  75                  80

Arg Asp Arg Arg Leu Tyr Arg Ser Thr His Arg Thr Phe Glu Glu Tyr
                 85                  90                  95

Cys Arg Glu Arg Phe Asn Tyr Ser Arg Asp Ala Ala Tyr Leu Lys Ile
            100                 105                 110

Ser Ala Thr Val Val Tyr Glu Asn Leu Gln Lys Phe Leu Pro Thr Ile
        115                 120                 125
```

```
Gly Arg Gln Ile Pro Met Pro Thr Asn Glu Arg Gln Leu Arg Phe Leu
        130                 135                 140

Ala Lys Ala Glu Leu Glu Pro Ala Val Gln Ala Asp Val Trp Arg Gln
145                 150                 155                 160

Ala Val Glu Gln Ala Gly Asn Lys Ile Pro Ser Gly Arg Ile Val Lys
                165                 170                 175

Asp Val Val Asp Arg Ile Arg Glu Arg Thr Lys Val Pro Asn Pro Tyr
            180                 185                 190

His Val Gly Glu Ile Cys Val Leu Leu Pro Lys Asp Asn Ala Asp Leu
        195                 200                 205

Arg Gly Lys Ala Gly Tyr Trp Gly Val Val Ser His Val Gly Glu Tyr
210                 215                 220

Ser Cys Thr Leu Gln Ile Trp Asp Gly Asp Tyr Thr Val Lys Ile Glu
225                 230                 235                 240

His Leu Lys Ser Leu Glu Leu Leu Asp Glu Asp Cys Gln Phe Met Gln
                245                 250                 255

Gln Leu Cys Val Arg Leu Arg Gln Leu His Gln Val Asp Arg Arg Asp
            260                 265                 270

Glu Ala Val Asp Trp Leu Leu Gln Trp Leu Gly Lys Gln Ala Lys Pro
        275                 280                 285

Tyr Leu Ser Ser Leu Gln Ser Lys Leu Leu Ala Phe Val Glu Arg Glu
290                 295                 300

Tyr Asn Leu Val Trp Lys Gln Gln Lys
305                 310

<210> SEQ ID NO 20
<211> LENGTH: 633
<212> TYPE: DNA
<213> ORGANISM: Nostoc species

<400> SEQUENCE: 20
atgacgaagw taagatgggg atrktctygk mtcgwartat cagttataca aaatactaca    60
atcttaaaca tacaattgtt agcttcgaca actattcaat caaagtatat atttaatatg   120
gctatcaaac acccttttttt atttgcactg ttaacgctct ccattatttg tgttggtacg   180
agttctggct ctgcactact gacagatatt gctcaacaaa cagacaacca aaagtcccca   240
tcgattattt tcttcctgcc caagaacga cctcagaccg gagtcggttg ggaaatcact   300
accacttcag ggaaggcaga actagccttg gcgaagcatt tggtgtatat cggggcaaaa   360
gaatatgttt cttggtggtg tcctcactgt cacgaacaaa agttaatctt tgggaagcaa   420
gcctaccaaa taatcaacga cagtattaaa gttgagtgcg ataagagagg tatcaatccc   480
cacccagact tgtgcaatgc ggcgaaagtc ccaggtgtac caacttgggt tatcaatgga   540
catcagtata ccggcgtgca aaactttaag gatcttgcga aagcttctgg ctacaagggg   600
gatatgaact ttcgttatat ccaaagcgaa taa                                 633

<210> SEQ ID NO 21
<211> LENGTH: 210
<212> TYPE: PRT
<213> ORGANISM: Nostoc species
<220> FEATURE:
<221> NAME/KEY: VARIANT
<222> LOCATION: 4, 8, 10-13
<223> OTHER INFORMATION: Xaa =Unknown

<400> SEQUENCE: 21

Met Thr Lys Xaa Arg Trp Gly Xaa Ser Xaa Xaa Xaa Xaa Ser Val Ile
```

```
              1               5                   10                  15
Gln Asn Thr Thr Ile Leu Asn Ile Gln Leu Leu Ala Ser Thr Thr Ile
                20                  25                  30

Gln Ser Lys Tyr Ile Phe Asn Met Ala Ile Lys His Pro Phe Leu Phe
            35                  40                  45

Ala Leu Leu Thr Leu Ser Ile Ile Cys Val Gly Thr Ser Ser Gly Ser
        50                  55                  60

Ala Leu Leu Thr Asp Ile Ala Gln Gln Thr Asp Asn Gln Lys Ser Pro
65                  70                  75                  80

Ser Ile Ile Phe Phe Leu Pro Lys Glu Arg Pro Gln Thr Gly Val Gly
                85                  90                  95

Trp Glu Ile Thr Thr Thr Ser Gly Lys Ala Glu Leu Ala Leu Ala Lys
            100                 105                 110

His Leu Val Tyr Ile Gly Ala Lys Glu Tyr Val Ser Trp Trp Cys Pro
        115                 120                 125

His Cys His Glu Gln Lys Leu Ile Phe Gly Lys Gln Ala Tyr Gln Ile
    130                 135                 140

Ile Asn Asp Ser Ile Lys Val Glu Cys Asp Lys Arg Gly Ile Asn Pro
145                 150                 155                 160

His Pro Asp Leu Cys Asn Ala Ala Lys Val Pro Gly Val Pro Thr Trp
                165                 170                 175

Val Ile Asn Gly His Gln Tyr Thr Gly Val Gln Asn Phe Lys Asp Leu
            180                 185                 190

Ala Lys Ala Ser Gly Tyr Lys Gly Asp Met Asn Phe Arg Tyr Ile Gln
        195                 200                 205

Ser Glu
    210

<210> SEQ ID NO 22
<211> LENGTH: 468
<212> TYPE: DNA
<213> ORGANISM: Nostoc species

<400> SEQUENCE: 22
atgatacagt gtaattttc gttgccacct gagtatgttc ttcgtaaggc caagcctttt      60
gatatgtggt taatagtatt ttttgtgttt agagcaaggc tagacccag tcaattaaga    120 tggcagcaat tttgggtcat tgaatgtgat ggacatttag tagccttcgg gcagatccga    180
aactttcact tagcacaaga gctaggcagt ttatttgttg caccgacttg gcgaaaccgt    240
ggtttaggga ctgttttgat acagcattta attactcaag ctagtcaacc gctttatta    300 aaatgcttaa aatatcaatt ggtgaatttt tacattaaaa gaggctttgt atccgttaat    360
tttaaagatt taccaccatc cctcaagcca agtttggac tatcccaatt acgaaagagg    420
ttaacgaaag cttttgtgct gtttatgaag tatgaatatc ccaactga                 468

<210> SEQ ID NO 23
<211> LENGTH: 155
<212> TYPE: PRT
<213> ORGANISM: Nostoc species

<400> SEQUENCE: 23

Met Ile Gln Cys Asn Phe Ser Leu Pro Pro Glu Tyr Val Leu Arg Lys
1               5                   10                  15

Ala Lys Pro Phe Asp Met Trp Leu Ile Val Phe Phe Val Phe Arg Ala
            20                  25                  30
```

-continued

```
Arg Leu Asp Pro Ser Gln Leu Arg Trp Gln Gln Phe Trp Val Ile Glu
         35                  40                  45
Cys Asp Gly His Leu Val Ala Phe Gly Gln Ile Arg Asn Phe His Leu
 50                  55                  60
Ala Gln Glu Leu Gly Ser Leu Phe Val Ala Pro Thr Trp Arg Asn Arg
 65                  70                  75                  80
Gly Leu Gly Thr Val Leu Ile Gln His Leu Ile Thr Gln Ala Ser Gln
                 85                  90                  95
Pro Leu Tyr Leu Lys Cys Leu Lys Tyr Gln Leu Val Asn Phe Tyr Ile
             100                 105                 110
Lys Arg Gly Phe Val Ser Val Asn Phe Lys Asp Leu Pro Pro Ser Leu
             115                 120                 125
Lys Pro Lys Phe Gly Leu Ser Gln Leu Arg Lys Arg Leu Thr Lys Ala
         130                 135                 140
Phe Val Leu Phe Met Lys Tyr Glu Tyr Pro Asn
145                 150                 155

<210> SEQ ID NO 24
<211> LENGTH: 2355
<212> TYPE: DNA
<213> ORGANISM: Nostoc species

<400> SEQUENCE: 24
atgtcagtgc cagttagcgc acagattata ccagataaaa cactacctat taattccaat     60
gttgaacatg aaggtaatac taaccgcata gaaggtggca ctataaaagg gagcaacttg    120
ttccacagtt ttgaacaatt ytccgtgctt actggaaatg aagcttactt taacaacgat    180
ataaatatcc aaaacattat tactcgtatt actgggaagt ctatttctaa tatcgatggc    240
attctcaaag ccaatggcac ggctaatttg tttctgctca atcccaatgg cattatttt     300 ggtaataatg ccaaactaaa tattggtggt tcatttctag ctactactgc aaatcaaatt    360
aattttgctg atgatactaa atttagtaca acaatcccc aacctaatcc tttactgaca     420
gtaagtgtgc ctataggact gcaaattgat agcaaccccg gtacaattcg catccaaggt    480
acaggtcaca atctaattgg ccctcctttt tctcctctaa tcacaagtag tagcgccgca    540
aatttacaag tgcaaccaga agaactgta gcaattgttg gtggtgatgt aattttagag    600
ggaggtgtga taacggctag gggagggcga attgaattgg gtagcctcag caatggttca    660
gtcagtatta atcctacgac ctctggttgg aaactgggct atgaaaatgt accttatttc    720
caagatatta acctctcaaa cgcgctkta gttaatacta gtggcattgg cagtggatct    780
atacagatag agggacgcak agttacgctt acagatggct cagtaatctt aaatcaaaat    840
caaggaacac taccaggagg cacactaaac gtgaatgctt cggagtcttt gtcagtgagt    900
ggtagcgatc caattgctag gacagctggt ggtttgcgga gcgaaacttt gggattyggc    960
aaagctggag acattgcaat ttcaaccaaa caggtaatta ttaaaatgg aggacaaata    1020 ataatttaa cctttggtgc tgcaacaagt ggcaatataa atgtgaatgc ctctgattct    1080
atacaattgc ttggggtttc gccttttgac cctgctgttt tagtactat cagcactgca     1140 actttcaatt ctggaaacgc aaacaatatt acagtgtcaa caggacaatt cgttgccacg    1200
gatggaggta acttgtcctc ttcaaccttt ggaactggta gaggagga tgtcactgta    1260 agtgcaactg actctataga aataatagga gcttcaccaa taccttca gccaagtatt    1320 ttatcttcca tatcgctcaa tgctggcaaa gctggcagcc taacaatcag tacatcaaag    1380
ttgatggttc aagatggcgg gagggttgac gcttctactt tagcaagtgg ggagggcggt    1440
```

-continued

```
agtgttacga ttaacgcctt taaatctgta gaggtaagtg gtaagatact tggttttgga    1500
gagcctagtt tggtgatctc cagtgctaat atcgtctctc caatcttgca aaagttatac    1560
agactcccTT cagtgccttc tggaaaatct ggaaacgtga cgattaatac tggtcagttg    1620
agtgttacag acggtgctga agttaacgtg agaaatgacg gttctarcga tgctggaaca    1680
ctcagaatca atgctgtttc tgtttcttta acaaacaaa gtgccattac agcaactact    1740
gctaacggcg aaggcggtaa tattttcgtg aatacacggt atttgcagct aagtaattac    1800
agtgttgtaa cgacgaccgc aggtagtaga ggcaatggcg gtaatataaa catcaatgca    1860
gatatattaa gtgcttgggg aagagcagt attgctgcca atgctttcta tgggtatgga    1920
ggaaatgtac taattaatac tagaggactt tttattgctc gtgacagtca aatttctgca    1980
agttctaaat acggaattaa cggcactgtt agcattaaca atactggtgg tgaaatttat    2040
cctactaaac tcaaatcaga atcgattcca gtagctcctc aaatagcatc agtttgtcaa    2100
aaaaattcag atataccaat cagtaaattt gtgaatgttg gcaccggtgg actgccagct    2160
aattctgatg atatgccata tatgaattat gaacagcaaa ataactctgt ttcaatccac    2220
aataataata acttagaggc atcgaaggca tcacaaactg aagaacctat acagataata    2280
gaagctcagg gttggataat aaatcttgat ggggaatgtc gtcttaactg cacaaaacaa    2340
tacagcaacc cctaa                                                    2355
```

<210> SEQ ID NO 25
<211> LENGTH: 784
<212> TYPE: PRT
<213> ORGANISM: Nostoc species
<220> FEATURE:
<221> NAME/KEY: VARIANT
<222> LOCATION: 47, 250, 267, 319, 556
<223> OTHER INFORMATION: Xaa = Unknown

<400> SEQUENCE: 25

```
Met Ser Val Pro Val Ser Ala Gln Ile Ile Pro Asp Lys Thr Leu Pro
 1               5                  10                  15

Ile Asn Ser Asn Val Glu His Glu Gly Asn Thr Asn Arg Ile Glu Gly
            20                  25                  30

Gly Thr Ile Lys Gly Ser Asn Leu Phe His Ser Phe Glu Gln Xaa Ser
        35                  40                  45

Val Leu Thr Gly Asn Glu Ala Tyr Phe Asn Asn Asp Ile Asn Ile Gln
    50                  55                  60

Asn Ile Ile Thr Arg Ile Thr Gly Lys Ser Ile Ser Asn Ile Asp Gly
65                  70                  75                  80

Ile Leu Lys Ala Asn Gly Thr Ala Asn Leu Phe Leu Leu Asn Pro Asn
                85                  90                  95

Gly Ile Ile Phe Gly Asn Asn Ala Lys Leu Asn Ile Gly Gly Ser Phe
            100                 105                 110

Leu Ala Thr Thr Ala Asn Gln Ile Asn Phe Ala Asp Asp Thr Lys Phe
        115                 120                 125

Ser Thr Asn Asn Pro Gln Pro Asn Pro Leu Leu Thr Val Ser Val Pro
    130                 135                 140

Ile Gly Leu Gln Ile Asp Ser Asn Pro Gly Thr Ile Arg Ile Gln Gly
145                 150                 155                 160

Thr Gly His Asn Leu Ile Gly Pro Pro Phe Ser Pro Leu Ile Thr Ser
                165                 170                 175

Ser Ser Ala Ala Asn Leu Gln Val Gln Pro Glu Arg Thr Val Ala Ile
```

-continued

```
            180                 185                 190
Val Gly Gly Asp Val Ile Leu Glu Gly Gly Val Ile Thr Ala Arg Gly
        195                 200                 205

Gly Arg Ile Glu Leu Gly Ser Leu Ser Asn Gly Ser Val Ser Ile Asn
    210                 215                 220

Pro Thr Thr Ser Gly Trp Lys Leu Gly Tyr Glu Asn Val Pro Tyr Phe
225                 230                 235                 240

Gln Asp Ile Asn Leu Ser Lys Arg Ala Xaa Val Asn Thr Ser Gly Ile
                245                 250                 255

Gly Ser Gly Ser Ile Gln Ile Glu Gly Arg Xaa Val Thr Leu Thr Asp
        260                 265                 270

Gly Ser Val Ile Leu Asn Gln Asn Gln Gly Thr Leu Pro Gly Gly Thr
            275                 280                 285

Leu Asn Val Asn Ala Ser Glu Ser Leu Ser Val Ser Gly Ser Asp Pro
        290                 295                 300

Ile Ala Arg Thr Ala Gly Gly Leu Arg Ser Glu Thr Leu Gly Xaa Gly
305                 310                 315                 320

Lys Ala Gly Asp Ile Ala Ile Ser Thr Lys Gln Val Ile Ile Lys Asn
                325                 330                 335

Gly Gly Gln Ile Asn Asn Leu Thr Phe Gly Ala Ala Thr Ser Gly Asn
            340                 345                 350

Ile Asn Val Asn Ala Ser Asp Ser Ile Gln Leu Leu Gly Val Ser Pro
        355                 360                 365

Phe Asp Pro Ala Val Phe Ser Thr Ile Ser Thr Ala Thr Phe Asn Ser
    370                 375                 380

Gly Asn Ala Asn Asn Ile Thr Val Ser Thr Gly Gln Phe Val Ala Thr
385                 390                 395                 400

Asp Gly Gly Asn Leu Ser Ser Thr Phe Gly Thr Arg Gly Gly
                405                 410                 415

Asp Val Thr Val Ser Ala Thr Asp Ser Ile Glu Ile Gly Ala Ser
        420                 425                 430

Pro Ile Thr Phe Gln Pro Ser Ile Leu Ser Ser Ile Ser Leu Asn Ala
    435                 440                 445

Gly Lys Ala Gly Ser Leu Thr Ile Ser Thr Ser Lys Leu Met Val Gln
    450                 455                 460

Asp Gly Gly Arg Val Asp Ala Ser Thr Leu Ala Ser Gly Glu Gly Gly
465                 470                 475                 480

Ser Val Thr Ile Asn Ala Phe Lys Ser Val Glu Val Ser Gly Lys Ile
                485                 490                 495

Leu Gly Phe Gly Glu Pro Ser Leu Val Ile Ser Ser Ala Asn Ile Val
            500                 505                 510

Ser Pro Ile Leu Gln Lys Leu Tyr Arg Leu Pro Ser Val Pro Ser Gly
        515                 520                 525

Lys Ser Gly Asn Val Thr Ile Asn Thr Gly Gln Leu Ser Val Thr Asp
    530                 535                 540

Gly Ala Glu Val Asn Val Arg Asn Asp Gly Ser Xaa Asp Ala Gly Thr
545                 550                 555                 560

Leu Arg Ile Asn Ala Val Ser Val Ser Leu Asn Lys Gln Ser Ala Ile
                565                 570                 575

Thr Ala Thr Thr Ala Asn Gly Glu Gly Gly Asn Ile Phe Val Asn Thr
            580                 585                 590

Arg Tyr Leu Gln Leu Ser Asn Tyr Ser Val Val Thr Thr Ala Gly
        595                 600                 605
```

```
Ser Arg Gly Asn Gly Asn Ile Asn Ile Asn Ala Asp Ile Leu Ser
    610                 615                 620

Ala Trp Gly Lys Ser Ser Ile Ala Ala Asn Ala Phe Tyr Gly Tyr Gly
625                 630                 635                 640

Gly Asn Val Leu Ile Asn Thr Arg Gly Leu Phe Ile Ala Arg Asp Ser
                645                 650                 655

Gln Ile Ser Ala Ser Ser Lys Tyr Gly Ile Asn Gly Thr Val Ser Ile
                660                 665                 670

Asn Asn Thr Gly Gly Glu Ile Tyr Pro Thr Lys Leu Lys Ser Glu Ser
                675                 680                 685

Ile Pro Val Ala Pro Gln Ile Ala Ser Val Cys Gln Lys Asn Ser Asp
    690                 695                 700

Ile Pro Ile Ser Lys Phe Val Asn Val Gly Thr Gly Gly Leu Pro Ala
705                 710                 715                 720

Asn Ser Asp Asp Met Pro Tyr Met Asn Tyr Glu Gln Gln Asn Asn Ser
                725                 730                 735

Val Ser Ile His Asn Asn Asn Leu Glu Ala Ser Lys Ala Ser Gln
                740                 745                 750

Thr Glu Glu Pro Ile Gln Ile Glu Ala Gln Gly Trp Ile Ile Asn
    755                 760                 765

Leu Asp Gly Glu Cys Arg Leu Asn Cys Thr Lys Gln Tyr Ser Asn Pro
    770                 775                 780

<210> SEQ ID NO 26
<211> LENGTH: 399
<212> TYPE: DNA
<213> ORGANISM: Nostoc species

<400> SEQUENCE: 26
atggtgatta ttcaagccac gcagcatttc tgtagattta gtcttggtgt tttcttagca      60
caatcaagag tagagataga gcagagttta acaatgtcaa ctcctaacta tcgtcaagag     120
attgatattg taaaacgttt attttcgcaa atcctaatt tatgcgttga tattatgcta      180
gcgactgaag aaaggtgtaa tgctattagc tttttagcta aaacttacag ccgattggct     240
agactggtgg ctaggaagga tagagaggca ttaattaaag agtttgaaaa tactcaaagt     300
ttttttgaag agaaaattaa tagttttctc cagcctttaa atacaacggc tctgcaacga     360
gattttaaac cccagatgca cacaaatatt agcatttga                            399

<210> SEQ ID NO 27
<211> LENGTH: 132
<212> TYPE: PRT
<213> ORGANISM: Nostoc species

<400> SEQUENCE: 27

Met Val Ile Ile Gln Ala Thr Gln His Phe Cys Arg Phe Ser Leu Gly
 1                  5                  10                  15

Val Phe Leu Ala Gln Ser Arg Val Glu Ile Glu Gln Ser Leu Thr Met
                 20                  25                  30

Ser Thr Pro Asn Tyr Arg Gln Glu Ile Asp Ile Val Lys Arg Leu Phe
             35                  40                  45

Ser Gln Asn Pro Asn Leu Cys Val Asp Ile Met Leu Ala Thr Glu Glu
         50                  55                  60

Arg Cys Asn Ala Ile Ser Phe Leu Ala Lys Thr Tyr Ser Arg Leu Ala
65                  70                  75                  80
```

```
Arg Leu Val Ala Arg Lys Asp Arg Glu Ala Leu Ile Lys Glu Phe Glu
                85                  90                  95

Asn Thr Gln Ser Phe Phe Glu Glu Lys Ile Asn Ser Phe Leu Gln Pro
            100                 105                 110

Leu Asn Thr Thr Ala Leu Gln Arg Asp Phe Lys Pro Gln Met His Thr
            115                 120                 125

Asn Ile Ser Ile
        130
```

```
<210> SEQ ID NO 28
<211> LENGTH: 645
<212> TYPE: DNA
<213> ORGANISM: Nostoc species

<400> SEQUENCE: 28
atgctgatag atatctttca tgataccgtt tgcccttggt gcagaattgg gaaaaaacat      60
ctatttgatg cactggcaca atggcaagaa caagaagtaa atatccgatg catcccttt     120 cttctggatg atactgttcc tgctgagggg tacgaattta gtagctttat gcaaaataga    180
aaaggcatta aagcgccaga atgcaacag atgtttgatt atacgcaacg cgcaggggag     240
gcggctgggg ttaagctaga ttttgaaaaa atccgtttgg ctgtcaatac taagcttgct    300
caccaactga ttgcattagc accgacaaac ataaaaaatg atgtcgttga agctatttat    360
agagcttact ttgaagaggg tttgaatatt ggagatatta cgttattgt tgccatcggt     420 acagcatacc agatggatgc taccgaatta aagttgcaat taaacgatcg cgatgtcgtt    480
gatacagttg ttgctgaatc ggcatttgct cgcttaaatg gcatcaacag cgtgccgttt    540
ttcatcatga ataatcaagt caaggtaaat ggttctcact cggttgaggt tttccttgaa    600
gctttgaata gtactgcact tttagatata cctgcaaaaa tatga                    645
```

```
<210> SEQ ID NO 29
<211> LENGTH: 214
<212> TYPE: PRT
<213> ORGANISM: Nostoc species

<400> SEQUENCE: 29

Met Leu Ile Asp Ile Phe His Asp Thr Val Cys Pro Trp Cys Arg Ile
  1               5                  10                  15

Gly Lys Lys His Leu Phe Asp Ala Leu Ala Gln Trp Gln Glu Gln Glu
             20                  25                  30

Val Asn Ile Arg Trp His Pro Phe Leu Leu Asp Asp Thr Val Pro Ala
         35                  40                  45

Glu Gly Tyr Glu Phe Ser Ser Phe Met Gln Asn Arg Lys Gly Ile Lys
 50                  55                  60

Ala Pro Glu Met Gln Gln Met Phe Asp Tyr Thr Gln Arg Ala Gly Glu
 65                  70                  75                  80

Ala Ala Gly Val Lys Leu Asp Phe Glu Lys Ile Arg Leu Ala Val Asn
                 85                  90                  95

Thr Lys Leu Ala His Gln Leu Ile Ala Leu Pro Thr Asn Ile Lys
            100                 105                 110

Asn Asp Val Val Glu Ala Ile Tyr Arg Ala Tyr Phe Glu Glu Gly Leu
            115                 120                 125

Asn Ile Gly Asp Ile Asn Val Ile Ala Ile Gly Thr Ala Tyr Gln
        130                 135                 140

Met Asp Ala Thr Glu Leu Lys Leu Gln Leu Asn Asp Arg Asp Val Val
145                 150                 155                 160
```

-continued

Asp Thr Val Val Ala Glu Ser Ala Phe Ala Arg Leu Asn Gly Ile Asn
                165                 170                 175

Ser Val Pro Phe Phe Ile Met Asn Asn Gln Val Lys Val Asn Gly Ser
            180                 185                 190

His Ser Val Glu Val Phe Leu Glu Ala Leu Asn Ser Thr Ala Leu Leu
        195                 200                 205

Asp Ile Pro Ala Lys Ile
    210

<210> SEQ ID NO 30
<211> LENGTH: 273
<212> TYPE: DNA
<213> ORGANISM: Nostoc species

<400> SEQUENCE: 30
atgatagttg acatcaagca aaaaaataga ttaattcatc aacgtgtttc ggttactttt      60
aactatgaga tttacttcac ccaaaattta tttgagttga aaaacccgac gctagcgcaa     120
gtaatttcgg cagatgagga gacaaagccg aagaaaatag ttgcggtggt agacgcagga     180
atattaaagt atcaaccgga attggtgaag caattagttg cgtataccaa gttttatgga     240
gaggtactag cgatcaatgt gcccaaatat tag                                  273

<210> SEQ ID NO 31
<211> LENGTH: 90
<212> TYPE: PRT
<213> ORGANISM: Nostoc species

<400> SEQUENCE: 31

Met Ile Val Asp Ile Lys Gln Lys Asn Arg Leu Ile His Gln Arg Val
1               5                   10                  15

Ser Val Thr Phe Asn Tyr Glu Ile Tyr Phe Thr Gln Asn Leu Phe Glu
            20                  25                  30

Leu Lys Asn Pro Thr Leu Ala Gln Val Ile Ser Ala Asp Glu Glu Thr
        35                  40                  45

Lys Pro Lys Lys Ile Val Ala Val Val Asp Ala Gly Ile Leu Lys Tyr
    50                  55                  60

Gln Pro Glu Leu Val Lys Gln Leu Val Ala Tyr Thr Lys Phe Tyr Gly
65                  70                  75                  80

Glu Val Leu Ala Ile Asn Val Pro Lys Tyr
                85                  90

<210> SEQ ID NO 32
<211> LENGTH: 3690
<212> TYPE: DNA
<213> ORGANISM: Artificial Sequence
<220> FEATURE:
<223> OTHER INFORMATION: 75% sequence identity to SEQ ID NO::2

<400> SEQUENCE: 32
atggggcata gagcttgggg atatctggga gggacagtcg caggtatgtt cactttggaa      60
gattttttaa gagtgattcg tcatagtggt agaccaatgg cacaggtacc ctgaggaggc     120
gaaacgttat ctataaggag ttcaatcgta aagataagtg aagtaatcgc gccatacgct     180
ccaaacgtcg cgatctcata aattgacggg cccccaagca ctgtcaattc aggtgggcca     240
gttgcaattg gaacgcttcg aaatctctta gccgcagtag agattttgac acgacgacgg     300
gaagtatccc gcgcgttcaa tgcatatccg atgaaacgaa cgttaacgga gtttgaagca     360

-continued

```
gcagcaccag ccctaacgta cgatccacta aacataccat cagtaccaaa tgtatcggga    420
gcgattgcgg agcagagtat aacctgagca agcggttgcc taattcatca ccggctaccg    480
cagaaatttg cgcatagtac ggacagataa cagcacgaag gttaatacct ctgcgtagac    540
cttggaccag aaccagcttt cttaagcgtg gcaagacagt acccgccaga ggacgtgggt    600
ccttgggtgc gatctgtcat actaggacaa gtacactcgc atccaatgct agaaacttag    660
gctcaacttt atgcgcaagg agttaaacat gattggttac ggttcattaa agattattgt    720
ggtagtacgg aagtagtctc gacttttgcc ttccatcgcc aacgttattg gtaggagaga    780
tataatagtc tcatagataa ggaacagatt tcataaaatc atattaatct ccaagctcta    840
gtcggtaata gatcacaagt agcagcgttt gaaaagtgaa ttcggtttaa atgccaaaat    900
ggtgcttctc atccaagtta ccagctacag cagtgagtct ttcctgtacc tctttaccaa    960
gctacagatt agttggtaat acccatacca ggaggtacaa ctttatttaa gtcaggtgat   1020
agaaccctat aagatattgt aatagaaaag gcatgaattt tatcgacggt aaaaattcag   1080
agaattcaaa tagtgttaat cttacggtta ctacagagat atagattaca tatttttggt   1140
ctggaaacaa atactgctac ttaagaacct agctggatac tacatgttca aggataaatg   1200
ttagtaagga acaaagtccc agaattagag accacatact tgaaagcggt caaagaaggg   1260
tataaggaaa agattttacc taatgagttt tacaagaaac atgaagaaag gcggctttat   1320
aacgctgctt ctatctaagc cgttggacaa ctgaggcaga gcgatagcaa aagactaagt   1380
ggaatttagt tgccaaaaac acaggtcata gttgcaaatt tatgacaact gcgcctaaat   1440
gtttaagatg atatgttcca ggtatttcca gctgttgtgg ttagaacgga caagcatgga   1500
gcttatgtgc acttggaaag aaaccgtcaa caaatatagc ggactgttag taatggttcg   1560
tcgacagaag tataggtaga tgtagcagaa cctaagaaaa ccactttgag atgtaacgtt   1620
gattcattat atgaacgcgg aatagtatga gcaagaattc aagcttaaag tttattatgt   1680
agttcacggg aggcattgtg ttgtagtatc gagccgcaag ttaacaaggg gttataacac   1740
atccagtggc agacccgatc acttgcacca catcacgaaa caattgactt gacaaactca   1800
ggtggctagt ttttggcttc accagccacc gggatagaga atcatatggt ggaatcgttc   1860
gcactgcaaa gctgacattg tatatttgta ggaccagggc agaacttcca ggagttagaa   1920
actccacagt atcatatcga ccgcaatcaa ccagacgaat tcatggactt gatgaaagca   1980
cggttggtgc agcaaccca ggtaccagca attatgcacc tacggggttt cgactaaaca   2040
atatcactaa agactggtgc gcagcacttg ctaaattaac gagtactcgg ttgtggcaac   2100
gaactgcatc gagtcaaggc cttcgtaata gatcgagata aggagagtgc cccttattg    2160 taagtggctc aagcctctca ttctgaggga atgaataac taccgatacc attccgacaa    2220
gcaactatgt gcgcgttatg tggagtattt gcacggggcc aaaggcaatt agaaagccag   2280
tgtttaggct tacatccatc taaggaagct tccgaaagat tagcagctat ctttgaggga   2340
ctattctctt ctgctgatga aacgtaaat gctaactctc aatggttaag tcgcgttcct    2400
gagtaagaga ggcgataaag aatgagaaca tgtacacatt ccgaatgaga aatatcgtcg   2460
catcaatcat gtctactgca gctagcagta tatagctcat ggacaccct tatcgaactc    2520 gaggccattt actcaattgc cgtaagtctg agagctccgg gctaaaaagc cgctaagtgg   2580
ttgataccac aagcggtaat aaatttcgtg cttactggac atacgcaggc aacagtaaga   2640
ggtctgcaaa cccttgatca aatacacatg gcagaagcgc cagtgttatt catctggtga   2700
gaaatttcgc atcaagagac tgtcgcaaga tttataaagt ccagcaaagc attattgcga   2760
```

-continued

| | |
|---|---|
| gcactatcag gaaaaataca ggccgccggg aaatgggttg gtggtcttct gttagatatc | 2820 |
| aagtgggtta aagttacata cgtggtggaa cataaactac atcggacttg gtatttccag | 2880 |
| aatatgactc tgaatctgcc tatggacctt gttttatgtt ttgcctccat tgattcgatc | 2940 |
| tttggttcga ctggtcgcgg gtattaagct ggtgccattg agtttatggg tggtttatcc | 3000 |
| cataatggac gtgatatgcg ataacctggg tcgagtatta aatggcgatc atggccacta | 3060 |
| gaagcaatgg ctgcaaatat gggtagccgt cttcgagatt gagcggtgac caaggcaatg | 3120 |
| tctgttatgg tttcagagca gggaatgcag cttcgaagtc aaaaactcta agaatcatta | 3180 |
| gcacaagtgg gagtgcttcc aaatgaatgg ccagtgatcc aagggccatt aaggttcggt | 3240 |
| gatcaattag cattactctc ctaaatgggc aatggaagca aaacacacca tatagccatc | 3300 |
| gagactcaga cacagtacaa tgggttctaa gaacacctaa aagctgctgt acaaagagta | 3360 |
| agacataaga ttgtgttaaa ttacgtcaaa ggtgtaatat ctaaactatt ttgttagagc | 3420 |
| atatctcgac ttgttatgga tcaccccctc aacacaatcg gtctagattc tttaaaggcc | 3480 |
| gtccaagtgc acactagtct tcgaactgat ttgctcctga atatgtcgct agtcataatt | 3540 |
| gtataaaata cctgtatcgt acatataggc tctgaactgt atcagcaagt gagcctaatt | 3600 |
| acgcagactc aatgagatga gtgagacaat aatggtaaac tcgaccaaac taaaagcaac | 3660 |
| gataaagacc gcattagtag tggattacgt | 3690 |

<210> SEQ ID NO 33
<211> LENGTH: 3690
<212> TYPE: DNA
<213> ORGANISM: Artificial Sequence
<220> FEATURE:
<223> OTHER INFORMATION: 80% sequence identity to SEQ ID NO:2

<400> SEQUENCE: 33

| | |
|---|---|
| atggggcatt atgccgggga atctgtgcca gccatagtgg ctggactatt tggtctagaa | 60 |
| gacgttttaa acccgcttgc ttatataggga cgactaatcc atcaattacc atctgggagt | 120 |
| gagatcttat ctgtaattgc atctattgaa cagctaaatc agctatttgc atcataccct | 180 |
| cagagagtag tgatcgcttc gatcaacgta caccaatgca tagtcatctc tgctgatgca | 240 |
| gacgcatttg gaccgggtca acatagctaa gtagcacaag acaggaagac aacacgagtg | 300 |
| caaatatgcc acccatttca tacacatctg ctggaatcaa agttggtgga atttgacgca | 360 |
| gtcgcttcag acataacgta cgatcatcca actattcgat tagcatgaaa tgtatctgga | 420 |
| gcgagcgcag agaatcgttt agcgacagca agctcttttgg gtaatcacgt ctggctaccg | 480 |
| gtgtaacttg ccaaaagaat gcacaaatta cagaatgaag gctattacat catcttataa | 540 |
| atcggaccaa aacctacatt gtaaggcatc agaagccagt gcatgtcaga acatgaggga | 600 |
| gtatgggtgc catcattgaa gctagcgcaa gacgactgac ggcacatgcc acgaagcttg | 660 |
| gcagaattat ctgtccatgg cgttatagtt cattgtttag cgttagataa cgaatattct | 720 |
| cctagaaagg gagtattacc tacttgtccc tgtcaatggc agcgctattg cattgtgaca | 780 |
| gataatcatc taattcacca gagacagttt caatcaaatc ataagagtct tcatcatcta | 840 |
| ctcagtcata cattacatat agaagcatta gatcagcata tacggtttga atgacatatt | 900 |
| agtgcatcac taccagctta cgttcaacac cgctgcgttt tatcacaacc tgttatccta | 960 |
| gaagctgctt actaggtaat cgccttagga gcgggtacaa tattaatcaa tgcagaggat | 1020 |
| ttcatcctac atgatatatc aaactaaaaa gtagtaactt tatctaaaga agaagttaat | 1080 |

```
acacttcata aaggtttaaa cttacagttt atacaaggct atcaattcct gatcttcagt    1140
atggctataa gcactaattg atccgaacct agatgcattc aacatgttga aggacagata    1200
atagtgggta atcaataccc cgaattacaa acaccaatct tcaacgcgat tacagaggag    1260
tagaactaac ggatactacc tgctgcattc taccgaacat ttgcagactg gtgtcttaac    1320
tccggtcctt cgttctaagc cgttcaacta ctgcgggaca cgcaggata  agcattagat    1380 gtaattccgt tacgagacac cgagatgaat gtaacaactt catactaact acacctaatt    1440
cgtttcgatg ctcgctgcca cgtgttcgca gcatttaggg gtaacacgca cagccatgaa    1500
tcttatatgc gattgcaaat agaacgatta cgaattcatc ggagtggtac taatcgtttc    1560
tggactcaag gagagatcgg tgcgacacaa cctagtaaac aagctttgac cggtcaagtg    1620
cgtttattcg ctgatcaagg cataggagta ggatgagttg caggtgtaac cgtattacgt    1680
gcttttcgcg cgggtttgtt gcctattatt gaagcaatat gtattaattg cttagatcac    1740
atccactggc taatccaatc attttcgccg catatccaag caatcgactg aaccaaatca    1800
ggtacgtgtc tagtgttttc ggcacccaca cgtaaaggcc aacttctggg agactcctta    1860
taacaacaag ctcggcattg tagactagta acacaacggg acatttacca ggagctagaa    1920
ccgcaacatg aacaaatcaa cctcagccaa cttgaggaat tcgggcaccc atggcaatcc    1980
agctcggagg agtaaccccc aggacgaggc attgttcacc tgcggacttg gtactcaacc    2040
ataccactaa ccactgggggg acacgagttg ctacaatccc atgagctggc cggtggcagc    2100
gtacgacatt tagacgaagg attagtaaag attcaagata cgcaaagtgg gccattatgg    2160
taattgactc aatgctgaca ctctgggggt aataactccc tgcatataca attgcatcag    2220
acatctttac gcgggttagg tcgcggaatc gcccaagaat acaggaatt  actattccgc    2280 tttttagaca tatatccaag tatagaagat cccaaaacag caggtgcttc gttataggat    2340
ctatcatctc atggtcatgt taaccaaata gtttactgtc atgaggtacg tcactttacc    2400
atgttagagc ggcaatagag aacgagtacg tctatacagt cggcattacc attttcctcg    2460
ctacaagcat atcagctgaa gctagcagct tacaagtctt aagtcaacct agtcctagcc    2520
gatgcgagtt acgtagttag cggatgtctg gcagtactgg ggttaattac ggccgagtgg    2580
acggtagaac atggggtgag atgtttagta ctcacccgac gtcgggagcg atcagaaaag    2640
ggtcaacaat ccagtgaacc attgcagaag ccaggggcgg aaatattagt ccagtggggc    2700
ggtatttccc gacacgaaag tgtgacaagg attctagaga cattcaaagg atccttgccg    2760
gccttacgag aaatgattcc tactgctggc atattagatc atgatttgcg gtcaaacatg    2820
actggggaac catttacacg ggtaatggcg cccaaagtac taggtgcttg tcatgtgcat    2880
accttgactc ataatgtacc gtgggacttt gttctttgtt cttgctctat gccttgaata    2940
atcggttcgc gtggccaagg gactaatgcg gctactaatg catacatggt tagtttagcc    3000
gatcaccgac gaggtacggg cttagctggc tggaggatta tctgggaacc atggacacga    3060
gcggaaatgg cacctaattt gcattgtcct catcgacata gtatgctgtc catgggtatg    3120
actattatgt ctatagaaca gtgattccag cttataggac agttacccga acagtcgata    3180
ccacgagtcg cagtgctacc acttgaatgg tcactgatcc aagaacattt tagttgtggt    3240
actcaagtac cactgcggtc ctagttggtg acagaaagca tatcacggca ccaagccctc    3300
aattcaaaga catagcagaa tgaagttata ggatagctaa cagcagcttt accaggacaa    3360
ggagcaaagc atatgataat gtacattata gatgcagttt cccgagtact atctctgagc    3420
agttatcaaa gtcatatgca tcagctcctg agcagtatgg cccttgattc tcaattggct    3480
```

```
gtccaattgc acattacgct acaagctgac atgctggtgg agataactat actcagattt    3540
ataccagatt tcactatcgt tgctatagcc agtgatgtgc atgaggaact gaccctagtt    3600
gcttagcatc aacgagatga gtcagcatat accgggcaac tctacgatag cattaggtaa    3660
gcaagcgagc ggattagacg tcaataatga                                     3690
```

<210> SEQ ID NO 34
<211> LENGTH: 3690
<212> TYPE: DNA
<213> ORGANISM: Artificial Sequence
<220> FEATURE:
<223> OTHER INFORMATION: 85% sequence identity to SEQ ID NO:2

<400> SEQUENCE: 34

```
atgggcata gcgctgggga atatgttgca gcaacagtac catgaatttt tagattagga      60
gatggttcaa aacagattgc tcagagagca agacttatgc aacaattacc gtctggcggt    120
taaatgtttt ctgtaaaggc ttgaatcgta aaagtgaatc aactcattgc actatactct    180
caataagtag cggtcgcatc gattgaccga cctcaaagca ttgacatgtc tggcgaggca    240
gtagcaaatg gagcggctga aaaaagcttg gaaccagaag acataaagac aaaatgactg    300
caagtgtcac aggcattcct ttcacgtttg ttggacccaa tgttagcgga cattgaagcg    360
gtagcctcag aattaaccta cagtcaagca aatatttcat aaggatcaaa tgtaagggta    420
gctaaggcag cgaatagtat ttccaaagca acctattggt tatatcgtgt ccggcaaccg    480
gtgaattttg cgcaatgtat ggtcacaata tagcaagaag attattcctt cttgttagaa    540
attgcacaca aatcaacttt gtaaggcgtg ggcagacagt gcttgccaga tgatgttgta    600
gtatgggtgc ctccgttgaa accaggtcaa gaatacttgc agcagatgct ccaaagtatg    660
gcttaaccat ttgtgcatgc agtttaagtt gattggtttg ggtttaataa ggattattct    720
cctagtaaag tagtatggcc gatttatccc tatcaaccgc aacgatattg gagtgcgaca    780
aattataatc taaaacagca gaaacagcta ttatcaaatc ataagaatcc tcaccctcaa    840
ctcggtgaaa gataacattc tgcagcctta gtactgcaaa ttcattttga gtgtcgaatt    900
agtgcatctc aagcaactta cccgcaacac tactgggttt ttttttcagcc tcttttctca    960 gcagtagctt gcttcgaaaa agccttacca gcaggtgcaa ttatattcaa gtcagatgat   1020
ttcatcctat aaggtatagc aatcccaaaa gtatttatta tatgaaacga tgaaaataat   1080
gcaattccga tagtattgaa attacattta gtgcaaagcc ataaatacca aattctcagt   1140
ttggatgtaa tcactagttc tccaaaaccc aaatggattc tacgtattga agaaaatta    1200 ttagaaggta gtaaagcctc ccaattaaaa acaacaaact tagaagcgct ttaagacggg   1260
tattacctac agataatacc tgctgaattc tcctaaaaat ttgaaggatg cggtcttatt   1320
tacggatcgt ctctccaagc cttttaaacaa atgtggcaca ccgaagtaaa ggcaccaggt   1380
aaaattccgt gaccaaaaac tgaggtaaat gtggcatctt catacgaact gcacccaaat   1440
ctattagatc ctagcttccg ggtgtttgct gcagtaatgc gtaaatcgga cagccaagaa   1500
gctaattggc cattggaaat acaacgacta caatttatc gcaatggtgg taacagtatg    1560
aggactcgag tagcgatagg tgctacagaa actagtacac agactttaag cggcaaggat   1620
tgtttactgg atgaacgagg aacagtagta acaagagttc aaggtttatc tttataacgt   1680
actactcgcc aggcttagtt acgtgatatt caacctaaat ttaataaatg gttatgtcaa   1740
atgcataggc aaacccgatc aatctctccg cataaccaaa caattgactt gacaaattca   1800
```

```
ggaaggtggt tattgtttcc cccactcaca agtataggca agcatctcgt agtaaccttA    1860
caacgacaag gatggcattg tgtattagca acacctgggg aagattagca ccagttagaa    1920
tcactacatt atcaattcaa cccctaccat ccagagggat tcctggacct atagcaatcc    1980
agcttggaac aggaaccgcc ataacgagga gttatttacc tgtagagtta cgactcaaca    2040
attgcacaaa gggctggggc acacgacttg ctaaattccc aaggagtggg ctttggcagc    2100
gtgcttcctt tagagcaagc catagtagaa aaccaagata tggaaagttc cccattgtgg    2160
ttactgacac aacgctcaca gtctttgggt catgagtccc ttcctgtacc attccaacat    2220
acaccgttat ggggattacg tcgggtaatt gcctagggac attggaaatt acattgcccg    2280
tgttttgact taggtccaac tatataagat tgcgaaacag tagcttctta gttagaggaa    2340
atattatgtc ctggttatca aatccaaatt gattactggc aaggggtgcg tcacgtttcc    2400
cggttagggc ggcaacaaca tatgagtgca tctacatagt caggataact aatttccttg    2460
caacacccgt ttctactgaa gctagcagaa tgtaactctt taggcaacct actccatgcc    2520
ggagccagtt agttaattac aggacgtctg gtagcactgg ggttgaaaac tgctgggtgg    2580
atggtccaac aagcggttaa atttttacta ctttccggtg gtagccagcc atctgcaaaa    2640
gctcaacaaa gcattgtaca attacggaag gcaggaccgc atgtgttcgt catgtgtgga    2700
gaaaattgcc aacaagataa agtggcagca attatatagt caagcaaact atctttgcca    2760
ccattacgtg gtataattca tgctggtggg aaattgggtg atggtatgct cttaatcatg    2820
agttgggtaa aattaacaca ggtgatggca caaaaagtac aggggggcctg gcgtttgcat    2880
tatttgactg agaatgtacg ttacgacttt tttgtgtgtt attccggtat ggtttcaata    2940
ttgggtacgc ctcgtcaagg ggattattat gctgcgaatg cttccatgga tggtttagct    3000
catcgtcgac ggggtatgcg tttatttggc ttgggcatta agtgcggact atggccacag    3060
gagggattgg cagcgaattt gcatagtcct caacaaggta gaaaggtgtc caagggaatg    3120
aggttcttgt catcagaaca gggattccag cttctaggtc aaatactcga agaatctata    3180
acacaagtac gagtccaacc agtccaatgg tgagtgatcg aagagcaatt tagttgtggt    3240
aatgaaatac catagctctc ccgattggaa aaggacagca tatctcagca aaaaccctc     3300
aagaccaaga ctaagcacaa tgagtttata gaacagctta aggctgcttt accaacagaa    3360
aaaggaaagc atttgaaaat tgacactaaa gatgaagttt ctaaagtgct tactttgagc    3420
ccttctgaaa tagatatgca tcagcgcctg aactctatgg ggcttgaatc tctaatcgct    3480
gtagaagtgc acattagcct tcagactgac ttgctggtgt atatatcaag agtctaattt    3540
acagaaagta tcagtaccgt tggtttagcc actgatgtga atgggcaacc gagccaagct    3600
actcacaatc aagtgttaa gtcaggaaat caagggcagc tttaccaaaa caatacgaaa    3660
gataacgtgc gggtaagagg tgaaatatga                                    3690

<210> SEQ ID NO 35
<211> LENGTH: 3690
<212> TYPE: DNA
<213> ORGANISM: Artificial Sequence
<220> FEATURE:
<223> OTHER INFORMATION: 90% sequence identity to SEQ ID NO:2

<400> SEQUENCE: 35
atggggcata gtggtgggga atatatcgca gccactgtag aaggaatatt taggttagaa      60
gatggcttaa aacttattgc acatagagga agactaaggc aaccgttacc ctcttggggt     120
gaaatattat ctgtgatggc ttcacttgaa aaggtaattc aaataattgc accagactct     180
```

-continued

```
caaacagtag cgatcgcatt gattaaagga ccccaaggca ttgtcacttc tgttgaggca      240
gaaacaattg gagcgggtca aaatagccta gaagctgaag acataaagac aaagcgactg      300
caactatccc acgtattcca ttcaaatttg atggagccaa tgctggcgga cttttaagca      360
gtagcaacag aaataagcta caatcaccca aatatttcat tagaatcaaa tgtgacggga      420
gctcgggcag agattagtat tgcaacagca agcgattggg taactcatgt ccgtcaaccg      480
gtaaaatttg ccgaaagtat ggccacatta catcaagaag gtaattccat cttgttagaa      540
attcgaccca aactaacttt gtaaggcatg gggagacagt gcctgccaga agttgtggga      600
gtatggttgc ctgctttgaa acccggtcaa gaatactggc agcaaaagct acaaaggttg      660
gctgacctat atgtgcttgg agtaaaagtt gatgggttag ggtctgataa agtttattct      720
cgaagcaagg taggattgcc gactcatccc tttctacggc aacgatattg gatggagaca      780
aatcataatc taattcatca aaaaagtttt ttagcaaatc ataacaatct tcactctcta      840
ctcggacaaa gattagattt agcacccttt gaactgcaaa ttcgatttga atgtgaaatt      900
agtccttctc aactaactta cctacaacac cacggtgttt ttcctcaacc tgttttttcca     960 gcagcaactt acttgggaat agccttcgca gcagtttcaa tattattcaa tgcagatgat     1020
tcaatcctag atgatatagc aaaccaaaaa gtgttaattt taccaaagga tgtaattaat     1080
acaatacaga tagttgtaaa tttaccgtta gtacaatgct ataaataccaa aattttgagt     1140 ttggatctaa acactatttc ttcaaaacct aaagggattc tacctattga aggtaaaata     1200
ttaataggta atagagaccc ccacttagaa acatcaaact taaaagagat taagaggag      1260 tataacccac agatatttcc tactgaaatc taccaaagat ttgaagcatg gggtctttat     1320 tacgttatt ctttccaggc cgttaaccaa ctgtggtaca gcgaagaaaa agcactgggt      1380
gaaatccagt tacctgaaac tgaggagaat gttgcagctt tatcccaact gtacccaatt     1440
ctattagatg ctggcttcca ggcgttagca gctgttatgg gtaaaacaga caaccgagaa     1500
acttacttgc cattgtaaat aaaacaacta caaatgtatc ggagtcgtag taatattttg     1560
tggacacaag tagaggtagg tgcaccagaa actattaaac aaacattgag cggtgaagtt     1620
tgttcattgg atgatcaagg aataatagta gcaagggttg aaggtctaac tttattacgt     1680
acttcacgcg aggcttggtt gcgtactatt gaacctaaat ttaaaaattg gtgatatcaa     1740
atcccttggc aaactcaatc aatatcaccc catagccaat caatcgactt aacaatatca     1800
ggtagatggt tattgtgttc cccacctaca ggtatgggca aacatgtggt agaatgctta     1860
gaacagcaag gttgggattg tatatgagta acaccggggg aaaatgacca gcagtgagaa     1920
tctcagcatt atcaagtcaa ccccagccat cctggggaat tccggcacct attggaatca     1980
agctgggagc agcagccccc attaggagga attatgcacc tgtggggttt ggactgaaca     2040
atagcgctaa ggacggggc acaggggttg caaaagtccc aagaacgggg ctgtgggagc     2100
gtacttgatt tagtccgagc cttagtgaaa aatcaaggta tggaaagggc cccattaggg     2160
ttagtgagtc aaggctcgca atctgggggt aatgggtccc ttccgataca attcgaacaa     2220
acacgtttat gggggtagg tcgaggaatt gcccaagaac ataggaaatt acaaagccgg     2280
tgttaagact tagaaccaac tatgaaagat tccaaaacag tagatgcttt gttaaaggaa     2340
ctataatctc ctggagatga aaacaaaatt gcttaatgtc aagggatacg tcacgatgcc     2400
cggtaagagc ggcaaaaaaa aatgactaca tctacccagt ccggtttaca aattttctcg     2460
caacatccat ttcaattgaa gctattagaa tataattctt tagactacct aatcctagcc     2520
```

-continued

```
gaagctagtt acttatttac cggagttctg ggagctctgg ggttataaac cgctgtgtgg       2580
atggttcaac aagggttcaa atatcttgta cttactggac gtaggtagcc atcagctaaa       2640
gctcaactaa ccattgatca attacagtag gcaggagtgc aagtatttgt cctgtgttga       2700
gatattttcc aacaagataa tgtggctaga attattgagt caatctaagt atcttttcca       2760
gcattactag gaatatttca tgctgtcggg atatttgatg atggtttgct gttaaatatg       2820
aattgggtaa aatttaaaca ggtgatagca ccaaaaatac aaggggattg gcatttacat       2880
aatttaactc agaatatacc tttgaacttt tttgtatgtt tttccactat ggcttaaata       2940
ttgggatcgc ctggtaaagg gaattatgct gctgcaaatg ctttcaagga aggtttagcc       3000
aatcatcgac cgggtatggg cttacctggc ctgagcatta cctggggacc ctgggcacaa       3060
cagggaatgg ccgcaaattt cgatagtcct cctcaagata caatggtgtc ccagggaatg       3120 cctttttttgt cctcagaaca cggattgcag cttctaggac cattactcga ccaatccata       3180
ccccaagtag cagtcctacc cattcaatgg ccagtgttcc cagagcaatt cagttttggt       3240
catcaaatac ccttgctgtc cccattggta caagaaagca catcacagca caaagccctc       3300
caaacaaaga ccaagcacaa cgaatttttta ggacagctaa gagctgcttt gccaagagaa       3360
ggagaaaagc gtttgatatt gtacattaaa ggtgaaattt gtcaagtact gtctttgagc       3420
gcttctcaaa gtgatatgca gcagcccctg gacactatgg gggttgattc gctaatggct       3480
ggggaattgc gcaataggct gcaaactgac gtgctcgtgg gtatatctat ggtcaaattt       3540
gtagaagata gcagtatcgt ggatttagcc gctgaagtga gtgagcaact gggccaagtt       3600
ggtcagaatc agggagttga ggcagaaaat agtgggcaac tgtaccaaag gaataggaaa       3660
ggaaacgagc gggtaagagg ggaattatga                                        3690
```

<210> SEQ ID NO 36
<211> LENGTH: 3690
<212> TYPE: DNA
<213> ORGANISM: Artificial Sequence
<220> FEATURE:
<223> OTHER INFORMATION: 95% sequence identity to SEQ ID NO:2

<400> SEQUENCE: 36

```
atggggcatg gtgctgggga atatgtggca gccacagtag caggaatatt aagttaagaa        60
gattgtttaa aactgattgc tcatagagga agactcatgc aacagatacc ctctgggggt       120
aaaatgttat ctgtaatggc ttcaattgga aaggttaatc aactaattgc accatactct       180
caaaaagcag cgatcgcatc gattaacgga ccccgaagct ttgtcatttc tggtgaggca       240
gaagaaattg gagcgcttca aaaaagctta gaagcagaag acattaagac aaaacgactg       300
caagtaaccc gcgcattcct ttcacatttg atggaaccaa tgttggcggc ctttgaagca       360
ggagcatcag aaataaccta caatcaacca aatattccat tagtaacaaa tgtaacggga       420
gaaagggcag agaatagtat tgccacagca agcaattggg taaatcatgt ccggcaaccg       480
gtgaaatttg ccaaaagtat ggacacatca cagccagaag ttattccat cttcttagaa       540 attggacccc aaccaccttt gttaggcatg ggaagacagt gcttgccaga agatctggga       600
gtttggtttc cttctttgaa tccaggtcaa gaagactggc agcaaatgtt acaatgtttg       660
gctgaactat atgtgcatgg agttaaagtt gatttgttag ggtttgataa agattattct       720
cgtagcgagg tagtattgcc gacttatccc tttcaggggc aacgtgattg gattgagaca       780
aataataatc taatacagca aaaacagttt ttatcaaaac aaaaaaatct tcaccctcta       840
ctcggacaaa gaatacattt agcagcctta gaacagcaaa ttcgtattga atgtcaaatt       900
```

```
agtgcttctc acccaactca cctgccacac cactgtgttt tttctcaacc tgtcttcccc    960
gcagcagctt acttggaaat agccttagca gcaggttcaa ttttattcga tgcagatgat   1020
ttaatcctag aagatatagc aatccaaaag gtattaattg tatcaaagga tgaaattaat   1080
acaattcaga tagttttaga tttacagtta gtataaagct ttaaattcca aattttcagt   1140
ttggatataa acacttattc ttcataacct aaatggattc tacatattga aggaataata   1200
ttagtaggtg ataaagaccc ccaattagaa acaacaaact aaaagcgag taaggacgag    1260
tataaccaac agatattacc tactgaattc tagcagaaat tagaagaatg gggtcttaat   1320
tacggttctt ctttccaagc cataaaacaa cagtggcaca gcgaaggaaa agcactaggt   1380
gaaaatcagt taccagaaac agagatgaat gttgcaactt tataccaact gcacccaata   1440
cttatagatg ctagcttcca ggtgttagca gcagttatag gtaaaacgga caaccaagaa   1500
ggggatttgc cattggaaat aaaacgacta caaatttatg ggagtggtag taatagtttg   1560
tggactcaag tagagatagg tgcaacagaa actaataaac aaattttgtg tggtaaagtt   1620
tgtttattgg ataaacaagg aatagttgta tcaagagttg aaggtttaac tttattacgt   1680
acttctcgcg aggctttgtt aaaaaaaatt gaaccaaaat ttaataattg gttatatcaa   1740
atccattggc aaacccaatc aatttcaccc cataaccaat caattgactt aacaaaatca   1800
ggtaggggt tggtgttttc cccacccaca ggtataggca aacatcgggt agaatcctta    1860
gaacaacaag gttggcattg tatattagta acaccagggg aaatttacca gcatttagaa   1920
tctcaacatt atcaaatcaa ccctaacctt cctgaggaat tcctgcacct attgcaatca   1980
agcttggagt agcaaccccc ataacgagga attattcaca tgtggagttt gaactcaaca   2040
atagcactaa ggactgaggc acaggagtag caaaaatccc aagaactggg ctgtggcagc   2100
gtccttcatt tagtccaagc cttagtacac aatcaagata tgcaacgtgc cccattatgg   2160
ttagtgactc aaggctcaca atctgtgggt aatgagtccc ttcatataca attccaacaa   2220
acaccttat gggagttagg tcaagtaatt gcccaggaac atagggaatt acaatgccgg    2280
tatttagact tagatacaac tttggaatat tcccaaacag tagctgcttt gttagaggaa   2340
ctattatctc ctggtgatga taaccatatt gcttactgtc aaggtgtacg tcacgttgcc   2400
cgtttagagc ggcaacatat aatgagtaca tctacatagt ccggattact aatttcctcg   2460
caacaaccat ttcaactgaa gctatcagaa tataagtctt aagacaacct aatccaagcc   2520
gaagccagtt aattaattac cggaggtctg ggagaactgg agttaaaaac cgctgagtgg   2580
atggtacaac aagaggtcaa atatttagta cttaccggac gtaggccgcc atcagcaaaa   2640
gcccaacaaa ccattgaaca cttacagacg gcaggagcgc aagtattagt cctgtgtgca   2700
aatatttccc aaaaagaaaa tgtggcaaga attatagagt caatcaaagt atctttgaca   2760
gcattacaag gaataattca tgctgctggg aaattggatg atggtttgct gttaaacatg   2820
aattgtgata aatttacaca ggtgatggca cctaaagtac aatggtcttg gcatttgcat   2880
aatttgactc agaatctacc attggacttt attgtttgta ttacctctat ggcttcaata   2940
ttgggttcgc ctggtcaagg gaattatgct gctgctaatg ctttcatgga tggtttagcc   3000
aatcatcgac ggggtatgga tttaccaggc ttgagcatta atgggggacc atgagcacaa   3060
gagggaatgg cagcaaattt ggatagtcct catcaagata gcatggtgtc caagggaatg   3120
actcttctgt cttcagaaca cggattgcag gttctaggac aattactcga caatccata    3180
ccacaagtag cagtcctacc atttcaatgg tcagtgtttc aagatcaatt tagttttggt   3240
```

-continued

```
aatcaaattc cattgctgtc ccaattggta aagaaaagca aatcacagca aaaagccttc      3300
caaccaaaga caaagcacaa tgaacttta gaacagctaa aagctgcttt accaagagaa      3360
agacaacagc ttttgataat ttacattaaa gatgaaattt gtcaagtact ttctttgagc      3420
acgtctcaaa ttgatatgcg acagccctg aacactaggg ggcttgatgc tctaatggct      3480
gtggaattgc acaataggct acaaactgac ttgctcgtgg ataaatctat agtcaaattt      3540
atagaagata tcaatatcgt agatatagcc actgaagtga atgagcaact gagccaagtt      3600
gctcagaatc aaggagttga gtcagataat attgggcaac tctacctaag caataggata      3660
gtaaacgagc ggataagagg tgaattatga                                      3690
```

<210> SEQ ID NO 37
<211> LENGTH: 3690
<212> TYPE: DNA
<213> ORGANISM: Artificial Sequence
<220> FEATURE:
<223> OTHER INFORMATION: 99% sequence identity to SEQ ID NO:2

<400> SEQUENCE: 37

```
atggggcata gtgctgggga atatgtggca gccacagtag caggaatatt tagtttagaa        60
gatggtttaa aactgattgc tcatagagga agactaatgc gacagttacc ctctgggggt       120
gaaatgttat ctgtaatggc ttcaattgaa aaggtaaatc aactaattgc accatactct       180
caaaaagtag cgatcgcatc gattaacgga ccccaaagca ttgtcatttc tggtgaggca       240
gaagcaattg gagcggttca aaatagctta ggagcagaag acattaagac aaaacgactg       300
gaagtatccc acgcattcca ttcacatttg atggaaccaa tgttggcgga cttttgaagca      360 gtagcatcag aaataaccta caatcaacca aatattccat gagtatcaaa tgtaacggga       420
gctagggcag agaatagtat tgccacagca agctattggg taaatcatgt ccggcaaccg       480
gtgaaatttg cccaaagtat gggcacatta cagcaagaag gttattccat cttcttagaa       540
attggaccca accaactttt gttaggcatg ggaagacagt gcttgccaga agatgtggga       600
ggttggttgc cttcttttga accaggtcaa gaagactggc agcaaatgct acaaagtttg       660
gctgaactat atgtgcatgg agttaaagtt gattggttag ggtttgataa agattattct       720
cgtagcaagg tagtattgcc gacttatccc tttcaacggc aacgttattg ggttgagaca       780 ataataatc taatacatca acaacagttt ttatcaaatc ataaaaatct tcaccctcta        840
ctcggtcaaa gattacattt agcagcctta gaacagcaaa ttcgttttga atgtcaaatt       900
cgtgcttctc aaccaactta cctgcaacac cactgtgttt ttctcaacc tgttttccca       960 gcagcagctt acttggaaat agccttagca gcaggttcaa ctttattcaa ttcagatgat      1020
ttaatcctag aagatatagc aatccaaaaa gtattaattt tatcaaagga tgaaattaat      1080
acaattcaga tagtttttaaa cttacagtta gtacaaagct ataaattcca aattttcagt    1140
ttggatataa acactaattc ttcagaacct aaatggattc tacatattga aggaaaaata      1200
ctagtaggta ataaagaccc ccaattagaa acaacaaact taaaagcgat taaagacgag      1260
tataaccaac agatattacc tactgaattc taccaaaaat ctgaagaatg ggtcttaat      1320 tacggttctt ctttccaagc cgttaaacaa ctgtggcaca gcgaaggaaa agcactaggt      1380
gaaattcagt taccagaaac cgaggtgaat gttgcaactt taccaact gcacccaatt       1440 cttttagatg ctagcttcca ggtgttagca gcagttatgg gtaaaacgga caaccaagaa      1500
ccttatttgc cattggaaat aaaacgacta caaatttatc ggagtggtag taatagtttg      1560
tggactcaag tagagatagg tgcaacagaa actaataaac caactttgag cggtaaagtt      1620
```

-continued

```
tgtctattgg atgaacaagg aatagtagta gcaagagttg aaggtttaac tttattacgt    1680
acttctcgcg aggctttgtt ccgtaatatt gaaccaaaat ttaataattg gttatatcaa    1740
atccattggc aaacccaatc aatttcaccc cataaccaat caattgactt aacaaaatca    1800
cgtagctggt tattgttttc cccacccaca ggtataggca aacatctggt agaatcctta    1860
gaacaacaag gttggcattg tatattagta acaccagggg caaattacca gcagttagaa    1920
tctcaacatt atcaaatcaa ccccaaccat cctgaggaat tcctgcacct attgcaatca    1980
agcttggagc agcaaccccc cttacgagga attattcacc tgtggagttt ggactcaaca    2040
atagcactaa ggactggggc acaggagttg caaaaatccc aagaactggg ctgtggcagc    2100
ctacttcatt tagtccaagc cttagtaaaa aatcaagata tggaaagtgc cccattatgg    2160
ttagtgactc aaggctcaca atctgtgggt aatgagtccc ctcctataca attccaacaa    2220
acacctttat gggggttagg tcgagtaatt gcccaggaac ataggaatt acaatgccgg     2280 tgtttagact tagatccaac catggaagat tcccaaacag tagctgcttt gttagaggaa    2340
ctattatctc ctggtgatga aaaccaaatt gcttactgtc aagggtacg tcacgttgcc     2400 cggttagagc ggcaacaaaa aatgagtaca tctacacagt ccggattaca aatttcctcg    2460
caacaaccat tccaactgaa gctatcagaa tataagtctt cagacaacct aatccaagcc    2520
gaagccagtt acttaattac cggaggtctg ggagcactgg ggttaaaaac cgctgagtgg    2580
atggtacaac aaggggtcaa ctatttagta cttaccggac gtaggcagcc atcagcaaaa    2640
gctcaacaaa ccattgaaca attacagaag gcaggagcgc aagtattagt cctgtgtgga    2700
catatttccc aacaagaaaa tgtggcaaga attatagagt caatcaaagt atctttgcca    2760
gcgttacgag gaataattca tgctgctggg atattggatg ctggtttgct gttaaacatg    2820
aattgggaaa aatttacaca ggtgatggca ccaaaagtac aaggggcttg gcatttgcat    2880
aatttgactc agaatctacc cttggacttt tttgtttgtt tttcctctat ggcttcaata    2940
ttgggttcgc ctggtcaagg gaattatgct gctgctaatg ctttcatgga tggtttagcc    3000
catcatcgac ggggtatggg tttacctggc ttgagcatta actggggacc atgggcacaa    3060
gagggaatgg ccgcaaattt ggatagtcct catcaagata caatggtgtc caagggaatg    3120
acttttttgt cttcagaaca gggattgcag gttctaggac aattactcga acaatccata    3180
ccacaagtag gagtcctacc cattcaatgg tcagtgttcc aagagcaatt tagttttggt    3240
aatcaaatac cattgctgtc ccaattggta aagaaaagca aatcacagca aaagccctc     3300 caaacaaaga caaagcacaa tgaattttta gaacagctaa aagctgcttt accaagagaa    3360
agagaaaagc ttttgataat ttacattaaa gatgaaattt cccaagtact ttctttgagc    3420
acttctcaaa ttgatatgca acagcccctg aacactatgg ggcttgattc tctaatggct    3480
gtggaattgc acaataggct ccaaactgac ttgctcgtgg atatatctat agtcaaattt    3540
atagaagata tcagtatcgt tgatttagcc actgaagtga atgagcaact gagccaagtt    3600
gctcagaatc aaggagttga gtcagaaaat aatgggcaac tctaccaaag caataggaaa    3660
gaaaacgagc ggataagagg tgaattatga                                    3690
```

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide
<220> FEATURE:

```
<221> NAME/KEY: misc_feature
<222> LOCATION: 3, 12, 18
<223> OTHER INFORMATION: n = A,T,C or G

<400> SEQUENCE: 38
gcnggyggyg cntaygtncc                                              20

<210> SEQ ID NO 39
<211> LENGTH: 17
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 3, 12
<223> OTHER INFORMATION: n = A,T,C or G

<400> SEQUENCE: 39
ccnggdatyt tnacytg                                                 17

<210> SEQ ID NO 40
<211> LENGTH: 32
<212> TYPE: DNA
<213> ORGANISM: Artificial Sequence
<220> FEATURE:
<223> OTHER INFORMATION: Oligonucleotide

<400> SEQUENCE: 40
atttatcata tgggttccga ttccggagcc ga                                32

<210> SEQ ID NO 41
<211> LENGTH: 36
<212> TYPE: DNA
<213> ORGANISM: Artificial Sequence
<220> FEATURE:
<223> OTHER INFORMATION: Oligonucleotide

<400> SEQUENCE: 41
aaataagaat cctcatcatt tttccaattg atgggt                            36
```

NUCLEIC ACIDS AND POLYPEPTIDES INVOLVED IN THE PRODUCTION OF CRYPTOPHYCIN

CROSS REFERENCE TO RELATED APPLICATIONS

This application claims priority under 35 U.S.C. §119(e) to U.S. Application Ser. No. 60/568,334, filed May 5, 2004, which is hereby incorporated by reference.

TECHNICAL FIELD

This invention relates to production of cryptophycin, and more particularly to the polypeptides involved in the biosynthesis of cryptophycin and the nucleic acids encoding such polypeptides.

BACKGROUND

Cryptophycins are novel macrolides first isolated from blue-green algae (*Nostoc* sp. GSV22 and *Nostoc* sp. ATCC 53789) and are potent tumor selective cytotoxins in vivo. Many syntheses of the major natural products, cryptophycins 1–4, and a wide range of analogs have been published. For example, cryptophycins have been synthesized by a convergent method in which four components, Unit A, Unit B, Unit C, and Unit D (Golakati et al., 1995, *J. Am. Chem. Soc.*, 117(49):12031), are coupled together to form the final product (see, for example, U.S. Pat. No. 6,013,626). In other methods, novel semi-synthetic compounds are generated, for example, by converting the epoxide of a natural cryptophycin to a carbon-carbon double bond (see, for example, U.S. Pat. Nos. 4,845,085 and 4,845,086). Stereo-selective addition of functional groups is often problematic during chemical synthesis of cryptophycins, however. Therefore, few of the methodologies for cryptophycin syntheses are considered viable or practical on a commercial scale.

SUMMARY

The present invention provides polypeptides involved in cryptophycin biosynthesis and the nucleic acid molecules that encode such polypeptides. The nucleic acid molecules and polypeptides of the invention or variants thereof can be used in the methods of the invention to produce cryptophycins.

In one aspect, the invention provides an isolated nucleic acid molecule that includes a nucleic acid sequence having at least 85% (e.g., 85%, 90%, 95%, 99%, or 100%) sequence identity to the sequence shown in SEQ ID NO:1 or to a fragment thereof. Such a sequence encodes at least one enzyme involved in biosynthesizing cryptophycin.

The invention further provides for a vector containing such a nucleic acid molecule, and host cells containing such vectors. The invention also provides for cryptophycin or cryptophycin analogues made by such host cells.

In another aspect, the invention provides methods of producing cryptophycin. Such a method generally includes the step of culturing the above-described host cells in the presence of an appropriate substrate and under conditions appropriate for the production of cryptophycin. Such a method can further include the step of purifying the cryptophycin.

In another aspect, the invention provides an isolated nucleic acid molecule comprising a nucleic acid sequence having at least 85% (e.g., 85%, 90%, 95%, 99%, or 100%) sequence identity to SEQ ID NOs: 2, 4, 6, 8, 10, 12, 14, 16, 18, 20, 22, 24, 26, 28, or 30, or to a fragment thereof, wherein the nucleic acid sequence encodes a polypeptide that exhibits functional activity.

The invention further provides for vectors containing such nucleic acid molecules, and host cells containing such vectors. The invention also provides for intermediates in cryptophycin biosynthesis made by such host cells.

The invention further provides a polypeptide encoded by the nucleic acid sequence having at least 85% (e.g., 85%, 90%, 95%, 99%, or 100%) sequence identity to SEQ ID NOs: 2, 4, 6, 8, 10, 12, 14, 16, 18, 20, 22, 24, 26, 28, or 30, or to a fragment thereof. Such polypeptides can have the sequence shown in 3, 5, 7, 9, 11, 13, 15, 17, 19, 21, 23, 25, 27, 29, or 31, respectively.

In still another aspect, the invention provides an isolated nucleic acid molecule comprising a nucleic acid sequence having at least 85% (e.g., 85%, 90%, 95%, 99%, or 100%) sequence identity to nucleotides 9,199 to 10,032 of SEQ ID NO:6, or to a fragment thereof, wherein the nucleic acid sequence encodes a polypeptide that exhibits thioesterase activity under appropriate conditions.

In yet another aspect, the invention provides an isolated nucleic acid molecule comprising a nucleic acid sequence having at least 85% (e.g., 85%, 90%, 95%, 99%, or 100%) sequence identity to the sequence shown in SEQ ID NO:8, or to a fragment thereof, wherein the nucleic acid sequence encodes a polypeptide that exhibits epoxidase activity under appropriate conditions.

In another aspect, the invention provides an isolated nucleic acid molecule comprising a nucleic acid sequence having at least 85% (e.g., 85%, 90%, 95%, 99%, or 100%) sequence identity to the sequence shown in SEQ ID NO:14, or to a fragment thereof, wherein the nucleic acid sequence encodes a polypeptide that exhibits halogenase activity under appropriate conditions.

In another aspect, the invention provides for methods of producing an intermediate in cryptophycin biosynthesis. Such a method includes culturing one or more host cells that contain one or more vectors comprising one or more of the nucleic acid sequences shown in SEQ ID NOs:2, 4, 6, 8, 10, 12, 14, 16, 18, 20, 22, 24, 26, 28, or 30 in the presence of one or more appropriate substrates under conditions appropriate for production of an intermediate in cryptophycin biosynthesis.

Representative appropriate conditions include pH, media, temperature, and/or the presence or absence of co-factors. Representative substrates and intermediates in cryptophycin biosynthesis include Cryptophycin 2, 3, 4, 5, 16, and 17 (see FIG. 1B).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 shows cryptophycin structures.

FIG. 5 is the nucleotide sequence of the cloned insert of pDAM163 (SEQ ID NO:1).

FIG. 6 is the nucleotide and amino acid sequences of the genes and polypeptides involved in cryptophycin biosynthesis (SEQ ID NOs:2–31).

FIG. 7 shows SEQ ID NOs:32–37, which have 75%, 80%, 85%, 90%, 95%, and 99% sequence identity, respectively, to SEQ ID NO:2.

DESCRIPTION OF SEQUENCES

Figure 1A:
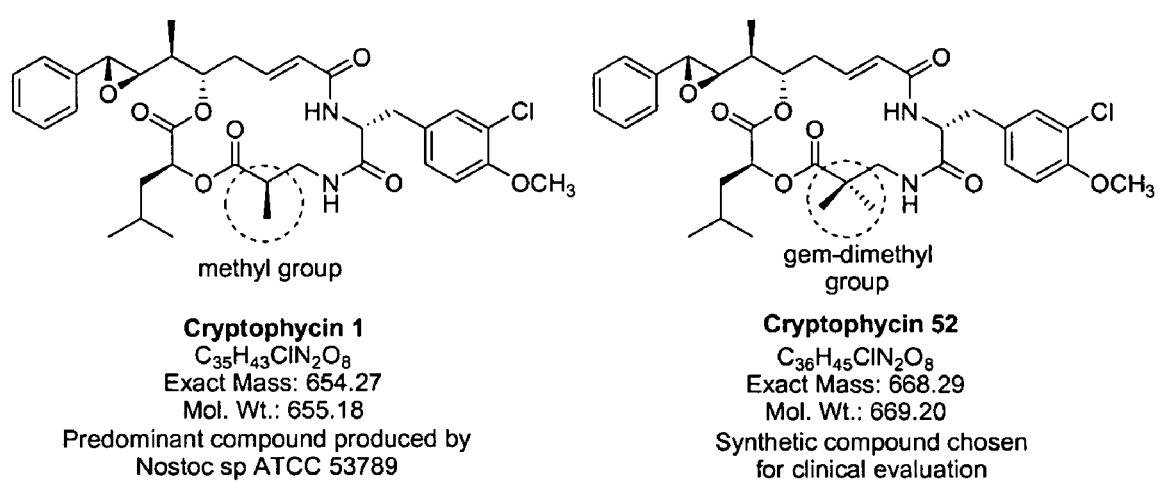
FIG. 1A is a natural cryptophycin, Cryptophycin 1, and a synthetic cryptophycin, Cryptophycin 52.
Figure 1B:
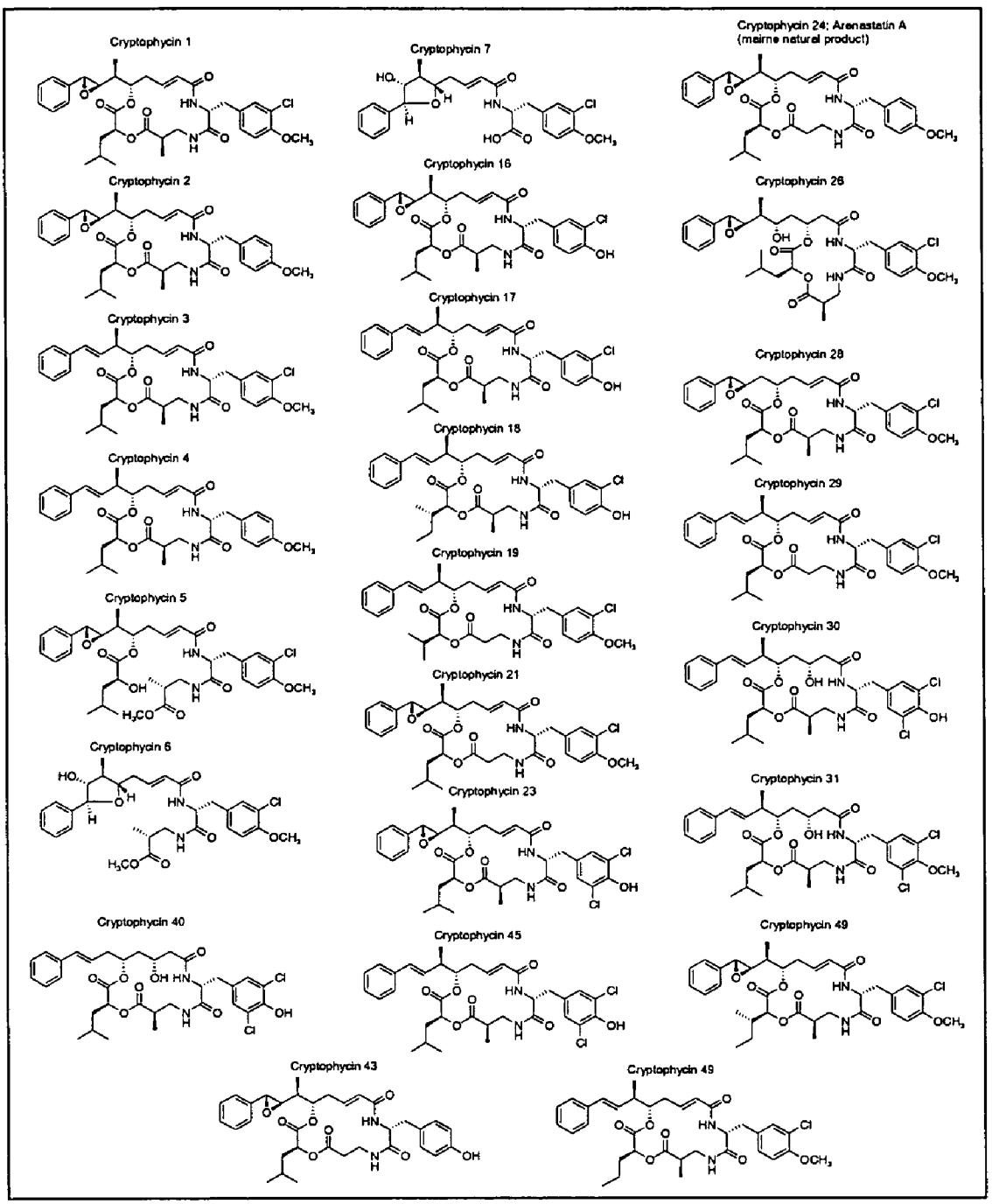
FIG. 1B illustrates the diversity of natural cryptophycins isolated from *Nostoc* spp.

SEQ ID NO:1 is the nucleotide sequence of the cloned insert of pDAM163.
SEQ ID NO:2 is the nucleotide sequence of crpA.
SEQ ID NO:3 is the amino acid sequence of CrpA.
SEQ ID NO:4 is the nucleotide sequence of crpB.
SEQ ID NO:5 is the amino acid sequence of CrpB.
SEQ ID NO:6 is the nucleotide sequence of crpC.
SEQ ID NO:7 is the amino acid sequence of CrpC.
SEQ ID NO:8 is the nucleotide sequence of crpF.
SEQ ID NO:9 is the amino acid sequence of CrpF.
SEQ ID NO:10 is the nucleotide sequence of crpG
SEQ ID NO:11 is the amino acid sequence of CrpG.
SEQ ID NO:12 is the nucleotide sequence of crpH.
SEQ ID NO:13 is the amino acid sequence of CrpH.
SEQ ID NO:14 is the nucleotide sequence of crpJ.
SEQ ID NO:15 is the amino acid sequence of CrpJ.
SEQ ID NO:16 is the nucleotide sequence of crpM.
SEQ ID NO:17 is the amino acid sequence of CrpM.
SEQ ID NO:18 is the nucleotide sequence of crpN.
SEQ ID NO:19 is the amino acid sequence of CrpN.
SEQ ID NO:20 is the nucleotide sequence of crpP.
SEQ ID NO:21 is the amino acid sequence of CrpP.
SEQ ID NO:22 is the nucleotide sequence of crpU.
SEQ ID NO:23 is the amino acid sequence of CrpU.
SEQ ID NO:24 is the nucleotide sequence of crpV.
SEQ ID NO:25 is the amino acid sequence of CrpV.
SEQ ID NO:26 is the nucleotide sequence of crpX.
SEQ ID NO:27 is the amino acid sequence of CrpX.
SEQ ID NO:28 is the nucleotide sequence of crpY.
SEQ ID NO:29 is the amino acid sequence of CrpY.
SEQ ID NO:30 is the nucleotide sequence of crpZ.
SEQ ID NO:31 is the amino acid sequence of CrpZ.
SEQ ID NO:32 is a nucleotide sequence having 75% sequence identity to SEQ ID NO:2.
SEQ ID NO:33 is a nucleotide sequence having 80% sequence identity to SEQ ID NO:2.
SEQ ID NO:34 is a nucleotide sequence having 85% sequence identity to SEQ ID NO:2.
SEQ ID NO:35 is a nucleotide sequence having 90% sequence identity to SEQ ID NO:2.
SEQ ID NO:36 is a nucleotide sequence having 95% sequence identity to SEQ ID NO:2.
SEQ ID NO:37 is a nucleotide sequence having 99% sequence identity to SEQ ID NO:2.
SEQ ID NO:38 is the sequence of an oligonucleotide.
SEQ ID NO:39 is the sequence of an oligonucleotide.
SEQ ID NO:40 is the sequence of an oligonucleotide.
SEQ ID NO:41 is the sequence of an oligonucleotide.

DETAILED DESCRIPTION

Cryptophycin biosynthesis is accomplished via a mixed Type I PKS/NRPS system. Manipulation of polyketide synthetases (PKSs) and non-ribosomal peptide synthetases (NRPSs) through mutasynthesis, combinatorial biosynthesis, and directed biosynthesis feeding (chemoenzymatic synthesis) has been described for many PKS and NRPS polypeptides. The identification of the corresponding genes allows for these types of approaches with the cryptophycin system. It is possible that altering the PKS enzyme for Unit A formation or the NRPS for Unit B, C, and D formation could generate a wide variety of new cryptophycins. With this invention, it is also possible to incorporate these enzymes in "total synthesis" of cryptophycins to lower the cost and increase the overall yields. For example, the ability of biosynthetic enzymes to exhibit high levels of stereochemical control and relaxed substrate specificity, and the sensitivity of the biological and chemical assays for identifying cryptophycins, allow for production of rational "biologically" derived cryptophycins that have superior properties.

Cryptophycins

FIG. 1A shows Cryptophycin 1 and Cryptophycin 52. Cryptophycin 52 is nearly identical to Cryptophycin 1, the most active natural compound, except for the presense of gem-dimethyl on the β-alanine unit of Cryptophycin 52 instead of the methyl group on Cryptophycin 1. FIG. 1B shows numerous other natural cryptophycins that have been isolated from *Nostoc* spp. A chlorohydrin analog (Cryptophycin 309; see U.S. Publication No. 20020065261 and FIG. 2 of the instant application) has been identified and has been shown to be much more active than the current clinical candidate, Cryptophycin 52.

Purification

Routine chromatographic techniques such as high-performance liquid chromatography (HPLC) or thin-layer chromatography (TLC) can be used to purify cryptophycins. See, for example, U.S. Pat. No. 5,952,298, which describes specific HPLC conditions for purifying different cryptophycins.

Structure Identification

The structures of cryptophycins can be determined using methodology that is well known to those of skill in the art.

Mass spectral analysis can be used, for example. Proton and carbon NMR data obtained from COSY, HMQC, HMBC, and NOESY spectra allows determination of the gross structures of the depsipeptide-type compounds. The presence of the various hydroxy and amino acid units in each compound can be detected by gas chromatographic mass spectral analysis. Total structures, including absolute stereochemistries, can be determined using a combination of chemical degradative and analytical techniques on cryptophycin compounds.

Anti-Fungal Activity

Cryptophycin compounds can be tested against fungal organisms known to be sensitive to such compounds using, for example, a disk-diffusion assay such as a Corbett assay (see, for example, Kemp, 1980, Organic Chemistry, Worth Publishers Inc.). The anti-fungal activity of a cryptophycin is usually correlated with the size of the zone of inhibition (i.e., an area of no microbial growth around an antimicrobial agent in a disk-diffusion test). An organism that can be used to evaluate the anti-fungal activity of a cryptophycin is *Candida albicans.*

Anti-Cancer Activity

The anti-cancer activity of a cryptophycin can be examined using a number of different assays such as cell proliferation assays and cell cycle arrest assays. In addition, cytoskeletal structures such as tubulin can be examined using, for example, immunofluorescence assays. See, for example, U.S. Pat. No. 5,945,315.

Cryptophycins can be evaluated for anti-cancer activity against a number of different cell types. For example, murine leukemia cells (e.g., L1210 or P388), murine solid tumor cells (e.g., colon adenocarcinoma 38, pancreatic ductal adenocarcinoma 03, mammary adenocarcinoma M16/M17), human solid tumor cells (e.g., colon CX-1, HCT8, H116, lung H125, mammary MX-1, MCF-7), low malignancy fibroblast cells (e.g., LML), human nasopharyngeal carcinoma cells (e.g., KB), human colon carcinoma cells (e.g., LoVo), and human ovarian carcinoma cells (e.g., SKOV3) can be used to evaluate the anti-cancer activity of a cryptophycin. For example, a disk diffusion assay much like the Corbett assay (Kemp, supra) commonly used in antifungal and antibacterial testing can be used to evaluate the anti-cancer activity of a cryptophycin. A zone of inhibition can be correlated with the anti-cancer activity of a cryptophycin.

Nucleic Acids and Polypeptides Involved in Cryptophycin Biosynthesis

Approximately 45 kb of DNA corresponding to the genes predicted to be involved in cryptophycin biosynthesis were cloned into a cosmid designated pDAM163 and sequenced. FIG. 4 shows a schematic of pDAM163, while FIG. 5 shows the nucleotide sequence of the cloned insert of pDAM163 (SEQ ID NO:1). This cosmid replicated efficiently and stably in well-developed fermentation strains such as *E. coli* B (*E. coli* BL21pLys) and *E. coli* K (DH5α) derivatives. Expressing the coding regions contained within pDAM163 can result in the production of cryptophycin in the *E. coli* strains. A variety of microorganisms such as bacteria (e.g., *Escherichia coli*), yeast (e.g., *Pichia pastoris* or *Saccharomyces cerevisiae*), or fungi (e.g., *Neurospora crassa*) that include expression constructs such as pDAM163 or variants thereof can be used to generate cryptophycins.

The components of the biosynthetic pathway are summarized in Table 1, which provides information related to the putative function of each polypeptide.

TABLE 1

Nucleic Acids and Polypeptides Involved in Cryptophycin Biosynthesis

| Designation (SEQ ID NO: Nucleic Acid/Polypeptide) | Length (nt/amino acids) | Putative Function |
|---|---|---|
| crpA (SEQ ID NO:2/3) | 3690/1229 | Polyketide synthetase (PKS) |
| crpB (SEQ ID NO:4/5) | 5832/1943 | Nonribosomal Peptide Synthetase (NRPS) |
| crpC (SEQ ID NO:6/7) | 10,032/3343 | NRPS |
| crpF (SEQ ID:NO:8/9) | 1353/450 | Cytochrome p450 (epoxidase) |
| crpG (SEQ ID NO:10/11) | 885/294 | Iron-dependent non-heme hydroxylase |
| crpH (SEQ ID NO:12/13) | 333/110 | Aspartate decarboxylase |
| crpI | —[a] | IS1327 Transposase |
| crpJ (SEQ ID NO:14/15) | 1476/491 | Non-heme halogenase |
| crpK | —[a] | IS892-orf2 |
| crpL | —[a] | IS892-orf1 |
| crpM (SEQ ID NO:16/17) | 1383/460 | ISRSO13 Transposase |
| crpN (SEQ ID NO:18/19) | 942/313 | Benzoyl-CoA reductase/2-Hydroxyglutaryl-CoA dehydratase |
| crpO | [b] | pvdE type regulator |
| crpP (SEQ ID NO:20/21) | 633/210 | Thioredoxin |
| crpU (SEQ ID NO:22/23) | 468/155 | N- acetyltransferase |
| crpV (SEQ ID NO:24/25) | 2355/784 | Large exoprotein involved in heme utilization |
| crpW | —[a] | TPR repeat protein |
| crpX (SEQ ID NO:26/27) | 399/132 | Chorismate mutase/Prephenate dehydrogenase |
| crpY (SEQ ID NO:28/29) | 645/214 | 2-Hydroxychromenene-2-carboxylate isomerase |
| crpZ (SEQ ID NO:30/31) | 273/90 | 3-Dehydroquinate synthase |

[a]no open reading frame identified;
[b]multiple open reading frames identified.

Nucleic Acid Molecules

The present invention is based, in part, on the identification of nucleic acid molecules that encode polypeptides involved in cryptophycin synthesis. Particular nucleic acid molecules of the invention include the sequences shown in SEQ ID NOs:1, 2, 4, 6, 8, 10, 12, 14, 16, 18, 20, 22, 24, 26, 28, and 30. As used herein, the term "nucleic acid molecule" can include DNA molecules and RNA molecules and analogs of the DNA or RNA molecule generated using nucleotide analogs. A nucleic acid molecule of the invention can be single-stranded or double-stranded, and the strandedness will depend upon its intended use.

The invention further encompasses nucleic acid molecules that differ from the nucleotide sequence of SEQ ID NOs: 1, 2, 4, 6, 8, 10, 12, 14, 16, 18, 20, 22, 24, 26, 28, and 30. Nucleic acid molecules of the invention include molecules that are at least 10 nucleotides in length and that have at least 75% sequence identity (e.g., at least 80%, 85%, 90%, 95%, or 99% sequence identity) to any of SEQ ID NOs: 1, 2, 4, 6, 8, 10, 12, 14, 16, 18, 20, 22, 24, 26, 28, and 30. Nucleic acid molecules that differ in sequence from the nucleic acid sequences shown in SEQ ID NOs: 1, 2, 4, 6, 8, 10, 12, 14, 16, 18, 20, 22, 24, 26, 28, and 30 can be generated by standard techniques, such as site-directed mutagenesis or PCR-mediated mutagenesis. In addition, nucleotide changes can be introduced randomly along all or part of a nucleic acid molecule of the invention, such as by saturation mutagenesis. Alternatively, nucleotide changes can be introduced into a sequence by chemically synthesizing a nucleic acid molecule having such changes.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, Nucleic Acids Res., 25:3389–3402) as incorporated into BLAST (basic local alignment search tool) programs, available at ncbi.nlm.nih-.gov on the World Wide Web. BLAST searches can be performed to determine percent sequence identity between a nucleic acid molecule of the invention and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used. Sequence analysis of the nucleic acid sequences as performed herein used BLAST version 2.2.8 (updated on Feb. 10, 2004).

The sequences of representative nucleic acids of the invention having 75%, 80%, 85%, 90%, 95%, and 99% sequence identity to SEQ ID NO:2 are shown in FIG. 7 (SEQ ID NOs:32–37, respectively). Such sequences can be generated using a computer or by hand. The nucleic acid sequences shown in SEQ ID NOs:32–37 were generated by hand by randomly changing 25 nucleotides out of every 100 nucleotides of SEQ ID NO:2, 2 out of every 10, 15 out of every 100, 1 out of every 10, 5 out of every 100, or 1 nucleotide out of every 100 nucleotides of SEQ ID NO:2, respectively. By "changing," it is meant that the nucleotide at a particular position is replaced randomly with one of the other three nucleotides. It is apparent to those of ordinary skill in the art that any nucleic acid molecule within the scope of the invention can be generated using the same method described herein (i.e., by similarly changing nucleotides within the sequence of SEQ ID NOs: 1, 2, 4, 6, 8, 10, 12, 14, 16, 18, 20, 22, 24, 26, 28, and 30).

Nucleic acid fragments are included in the invention. Nucleic acid fragments suitable for use in the invention are those fragments that encode a polypeptide having functional activity. These fragments can be called "functional fragments," although it is understood that it is not the nucleic acid that possesses functionality.

For example, nucleic acid fragments of crpA (SEQ ID NO:2) can be at least 185 nucleotides in length (e.g., 185, 200, 269, 323, 392, 442, 481, 530, 590, 618, 678, 752, 804, 876, 922, 1033, 1146, 1278, 1399, 1478, 1567, 1645, 1712, 1888, 1907, 2061, 2154, 2233, 2357, 2491, 2543, 2677, 2781, 2802, 2944, 3012, 3143, 3257, 3368, 3459, 3548, or 3689); nucleic acid fragments of crpB (SEQ ID NO:4) can be at least 292 nucleotides in length (e.g., 292, 306, 382, 461, 592, 715, 825, 947, 1059, 1172, 1236, 1358, 1496, 1590, 1671, 1774, 1889, 1923, 2047, 2135, 2265, 2346, 2477, 2588, 2667, 2754, 2863, 2954, 3084, 3126, 3278, 3345, 3412, 3551, 3670, 3781, 3890, 3910, 4044, 4123, 4266, 4378, 4423, 4513, 4622, 4783, 4822, 4989, 5002, 5156, 5237, 5368, 5486, 5572, 5691, 5765, or 5831); nucleic acid fragments of crpC (SEQ ID NO:6) can be at least 502 nucleotides in length (e.g., 502, 624, 738, 829, 914, 1026, 1138, 1257, 1318, 1452, 1525, 1637, 1768, 1828, 1987, 2074, 2183, 2294, 2338, 2444, 2557, 2637, 2789, 2816, 2942, 3067, 3178, 3227, 3348, 3459, 3504, 3684, 3759, 3812, 3943, 4005, 4276, 4495, 4658, 4827, 5048, 5276, 5424, 5608, 5877, 6034, 6269, 6447, 6632, 6874, 7006, 7284, 7472, 7647, 7814, 8038, 8246, 8459, 8644, 8888, 9053, 9298, 9436, 9666, 9878, or 10,032); nucleic acid fragments of crpF (SEQ ID NO:8) can be at least 68 nucleotides in length (e.g., 68, 74, 82, 88, 95, 105, 168, 235, 367, 489, 524, 665, 784, 863, 925, 1064, 1138, 1279, or 1352); nucleic acid fragments of crpG (SEQ ID NO:10) can be at least 44 nucleotides in length (e.g., 44, 54, 58, 67, 74, 83, 97, 107, 189, 267, 345, 457, 536, 679, 772, or 884); nucleic acid fragments of crpH (SEQ ID NO:12) can be at least 33 nucleotides in length (e.g., 33, 45, 52, 68, 73, 84, 93, 108, 168, 216, 248, 293, 312, or 332); nucleic acid fragments of crpJ (SEQ ID NO:14) can be at least 74 nucleotides in length (e.g., 74, 106, 187, 254, 304, 379, 467, 522, 592, 667, 714, 781, 859, 911, 978, 1049, 1138, 1273, 1347, 1405, or 1475); nucleic acid fragments of crpM (SEQ ID NO:16) can be at least 69 nucleotides in length (e.g., 69, 136, 216, 362, 486, 592, 647, 781, 844, 919, 1049, 1138, 1274, or 1382); nucleic acid fragments of crpN (SEQ ID NO:18) can be at least 94 nucleotides in length (e.g., 94, 182, 261, 358, 442, 580, 625, 740, 862, or 941); nucleic acid fragments of crpP (SEQ ID NO:20) can be at least 32 nucleotides in length (e.g., 32, 85, 120, 175, 232, 286, 310, 379, 433, 561, or 632); nucleic acid fragments of crpU (SEQ ID NO:22) can be at least 23 nucleotides in length (e.g., 23, 74, 112, 178, 215, 280, 315, 369, 402, or 467); nucleic acid fragments of crpV (SEQ ID NO:24) can be at least 118 nucleotides in length (e.g., 118, 235, 366, 440, 521, 636, 783, 852, 918, 1044, 1168, 1238, 1350, 1448, 1569, 1722, 1838, 1924, 2052, 2167, 2288, or 2354); nucleic acid fragments of crpX (SEQ ID NO:26) can be at least 60 nucleotides in length (e.g., 60, 98, 137, 182, 214, 278, 308, 357, or 398); nucleic acid fragments of crpY (SEQ ID NO:28) can be at least 32 nucleotides in length (e.g., 32, 74, 121, 169, 204, 263, 298, 355, 391, 426, 484, 523, 577, 624, or 644); and nucleic acid fragments of crpZ (SEQ ID NO:30) can be at least 27 nucleotides in length (e.g., 27, 68, 103, 158, 193, 243, or 272). Based on contemporaneous public database searches, such fragments appear not to have more than 85% sequence identify to sequences in the public databases.

As used herein, an "isolated" nucleic acid molecule is a nucleic acid molecule that is separated from other nucleic acid molecules that are usually associated with the reference nucleic acid molecule in the genome. Thus, an "isolated" nucleic acid molecule includes, without limitation, a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

Isolated nucleic acid molecules of the invention can be obtained using techniques routine in the art. For example, isolated nucleic acids within the scope of the invention can be obtained using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid molecule of the invention. Isolated nucleic acids of the invention also can be chemically synthesized, either as a single nucleic acid molecule or as a series of oligonucleotides. In addition, isolated nucleic acid molecules of the invention also can be obtained by mutagenesis. For example, an isolated nucleic acid that shares identity with an art known sequence can be mutated using common molecular cloning techniques (e.g., site-directed mutagenesis). Possible mutations include, without limitation, deletions, insertions, substitutions, and combinations thereof.

Vectors containing nucleic acid molecules that encode polypeptides involved in cryptophycin synthesis also are provided by the invention. Vectors, including expression vectors, suitable for use in the present invention are commercially available and/or produced by recombinant DNA technology methods routine in the art. A vector containing a nucleic acid molecule of the invention can have elements necessary for expression operably linked to such a nucleic acid molecule, and further can include sequences such as those encoding a selectable marker (e.g., an antibiotic resistance gene), and/or those that can be used in purification of a polypeptide involved in cryptophycin synthesis (e.g., 6×His tag).

Elements necessary for expression include nucleic acid sequences that direct and regulate expression of nucleic acid coding sequences. One example of an element necessary for expression is a promoter sequence. Elements necessary for expression also can include introns, enhancer sequences, response elements, or inducible elements that modulate expression of a nucleic acid molecule of the invention. Elements necessary for expression can be of bacterial, yeast, insect, mammalian, or viral origin and vectors can contain a combination of elements from different origins. Elements necessary for expression are described, for example, in Goeddel, 1990, *Gene Expression Technology: Methods in Enzymology*, 185, Academic Press, San Diego, Calif. As used herein, operably linked means that a promoter and/or other regulatory element(s) are positioned in a vector relative to a nucleic acid molecule of the invention in such a way as to direct or regulate expression of the nucleic acid molecule. Many methods for introducing nucleic acids into host cells, both in vivo and in vitro, are well known to those skilled in the art and include, without limitation, calcium phosphate precipitation, electroporation, heat shock, lipofection, microinjection, and viral-mediated nucleic acid transfer.

Another aspect of the invention pertains to host cells into which a vector of the invention, e.g., an expression vector, or an isolated nucleic acid molecule of the invention has been introduced. The term "host cell" refers not only to the particular cell but also to the progeny or potential progeny of such a cell. A host cell can be any prokaryotic or eukaryotic cell. For example, nucleic acid molecules of the invention can be expressed in bacterial cells such as *E. coli*, or in insect cells, yeast or mammalian cells (such as Chinese hamster ovary cells (CHO) or COS cells). Other suitable host cells are known to those skilled in the art.

Conditions for amplification of a nucleic acid and detection of an amplification product are known to those of skill in the art (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188). Modifications to the original PCR also have been developed. For example, anchor PCR, RACE PCR, or ligation chain reaction (LCR) are additional PCR methods known in the art (see, e.g., Landegran et al., 1988, *Science*, 241:1077–1080; and Nakazawa et al., 1994, *Proc. Natl. Acad. Sci. USA*, 91:360–364).

Hybridization between nucleic acid molecules is discussed in detail in Sambrook et al. (1989, *Molecular Cloning: A Laboratory Manual*, $2^{nd}$ Ed., Cold Spring Harbor Laboratory Press, Cold Spring Harbor, N.Y.; Sections 7.37–7.57, 9.47–9.57, 11.7–11.8, and 11.45–11.57). For oligonucleotide probes less than about 100 nucleotides, Sambrook et al. discloses suitable Southern blot conditions in Sections 11.45–11.46. The Tm between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47–9.52). Hybridizations with an oligonucleotide greater than 100 nucleotides generally are performed 15–25° C. below the Tm. The Tm between a sequence greater than 100 nucleotides in length and a second sequence can be calculated using the formula provided in Sections 9.50–9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations and washes can be performed, where appropriate, under moderate or high stringency conditions. Such conditions are described, for example, in Sambrook et al. section 11.45–11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid of the invention but not to another nucleic acid if hybridization to a nucleic acid of the invention is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Detection of an amplification product or a hybridization complex is usually accomplished using detectable labels. The term "labeled" with regard to an agent (e.g., an oligonucleotide or a polypeptide) is intended to encompass direct labeling of the agent by coupling (i.e., physically linking) a detectable substance to the agent, as well as indirect labeling of the agent by reactivity with another reagent that is directly labeled with a detectable substance. Detectable substances include various enzymes, prosthetic groups, fluorescent materials, luminescent materials, bioluminescent materials, and radioactive materials.

Polypeptides

One aspect of the invention pertains to purified polypeptides involved in cryptophycin synthesis as well as polypeptide fragments, particularly those that possess enzymatic activity (i.e., functional fragments). Predicted amino acid sequences of polypeptides involved in cryptophycin synthesis are shown in SEQ ID NOs:3, 5, 7, 9, 11, 13, 15, 17, 19, 21, 23, 25, 27, 29, and 31.

The term "purified" polypeptide as used herein refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

Polypeptides involved in cryptophycin synthesis can be purified from natural sources (e.g., a biological sample) by known methods such as DEAE ion exchange, gel filtration, and hydroxyapatite chromatography. A purified polypeptide also can be obtained, for example, by expressing a nucleic acid molecule of the invention in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In addition to the naturally-occurring polypeptides involved in cryptophycin biosynthesis, the skilled artisan will further appreciate that changes can be introduced into a nucleic acid molecule (e.g., those having the sequence shown in SEQ ID NOs: 1, 2, 4, 6, 8, 10, 12, 14, 16, 18, 20, 22, 234, 26, 28, and 30) as discussed herein, thereby leading to changes in the amino acid sequence of the encoded polypeptide. For example, changes can be introduced into nucleic acid coding sequences leading to conservative and/or non-conservative amino acid substitutions at one or more amino acid residues. A "conservative amino acid substitution" is one in which one amino acid residue is replaced with a different amino acid residue having a similar side chain. Similarity between amino acid residues has been assessed in the art. For example, Dayhoff et al. (1978, in *Atlas of Protein Sequence and Structure,* 5(Suppl. 3):345–352) provides frequency tables for amino acid substitutions that can be employed as a measure of amino acid similarity. A non-conservative substitution is one in which an amino acid residue is replaced with an amino acid residue that does not have a similar side chain.

The invention also provides for chimeric or fusion polypeptides. As used herein, a "chimeric" or "fusion" polypeptide includes a polypeptide involved in cryptophycin synthesis operatively linked to a heterologous polypeptide. A heterologous polypeptide can be at either the N-terminus or C-terminus of a polypeptide involved in cryptophycin synthesis. Within a chimeric or fusion polypeptide, the term "operatively linked" is intended to indicate that the two polypeptides are encoded in-frame relative to one another. In a fusion polypeptide, the heterologous polypeptide generally has a desired property such as the ability to purify the fusion polypeptide (e.g., by affinity purification). A chimeric or fusion polypeptide of the invention can be produced by standard recombinant DNA techniques, and can use commercially available vectors.

A polypeptide commonly used in a fusion polypeptide for purification is glutathione S-transferase (GST), although numerous other polypeptides are available and can be used. In addition, a proteolytic cleavage site can be introduced at the junction between a polypeptide and a heterologous polypeptide to enable separation of the two polypeptides subsequent to purification of the fusion polypeptide. Enzymes that cleave such proteolytic sites include Factor Xa, thrombin, or enterokinase. Representative expression vectors encoding a heterologous polypeptide that can be used in affinity purification of a polypeptide involved in cryptophycin synthesis include pGEX (Pharmacia Biotech Inc; Smith & Johnson, 1988, *Gene,* 67:31–40), pMAL (New England Biolabs, Beverly, Mass.) and pRIT5 (Pharmacia, Piscataway, N.J.).

Antibodies can be used to detect the presence or absence of polypeptides involved in cryptophycin synthesis. Techniques for detecting polypeptides using antibodies include enzyme linked immunosorbent assays (ELISAs), Western blots, immunoprecipitations and immunofluorescence. An antibody can be polyclonal or monoclonal, and usually is detectably labeled. An antibody having specific binding affinity for a polypeptide involved in cryptophycin synthesis can be generated using methods well known in the art. The antibody can be attached to a solid support such as a microtiter plate using methods known in the art (see, for example, Leahy et al., 1992, *BioTechniques,* 13:738–743). In the presence of a polypeptide involved in cryptophycin synthesis, an antibody-polypeptide complex is formed.

Detection of a polypeptide-antibody complex is usually accomplished by detectably labeling the antibody. The term "labeled" with regard to an antibody is intended to encompass direct labeling of the antibody by coupling (i.e., physically linking) a detectable substance to the antibody, as well as indirect labeling of the antibody by reactivity with another reagent that is directly labeled with a detectable substance. Detectable substances are described above.

Biosynthesis of Cryptophycin

Figure 3:
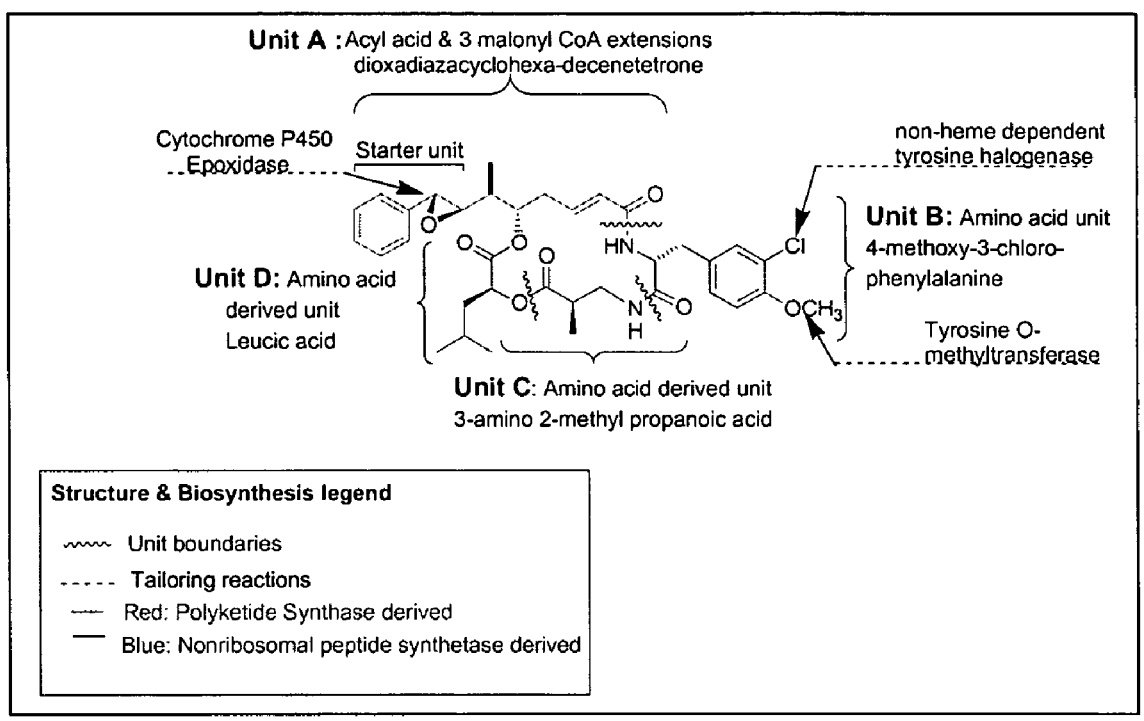
FIG. 3 is a schematic of the modular structure of the cryptophycins and retro-biosynthesis assembly.

FIG. 3 shows the modular structure of cryptophycins. Cryptophycin biosynthesis is a result of a mixed Type I PKS/NRPS system.

Figure 2:
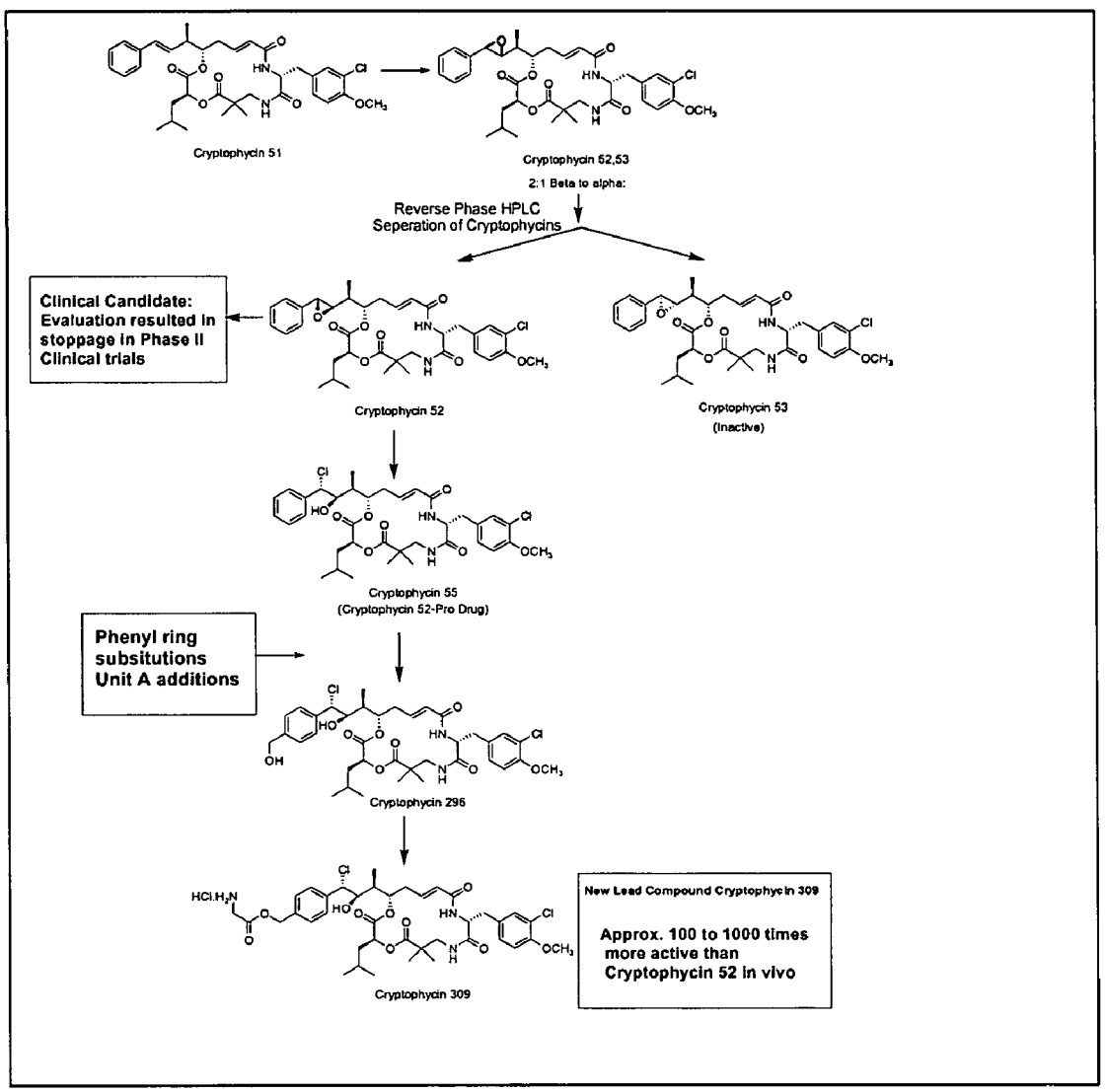
FIG. 2 is a schematic of the lineage of biologically active cryptophycins.
Figure 8:
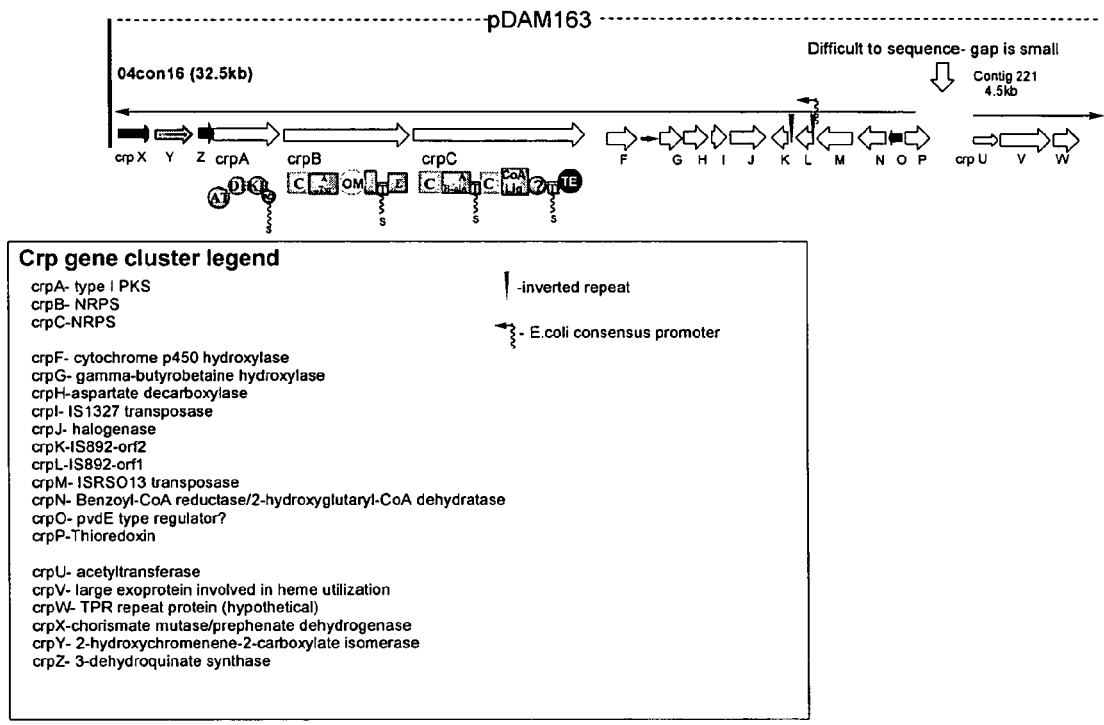
FIG. 8 is a schematic depicting the predicted cryptophycin assembly line.
Figure 9:
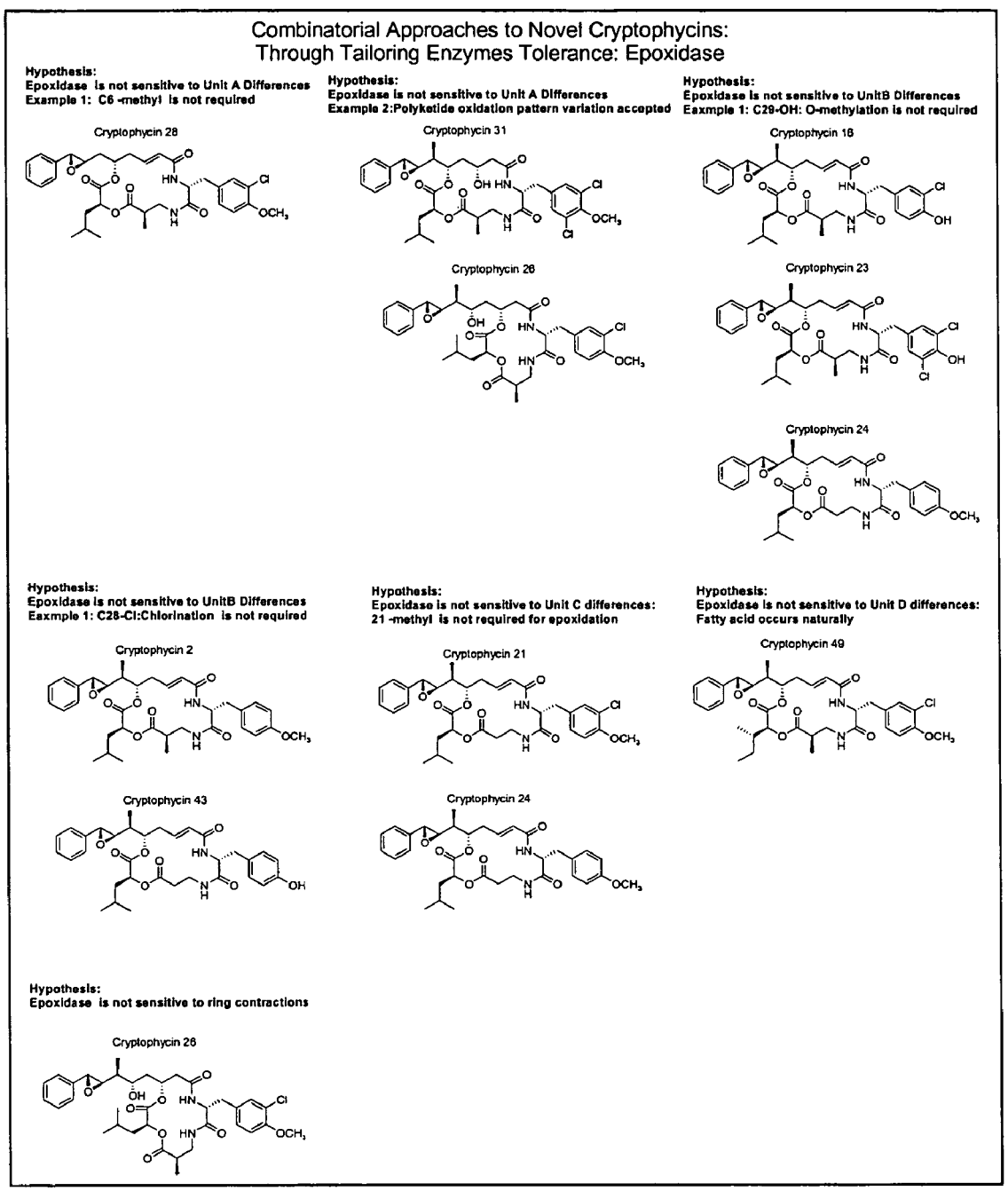
FIG. 9 is a schematic demonstrating that the cryptophycin epoxidase (CrpE) has substrate flexibility but a high degree of steroselectivity.

Unit A is a polyketide synthetase derived unit. Incorporation and linkage of unnatural amino acids such as chlorinated methoxy D-tyrosine amino acid (Unit B) and β-methyl β-alanine (Unit C) are consistent with activities of non-ribosomal peptide synthetase domains. The final terminating unit, the rare carboxylic acid of leucine, leucic acid, could be the result of a NRPS system. However, the ester linkage between Unit C and D is not consistent with a peptide bond forming condensation domain of such a system. It is possible that incorporation of this ester occurs by a novel domain as part of a larger NRPS system. Alternatively, incorporation of the ester may be directed by an enzyme that previously has not been described. The generation of the macrocycle to form the core cryptophycin chemical skeleton involves a chain-terminating cyclization step, likely completed by a member of the hydrolase superfamily of enzymes or domains. The lactone formed between Unit A (the hydroxyl group) and Unit D points to a classic thioesterase dependent mechanism. Additional enzymes such as a cytochrome p450-dependent hydroxylase (likely a cryptophycin epoxidase), a non-heme dependent halogenase, o-methyltransferase, and enzymes involved in activation and methylation of the β-carbon of 3-amino propanoic acid are involved in Unit A, B, C, or D synthesis or in final structural components of cryptophycin. Many of these types of enzymes have been previously described from other polyketide and nonribosomal peptide synthetases. For an overview of the predicted pathway of cryptophycin biosynthesis, see FIG. 8. See also, FIG. 2.

Polyketide Synthetase

Based on homology searches of the GenBank database, the nucleotide sequence designated crpA (SEQ ID NO:2) appears to encode a PKS (CrpA; SEQ ID NO:3). Sequence analysis indicated that CrpA contains a PKS domain (positioned at approximately nucleotides 1–450 of SEQ ID NO:2), an acyltransferase domain (positioned at approximately nucleotides 1–220 of SEQ ID NO:2), a dehydrogenase domain (positioned at approximately nucleotides 760–1000 or 860–1000 of SEQ ID NO:2), a ketoreductase domain (positioned at approximately nucleotides 850–1000 of SEQ ID NO:2), and an acyl carrier protein domain.

Polyketides are diverse biologically active molecules with a wide variety of structures. Polyketides are synthesized from 2-carbon units through a series of condensations and subsequent modifications, and occur in many types of organisms including fungi and mycelial bacteria. Polyketide synthetases (PKSs) catalyze the biosynthesis of polyketides through repeated, decarboxylative Claisen condensations between acylthioester building blocks. The building blocks used to form complex polyketides are typically acylthioesters such as acetyl, butyryl, propionyl, malonyl, hydroxymalonyl, methylmalonyl, and ethylmalonyl CoA.

The sequencing of several genes encoding enzymes that produce type 1 modular PKSs has revealed a linear organization of modules, each of which contains the activities needed for one cycle of polyketide chain elongation. The minimal module contains a ketosynthase (KS), an acyltransferase (AT), and an acyl carrier protein (ACP) that together catalyze a 2-carbon extension of the chain similar to the condensation of 2-carbon units in the biosynthesis of fatty acids. In PKS polypeptides, the regions that encode enzymatic activities are separated by linker regions, also called scaffold regions. These scaffold regions encode amino acid sequences that space the enzymatic activities at the appropriate distances and in the correct order.

PKS is likely responsible for synthesis of the Unit A region, which is one of the most challenging aspects in the chemical synthesis of cryptophycins. The Unit A portion of the molecule is a dioxadiazacyclo, hexadecenetetrone moiety and represents the beginning polyketide unit (FIG. 3).

Non-Ribosomal Peptide Synthetase

Based on homology searches of the GenBank database, the nucleotide sequence designated crpB (SEQ ID NO:4) appears to encode a non-ribosomal peptide synthetase (NRPS) (CrpB; SEQ ID NO:5) involved in production of the Unit B peptide portion of cryptophycin. Sequence analysis indicated that CrpB may contain one or more NRPS domains (positioned at approximately nucleotides 300–950 and 1290–1425 of SEQ ID NO:4), one or more condensation domains (positioned at approximately nucleotides 50–350 and 1475–1780 of SEQ ID NO:4), an adenylation domain, an o-methyltransferase domain (positioned at approximately nucleotides 1000–1200 of SEQ ID NO:4), one or more peptidyl carrier protein domains, an epimerase domain, and one or more acyl CoA synthetase (positioned at approximately nucleotides 525–1000 of SEQ ID NO:4).

Based on homology searches of the GenBank database, the nucleotide sequence designated crpC (SEQ ID NO:6) appears to encode a NRPS (Crp C; SEQ ID NO:7) involved in production of the Units C and D peptide portions of cryptophycin. CrpC also apparently generates a 16-membered peptolide ring during cryptophycin biosynthesis. Sequence analysis indicated that CrpC contains one or more NRPS domains (positioned at approximately nucleotides 250–975, 1350–1600, 1850–2300, and 2950–3100 of SEQ ID NO:6), one or more condensation domains (positioned at approximately nucleotides 1–300 and 1150–1450 of SEQ ID NO:6), an adenylation domain, one or more peptidyl carrier protein domains, one or more acyl CoA ligase domains (positioned at approximately nucleotides 500–1000 and 1900–2400 of SEQ ID NO:6), one or more acyl CoA synthetase domains (positioned at approximately nucleotides 475–1000 and 1900–2400 of SEQ ID NO:6), and a thioesterase domain.

NRPSs are modular in nature, where a module is usually defined as a segment of the NRPS necessary to catalyze the activation of a specific amino acid and result in the incorporation of that amino acid into a non-ribosomal peptide. A minimal module typically contains three domains: (1) an adenylation domain (about 60 kDa) responsible for selecting and activating an amino acid and transferring the aminoacyl adenylate to a peptidyl carrying center; (2) a thiolation domain, also referred to as a peptidyl carrier protein (8–10 kDa), containing a serine residue that is post-translationally modified with a 4-phosphopantetheine group (Ppant) and acts as an acceptor for the aminoacyl adenylate; and (3) a condensation domain (50–60 kDa), which catalyzes peptide bond-forming chain-translocating steps between an upstream peptidyl-s-Ppant and the downstream aminoacyl-Ppant of the adjacent module. This minimal module for chain extension is typically repeated within a NRPS. A co-linear relationship exists between the number of modules present and the number of amino acids in the final product, with the order of the modules in the synthetase determining the order of the amino acids in the peptide.

Thioesterase Domain

Based on homology searches of the GenBank database, a thioesterase domain is positioned at approximately nucleotide 9,199 to nucleotide 10,032 of CrpC (SEQ ID NO:6).

The cryptophycin thioesterase is likely responsible for the cyclization and release of the cryptophycins from the phosphopantethienyl group of the C-terminal phosphopantetheinyl carrier protein (PCP) of a NRPS. The synthetic methods used for ring closure of cryptophycin thus far limit the scope and ease of derivatization of cyptophycins.

The utility of thioesterase domains as semi-synthetic tools for cylization of synthetic molecules has been demonstrated for gramicidin, epothilone C, and tyrocidine semi-synthesis. See, for example, Wu et al., 2003, *Org. Lett.,* 5:1749; Kohli et al., 2003, *J. Am. Chem. Soc.,* 125:7160; Kohli et al., 2002, *Nature,* 418:658; and Boddy et al., 2003, *J. Am. Chem. Soc.,* 125:3428. Use of the cryptophycin thioesterase for semi-synthesis of cryptophycin provides a new route to synthesis of cyptophycin and its analogues that allows for rapid generation in diversity throughout the entire cyptophycin molecule. Use of a thioesterase domain of the invention to cyclize a cryptophycin chain elongation intermediate (e.g., a seco-SNAC-cryptophycin thioester) provides an approach for generating novel cryptophycins.

Cytochrome p450

Based on homology searches of the GenBank database, the crpF nucleic acid sequence (SEQ ID NO:8) appears to encode a cytochrome p450 (CrpF; SEQ ID NO:9), which is likely an epoxidase involved in cryptophycin biosynthesis.

A survey of the structure-activity relationship of cryptophycins has demonstrated the necessity of the epoxide for high-level tubulin depolymerization and anti-proliferative activities toward tumor cells. Opening of the epoxide, however, is one of the major problems encountered in clinical uses of cryptophycins. A new generation of compounds has been synthesized containing a chlorohydrin. Chlorohydrin analogs are generated from cryptophycins containing an epoxide, and act as pro-drugs. Once chlorohydrins are injected into the serum, the compounds are rapidly converted back to the corresponding epoxides.

High-level tubulin depolymerization and anti-proliferative activities toward tumor cells also requires proper stereochemistry of the epoxide group (β epoxide). Synthesis of cryptophycins containing an epoxide often results in a mixture of two diastereomers. One of the diastereomers is usually inactive, thereby requiring reverse-phase HPLC to separate the two compounds. See, for example, FIG. 2. In addition to the extra expense and time required for separation, separation of the diastereomers results in a significant loss of starting material.

Using a recombinant cell line expressing an epoxidase or a purified form of an epoxidase could dramatically increase overall yields, eliminate a separation step (e.g., HPLC), and allow more flexibility in synthetic strategies. Since no known natural cryptophycin contains the α-epoxide, the native epoxidase enzyme seems to be highly efficient at generating the desired epoxide diastereomer (see FIG. 9). Further, the cryptophycin epoxidase apparently exhibits a high degree of flexibility since it is able to use various substrates (e.g., those having different ring sizes).

Additional Enzymes

Additional enzymes having a variety of functions are involved in cryptophycin biosynthesis. In addition to the PKS, the NRPS, and the epoxidase discussed above, sequence analysis indicated that the following types of enzymes are likely involved in cryptophycin biosynthesis.

Based on homology searches of the GenBank database, crpG (SEQ ID NO:10) appears to encode an iron-dependent non-heme hydroxylase (CrpG; SEQ ID NO:11), which is a member of the γ-butyrobetaine hydroxylase group. Non-heme iron-dependent enzymes generally catalyze a wide variety of $O_2$ reactions. An iron-dependent non-heme hydroxylase is likely involved in hydroxylation of cryptophycins.

Based on homology searches of the GenBank database, crpH (SEQ ID NO:12) appears to encode an aspartate decarboxylase (CrpH; SEQ ID NO:13). An aspartate decarboxylase (EC 4.1.1.11) is likely involved in production of β-alanine or methyl-β-alanine, which is a precursor for NRPS. See, for example, Williamson & Brown, 1979, *J. Biol. Chem.,* 254:8074–82; and Ramjee et al., 1997, *Biochem. J.,* 323:661–9.

Based on homology searches of the GenBank database, crpI appears to be the remnants of an IS1327 transposition event. The sequences identified as having homology to IS1327 are positioned at approximately nucleotides 9154–8514 of SEQ ID NO:1 (pDAM163). No open reading frame or coding sequences, however, were identified.

Based on homology searches of the GenBank database, crpJ (SEQ ID NO:14) appears to encode a non-heme-dependent, flavin-dependent halogenase (CrpJ; SEQ ID NO:15). See, for example, van Pee & Unversucht, 2003, *Chemosphere,* 52:299–312; and Littlechild, 1999, *Curr. Opin. Chem. Biol.,* 3:28–34. A halogenase is likely involved in chlorination of the Unit B amino acid, o-methyl tyrosine.

Based on homology searches of the GenBank database, crpK appears to be the remnants of an IS892-orf2 transposition event. The sequences identified as having homology to IS892-orf2 are positioned at approximately nucleotides 4730–7039 of SEQ ID NO:1 (pDAM163). No open reading frame or coding sequences, however, were identified.

Based on homology searches of the GenBank database, crpL appears to be the remnants of an IS892-orf1 transposition event. The sequences identified as having homology to IS892-orf2 are positioned at approximately nucleotides 4730–7039 of SEQ ID NO:1 (pDAM163). No open reading frame or coding sequences, however, were identified.

Based on homology searches of the GenBank database, crpM appears to be an ISRSO13 transposase sequence. The identified coding sequence (crpM; SEQ ID NO:16) encodes a polypeptide designated CrpM (SEQ ID NO:17) with unknown function.

Based on homology searches of the GenBank database, crpN (SEQ ID NO:18) appears to encode a non-heme-dependent, iron-dependent hydroxylase (CrpN, SEQ ID NO:19). See, for example, Solomon et al., 2003, *PNAS USA,* 100:3589–94; and Ryle et al., *PNAS USA,* 100:3790–5.

Based on homology searches of the GenBank database, crpO appears to encode a pvdE-type regulator (CrpO). The sequences identified as having homology to a pvdE-type regulator are positioned at approximately nucleotides 786–1768 of SEQ ID NO:1 (pDAM163). A pvdE-type regulator is likely involved in regulating cyptophycin biosynthesis. See, for example, Wilson et al., 2001, *J. Bacteriol.,* 183:2151–5.

Based on homology searches of the GenBank database, crpP (SEQ ID NO:20) appears to encode a thioredoxin (CrpP, SEQ ID NO:21). Thioredoxins are generally reduction/oxidation (redox)-regulatory proteins thought to have anti-apoptotic effects. Thioredoxin is likely involved in redox reactions (e.g., cytochrome p450-dependent hydroxylations) associated with cryptophycin biosynthesis.

Based on homology searches of the GenBank database, crpU (SEQ ID NO:22) appears to encode an N-acetyltransferase (EC 2.3.1.5) (CrpU, SEQ ID NO:23). N-acetyltransferases usually catalyze the transfer of acetyl groups from acetyl-CoA to arylamines.

Based on homology searches of the GenBank database, crpV (SEQ ID NO:24) appears to encode a large exoprotein involved in heme utilization (CrpV, SEQ ID NO:25). A large exoprotein involved in heme utilization may be involved in redox reactions associated with cryptophycin formation (i.e., cytochrome p450-dependent hydroxylations).

Based on homology searches of the GenBank database, crpW appears to encode a tetratricopeptide repeat (TPR) protein (CrpW). A TPR is a 34 amino acid repeated sequence motif found in a number of diverse proteins that may be involved in transcriptional repression, mitochondrial and/or peroxisomal protein transport, cell cycle regulation, protein kinase inhibition, heat shock response, and/or mediating protein-protein interactions. See, for example, Sikorski et al., 1991, *Cold Spring Harbor Symp. Quant. Biol.*, 56:663–73; and Lamb et al., 1995, *Trends Biosci.*, 20:257–9.

Based on homology searches of the GenBank database, crpX (SEQ ID NO:26) appears to encode a chorismate mutase-prephenate dehydrogenase (CrpX, SEQ ID NO:27). A chorismate mutase-prephenate dehydrogenase (EC 1.3.1.12) usually catalyzes the first two steps in the biosynthesis of tyrosine (the chorismate mutase activity) and the conversion of prephenate to p-hydroxyphenylpyruvate in the presence of NAD (the prephenate dehydrogenase activity). A chorismate mutase-prephenate dehydrogenase is likely involved in the production of shikimate-derived PKS starter units in cryptophycin biosynthesis.

Based on homology searches of the GenBank database, crpY (SEQ ID NO:28) appears to encode a 2-hydroxychromene-2-carboxylate isomerase (CrpY, SEQ ID NO:29). A 2-hydroxychromene-2-carboxylate isomerase is involved in the naphthalene catabolic pathway and catalyzes the reaction of 2-hydroxychromene-2-carboxylate into trans-o-hydroxybenzylidenepyruvate. See, for example, Eaton, 1994, *J. Bacteriol.*, 176:7757–62; and Zylstra et al., 1997, *FEMS Microbiol. Lett.*, 153:479–84. A 2-hydroxychromene-2-carboxylate isomerase is likely involved in the production of shikimate-derived PKS starter units in cryptophycin biosynthesis.

Based on homology searches of the GenBank database, crpZ (SEQ ID NO:30) appears to encode a 3-dehydroquinate synthase (CrpZ, SEQ ID NO:31). A 3-dehydroquinate synthase (EC 4.2.3.4) usually catalyzes the cyclization of 3-deoxy-D-arabino-heptulosonic acid 7-phosphate (DAHP) to dehydroquinate. A 3-dehydroquinate synthase may be involved in the production of shikimate-derived PKS starter units.

Combinatorial Techniques and Domain Swapping

Figure 4:
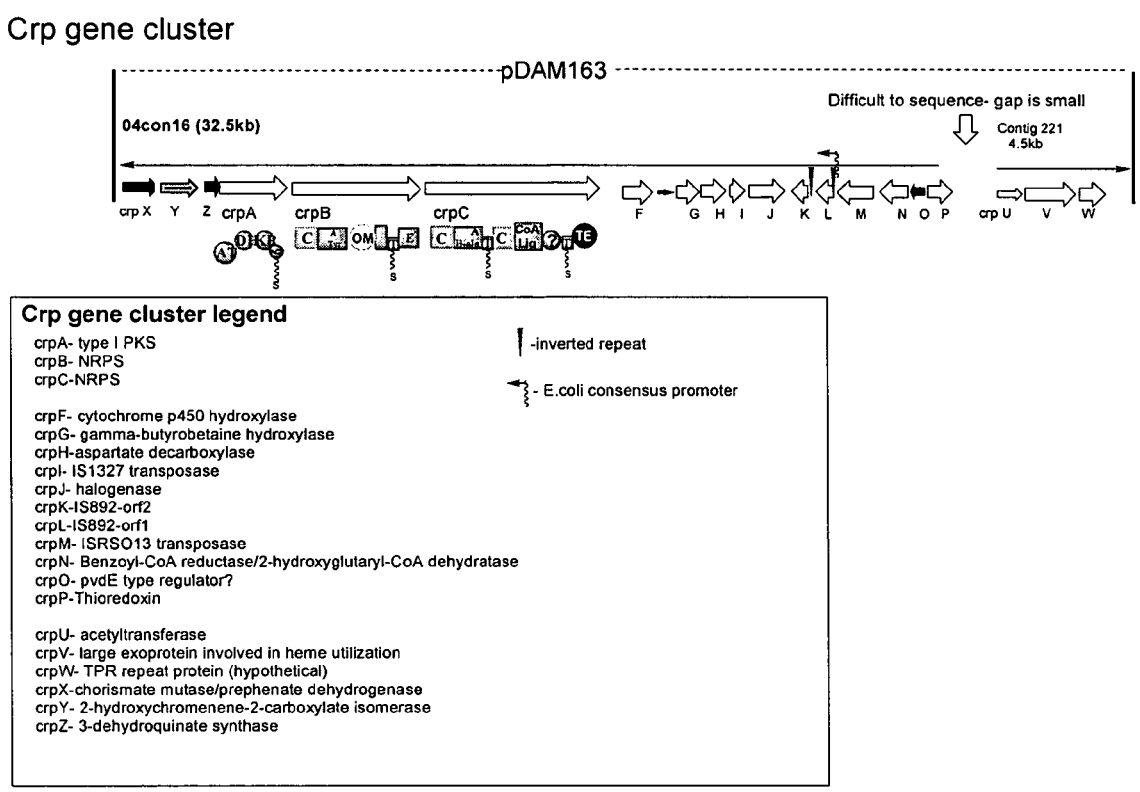
FIG. 4 is a schematic of cosmid pDAM163 and genes identified with relationships to cryptophycin biosynthesis.

It will be apparent to one of skill in the art that any number and/or combination of nucleic acid molecules of the invention (e.g., SEQ ID NOs:2, 4, 6, 8, 10, 12, 14, 16, 18, 20, 22, 24, 26, 28, and/or 30) can be joined together to generate a longer nucleic acid molecule (e.g., pDAM163; shown in FIGS. 4 and 5 and SEQ ID NO:1). In addition, the nucleic acid molecules (SEQ ID NOs:2, 4, 6, 8, 10, 12, 14, 16, 18, 20, 22, 24, 26, 28, and 30) can be manipulated using standard techniques to delete or inactivate activity encoding regions, insert regions from different molecules encoding corresponding activities from the same or different biosynthesis systems, or be otherwise mutated using standard procedures for obtaining genetic alterations. Mutations can be made to the native sequences using conventional techniques such as those described above.

Chemical approaches have lead to highly informative structure-activity relationships. Therefore, the regions suggested for modifications are well defined, particularly in view of the modular-type structure of the PKSs and NRPSs.

In addition to approaches that provide mutated polypeptides, it is possible to manipulate entire domains or portions of domains. For example, a domain having a particular activity from one biosynthetic pathway can be exchanged or replaced with a domain having a corresponding activity from a different biosynthetic pathway. Alternatively, a domain having a particular activity from a biosynthetic pathway can be exchanged or replaced with a domain having an unrelated activity from the same or a different biosynthetic pathway.

If replacement of a particular nucleic acid region encoding a host enzyme is to be made, this replacement can be conducted in vitro using suitable restriction enzymes and cloning techniques or can be effected in vivo using recombinant techniques involving homologous sequences framing the replacement region in a donor plasmid and a receptor region in a recipient plasmid. A representative exchange system that involves plasmids that have different temperature sensitivities is described in PCT Publication No. WO 96/40968.

The various nucleic acid molecules involved in cyrptophycin biosynthesis, individually or as a cocktail of such molecules, can be cloned into one or more recombinant vectors. When more than one molecule is cloned together, such elements can be under the control of a single element for expression (e.g., a promoter) or each molecule can be under the control of an element for expression. The nucleotide sequences encoding an enzymatic subunit or a cocktail of such molecules can include flanking restriction sites to allow for the easy deletion and insertion of other molecules or regions of a molecule. In this manner, nucleotide sequences encoding hybrid or chimeric enzymes can be generated. The design of such unique restriction sites is known to those of skill in the art and can be accomplished using the techniques described above such as site-directed mutagenesis and PCR.

Expression vectors containing nucleotide sequences encoding a variety of enzymatic activities can be transformed into an appropriate host cell to construct a library. In one approach, a mixture of such vectors is transformed into host cells and the resulting cells plated into individual colonies and selected for successful transformants. Each individual colony represents a colony expressing an enzyme having a particular activity and, ultimately, the ability to produce a particular product. Alternatively, expression vectors can be used individually to transform host cells, which are then assembled into a library. Methods are known for screening a library or isolates from a library for substrate-specificity and/or production of a particular product. Another strategy for preparing a variety of products is by random digestion-religation leading to chimeric domains or modules. A similar such method has been described as a "DNA shuffling method" (see Patten et al., 1997, *Curr. Op. Biotechnol.*, 8: 724–733).

As one non-limiting example, the creation of novel macrolides can be achieved through genetic manipulation of polyketide synthases. The modular nature of polyketide synthases allows for domain exchange between different polyketide synthase genes, resulting in hybrid genes that produce polyketide synthases with altered properties that, in turn, produce modified macrolide structures. Thus, it is possible to control chain length, choice of chain extender unit, degree of β-carbon oxidation level, and stereochemistry. See, for example, PCT Publication Nos. WO 93/13663; WO 95/08548; WO 96/40968; WO 97/02358; WO 98/27203; and WO 98/49315; U.S. Pat. Nos. 4,874,748; 5,063,155; 5,098,837; 5,149,639; 5,672,491; 5,712,146;

5,830,750; and 5,843,718; and Fu et al., 1994, *Biochemistry*, 33:9321–9326; McDaniel et al., 1993, *Science*, 262:1546–1550; and Rohr, 1995, *Angew. Chem. Int. Ed. Engl.*, 34(8):881–888.

The application of innovative combinatorial techniques to this type of genetic organization has prompted the generation of novel natural products, by adding, deleting, or exchanging domains or entire modules. See, for example, U.S. Pat. Nos. 5,672,491; 5,712,146; 5,830,750; 5,843,718; 5,962,290; and 6,022,731; and Tang et al., 2000, *Science*, 287:640–2). The invention allows for combinatorial biosynthesis technology to produce a diversity of cryptophycin analogues in addition to those cryptophycin analogues produced to date.

The invention will be further described in the following examples, which do not limit the scope of the invention described in the claims.

EXAMPLES

Example 1

Cloning and Sequencing the crp Gene Cluster Contained within pDAM163

Primer synthesis and cosmid sequencing was preformed at the University of Minnesota Advanced Genetic Sequencing and Analysis Center-AGAC (St. Paul, Minn.). Degenerate PCR primers specific for conserved core motifs of peptide synthetase adenylation domains A2 and A8 (Marahiel et al., 1997, *Chem. Rev.*, 97:2651–74) were used and consisted of the following sequences: MTF2' forward primer (5'-GCNGG (ct) GG (ct) GCNTA (ct) GTNCC-3' (SEQ ID NO:38)) and MTR reverse primer (5'-CCNGG (agt) AT (tc) TTNAC (tc) TG-3' (SEQ ID NO:39)) (Neilan et al., 1999, *J. Bacteriol.*, 181:4089–97). Adenylation domain containing DNA fragments of approximately 1100 bp in length were synthesized by PCR using a Hybaid Express PCR thermocycler (30 cycles: 95° C. for 1 min, 55° C. for 1 min, 72° C. for 1 min) with *Nostoc* sp ATCC 53789 genomic DNA as a template. End sequencing of one fragment, pNAM124, using an Applied Biosystems, Inc. ABI3700 sequencer (Foster City, Calif.) confirmed that the fragment contained an adenylation domain. Prediction of its substrate specificity (aromatic amino acid activating) was determined using methods described previously (Challis et al., 2000, *Chem. Biol.*, 7:211–24). The fragment was radiolabeled using the RadPrime labeling kit (Pharmacia) with [$\alpha$-$^{32}$P] dCTP (Amersham) according to the manufacter's directions. The radiolabeled fragment was used to probe the genomic library using standard colony hybridization protocols (Sambrook & Russell, 2000, *Molecular Cloning: A Laboratory Manual*, Cold Spring Harbor Laboratory Press). One cosmid, pDAM163, was selected because it hybridized to the adenylation domain encoding DNA probe contained within pNAM124. The DNA sequence of pDAM163 was obtained by creating a shotgun library of the cosmid within the sequencing vector, pUC18. Sequences obtained were assembled using SeqMan version 5.06 (DNAStar, Madison, Wis.) and Frameplot 2.3.2 (Ishikawa & Hotta, 1999, *FEMS Microbiol. Lett.*, 174:251–3) used to identify individual open reading frames. The putative functions of the crp biosynthesis genes were assessed by using the open reading frames and their putative protein products versus genes/proteins contained within the GenBank database using BlastN and BlastP.

Example 2

Cloning Genes Involved in Cryptophycin Biosynthesis

DNA encoding a putative cryptophycin biosynthetic gene cluster was contained on a cosmid designated pDAM163. pDAM163 DNA was prepared using a Qiagen large construct DNA extraction kit from a 500 mL culture grown overnight at 25° C. in LB media containing 50 µg/mL ampicillin.

Example 3

Cryptophycin Production

The cosmid, pDAM163, or sub-vectors such as cosmid, plasmids, yeast artifical chromosomes, bacterial artificial chromosomes, or phage vectors containing pDAM163 sequences can be used to biosynthetically prepare cryptophycins in a non-*Nostoc* spp. host. pDAM163 is introduced into an *Escherichia coli* strain that harbors a phosphopantetheinyl transferase gene required for expressing active polyketide synthase and nonribosomal peptide synthetase enzymes. Fermentation of the resulting strain on a large scale, and extracting and detecting cryptophycins are performed as decribed previously (Subbaraju et al., 1997, *J. Nat. Prod.*, 60:302–5; and Golakoti et al., 1994, *J. Am. Chem. Soc.*, 116:4729–37).

Example 4

Cloning Strategy of the Thioesterase Domain

DNA encoding the cryptophycin thioesterase domain is contained at the 3'-end of the 3'-terminal open reading frame of CrpC, which also codes for domains necessary for incorporation of units C and D of cryptophycin. Therefore, truncation of the DNA in the final ORF was necessary in order to isolate the cryptophycin thioesterase. Identification of the DNA encoding the cryptophycin thioesterase was elucidated through use of the NCBI "CDART" program for identification of conserved domains. The "nnpredict" secondary structure prediction program (Kneller et al., 1990, *J. Mol. Biol.*, 214:171) was used to determine the putative secondary structure of the gene product of the putative thioesterase domain and a domain capable of being phosphopantetheinlyated. The forward primer, 5'-ATT TAT CAT ATG GGT TCC GAT TCC GGA GCC GA-3' (SEQ ID NO:40), was designed to a position immediately 3' of a nucleic acid sequence predicted to encode a protein capable of being phosphopantethionylated in a region appearing to lack secondary structure based on the "nnpredict" program results and contained an NdeI restriction site. The reverse primer, 5'-AAA TAA GAA TCC TCA TCA TTT TTC CAA TTG ATG GGT-3' (SEQ ID NO:41), was constructed to anneal to the 3' end of the open reading frame and contained a BamHI restriction site.

PCR reactions were performed with 0.1 µL of pDAM163 DNA from the extraction, 1 µM forward primer, 1 µM reverse primer, 1× ExTaq buffer (Takara), 1 µL ExTaq polymerase (Takara), and 1 µM dNTP (Takara) to a final volume of 50 µL with water. The PCR program consisted of 30 cycles of the following amplification conditions: denaturation 1 min at 95° C., 1 min annealing at 50° C., 1.5 min extension at 72° C. PCR fragments corresponding to the desired length were separated on a 1% agarose gel and purified from the gel using a Qiagen gel extraction kit. The PCR fragment was cloned into a pGEM T-Easy vector (Promega) using T-overhang cloning with the pGEM T-Easy kit (Promega).

Clones were transformed into XL-1 Blue competent cells using heat shock protocols as described in the pGEM T-Easy kit. Constructs containing inserts were identified using blue/white screening according to the pGEM T-Easy kit protocol. Five clones containing insert were re-plated and half of the colony was subjected to PCR to verify insert of the desired DNA size using the same PCR condition listed above, with the exception of a 5 min incubation of each clone at 96° C. prior to the amplification cycles.

One clone containing the desired size insert was grown in a 2 mL culture overnight in LB media containing ampicillin (50 μg/mL; Research Products International Corp). DNA was purified using a Qiagen mini-prep kit. DNA was submitted for sequencing to the University of Michigan DNA Sequencing Core Lab and sequenced 3 times from the 5' end using the T7 primer binding site and 3 times from the 3' end using the SP6 primer-binding site. DNA from the sequenced clone was ligated into the NdeI and BamHI sites in pET28b (Novagen) and transformed into BL21 competent cells using electroporation. All cells were plated on LB plates containing kanamycin (50 μg/mL; Research Products International Corp) and incubated overnight at 37° C. Ten colonies were subjected to PCR verification of the desired DNA insert using the primers and protocols listed above.

Example 5

Expression and Purification of the Cryptophycin Thioesterase Domain

A clone containing the desired insert size, as visualized by agarose gel electrophoresis, was grown overnight in 25 mL of 2YT broth (16 g tryptone, 10 g yeast extract, 10 g NaCl) containing 50 μg/mL kanamycin at 37° C. 5 mL of the overnight culture were used to inoculate 1L of 2YT media containing 50 μg/mL kanamycin, which was grown at 37° C. The culture was induced at an $OD_{595}$ of 0.7 with 0.2 mM IPTG and grown overnight at 30° C. Cells were harvested at 5000 g for 30 min. The pellet was resuspended in 20 mL 0.1 M sodium phosphate buffer (pH 8) containing 20 mM imidazole and 300 mM NaCl. 4 mg of lysozyme and 2 g sucrose were added to the cell suspension and incubated at room temperature for 30 min until the viscosity of the solution increased. The solution was put on ice and subjected to sonication (5 times for 20 sec) at a level of 6 on the sonicator until the solution became less viscous. The suspension was centrifuged at 17,000 g for 1 hour at 4° C.

The supernatant was collected and incubated with 7 mL of Qiagen Ni-Agarose overnight at 4° C. The agarose was then loaded into a column and washed with 10 column volumes of 0.1 M sodium phosphate buffer (pH 8) containing 20 mM imidazole and 300 mM NaCl. The column was washed with 10-column volumes wash buffer containing 50 mM imidazole. Protein was eluted with wash buffer containing 100 mM imidazole. The eluted sample contained ~50 mg of protein as determined using a BioRad Bradford assay kit. Samples were run on a 4–20% SDS-PAGE gel to check for purity. A band corresponding the expected molecular weight was observed at >95% purity. Protein was subjected to a PD-10 column prior to kinetic assays for buffer exchange to 100 mM sodium phosphate buffer (pH 8).

Example 6

Preparation of Substrates

Figure 10:
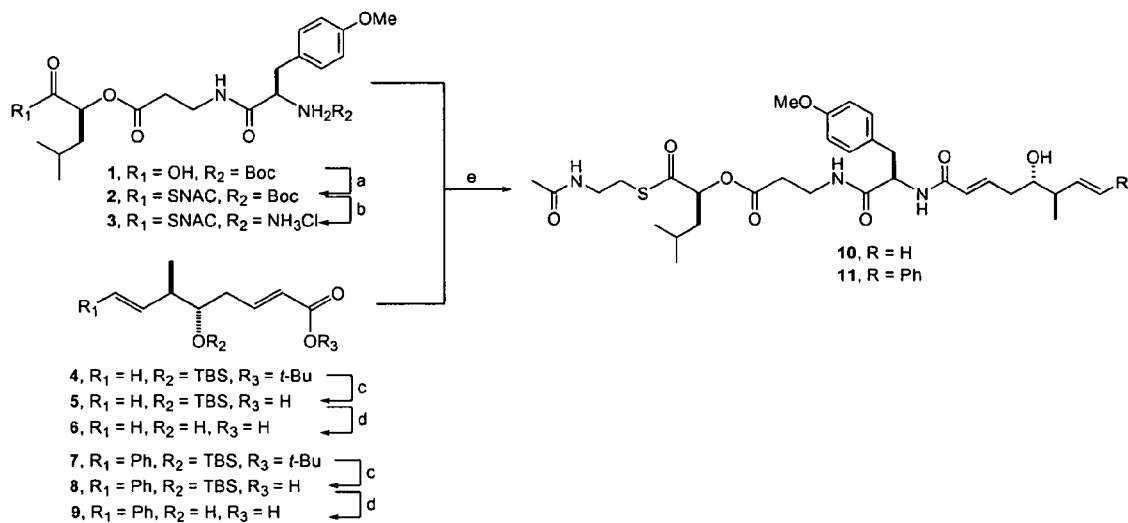
FIG. 10 is a schematic of the synthesis of SNAC substrates.

Referring to FIG. 10, substrate 3 represents the tri-depsipeptide sector of cryptophycin except that the methyl β-alanine residue has been replaced by β-alanine. The remaining functionality has been preserved. The halogenation of the tyrosine residue likely is a tailoring modification, which is performed after thioesterase-mediated cyclization. Therefore, a simple tyrosine methyl ether was employed. The SNAC thioester substrate 3 was prepared from known tri-depsipeptide 1 (Georg et al., *J. Org. Chem.*, 2000, 65:7792–7799) by PyBOP coupling of N-acetylcysteamine followed by Boc deprotection with 4 N HCl in 1,4-dioxane to provide 3 as the hydrochloride salt (FIG. 10).

Similarly, the Unit A analogs 6 and 9 were prepared by stepwise deprotection of the t-butyl ester with TFA containing 1% triethylsilane followed by TBS cleavage with 5% hydrofluoric acid in acetonitrile from known Unit A fragments 4 and 7 (Georg et al., supra). PyBOP mediated coupling of subunit 3 with fragments 6 and 9 afforded the seco-SNAC-cryptophycin thioester substrates 10 and 11 respectively, which were purified by reverse-phase semi-preparative HPLC (C18, Alltech Econosil 10×250 mm, 5 mL/min, 10–100% AcCN/$H_2O$+0.1% TFA, 30 minutes).

Example 7

Kinetic Characterization of Cryptophycin Thioesterase Activity with a Substrate

A standard curve of the cleaved product was determined on a 10–67% acetonitrile/water (0.1% TFA) gradient over 30 min. Cleavage reactions were run for 15 min at 30° C. with 1.4 μM cryptophycin thioesterase with substrate concentrations of 0.3125, 0.625, 1.25, 2.5, and 5 mM substrate containing 4% DMSO in 0.1 M $NaH_2PO_4$ buffer at pH 7, 8, and 8.75. The hydrolyzed version of substrate 3 was monitored in order to determine the rate of hydrolysis for the reactions. All reactions were run in triplicate.

Example 8

Cyclization of Cryptophycin Substrates

A 1 mL solution containing 100 μM substrate 10 or substrate 11, with 7 μM cryptophycin thioesterase, 0.095 M $NaH_2PO_4$ buffer (pH 7), and 5% DMSO was incubated for 1 hour at 30° C. Negative control reactions containing all reagents except for the cryptophycin thioesterase were run in parallel. The total contents of each reaction were separated using reverse phase chromatography with a 10–100% gradient (acetonitrile+0.1% TFA/water+0.1% TFA) over 37 min on an Alltech Econosil 10 U C18 column with dimensions 250 mm×4.6 mm. The products were analyzed by electrospray mass spectrometry (ES+). The relative concentration of the products was determined by comparing absorption at 245 nM, which corresponds to the enone functionality contained within each molecule examined.

Example 9

Results

Immediately 5' of the nucleotide sequences encoding the cryptophycin thioesterase are sequences that putatively encode a phosphopantetheinylation domain. The thioesterase domain was, therefore, constructed to begin immediately following the 3' end of DNA predicted to encode the phosphopantetheinylation domain.

The molecular weight of cryptophycin TE was determined to be 35,424 Da by ES+ mass spectrometry and 35,410 by MALDI-TOF mass spectrometry. The calculated average mass for the cryptophycin TE was 35,550.08, and the monoisoptopic mass was determined to be 35527.66. The mass spectrometry determined that the molecular weight of cryptophycin thioesterase corresponds to a thioesterase that is missing its N-terminal methionine. Processing of the N-terminal methionine commonly occurs when proteins are expressed small amino acids adjacent to the N-terminal methionine, such as the glycine that is located adjacent to the N-terminal methionine in the engineered construct.

The cyclized cryptophycins are fairly insoluble in water and, therefore, kinetic characterization of hydrolytic rate of the cryptophycin thioesterase was determined using a substrate modeled after the depsipeptide fragment corresponding to Units B, C and D of Cryptophycin 1.

Figure 11:
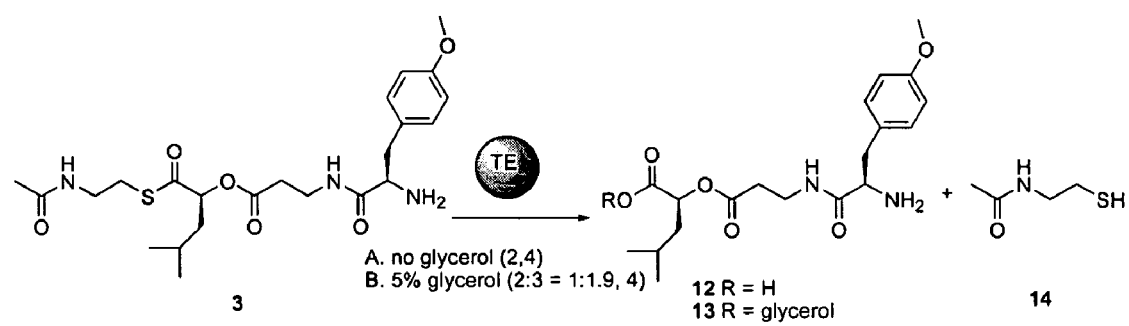
FIG. 11 is a schematic of cryptophycin thioesterase-catalyzed conversion of substrate 1 to products 2, 3, and 4 in 0.1 M NaPi buffer (pH 8.0) containing 4% DMSO.

Characterization of the cryptophycin thioesterase-catalyzed hydrolysis of the substrate 3 was monitored by HPLC. The two hydrolysis products produced by the reaction were determined using ES+ mass spectrometry to be N-acetyl cystamine and molecule 12 (FIG. 11).

Initially, the cryptophycin thioesterase was stored in 5% glycerol containing buffer. However, analysis by HPLC/MS of hydrolysis of the substrate 3 with cryptophycin thioesterase containing 5% glycerol revealed that the glycerol adduct was the major product of the reaction with a minor product of the hydrolyzed substrate. Therefore, the expression strain containing cryptophycin thioesterase was recultured and the cryptophycin thioesterase was purified in the absence of glycerol. Subsequent analysis of the cryptophycin thioesterase-catalyzed hydrolysis of the substrate 3 did not reveal a glycerol adduct peak. The generation of the glycerol adduct (molecule 13, FIG. 11) warrants caution when determining kinetics using buffers containing glycerol (especially using indirect methods).

Figure 12:
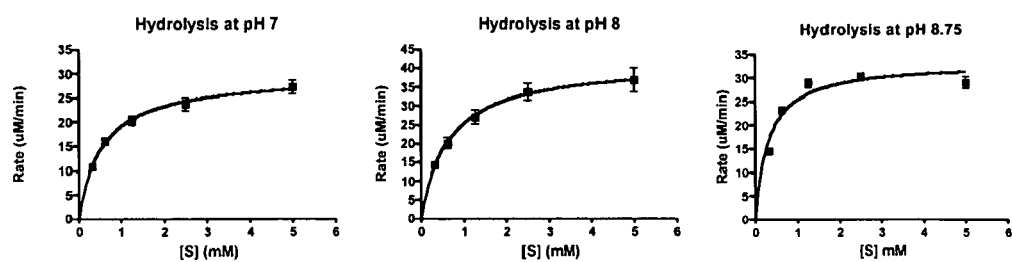
FIG. 12 are graphs of cryptophycin thioesterase-catalyzed hydrolysis of substrate 1 using 1.4 µM thioesterase in 50 µL reactions containing 0.1 M $NaH_2PO_4$ and 4% DMSO.

The hydrolytic activity of cryptophycin thioesterase was determined for the substrate 3 using steady state kinetic analysis utilizing HPLC analytical methods. FIG. 12 outlines the catalytic rate constants for hydrolysis of the substrate 3 with cryptophycin thioesterase at pH 7, pH 8, and pH 8.75.

Figure 13:
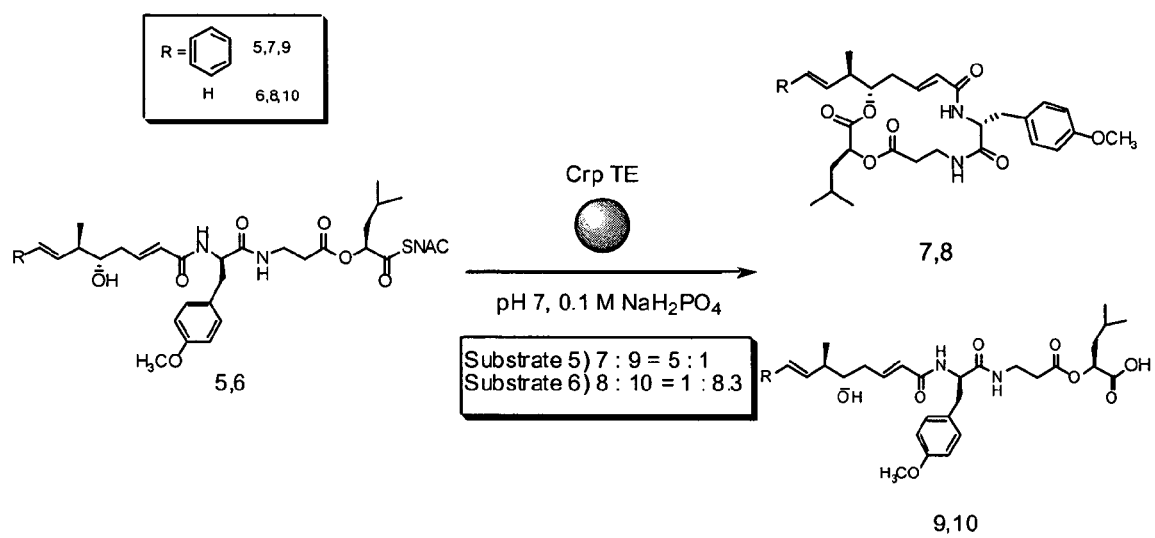
FIG. 13 is a schematic of cryptophycin thioesterase-catalyzed cyclization and hydrolysis of the seco-SNAC-ester of arenastatin and the seco-SNAC-ester of the vinyl derivative of arenastatin.

The ability of the cryptophycin thioesterase to cyclize substrates was examined using seco-SNAC-des-epoxy-arenastatin 11 and the des-benzyl derivative of seco-SNAC-des-epoxy-arenastatin 10 as substrates (FIG. 13).

The partition ratio of cyclization to hydrolysis for the cryptophycin catalyzed reaction with seco-SNAC-des-epoxy arenastatin 11 was 5: 1, while the partition ratio of cyclization to hydrolysis with the seco-SNAC-des-benzyl-des-epoxy-arenastatin 10 was 1:8.3, as determined by HPLC/MS with quantitation of the quantity of enone functionality at 245 nM. Therefore, the cryptophycin thioesterase preferentially cyclized the SNAC thioester of seco-des-epoxy-arenastatin over the SNAC thioester of seco-des-benzyl-des-epoxy-arenastatin.

The specificity constant ($k_{cat}/K_M$) for the cryptophycin thioesterase catalyzed hydrolysis of the substrate 3 increased over the pH range from 7 to 8.75 (FIG. 12). The increase in the specificity constant was due to an increase in the $k_{cat}$ from pH 7 to pH 8, and a decrease in $k_{cat}$ from pH 8 to pH 8.75. The $K_M$ for the hydrolysis of the substrate 3 decreased slightly from pH 8 to pH 8.75, although the $k_{cat}$ for hydrolysis also decreased, resulting in an overall increase in the specificity constant.

Interestingly, although substrate 3 contains both a thioester bond and an ester bond, hydrolysis occured specifically at the thioester, even after complete hydrolysis of the thioester, indicating a selective preference for that site.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a nucleic acid sequence having at least 95% sequence identity to SEQ ID NO:6, or to a fragment thereof, wherein said nucleic acid sequence or fragment thereof encodes a polypeptide that exhibits non-ribosomal peptide synthase (NRPS) activity.

2. The nucleic acid molecule of claim 1, wherein said nucleic acid sequence has at least 99% sequence identity to ID NO:6 or a fragment thereof encoding a polypeptide having NRPS activity.

3. The nucleic acid molecule of claim 1, wherein said nucleic acid sequence is SEQ ID NO:6 or a fragment thereof encoding a polypeptide having NRPS activity.

4. An isolated polypeptide encoded by the nucleic acid sequence of claim 1.

5. The polypeptide of claim 4, wherein said polypeptide has the sequence of SEQ ID NO:7.

6. A vector comprising the nucleic acid molecule of claim 1.

7. An isolated host cell containing the vector of claim 6.

8. An isolated nucleic acid molecule comprising a nucleic acid sequence having at least 95% sequence identity to nucleotides 9,199 to 10.032 of SEQ ID NO:6, or to a fragment thereof, wherein said nucleic acid sequence or fragment thereof encodes a polypeptide that exhibits thioesterase activity under appropriate conditions.

9. The isolated nucleic acid of claim 8, wherein said appropriate conditions are pH, media, temperature, and/or the presence or absence of co-factors.

* * * * *

UNITED STATES PATENT AND TRADEMARK OFFICE
CERTIFICATE OF CORRECTION

PATENT NO. : 7,229,814 B2 Page 1 of 1
APPLICATION NO. : 11/122396
DATED : June 12, 2007
INVENTOR(S) : David H. Sherman It is certified that error appears in the above-identified patent and that said Letters Patent is hereby corrected as shown below:

Title page (Page 2), line 20, Col. 1, References Cited, Other Publications, Kinzie et al. reference, please delete "Coordinaiton" and insert --Coordination-- therefor;

Title page (Page 2), line 1, Col. 2, References Cited, Other Publications, Neilan et al. reference, please delete "Cyanobacterial" and insert --Cyanobacteria-- therefor;

Title page (Page 2), line 3, Col. 2, References Cited, Other Publications, Pattern et al. reference, please delete "Pattern" and insert --Patten-- therefor;

Column 155, line 52 (Claim 2), before "ID" please insert --SEQ--;

Column 156, line 48 (Claim 7), please delete "ceil" and insert --cell-- therefor;

Column 156, line 51 (Claim 8), please delete "10.032" and insert --10,032-- therefor.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,229,814 B2 |
| APPLICATION NO. | : 11/122396 |
| DATED | : June 12, 2007 |
| INVENTOR(S) | : David H. Sherman |

It is certified that error appears in the above-identified patent and that said Letters Patent is hereby corrected as shown below:

Column 1, line 4, please insert:

--STATEMENT REGARDING GOVERNMENT FUNDING

This invention was made with government support under CA83155 awarded by the National Institutes of Health. The government has certain rights in the invention.--

Signed and Sealed this

Ninth Day of December, 2008

JON W. DUDAS
*Director of the United States Patent and Trademark Office*